United States Patent
Smith et al.

(10) Patent No.: US 7,858,785 B2
(45) Date of Patent: Dec. 28, 2010

(54) AMINOPYRIMIDINE COMPOUNDS AND METHODS OF USE

(75) Inventors: Adrian Leonard Smith, Simi Valley, CA (US); Paul Edward Brennan, Canterbury (GB); Fenel F. Fils, Thousand Oaks, CA (US); Gang Liu, Oak Park, CA (US); Nick A. Paras, Glendale, CA (US); Daniel Martin Retz, Newbury Park, CA (US); Elizabeth Rainbeau, Port Hueneme, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/562,853

(22) Filed: Sep. 18, 2009

(65) Prior Publication Data

US 2010/0010014 A1    Jan. 14, 2010

Related U.S. Application Data

(63) Continuation of application No. 11/304,901, filed on Dec. 16, 2005, now Pat. No. 7,786,132.

(60) Provisional application No. 60/636,604, filed on Dec. 17, 2004.

(51) Int. Cl.
  *C07D 417/14*    (2006.01)
  *A61K 31/506*    (2006.01)
  *A61P 19/02*    (2006.01)
  *A61P 35/00*    (2006.01)

(52) U.S. Cl. .................. 544/316; 544/331; 544/333; 514/275; 514/256; 514/269

(58) Field of Classification Search ............... 544/316, 544/331, 333; 514/275, 256, 269
See application file for complete search history.

(56) References Cited

U.S. PATENT DOCUMENTS

| | | |
|---|---|---|
| 6,417,185 B1 | 7/2002 | Geoff et al. |
| 6,489,344 B1 | 12/2002 | Nuss et al. |
| 6,531,479 B2 | 3/2003 | Wang et al. |
| 6,762,179 B2 | 7/2004 | Cochran et al. |
| 2003/0149057 A1 | 8/2003 | Wang et al. |

FOREIGN PATENT DOCUMENTS

| | | |
|---|---|---|
| EP | 02/033461 | 8/1987 |
| EP | 04/071261 | 2/1992 |
| WO | 95/09852 | 4/1995 |
| WO | 97/19065 | 5/1997 |
| WO | 00/39087 | 12/1999 |
| WO | 01/14333 | 3/2001 |
| WO | 02/20495 | 3/2002 |
| WO | 2004/014899 | 2/2004 |

*Primary Examiner*—Venkataraman Balasubramanian
(74) *Attorney, Agent, or Firm*—Joseph W. Bulock; Ronald S. Hermenau

(57) ABSTRACT

The invention relates to aminopyrimidine compounds useful for treating diseases mediated by polo-like kinase 1 (Plk1). The invention also relates to the therapeutic use of such aminopyrimidine compounds and compositions thereof in treating disease states associated with abnormal cell growth and unwanted cell proliferation.

12 Claims, No Drawings

AMINOPYRIMIDINE COMPOUNDS AND METHODS OF USE

This application is a continuation of U.S. application Ser. No. 11/304,901 filed on Dec. 16, 2005, now U.S. Pat. No. 7,786,132, which claims benefit of U.S. Provisional Ser. No. 60/636,604 filed on 17 Dec. 2004, which are hereby incorporated by reference.

1. FIELD OF THE INVENTION

The invention relates to aminopyrimidine compounds useful for treating diseases mediated by polo-like kinase 1 (Plk1). The invention also relates to the therapeutic use of such aminopyrimidine compounds and compositions thereof in treating disease states associated with abnormal cell growth and unwanted cell proliferation.

2. BACKGROUND OF THE INVENTION

Protein kinases represent a large family of proteins which play a central role in the regulation of a wide variety of cellular processes, maintaining control over cellular function. A partial list of such kinases includes ab1, AKT, bcr-ab1, Blk, Brk, Btk, c-kit, c-met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, GSK3α, GSK3β, Hck, IGF-1R, INS-R, Jak, KDR, Lck, Lyn, MEK, MK2, MSK1, p38, PDGFR, PIK, PKB, PKA, PRAK, PRK2, PKC, PYK2, P70S6, ROCK2, ros, tie, tie2, TRK, Yes, and Zap70. Inhibition of such kinases has become an important therapeutic target.

Plk1 is a mitosis specific serine/threonine protein kinase that is overexpressed in a variety of human tumors. Three mammalian Plks have been identified; Plk1 is expressed during M phase and cytokinesis, whereas Plk2 (Snk) and Plk3 (Fnk) are expressed in other phases of the cell cycle. These enzymes are characterized by their similar N-terminal catalytic domains, as well as a C-terminal domain with highly conserved sequences termed the polo box. Plk1 localizes to centrosomes and the spindle poles at metaphase, in the central spindle during anaphase, and at the midbody during cytokinesis. Plk1 has been implicated in centrosome maturation, bipolar spindle formation and activation of the anaphase-promoting complex.

Plk1 phosphorylated substrates regulate four key pathways that control the coordinated progression of mitosis. Inhibiting Plk1 function using antibody injection, expression of a dominant negative Plk1, and antisense mRNA reduction produces aberrant chromosome segregation, cell cycle arrest, and mitotic cell death in tumor cell lines but reversible G2 arrest in normal nontransformed primary cell lines.

Plk1 has been shown to be overexpressed in many human tumors, such as breast, colorectal, non-small cell lung, oesophageal and ovarian cancers. It plays a central role in the regulation of the cancer cell cycle. Among other functions, Plk1 is thought to regulate initiation, progression and exit from mitosis, the stage when cancer cells divide. Consequently, blocking Plk1 in cancer cells prevents their division or mitosis. For example, the taxanes, highly successful drugs that are widely used in clinical practice to treat cancer, also work by blocking mitosis. However, these drugs cause considerable side effects upon normal, non-dividing cells especially in the nervous system. Plk inhibitor drugs specifically target dividing cells and may be able to avoid the undesirable toxicities of the taxanes. Despite the attractiveness of Plk1 as an anticancer drug target, little progress has been reported with regard to the discovery of chemical inhibitors of the Plk1 kinase.

Modulation of Plk1 by small molecules can be achieved by identifying compounds that bind to and activate or inhibit Plk1. Schwede et al. in International Publication no. WO 03/093249, published Nov. 13, 2003, disclose certain thiazolidinone derivatives and thiophene analogs as inhibitors of Plk1. Certain thiophene compounds have also been reported to inhibit Plk. Andrews et al., International Publication no. WO 03/093249, published Feb. 19, 2004.

3. SUMMARY OF THE INVENTION

This invention encompasses novel compounds useful for treating diseases or conditions mediated by Plk1. The invention also encompasses the therapeutic use of such compounds and compositions thereof in the treatment of disease states associated with abnormal cell growth or unwanted cell proliferation, such as cancer.

In one aspect the invention comprises a compound of Formula I

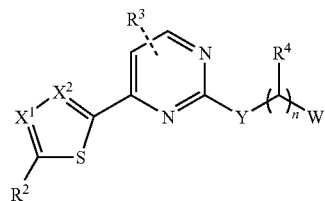

wherein:
$X^1$ is C—$R^1$ or N;
$X^2$ is CH or N;
Y is O, S, CH($R^7$), or N($R^7$);
W is selected from CN,

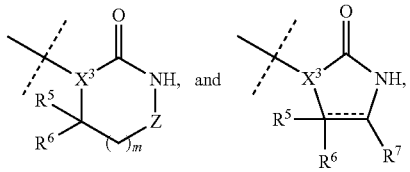

wherein m is 0 or 1, $X^3$ is CH or N, and Z is $CH_2$ or C(O);

$R^1$ and $R^2$ are each independently selected from the group consisting of H, halo, CN, $C_1$-$C_6$ alkyl which may be interrupted by one or more hetero atoms, —$(CR^8R^9)_t$(aryl), —$(CR^8R^9)_t$(heteroaryl), —$(CR^8R^9)_t$(cycloalkyl), —$(CR^1R^9)_t$(heterocyclyl), —$(CR^8R^9)_tN(R^{10})(R^1)$, —$(CR^1R^9)_tSO_2(R^{11})$, —$(CR^1R^9)_tSO_2(N)(R^{10})(R^{11})$, —$(CR^8R^9)_tSO_2$(cycloalkyl), —$(CR^8R^9)_tSO(R^{10})$, or —$(CR^8R^9)_tS(R^{10})$, or $R^1$ and $R^2$ together with the carbon atoms to which they are attached join to form a $C_3$-$C_{10}$ heterocyclic or carbocyclic;

$R^3$ is H, OH, halo, $NO_2$, $NH_2$, CN, $C_1$-$C_6$ alkyl, $C_1$-$C_6$ alkoxy, $C_1$-$C_6$ alkylamino, $C_2$-$C_6$ alkenyl, $C_2$-$C_6$ alkynyl, or an aryl or heteroaryl;

$R^4$, $R^7$, $R^8$, and $R^9$ are independently selected from —H and $C_1$-$C_6$ alkyl;

$R^5$ and $R^6$ are independently selected from —H, $C_1$-$C_6$ alkyl, alkenyl, aryl, heteroaryl, cycloalkyl, or heterocyclyl, or $R^5$ and $R^6$ together with the atoms to which they are linked join to form a 3 to 6-membered carbocyclic or heterocyclic;

$R^{10}$ and $R^{11}$ are independently selected from $C_1$-$C_6$ alkyl, aryl, heteroaryl, cycloalkyl, and heterocyclyl;

wherein n is an integer from 1 to 6, and each t is an integer from 0 to 2;

wherein the above alkyl, alkenyl, aryl, heteroaryl, cycloalkyl, heterocyclyl, heterocyclic, and carbocyclic moieties are optionally substituted by 1-3 substituents selected from
alkanoyl,
alkylamine,
amino,
aryl, heteroaryl, cycloalkyl, heterocyclyl,
$C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine,
$C_1$-$C_6$ dialkylamine, $C_2$-$C_6$ alkenyl, or $C_2$-$C_6$ alkynyl, wherein each of which may be interrupted by one or more hetero atoms,
carboxyl,
cyano,
halo,
hydroxy,
nitro,
—N=N—NH$_2$,
—C(O)$_2$—($C_1$-$C_6$ alkyl), —C(O)$_2$-(aryl), —C(O)$_2$-(heteroaryl), —C(O)$_2$-(cycloalkyl),
—C(O)$_2$-(heterocyclyl),
—O—($C_1$-$C_6$ haloalkyl), —O—($C_1$-$C_6$ alkyl)aryl, —O—($C_1$-$C_6$ alkyl)heteroaryl, —O—($C_1$-$C_6$ alkyl)cycloalkyl, —O—($C_1$-$C_6$ alkyl)heterocyclyl, —O—($C_1$-$C_6$ alkyl)amino, —O—($C_1$-$C_6$ alkyl)alkylamino, —O—($C_1$-$C_6$ alkyl)dialkylamino, —O-aryl, —O-heteroaryl,
—NHC(O)—($C_1$-$C_6$ alkyl), —NHC(O)—($C_1$-$C_6$ alkylene), —NHC(O)-(aryl),
—NHC(O)-(heteroaryl), —NHC(O)-(cycloalkyl), —NHC(O)-(heterocyclyl),
—NHC(O)—($C_1$-$C_6$ alkyl)aryl, —NHC(O)—($C_1$-$C_6$ alkyl)heteroaryl, —NHC(O)—($C_1$-$C_6$ alkyl)cycloalkyl, —NHC(O)—($C_1$-$C_6$ alkyl)heterocyclyl, —NHC(O)—($C_1$-$C_6$ alkyl)amino, —NHC(O)—($C_1$-$C_6$ alkyl)alkylamine, —NHC(O)—($C_1$-$C_6$ alkyl)dialkylamine, —NHC(O)—($C_1$-$C_6$ alkyl)C(O)amino, —NHC(O)—($C_1$-$C_6$ alkyl)C(O)alkylamine, —NHC(O)—($C_1$-$C_6$ alkyl)C(O)dialkylamine, —NHC(O)—($C_1$-$C_6$ alkyl)N(H)—($C_1$-$C_6$ alkyl)C(O)$_2$—($C_1$-$C_6$ alkyl), —NHC(O)—($C_1$-$C_6$ alkyl)S(O)$_2$($C_1$-$C_6$ alkyl), —NHC(O)—($C_1$-$C_6$ alkyl)-S-(heterocyclyl), —NHS(O)$_2$—($C_1$-$C_6$ alkyl),
—NHS(O)$_2$-(aryl), —NHS(O)$_2$-(heteroaryl), —NHS(O)$_2$-(cycloalkyl), —NHS(O)$_2$-(heterocyclyl), —NHS(O)($C_1$-$C_6$ alkyl), —NHS(O)(aryl),
—NHS(O)(heteroaryl), —NHS(O)(cycloalkyl), —NHS(O)(heterocyclyl), —NHS($C_1$-$C_6$ alkyl), —NHS(aryl), —NHS(heteroaryl), —NHS(cycloalkyl), —NH—S-(heterocyclyl),
wherein each of the above substituents can be further optionally substituted by 1-5 substituents selected from
amino,
$C_1$-$C_6$ alkylamine, $C_1$-$C_6$ dialkylamine,
$C_1$-$C_6$ alkyl, $C_1$-$C_6$ alkoxy, $C_1$-$C_6$ alkenyl, $C_1$-$C_6$ hydroxyl, and $C_1$-$C_6$ hydroxyalkyl, each optionally substituted by halo,
cyano,
halo, and
nitro,
or a pharmaceutically acceptable salt, hydrate, or stereoisomer thereof.

In one embodiment the invention comprises a compound of Formula I wherein Y is NH.

In another embodiment the invention comprises a compound of Formula I wherein n is 2 and $R^4$ is H.

In another embodiment the invention comprises a compound of Formula I wherein $R^3$ is halo, haloalkyl, aryl, or CN.

In another embodiment the invention comprises a compound of Formula I wherein W is

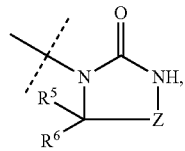

wherein Z is Z is CH$_2$ or C(O) and $R^5$ and $R^6$ are independently selected from —H and $C_1$-$C_6$ alkyl. In another embodiment, $R^5$ and $R^6$ are each —CH$_3$.

In another embodiment the invention comprises a compound of Formula I wherein $X^1$ and $X^2$ are each CH. In another embodiment, $X^1$ is CH and $X^2$ is N. In a further embodiment, $X^1$ is N and $X^2$ is CH.

In another embodiment the invention comprises a compound of Formula I wherein $R^1$ and $R^2$ are each independently selected from the group consisting of $C_1$-$C_6$ alkyl, —(CR$^8$R$^9$)$_t$(aryl), —(CR$^8$R$^9$)$_t$(heterocyclyl), —(CR$^8$R$^9$)$_t$N(R$^{10}$)(R$^{11}$), —(CR$^8$R$^9$)$_t$SO$_2$(R$^{11}$), or —(CR$^8$R$^9$)$_t$S(R$^{10}$), or $R^1$ and $R^2$ together with the carbon atoms to which they are attached join to form a $C_3$-$C_{10}$ heterocyclic or carbocyclic, wherein t is an integer from 0 to 2, and $R^{10}$ and $R^{11}$ are independently selected from $C_1$-$C_6$ alkyl, aryl, and heterocyclyl.

In another embodiment, the invention comprises a compound of Formula I selected from 1-(2-{4-[5-(2-Azetidin-1-yl-ethoxy)-benzo[b]thiophen-2-yl]-5-bromo-pyrimidin-2-ylamino}-ethyl)-5,5-dimethyl-imidazolidine-2,4-dione; 1-(2-{4-[5-(2-Ethyl-phenylsulfanyl)-thiophen-2-yl]-pyrimidin-2-ylamino}-ethyl)-5,5-dimethyl-imidazolidine-2,4-dione; 1-(2-{4-[5-(2-Isopropylamino-ethoxy)-benzo[b]thiophen-2-yl]-5-trifluoromethyl-pyrimidin-2-ylamino}-ethyl)-5,5-dimethyl-imidazolidine-2,4-dione; 1-(2-{5-(1H-Indol-5-yl)-4-[5-(piperidine-1-sulfonyl)-thiophen-2-yl]-pyrimidin-2-ylamino}-ethyl)-imidazolidin-2-one; 1-(2-{5-(3-Hydroxy-phenyl)-4-[5-(piperidine-1-sulfonyl)-thiophen-2-yl]-pyrimidin-2-ylamino}-ethyl)-imidazolidin-2-one; 1-(2-{5-Bromo-4-[2-(4-fluoro-phenylamino)-thiazol-5-yl]-pyrimidin-2-ylamino}-ethyl)-5,5-dimethyl-imidazolidine-2,4-dione; 1-(2-{5-Bromo-4-[2-(methyl-phenyl-amino)-thiazol-5-yl]-pyrimidin-2-ylamino}-ethyl)-5,5-dimethyl-imidazolidine-2,4-dione; 1-(2-{5-Bromo-4-[5-(2-diethylamino-ethoxy)-benzo[b]thiophen-2-yl]-pyrimidin-2-ylamino}-ethyl)-5,5-dimethyl-imidazolidine-2,4-dione; 1-(2-{5-Bromo-4-[5-(2-dimethylamino-ethoxy)-benzo[b]thiophen-2-yl]-pyrimidin-2-ylamino}-ethyl)-5,5-dimethyl-imidazolidine-2,4-dione; 1-(2-{5-Bromo-4-[5-(2-isopropylamino-ethoxy)-benzo[b]thiophen-2-yl]-pyrimidin-2-ylamino}-ethyl)-5,5-dimethyl-imidazolidine-2,4-dione; 1-(2-{5-Bromo-4-[5-(2-piperidin-1-yl-ethoxy)-benzo[b]thiophen-2-yl]-pyrimidin-2-ylamino}-ethyl)-5,5-dimethyl-imidazolidine-2,4-dione; 1-(2-{5-Bromo-4-[5-(2-pyrrolidin- 1-yl-ethoxy)-benzo[b]thiophen-2-yl]-pyrimidin-2-ylamino}-ethyl)-5,5-dimethyl-imidazolidine-2,4-dione; 1-(2-{5-Bromo-4-[5-(4-fluoro-benzenesulfonyl)-thiophen-2-yl]-pyrimidin-2-ylamino}-ethyl)-imidazolidin-2-one; 1-(2-{5-Bromo-4-[5-(4-fluoro-benzyl)-4-(2-hydroxy-ethyl)-thiophen-2-yl]-pyrimidin-2-ylamino}-ethyl)-5,5-dimethyl-imidazolidine-2,4-dione; 1-(2-{5-Bromo-4-[5-(4-fluoro-benzyl)-4-(2-isopropylamino-ethyl)-thiophen-2-yl]-pyrimidin-2-ylamino}-ethyl)-5,5-dimethyl-imidazolidine-2,4-dione; 1-(2-{5-Bromo-4-[5-(4-fluoro-benzyl)-4-(2-piperazin-1-yl-ethyl)-thiophen-2-yl]-pyrimidin-2-ylamino}-ethyl)-5,5-dimethyl-imidazolidine-2,4-dione; 1-(2-{5-Bromo-4-[5-(4-fluoro-benzyl)-4-(2-piperidin-1-yl-ethyl)-thiophen-2-yl]-pyrimidin-2-ylamino}-ethyl)-5,5-dimethyl-imidazolidine-2,4-dione; 1-(2-{5-Bromo-4-[5-(4-fluoro-benzyl)-4-(2-pyrrolidin-1-yl-ethyl)-thiophen-2-yl]-pyrimidin-2-ylamino}-ethyl)-5,5-dimethyl-imidazolidine-2,4-dione; 1-(2-{5-Bromo-4-[5-(4-fluoro-benzyl)-thiazol-2-yl]-pyrimidin-2-ylamino}-ethyl)-5,5-dimethyl-imidazolidine-2,4-dione; 1-(2-{5-Bromo-4-[5-(pyrrolidin-2-ylmethoxy)-benzo[b]thiophen-2-yl]-pyrimidin-2-ylamino}-ethyl)-5,5-dimethyl-imidazolidine-2,4-dione; 1-(2-{5-Chloro-4-[2-(methyl-phenyl-amino)-thiazol-5-yl]-pyrimidin-2-ylamino}-ethyl)-5,5-dimethyl-imidazolidine-2,4-dione; 1-(2-{5-Chloro-4[5-(4-fluoro-benzyl)-4-(2-morpholin-4-yl-ethyl)-thiophen-2-yl]-pyrimidin-2-ylamino}-ethyl)-5,5-dimethyl-imidazolidine-2,4-dione; 1-(2-{5-Chloro-4-[5-(4-fluoro-phenylimino)-4-methyl-4,5-dihydro-[1,3,4]thiadiazol-2-yl]-pyrimidin-2-ylamino}-ethyl)-5,5-dimethyl-imidazolidine-2,4-dione; 1-(2-{5-Chloro-4-[5-(4-methoxy-phenylamino)-[1,3,4]thiadiazol-2-yl]-pyrimidin-2-ylamino}-ethyl)-5,5-dimethyl-imidazolidine-2,4-dione; 1-(2-{5-Fluoro-4-[2-(4-fluoro-phenylamino)-thiazol-5-yl]-pyrimidin-2-ylamino}-ethyl)-5,5-dimethyl-imidazolidine-2,4-dione; 1-(2-{5-Fluoro-4-[2-(methyl-phenyl-amino)-thiazol-5-yl]-pyrimidin-2-ylamino}-ethyl)-5,5-dimethyl-imidazolidine-2,4-dione; 1-(2-{5-Fluoro-4-[5-(2-isopropylamino-ethoxy)-benzo[b]thiophen-2-yl]-pyrimidin-2-ylamino}-ethyl)-5,5-dimethyl-imidazolidine-2,4-dione; 1-(2-{5-Fluoro-4-[5-(4-fluoro-benzyl)-thiazol-2-yl]-pyrimidin-2-ylamino}-ethyl)-5,5-dimethyl-imidazolidine-2,4-dione; 1-[2-(5-Bromo-4-{2-[1-(4-fluoro-phenyl)-ethyl]-thiazol-5-yl}-pyrimidin-2-ylamino)-ethyl]-5,5-dimethyl-imidazolidine-2,4-dione; 1-[2-(5-Bromo-4-{5-(4-fluoro-benzyl)-4-[2-(2-hydroxymethyl-pyrrolidin-1-yl)-ethyl]-thiophen-2-yl}-pyrimidin-2-ylamino)-ethyl]-5,5-dimethyl-imidazolidine-2,4-dione; 1-[2-(5-Bromo-4-{5-(4-fluoro-benzyl)-4-[2-(4-methyl-piperazin-1-yl)-ethyl]-thiophen-2-yl}-pyrimidin-2-ylamino)-ethyl]-5,5-dimethyl-imidazolidine-2,4-dione; 1-[2-(5-Bromo-4-{5-[(4-fluoro-phenyl)-hydroxy-methyl]-thiazol-2-yl}-pyrimidin-2-ylamino)-ethyl]-5,5-dimethyl-imidazolidine-2,4-dione; 1-[2-(5-Bromo-4-{5-[2-(2-methyl-pyrrolidin-1-yl)-ethoxy]-benzo[b]thiophen-2-yl}-pyrimidin-2-ylamino)-ethyl]-5,5-dimethyl-imidazolidine-2,4-dione; 1-[2-(5-Bromo-4-{5-[2-(3-hydroxy-pyrrolidin-1-yl)-ethoxy]-benzo[b]thiophen-2-yl}-pyrimidin-2-ylamino)-ethyl]-5,5-dimethyl-imidazolidine-2,4-dione; 1-[2-(5-Bromo-4-{5-[2-(4-methyl-piperazin-1-yl)-ethoxy]-benzo[b]thiophen-2-yl}-pyrimidin-2-ylamino)-ethyl]-5,5-dimethyl-imidazolidine-2,4-dione; 1-[2-(5-Bromo-4-{5-[2-(isopropyl-methyl-amino)-ethoxy]-benzo[b]thiophen-2-yl}-pyrimidin-2-ylamino)-ethyl]-5,5-dimethyl-imidazolidine-2,4-dione; 1-[2-(5-Chloro-4-{5-[(4-fluoro-phenyl)-methyl-amino]-[1,3,4]thiadiazol-2-yl}-pyrimidin-2-ylamino)-ethyl]-5,5-dimethyl-imidazolidine-2,4-dione; 1-[2-(5-Fluoro-4-{2-[(4-fluoro-phenyl)-(2-pyrrolidin-1-yl-ethyl)-amino]-thiazol-5-yl}-pyrimidin-2-ylamino)-ethyl]-5,5-dimethyl-imidazolidine-2,4-dione; 1-[2-(5-Fluoro-4-{2-[(4-fluoro-phenyl)-(3-hydroxy-propyl)-amino]-thiazol-5-yl}-pyrimidin-2-ylamino)-ethyl]-5,5-dimethyl-imidazolidine-2,4-dione; 1-[2-(5-Fluoro-4-{2-[(4-fluoro-phenyl)-(3-morpholin-4-yl-propyl)-amino]-thiazol-5-yl}-pyrimidin-2-ylamino)-ethyl]-5,5-dimethyl-imidazolidine-2,4-dione; 1-[2-(5-Fluoro-4-{2-[(4-fluoro-phenyl)-methyl-amino]-thiazol-5-yl}-pyrimidin-2-ylamino)-ethyl]-5,5-dimethyl-imidazolidine-2,4-dione; 1-[2-(5-Fluoro-4-{5-[(4-fluoro-phenyl)-methyl-amino]-thiazol-2-yl}-pyrimidin-2-ylamino)-ethyl]-5,5-dimethyl-imidazolidine-2,4-dione; 1-{2-[4-(5-Amino-benzo[b]thiophen-2-yl)-5-bromo-pyrimidin-2-ylamino]-ethyl}-5,5-dimethyl-imidazolidine-2,4-dione; 1-{2-[4-(5-Benzenesulfonyl-thiophen-2-yl)-5-bromo-pyrimidin-2-ylamino]-ethyl}-imidazolidin-2-one; 1-{2-[4-(5-Benzyl-[1,3,4]thiadiazol-2-yl)-5-chloro-pyrimidin-2-ylamino]-ethyl}-5,5-dimethyl-imidazolidine-2,4-dione; 1-{2-[4-(5-Benzyl-thiophen-2-yl)-5-bromo-pyrimidin-2-ylamino]-ethyl}-5,5-dimethyl-imidazolidine-2,4-dione; 1-{2-[4-(5-Benzyl-thiophen-2-yl)-pyrimidin-2-ylamino]-ethyl}-5,5-dimethyl-imidazolidine-2,4-dione; 1-{2-[4-[5-(3-Fluoro-benzenesulfonyl)-thiophen-2-yl]-5-(3-hydroxy-phenyl)-pyrimidin-2-ylamino]-ethyl}-5,5-dimethyl-imidazolidine-2,4-dione; 1-{2-[4-[5-(4-Fluoro-benzenesulfonyl)-thiophen-2-yl]-5-(3-hydroxy-phenyl)-pyrimidin-2-ylamino]-ethyl}-5,5-dimethyl-imidazolidine-2,4-dione; 1-{2-[5-Bromo-4-(5-(4-fluoro-benzyl)-4-{2-[2-(isopropylamino-methyl)-pyrrolidin-1-yl]-ethyl}-thiophen-2-yl)-pyrimidin-2-ylamino]-ethyl}-5,5-dimethyl-imidazolidine-2,4-dione; 1-{2-[5-Bromo-4-(7-phenyl-4,5,6,7-tetrahydro-thieno[3,2-c]pyridin-2-yl)-pyrimidin-2-ylamino]-ethyl}-5,5-dimethyl-imidazolidine-2,4-dione; 1-{2-[5-Chloro-4-(7-phenyl-4,5,6,7-tetrahydro-thieno[3,2-c]pyridin-2-yl)-pyrimidin-2-ylamino]-ethyl}-5,5-dimethyl-imidazolidine-2,4-dione; 2-[2-(5,5-Dimethyl-2,4-dioxo-imidazolidin-1-yl)-ethylamino]-4-(5-iodo-thiophen-2-yl)-pyrimidine-5-carbonitrile; 5,5-Dimethyl-1-(2-{4-[5-(2-pyrrolidin-1-yl-ethoxy)-benzo[b]thiophen-2-yl]-5-trifluoromethyl-pyrimidin-2-ylamino}-ethyl)-imidazolidine-2,4-dione; 5,5-Dimethyl-1-{2-[4-(2-phenylsulfanyl-thiazol-5-yl)-pyrimidin-2-ylamino]-ethyl}-imidazolidine-2,4-dione; 5,5-Dimethyl-1-{2-[4-(5-phenylsulfanyl-thiophen-2-yl)-pyrimidin-2-ylamino]-ethyl}-imidazolidine-2,4-dione; N-(2-{2-[2-(5,5-Dimethyl-2,4-dioxo-imidazolidin-1-yl)-ethylamino]-pyrimidin-4-yl}-benzo[b]thiophen-5-yl)-2-pyridin-3-yl-acetamide In another aspect, the invention comprises a pharmaceutically acceptable salt, hydrate, or solvate of a compound of Formula I.

In another aspect, the invention comprises a pharmaceutical composition comprising a pharmaceutically-acceptable carrier and a compound of Formula I.

In another aspect, the invention comprises a method for treating a kinase-mediated disorder in a mammal comprising administering to the mammal a therapeutically effective amount of a compound of Formula I. In one embodiment, the disorder can be one that is mediated by Plk1.

In another embodiment, the invention encompasses Formula I compounds that have selective kinase activity—e.g., they possess significant activity against Plk1 while possessing less or minimal activity against a different kinase.

Another embodiment of the invention comprises treating abnormal cell growth by administering a therapeutically effective amount of a compound of the invention to a subject in need thereof. The abnormal cell growth can be a benign growth or a malignant growth. In particular, the abnormal cell growth can be a carcinoma, sarcoma, lymphoma, or leukemia. In one embodiment of this method, the abnormal cell growth is a cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. The method of the invention also comprises treating a patient having cancer wherein the cancer is selected from the group consisting of small cell lung carcinoma, non-small cell lung carcinoma, esophageal cancer, kidney cancer, pancreatic cancer, melanoma, bladder cancer, breast cancer, colon cancer, liver cancer, lung cancer, sarcoma, stomach cancer, cholangiocarcinoma, mesothelioma, or prostate cancer. In another embodiment of said method, said abnormal cell growth is a benign proliferative disease, including, but not limited to, psoriasis, benign prostatic hypertrophy or restenosis.

In another embodiment, the invention encompasses a method for treating or preventing cancer in a patient in need thereof, comprising administering to the patient a therapeutically or prophylactically effective amount of a compound according to Formula I and a pharmaceutically acceptable excipient, carrier, or vehicle.

In another aspect, the invention encompasses a method for treating or preventing cancer in a patient in need thereof, comprising administering to the patient a therapeutically or prophylactically effective amount of a Formula I compound and at least one additional therapeutic agent.

4. DETAILED DESCRIPTION OF THE INVENTION

4.1 Definitions

Where the following terms are used in this specification, they are used as defined below:

The terms "comprising" and "including" are used herein in their open, non-limiting sense.

As used herein, unless otherwise specified, the term "alkyl" means a saturated straight chain or branched non-cyclic hydrocarbon having from 1 to 20 carbon atoms, preferably 1-10 carbon atoms and most preferably 1-4 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group can be unsubstituted or substituted.

As used herein, unless otherwise specified, the term "alkenyl" means an unsaturated straight chain or branched non-cyclic hydrocarbon having from 2 to 20 carbon atoms and at least one carbon-carbon double bond. Preferably an alkenyl has 2 to 10 carbon atoms and most preferably 2 to 4 carbon atoms. Exemplary straight chain alkenyls include -but-3-ene, -hex-4-ene, and -oct-1-ene. Exemplary branched chain alkenyls include-2-methyl-obut-2-ene, -1-methyl-hex-4-ene, and -4-ethyl-oct-1-ene. An alkenyl group can be substituted or unsubstituted.

As used herein, and unless otherwise specified, the term "alkynyl" means an alkyl group in which one or more carbon-carbon single bonds is replaced with an equivalent number of carbon-carbon triple bonds. An alkynyl group must comprise at least two carbon atoms, and can be substituted or unsubstituted.

As used herein, unless otherwise specified, the term "haloalkyl" means an alkyl group in which one or more hydrogens has been replaced by a halogen atom. A halogen atom is a fluorine, chlorine, bromine, or iodine atom.

As used herein, unless otherwise specified, the term "hydroxyalkyl" means an alkyl group in which one or more hydrogens has been replaced with a hydroxyl group.

The term "alkoxy" means a structure of the formula —O-alkyl.

The term "alkylsulfonyl" means a structure of the formula —$S(O)_2$-alkyl.

The terms "alkylamine" and "dialkylamino" mean a structure of the formula —N-alkyl and —NH(alkyl)alkyl, respectively, wherein the alkyl is defined as above.

The term "alkanoyl", alone or in combination with another term, means a radical of the type "R—C(O)—" wherein "R" is an alkyl radical as defined above and "—C(O)—" is a carbonyl radical. Examples of such alkanoyl radicals include acetyl, trifluoroacetyl, hydroxyacetyl, propionyl, butyryl, valeryl, 4-methylvaleryl, and the like.

The terms "alkanoylamino," and "alkanoyloxy" mean —NH-alkanoyl and —O-alkanoyl, respectively.

The term "alkoxy carbonyl amino" means a structure of the formula —NHC(O)O-alkyl.

The term "alkylsulfonyl amino" means a structure of the general formula —$NHS(O)_2$-alkyl.

As used herein, unless otherwise specified the term "aryl" means a carbocyclic ring or ring system containing from 5 to 14 ring atoms wherein at least one ring is aromatic. The ring atoms of a carbocyclic aryl group are all carbon atoms. Aryl groups include mono-, bi-, or tricyclic groups as well as benzo-fused carbocyclic moieties such as 5,6,7,8-tetrahydronaphthyl and the like. Preferably, the aryl group is a monocyclic ring or bicyclic ring. Representative aryl groups include phenyl, tolyl, anthracenyl, fluorenyl, indenyl, azulenyl, phenanthrenyl and naphthyl. An aryl group can be unsubstituted or substituted.

The term "heteroaryl" means an aryl group in which one or more, but not all, of the ring carbon atoms is substituted by a hetero atom. Exemplary heteroatoms are N, O, S, and Si. A heteroaryl group can be unsubstituted or substituted.

The term "cycloalkyl" means an unsaturated or saturated hydrocarbon that forms at least one ring, having from 3 to 20 ring carbon atoms, preferably from 3 to 10 ring carbon atoms. The rings in a cycloalkyl group are not aromatic. A cycloalkyl group can be unsubstituted or substituted.

The term "heterocyclyl" means a cycloalkyl in which at least one but not all ring carbon atoms is substituted by a heteroatom. Exemplary heteroatoms are NH, O, and S.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "Plk1" refers to polo-like kinase-1.

The term "treating" refers to:

(i) preventing a disease, disorder, or condition from occurring in a mammal that may be predisposed to the disease, disorder and/or condition, but has not yet been diagnosed as having it;

(ii) inhibiting the disease, disorder, or condition, i.e., arresting its development; and (iii) relieving the disease, disorder, or condition, i.e., causing regression of the disease, disorder, and/or condition, or one or more of its symptoms.

The term "preventing" refers to the ability of a compound or composition of the invention to prevent a disease identified herein in mammals diagnosed as having the disease or who are at risk of developing such disease. The term also encompasses preventing further progression of the disease in mammals who are already suffering from or have symptoms of such disease.

The term "mammal" refers to non-human animals or humans.

As used herein, the term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of a cancer, the term "patient" or "subject" preferably means a monkey or a human, most preferably a human. In a specific embodiment the patient or subject is afflicted by a cancer.

As used herein, a "therapeutically effective amount" refers to an amount of a Formula I compound of the invention, or prodrug thereof, sufficient to provide a benefit in the treatment or prevention of a condition or disease such as cancer, to delay or minimize symptoms associated with the condition or disease, or to cure or ameliorate the disease or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

As used herein, a "prophylactically effective amount" refers to an amount of a compound of the invention or other active ingredient sufficient to result in the prevention of a condition or disease such as cancer, or recurrence or metastasis of cancer. A prophylactically effective amount may refer to an amount sufficient to prevent initial disease or the recurrence or spread of the disease. The term preferably encompasses a non-toxic amount that improves overall prophylaxis or enhances the prophylactic efficacy of or synergies with another prophylactic or therapeutic agent.

As used herein, "in combination" refers to the use of more than one prophylactic and/or therapeutic agents simultaneously or sequentially. The agents may be selected and administered in such a manner that their respective effects are additive or synergistic.

As used herein, the term "pharmaceutically acceptable salts" refers to salts prepared from pharmaceutically acceptable non-toxic acids or bases including inorganic and organic acids and bases. If the Formula I compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the Formula I compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The term "prodrug" is intended to mean any chemical entity that after administration is converted to a different therapeutically effective chemical entity.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

As used herein and unless otherwise indicated, the term "optically pure" or "stereomerically pure" means a composition that comprises one stereoisomer of a compound and is substantially free of other stereoisomers of that compound. For example, a stereomerically pure compound having one chiral center will be substantially free of the opposite enantiomer of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

The compounds of the invention may exhibit the phenomenon of tautomerism. While Formula I cannot expressly depict all possible tautomeric forms, it is to be understood that Formula I is intended to represent any tautomeric form of the depicted compound and are not to be limited merely to a specific compound form depicted by the formula drawings.

4.2 Methods of Treatment and Prevention of Disease States Mediated by Plk1 Activity The present invention provides methods for treating or preventing Plk1-mediated disease states, such as cancer.

4.2.1 Doses

The magnitude of a prophylactic or therapeutic dose of a Formula I compound of the invention, or a pharmaceutically acceptable salt, solvate, hydrate, or stereoisomer thereof, in the acute or chronic treatment or prevention of a disease or condition such as abnormal cell growth or cancer will vary with the nature and severity of the disease, and the route by which the active ingredient is administered. The dose, and in some cases the dose frequency, will also vary according to the abnormal cell growth to be treated, the age, body weight, and response of the individual patient. Suitable dosing regimens can be readily selected by those skilled in the art with due consideration of such factors.

The magnitude of a prophylactic or therapeutic dose of a Formula I compound of the invention or a pharmaceutically acceptable salt, solvate, hydrate, or stereoisomer thereof in the acute or chronic treatment or prevention of a cancer or condition will vary with the nature and aggressiveness of the condition, and the route by which the active ingredient is administered. The dose, and in some cases the dose frequency, will also vary according to the condition to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. In general, the dose per day is in the range of from about 0.001 to 100 mg/kg, preferably about 1 to 25 mg/kg, more preferably about 1 to about 5 mg/kg. For treatment of humans having a cancer, about 0.1 mg to about 15 g per day is administered in about one to four divisions a day, preferably 10 mg to 12 g per day, more preferably from 40 mg to 500 mg per day. In one embodiment the compounds of the invention are administered from 40 mg to 500 mg per day in about one to four divisions a day. Additionally, the recommended daily dose ran can be administered in cycles as single agents or in combination with other therapeutic agents. In one embodiment, the daily dose is administered in a single dose or in equally divided doses. In a related embodiment, the recommended daily dose can be administered one time per week, two times per week, three times per week, four times per week or five times per week.

The compounds of the invention can be administered to provide systemic distribution of the compound within the patient. In a related embodiment, the compounds of the invention are administered to produce a systemic effect in the body.

In another embodiment, the compounds of the invention are administered directly to the site affected by the condition, as, for example, an accessible skin or esophageal cancer.

In another embodiment the compounds of the invention are administered via oral, mucosal (including sublingual, buccal, rectal, nasal, or vaginal), parenteral (including subcutaneous, intramuscular, bolus injection, intra-arterial, or intravenous), transdermal, or topical administration. In a specific embodiment the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In a further specific embodiment, the compounds of the invention are administered via oral administration. In an alternative specific embodiment, the compounds of the invention are not administered via oral administration.

Different therapeutically effective amounts may be applicable for different conditions, as will be readily known by those of ordinary skill in the art. Similarly, amounts sufficient to treat or prevent such conditions, but insufficient to cause, or sufficient to reduce, adverse effects associated with conventional therapies are also encompassed by the above described dosage amounts and dose frequency schedules.

4.2.2 Combination Therapy

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to antibiotics, anti-emetic agents, antidepressants, and antifungal agents, anti-inflammatory agents, antiviral agents, other anticancer agents, immunomodulatory agents, alpha-interferons, β-interferons, alkylating agents, hormones or cytokines. In a preferred embodiment the invention encompasses the administration of an additional therapeutic agent that demonstrates anti-cancer activity.

The compounds of the invention and the other therapeutics agent can act additively or, preferably, synergistically. In a preferred embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent. In a separate embodiment, a compound of the invention is administered to a patient who has not previously undergone or is not currently undergoing treatment with another therapeutic agent.

In one embodiment, the methods of the invention comprise the administration of one or more Formula I compounds of the invention without an additional therapeutic agent.

4.3 Pharmaceutical Compositions and Dosage Forms

Pharmaceutical compositions and single unit dosage forms comprising a Formula I compound of the invention, or a pharmaceutically acceptable salt, hydrate, metabolite or stereoisomer thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intra-arterial, or intravenous), transdermal, or topical administration. Pharmaceutical compositions and dosage forms of the invention typically also comprise one or more pharmaceutically acceptable excipients. Sterile dosage forms are also contemplated.

In an alternative embodiment, pharmaceutical composition encompassed by this embodiment includes a Formula I compound of the invention, or a pharmaceutically acceptable salt, hydrate or stereoisomer thereof, and at least one additional therapeutic agent. Examples of additional therapeutic agents include, but are not limited to, those listed above in Section 4.2.2.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences,* 20th ed., Mack Publishing, Easton Pa. 2000. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms particularly suitable for parenteral administration to a patient; and sterile solids (e.g., crystalline or amorphous solids) that can be reconstituted to provide liquid dosage forms suitable for parenteral administration to a patient.

Like the amounts and types of excipients, the amounts and specific types of active ingredients in a dosage form may differ depending on factors such as, but not limited to, the route by which it is to be administered to patients. However, typical dosage forms of the invention comprise Formula I compounds of the invention, or a pharmaceutically acceptable salt, hydrate, or stereoisomers thereof comprise 0.1 mg to 1500 mg per unit to provide doses of about 0.01 to 200 mg/kg per day.

The foregoing demonstrates the pertinent and important features of the present invention. One of skill in the art will appreciate that numerous modifications and embodiments thereof may be devised. Therefore, it is intended that the appended claims cover all such modifications and embodiments.

5. WORKING EXAMPLES

The compounds of Formula I were prepared according to the following synthetic schemes and individual examples detailed therein. The compounds were named using AutoNom v.2.2 within Chemdraw Ultra, v.7.0.1. These schemes and examples are provided for the purpose of illustration only and are not intended as limiting the scope of the invention.

Unless otherwise noted, all materials were obtained from commercial suppliers and used without further purification. Anhydrous solvents such as DMF, THF, $CH_2Cl_2$ and toluene were obtained from the Aldrich Chemical Company. All reactions involving air- or moisture-sensitive compounds were performed under a nitrogen atmosphere. Flash chromatography was performed using Aldrich Chemical Company silica gel (200-400 mesh, 60 A) or Biotage pre-packed column. Thin-layer chromatography (TLC) was performed with Analtech gel TLC plates (250 mt). Preparative TLC was performed with Analtech silica gel plates (1000-2000 mt). Preparative HPLC was conducted on a Beckman or Waters HPLC system with 0.1% $TFA/H_2O$ and 0.1% $TFA/CH_3CN$ as mobile phase. The flow rate was at 20 mL/min. and gradient method was used. $^1H$ NMR spectra were determined with super conducting FT NMR spectrometers operating at 400 MHz or a Varian 300 MHz instrument. Chemical shifts are expressed in ppm downfield from internal standard tetramethylsilane. All compounds showed NMR spectra consistent with their assigned structures. Mass spectra (MS) were determined on a Perkin Elmer-SCIEX API 165 electrospray mass spectrometer (positive and/or negative) or an HP 1100 MSD LC-MS with electrospray ionization and quadrupole detection. All parts are by weight and temperatures are in Degrees centigrade unless otherwise indicated.

The following abbreviations are used: AcOH or HOAc (acetic acid), $Ac_2O$ (acetic anhydride), $Al_2O_3$ (alumina), AIBN (2,2'-azobisisobutyronitrile), Ar (argon), $AgSO_4$ (silver sulfate), ATP (adenosine triphosphate), 9-BBN (9-borabicyclo[3.3.1]nonane), $BH_3$ (borane), BINAP (2,2'-bis (diphenylphosphino)-1,1'-binaphthyl), Boc (tert-butyloxycarbonyl), $Boc_2O$ (Boc anhydride), BOP-Cl (bis(2-oxo-3-oxazolidinyl)phosphinic chloride), $Br_2$ (bromine), BSA (bovine serum albumin), t-BuOH (tert-butanol), CAN (ammonium cerium(IV) nitrate), $CH_3CN$ or AcCN (acetonitrile), $CH_2Cl_2$ (dichloromethane), $CH_3I$ or MeI (iodomethane or methyl iodide), $CCl_4$ (carbon tetrachloride), $CCl_3$ (chloroform), $CO_2$ (carbon dioxide), $Cs_2CO_3$ (cesium carbonate), DIEA (diisopropylethylamine), CuT (copper iodide), DCE (1,2-dichloroethane), DEA (diethylamine), DEAD (diethyl azodicarboxylate), DIEA (diisopropylethylamine), dppf (1,1-diphenylphosphinoferrocene), DMAP (4-(dimethylamino)pyridine), DMAC (N,N-dimethylacetamide), DMF (dimethylformamide), DMSO (dimethylsulfoxide), DTT (dithiothreitol), EDC or EDAC, 1-(3-dimethylaminopropyl)-3 (ethylcarbodiimide hydrochloride), EGTA (ethylene glycol-bis(β-aminoethyl ether)), N,N,N',N' (tetraacetic acid), EtOAc (ethyl acetate), EtOH (ethanol), $Et_2O$ (diethyl ether), Fe (iron), g (gram), h (hour), HATU (O-(7-azabenzotriazol-1-yl)-N,N,N',N' (tetramethyluronium) hexafluorophosphate), $H_2$ (hydrogen), $H_2O$ (water), HCl (hydrochloric acid), $H_2SO_4$ (sulfuric acid), $H_2NNH_2$ (hydrazine), $HC(OEt)_3$ (triethylorthoformate), HCHO or $H_2CO$ (formaldehyde), HCOOH (formic acid), $HCO_2Na$ (sodium formate), HOAc, AcOH (acetic acid), HOAt (1-hydroxy-7-azabenzotriazole), HOBt (hydroxybenzotriazole), ipOH, i-PrOH (isopropanol), $K_2CO_3$ (potassium carbonate), KHMDS (potassium hexamethylsilazane), $KNO_3$ (potassium nitrate), KOAc (potassium acetate), KOH (potassium hydroxide), LAH or $LiAlH_4$ (lithium aluminum hydride), LDA (lithium diisopropylamide), LiCl (lithium chloride), LiHMDS (lithium hexamethyldisilazide), LiOH (lithium hydroxide), $LiN(TMS)_2$ (lithium bis(trimethylsilyl)amide), MeOH (methanol), $MgCl_2$ (magnesium chloride), $NgSO_4$ (magnesium sulfate), mg (milligram), min (minute), mL (milliliter), $NnCl_2$ (manganese chloride), NBS (N-bromosuccinimide), NMO (4-methylmorpholine), N-oxide, NMP (N-methylpyrrolidone), $Na_2SO_4$ (sodium sulfate), $Na_2S_2O_5$ (sodium metabisulfite), $NaHCO_3$ (sodium bicarbonate), $Na_2CO_3$ (sodium carbonate), NaCl (sodium chloride), NaH (sodium hydride), NaI (sodium iodide), NaOH (sodium hydroxide), NaOMe (sodium methoxide), NaOtBu (sodium tert-butoxide), $NaCNBH_3$ (sodium cyanoborohydride), $NaBH_4$ (sodium borohydride), $NaNO_2$ (sodium nitrate), $NaBH(OAc)_3$ (sodium triacetoxyborohydride), $NH_4Cl$ (ammonium chloride), $N_2$ (nitrogen), Pd/C (palladium on carbon), $PdCl_2$, $(PPh_3)_2$ (palladium chloride bis(triphenylphosphine)), $Pd_2(dba)_3$ (palladium dibenzylideneacetone), $PdCl_2(dppf)$ (1,1-bis(diphenylphosphino)ferrocene, palladium chloride), $Pd(PPh_3)_4$ (palladium tetrakis triphenylphosphine), $Pd(OH)_2$ (palladium hydroxide), $Pd(OAc)_2$ (palladium acetate), PMB (para methoxybenzyl), $POCl_3$ (phosphorus oxychloride), $PPh_3$ (triphenylphosphine), $PtO_2$ (platinum oxide), RT (room temperature), $SiO_2$ (silica), $SOCl_2$ (thionyl chloride), TBAI (tetrabutylammonium iodide), TBTU (O-(1H-Benzatriazol-1-yl)), N,N,N,N (tetramethyluronium) tetrafluoroborate), TEA (triethylamine), $Tf_2NPh$ (N-phenyltrifluoromethanesulfonimide), TFA (trifluoroacetic acid), THF (tetrahydrofuran), TPAP (tetrapropylammoniumperruthenate), Tris-HCl (Tris(hydroxymethyl)aminomethane hydrochloride salt), and Zn (zinc).

Scheme 1

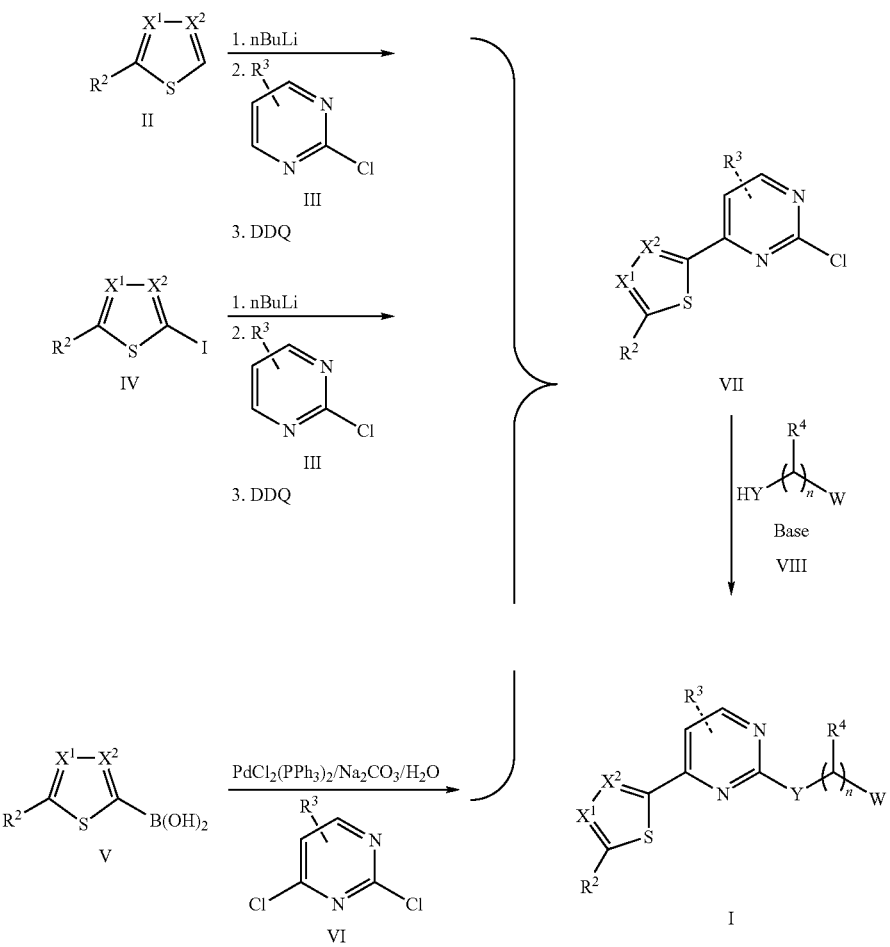

Certain embodiments of Formula I may be synthesized as outlined in Scheme 1. Deprotonation of Formula II or metallation of Formula IV with a strong base including, but not limited to, n-BuLi, tert-BuLi or LDA followed by treatment with Formula III and subsequent treatment with an oxidizing agent including DDQ gives Formula VII.

Alternatively, a compound of Formula VII may be prepared by other methods involving C—C bond formation such as a Suzuki coupling or a Stille coupling (exemplified by the coupling of a boronic acid of Formula V with a chloropyrimidine of Formula VI). Formula VII may be converted to Formula I by displacement of the chloro substituent by Formula VIII, preferably in the presence of base and heat.

Scheme 2

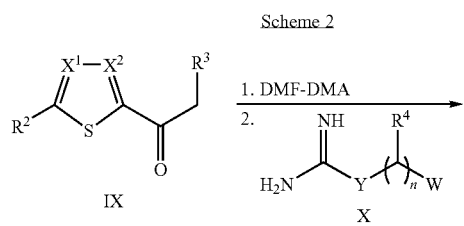

-continued

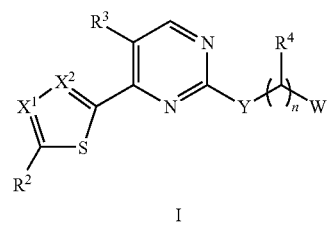

Certain embodiments of Formula I may be prepared conveniently as outlined in Scheme 2 by treatment of compounds of Formula IX with an amidine or guanidine derivative of Formula X.

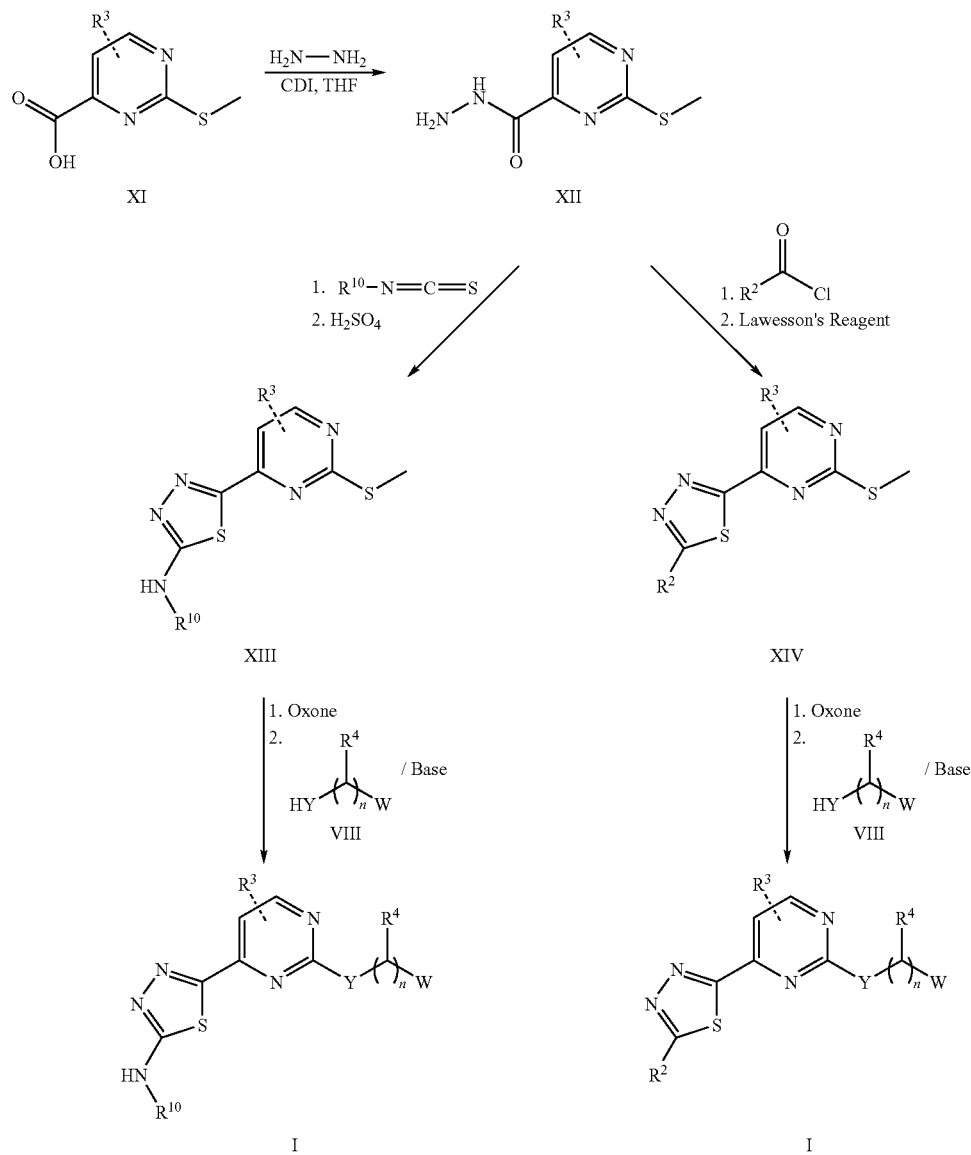

Scheme 3

When compounds of Formula I contain a thiadiazole moiety attached to the 4-position of the pyrimidine core, certain embodiments may be synthesized as outlined in Scheme 3. Coupling of Formula XI with hydrazine utilizing an amide coupling technique gives a hydrazide of Formula XII. This may be treated with an isothiocyanate followed by cyclization with a dehydrating agent such as sulfuric acid to give a compound of Formula XIII, or treated with an acid chloride or chloroformate followed by Lawesson's Reagent to give a compound of Formula XIV. Compounds of Formulae XIII and XIV may be converted to the corresponding sulfones by treatment with an oxidizing agent such as oxone, and then treated with Formula VIII to give the compounds of Formula I. This latter transformation (Formula XIV to Formula I) may also be utilized as part of a modification of the chemistry shown in Scheme 1.

Further structural elaboration of compounds of Formula I may be carried out by methods known to those experienced in the art and/or described in the following examples to give additional examples of Formula I.

Example 1

1-(2-Aminoethyl)-5,5-dimethyl-imidazolidine-2,4-dione (i) {2-[(Cyano-dimethyl-methyl)-amino]-ethyl}-carbamic acid tert-butyl ester (2-Aminoethyl)carbamic acid tert-butyl ester (25.07 g, 156.5 mmol) was dissolved in EtOH (500 mL), treated with acetone (13.75 mL, 187 mmol), and the stirred solution was cooled in an ice bath. After stirring for 30 min, TMS-CN (62 mL, 465 mmol; CAUTION—toxic) was added dropwise over 1 h. The solution was stirred for 16 h, allowing to warm gradually to room temperature. The solution was concentrated in vacuo [caution: HCN gas evolved: a dry pump venting to the back of the fume hood was used] resulting in a pale yellow solid. This was dissolved in EtOAc (100 mL) and concentrated to a viscous oil. Hexane (500 mL) was added rapidly and the resulting mixture was swirled vigorously until a thick white crystalline precipitate formed. The mixture was allowed to stand for 30 min, and the crystallized product (30.0 g) was collected by filtration, washing with a small amount of hexane to give a white crystalline solid. The filtrate was concentrated in vacuo to give a viscous gum (5 g). This was quickly purified by flash chromatography eluting with EtOAc [N.B. the product is somewhat unstable to silica gel and decomposes if allowed to stay on the column for a long time] resulting in an additional 1.7 g of product, which was combined with the recrystallized material. Total yield=31.7 g, 89%. $^1$H NMR: δ ($d_6$-DMSO, 400 MHz) 6.64 (1 H, t), 2.83 (2 H, m), 2.60 (1 H, t), 2.41 (2 H, m), 1.21 (9 H, s), 1.17 (6 H, s).

(ii) 1-(2-Aminoethyl)-5,5-dimethyl-imidazolidine-2, 4-dione

{2-[(Cyano-dimethyl-methyl)-amino]-ethyl}-carbamic acid tert-butyl ester (31.7 g, 139.5 mmol) was dissolved in dichloromethane (500 mL) and the stirred solution was cooled in an ice bath. After 15 min, chlorosulfonyl isocyanate (14.5 mL, 23.6 g, 167 mmol) was added by syringe over 2 min, and the resulting solution was stirred for an additional 30 min. The solution was concentrated in vacuo to give a pale yellow gum. Water (500 mL) was added, and the mixture was heated in an oil bath (bath temperature 101° C.) for 20 h, during which time the solid went into solution. The resulting pale brown solution was cooled and allowed to stand for 30 min before filtering through a fluted filter paper (removes a trace amount of an oily residue). The solution was applied to a 3" diameter flash column packed with SCX ion exchange resin (800 g; Varian Cat# 12213040) which had been previously conditioned with MeOH (2 L) followed by water (2 L). The resin was washed with water (2 L) followed by MeOH (2 L), and the product was then eluted with 2 M $NH_3$ in MeOH (2.4 L). Concentration in vacuo gave the product as a pale brown hygroscopic foam. This was dissolved in MeOH (150 mL), filtered through a fluted filter paper, and concentrated in vacuo to give pure product (16.7 g, 70%). Final purification was achieved by flash chromatography (DCM:MeOH:NH4OH; 80:20:1 v/v/v) to give a fluffy white solid. $^1$H NMR: δ ($d_6$-DMSO, 400 MHz) 3.60 (bs, NH & $H_2O$), 2.93 (2 H, t, $CH_2$), 2.45 (2 H, t, $CH_2$), 1.06 (6 H, S, $C(Me)_2$). MS (M+H)$^+$ 172.

Examples 2-11 were prepared in an analogous manner to Example 1.

Example 2

1-(2-Aminoethyl)-1,3-diaza-spiro[4.5]decane-2,4-dione

MS (M+H)$^+$ 212.

Example 3

1-(2-Aminoethyl)-8-methyl-1,3,8-triaza-spiro[4.5]decane-2,4-dione

MS (M+H)$^+$ 227.

Example 4

1-(2-Aminoethyl)-1,3-diaza-spiro[4.4]nonane-2,4-dione

MS (M+H)$^+$ 198.

Example 5

1-(2-Aminoethyl)-5-phenyl-imidazolidine-2,4-dione

MS (M+H)$^+$ 220.

Example 6

5-(2-Aminoethyl)-5,7-diaza-spiro[3.4]octane-6,8-dione

MS (M+H)$^+$ 184.

Example 7

1-(2-Aminoethyl)-5-ethyl-5-methyl-imidazolidine-2,4-dione

MS (M+H)$^+$ 186.

Example 8

1-(2-Aminoethyl)-5-benzyl-imidazolidine-2,4-dione

MS (M+H)$^+$ 234.

Example 9

1-(2-Aminoethyl)-5-dimethylaminomethyl-5-methyl-imidazolidine-2,4-dione

MS (M+H)$^+$ 215.

Example 10

1-(2-Aminoethyl)-5-methyl-imidazolidine-2,4-dione

MS (M+H)$^+$ 158.

Example 11

1-(2-Aminoethyl)-5-benzyl-5-methyl-imidazolidine-2,4-dione

MS (M+H)$^+$ 248.

Example 12

3-(2-Aminoethyl)-imidazolidine-2,4-dione hydrochloride (2-Aminoethyl)-carbamic acid tert-butyl ester (14.4 g, 90 mmol) was dissolved in DCM (100 mL) and was treated with a solution of isocyanatoacetic acid ethyl ester (11.6 g. 90 mmol) in DCM (100 mL) added dropwise over 30 min. The resulting solution was stirred for 1 h and concentrated to give a pale gum. Aqueous 5N HCl (250 mL) was added and the mixture stirred until dissolved. The resulting solution was heated at 100° C. for 16 h, concentrated, water (250 mL) was added and the solution again concentrated to give a solid.

Ethanol (100 mL) was added and the mixture was again concentrated. Ethanol (150 mL) was added and the mixture stirred for 16 h to give the product as a fine white powder which was collected by filtration. Yield=14.7 g, 91%. MS (M+H)+ 144.

Example 13

1-(2-Aminoethyl)-1,3-dihydroimidazol-2-one (i) [2-(2,5-Dioxo-imidazolidin-1-yl)-ethyl]-carbamic acid tert-butyl ester 3-(2-Aminoethyl)-imidazolidine-2,4-dione hydrochloride (14.7 g., 82 mmol) was suspended in DCM (300 mL) and DIPEA (28 mL, 160 mmol) was added. The mixture was stirred for 15 min, and then $BOC_2O$ (19.7 g, 90 mmol) was added. The suspension was stirred for 1 h, and then DMF (45 mL) was added. The stirred suspension gradually became a clear solution over the next several h. Stirring was continued for a further 16 h, after which time a thick precipitate had formed. The mixture was concentrated to dryness in vacuo, ensuring the last traces of DMF were removed, and then dissolved in boiling EtOAc (200 mL). Hexane (800 mL) was added, the mixture cooled and allowed to stand for 1 h. The resulting product was collected by filtration. Yield=14.6 g, 73%.

(ii) [2-(5-Hydroxy-2-oxo-imidazolidin-1-yl)-ethyl]-carbamic acid tert-butyl ester

[2-(2,5-Dioxo-imidazolidin-1-yl)-ethyl]-carbamic acid tert-butyl ester (14.6 g, 60 mmol) was dissolved in THF (1.5 L) and treated with 1.0 M $LiAlH_4$ in THF (77 mL, 77 mmol) added dropwise. The initial vigorous effervescence subsided and the solution became opaque white. The mixture was stirred for 16 h and then quenched (i. 2.0 mL of water; ii. 2.0 mL of 4 M aqueous NaOH; iii. 10 mL of water). The mixture was filtered and the resulting filtrate concentrated to give 12.1 g of solid. This was dissolved in 100 mL of hot EtOAc and applied (hot) to 250 g of silica pre-washed with EtOAc. The product was isolated by elution with EtOAc→2% MeOH/EtOAc→5% MeOH/EtOAc as a white solid (7.85 g, 53%). The compound has poor solubility in a number of organic solvents.

(iii) 1-(2-Aminoethyl)-1,3-dihydroimidazol-2-one

[2-(5-Hydroxy-2-oxo-imidazolidin-1-yl)-ethyl]-carbamic acid tert-butyl ester (7.85 g, 32 mmol) was suspended in DCM (250 mL) and a solution of TFA (100 mL) in DCM (250 mL) was added over 10 min to the stirred suspension, which dissolved. The solution was stirred for 16 h, concentrated, and azeotroped with MeCN. The resulting TFA salt of the product was dissolved in MeOH (10 mL) and purified on 50 g of SCX resin, washing with MeOH and eluting off with 2 M $NH_3$ in MeOH. Concentration gave the product as a pale yellow oil (3.66 g, 90%). MS (M+H)+ 128.

Example 14

1-(2-Amino-ethyl)-5,5-dimethyl-imidazolidin-2-one (i) [2-(5,5-Dimethyl-2-oxo-imidazolidin-1-yl)-ethyl]-carbamic acid tert-butyl ester {2-[(Cyano-dimethyl-methyl)-amino]-ethyl}-carbamic acid tert-butyl ester (0.74 g., 3.3 mmol) was dissolved in THF (2 mL), cooled in an ice bath, and a 1.0 M solution of $LiAlH_4$ in $Et_2O$ (6.5 mL, 6.5 mmol) was added dropwise. The resulting suspension was stirred in the ice bath for 3 h and then quenched (i. 0.17 mL of water; ii. 0.17 mL of 4 M aqueous NaOH; iii. 0.84 mL of water). The resulting mixture was diluted with THF (50 mL) and stirred for 15 min. The mixture was filtered and the filtrate concentrated to give an oil. The oil was dissolved in THF (10 mL), DIPEA (1.4 mL) was added, and the mixture was stirred in an ice bath. A solution of p-nitrophenyl chloroformate (800 mg, 4.0 mmol) in THF (8 mL) was added dropwise and the resulting yellow solution was stirred for 16 h. The mixture was concentrated, dissolved in DCM (50 mL) and washed with 0.5 M HCl (50 mL) followed by saturated aqueous $NaHCO_3$ solution (50 mL). The organic layer was dried ($Na_2SO_4$), concentrated and purified by flash chromatography (EtOAc) to give the product as a pale yellow gum (450 mg, 54%).

(ii) 1-(2-Amino-ethyl)-5,5-dimethyl-imidazolidin-2-one

[2-(5,5-Dimethyl-2-oxo-imidazolidin-1-yl)-ethyl]-carbamic acid tert-butyl ester (450 mg, 1.75 mmol) was dissolved in DCM (5 mL) and TFA (1 mL) was added. The mixture was allowed to stand for 16 h, concentrated, and purified by SCX ion exchange chromatography to give the product as a yellow oil (256 mg, 93%).

Example 15

1-(2-Aminoethyl)-1H-benzo[d]imidazol-2(3H)-one (i) tert-Butyl 2-(2-nitrophenylamino)ethylcarbamate A mixture of 1-fluoro-2-nitrobenzene (2 g, 14.2 mmol), tert-butyl 2-aminoethylcarbamate (2.7 g, 17.0 mmol) and triethylamine (1.7 g, 2.4 mmol) in tetrahydrofuran was refluxed for 7 h. After cooling to rt 100 mL of water was added and the mixture was extracted with ethyl acetate (3×100 mL). The combined organic layer was washed with brine (150 mL), dried over anhydrous sodium sulfate and filtered. The solvent was removed and the product was used in the next step without further purification.

(ii) tert-Butyl 2-(2-aminophenylamino)ethylcarbamate

A mixture of tert-butyl 2-(2-nitrophenylamino)ethylcarbamate (400 mg) and palladium (10% on activated carbon, 20 mg) in ethanol (50 mL) was stirred under hydrogen (1 atm) for 5 h. The mixture was filtered through Celite and washed with methanol. The solvent was removed and the product was used in the next step without further purification.

(iii) tert-Butyl 2-(2-oxo-2,3-dihydrobenzo[d]imidazol-1-yl)ethylcarbamate 1,1-carbonyldiimidazole (0.36 g, 2.23 mmol) was added to a solution of tert-butyl 2-(2-aminophenylamino)ethylcarbamate (0.56 g, 2.23 mmol) in dichloromethane (15 mL) and stirred at rt overnight. Water (50 mL) was added and the mixture was extracted with dichloromethane (3×50 mL). The combined organic layers were washed with brine (50 mL), dried over anhydrous sodium sulfate and filtered. The solvent was removed and the product was purified by column chromatography eluting with ethyl acetate/hexane (1:3) to give the title compound (230 mg, 37%).

(iv) 1-(2-Aminoethyl)-1H-benzo[d]imidazol-2(3H)-one tert-Butyl 2-(2-oxo-2,3-dihydrobenzo[d]imidazol-1-yl)ethylcarbamate (200 mg) was added to 15 mL of hydrogen chloride solution in diethyl ether (1 M) and the mixture was stirred at rt for 5 h. Evaporation of the solvent give the title compound as a white hydrochloride salt (100%).

Example 16

N-[2-(5,5-Dimethyl-2,4-dioxo-imidazolidin-1-yl)-ethyl]-guanidine hydrochloride 1-(2-Amino-ethyl)-5,5-dimethyl-imidazolidine-2,4-dione (5.00 g., 29 mmol) and pyrazole-1-carboxamidine hydrochloride (4.28 g., 29 mmol) were added to MeCN (100 mL) and heated at reflux for 16 h. The mixture was cooled, the supernatent MeCN layer was decanted off, and the residual gum was washed with MeCN twice. The gum was dissolved in MeOH (100 mL) and concentrated to give the product as a foam. Yield=7.29 g., 100%.

MS (M+H)$^+$ 214.

Examples 17-18 were prepared in an analogous manner to Example 16.

Example 17

N-[2-(2-Oxo-imidazolidin-1-yl)-ethyl]-guanidine hydrochloride

MS (M+H)$^+$ 172.

Example 18

N-[2-(2-Oxo-2,3-dihydro-imidazol-1-yl)-ethyl]-guanidine hydrochloride

MS (M+H)$^+$ 170.

Example 19

1-(Benzo[b]thiophen-5-yl)-2,5-dimethyl-1H-pyrrole (i) Methyl 5-nitrobenzo[b]thiophene-2-carboxylate Methyl thioglycolate (19.62 mL, 0.216 mol) was added dropwise, via syringe pump, to a stirred suspension of 95% sodium hydride (5.99 g, 0.237 mol) in dry N,N-dimethylformamide (400 mL) at r.t. under nitrogen (CAUTION: hydrogen evolution). Upon complete addition, the reaction was stirred for 10 min and then a solution of 2-chloro-5-nitrobenzaldehyde (40.0 g, 0.216 mol) in DMF (120 mL) was added. The solution turned orange and a gentle exotherm was observed. After 1 h, the now yellow mixture was heated to 100° C. for 5 h. The mixture turned amber in appearance. After cooling to r.t. the mixture was poured into 1 N aqueous hydrochloric acid (500 mL). The resulting yellow precipitate was filtered off and washed with water (250 mL). The solid was suspended in hot methanol/ethyl acetate (1:1) (1000 mL) and allowed to cool to r.t. The resulting solid was filtered off and air dried to yield methyl 5-nitrobenzo[b]thiophene-2-carboxylate (33.77 g, 66%) as a tan amorphous solid. $^1$H NMR δ (d$_6$-DMSO, 400 MHz) 3.92 (s, 3 H), 8.32 (dd, J=9, 2 Hz, 1 H), 8.37 (d, J=9 Hz, 1 H), 8.45 (s, 1 H), 9.00 (d, J=2 Hz, 1 H).

(ii) 5-Nitrobenzo[b]thiophene-2-carboxylic acid

A suspension of methyl 5-nitrobenzo[b]thiophene-2-carboxylate (32.49 g, 0.137) in methanol (400 mL) and 1 N aqueous sodium hydroxide (150 mL) was heated to reflux for 1 h after which time everything had gone into solution. After cooling to r.t. the solution was acidified with concentrated hydrochloric acid. The resulting solid was filtered off, washed with water (3×50 mL), air dried, and then placed in a vacuum oven at 60° C. for 20 h to yield 5-nitrobenzo[b]thiophene-2-carboxylic acid (29.87 g, 98%) as a cream amorphous solid. $^1$H NMR δ (d$_6$-DMSO, 400 MHz) 8.30 (dd, J=9, 2 Hz, 1 H), 8.35 (d, J=9 Hz, 1 H), 8.36 (s, 1 H), 8.98 (s, 1 H), 13.89 (br. s., 1 H).

(iii) 5-Nitrobenzo[b]thiophene

Copper (8.18 g, 0.129 mol) was added to a mechanically stirred slurry of 5-nitrobenzo[b]thiophene-2-carboxylic acid (28.73 g, 0.129 mol) and quinoxaline (160 mL). The thick mixture was heated to 190° C. Upon heating, stirring became easier, and at around 170° C. gas evolution was observed. Gas evolution ceased after 40 min and the reaction mixture was allowed to cool to r.t. overnight. The mixture was then poured over crushed ice and acidified with concentrated hydrochloric acid. The resulting brown suspension was warmed with diethyl ether (4×400 mL). The ether layers were combined, washed with 2 N aqueous hydrochloric acid (300 mL), water (300 mL) and brine (300 mL), and then separated, dried over sodium sulfate, filtered, and the solvent evaporated in vacuo. The crude yellow solid (26 g) was recrystallized from hot acetone (175 mL) to yield 5-nitrobenzo[b]thiophene (15.58 g, 68%) as pale yellow crystals. $^1$H NMR δ (d$_6$-DMSO, 400 MHz) 7.63 (d, J=5.5 Hz, 1 H), 7.95 (d, J=5.5 Hz, 1 H), 8.08 (dd, J=9, 2 Hz, 1 H), 8.20 (d, J=9 Hz, 1 H), 8.75 (d, J=2 Hz, 1 H).

(iv) Benzo[b]thiophen-5-amine

A mixture of 5-nitrobenzo[b]thiophene (3.09 g, 17.0 mmol) and 10% palladium on carbon (Aldrich, cat. No. 20, 569-9) (150 mg) in ethanol (90 mL) was shaken in a Parr flask under a hydrogen atmosphere of 3 bar. After 16 h the catalyst was filtered off over a celite pad and washed with ethanol (2×30 mL). The filtrate was evaporated in vacuo to yield benzo[b]thiophen-5-amine (2.57 g, 100%) as a dark purple amorphous solid. $^1$H NMR δ (CDCl$_3$, 400 MHz) 3.70 (br. s., 2 H), 6.78 (dd, J=8.61, 1.96 Hz, 1 H), 7.10 (d, J=2.35 Hz, 1 H), 7.14 (d, J=5.09 Hz, 1 H), 7.38 (d, J=5.48 Hz, 1 H), 7.63 (d, J=8.61 Hz, 1 H).

(v) 1-(Benzo[b]thiophen-5-yl)-2,5-dimethyl-1H-pyrrole

A stirred solution of benzo[b]thiophen-5-amine (2.48 g, 17.0 mmol), hexane-2,5-dione (1.95 mL, 17.0 mmol) and glacial acetic acid (0.2 mL) in benzene (35 mL) was heated to reflux under a Dean-Stark head. After 14 h the reaction was cooled to r.t., diluted with diethyl ether (40 mL), and successively washed with aqueous 2 N hydrochloric acid (30 mL), brine (30 mL), a saturated aqueous solution of sodium hydrogen carbonate (30 mL) and finally brine (30 mL). The organic layer was separated, dried over magnesium sulfate, filtered and the solvent evaporated in vacuo to yield 1-(benzo[b]thiophen-5-yl)-2,5-dimethyl-1H-pyrrole (3.67 g, 97%) as a light orange crystalline solid. $^1$H NMR δ (CDCl$_3$, 400 MHz) 2.04 (s, 6 H), 5.93 (s, 2 H), 7.19 (dd, J=8, 2 Hz, 1 H), 7.37 (d, J=5 Hz, 1 H), 7.55 (d, J=5 Hz, 1 H), 7.66 (d, J=2 Hz, 1 H), 7.94 (d, J=9 Hz, 1 H).

Example 20

4-Benzo[b]thiophen-2-yl-5-bromo-2-chloro-pyrimidine

A 2.5 M solution of n-butyllithium in hexanes (52.2 mL, 1.01 equiv.) was added dropwise, via syringe pump over 2.75 h, to a stirred solution of benzothiophene (17.52 g, 1.01 equiv.) in anhydrous diethyl ether (160 mL) at 0° C. under nitrogen resulting in a yellow/brown solution. The reaction was cooled to −78° C. (dry ice/acetone) and a solution of 5-bromo-2-chloropyrimidine (25.0 g, 0.13 moles, 1 equiv.) in anhydrous tetrahydrofuran (100 mL) was added, via dropping funnel, over 45 min. The mixture, now pale yellow, was maintained at −78° C. for an additional hour (LC/MS showed one major product) and then warmed to −24° C. (carbon tetrachloride/dry ice bath). Once stabilized, the reaction was quenched with a solution of acetic acid (7.5 mL, 1.01 equiv.) and methanol (5.8 mL, 1.1 equiv.) in tetrahydrofuran (65 mL). Everything goes into solution, dark yellow in color. After mixing thoroughly and allowing the reaction to re-cool to −24° C., a solution of 2,3-dichloro-5,6-dicyano-1,4-benzoquinone (29.63 g, 1.01 equiv.) in tetrahydrofuran (150 mL) was added dropwise at such a rate to maintain the temperature below −15° C. After complete addition the reaction was stirred for 1 h. The cold bath was removed and the reaction quenched with aqueous 1 M sodium hydroxide (131 mL, 1.01 equiv.). The resulting mixture was left to warm to room temperature overnight. The reaction mixture was diluted with ethyl acetate (200 mL) and shaken vigorously. An emulsion developed that was filtered and washed with water. The solid collected (26 g) was the desired product and was set to one side. The organic layer was separated and the aqueous layer extracted with ethyl acetate (3×200 mL). The ethyl acetate layers were combined, washed successively with a saturated aqueous solution of sodium hydrogen carbonate (150 mL), water (150 mL) and finally brine (150 mL). The organic layer was separated, dried over anhydrous sodium sulfate, filtered and the solvent evaporated in vacuo to yield a brown solid (3.7 g). The solids collected were combined and recrystallized from ethyl acetate to yield the title compound (26.3 g, 62%) as yellow crystals. $^1$H NMR: δ (CDCl$_3$, 400 MHz) 8.75-8.67 (2H, m), 7.92-7.88 (2H, m), 7.49-7.42 (2H, m). MS (M+H)$^+$ 325/327.

Examples 21-23 were prepared in an analogous manner to Example 20.

Example 21

2-(5-Bromo-2-chloro-pyrimidin-4-yl)-benzothiazole

MS (M+H)$^+$ 326/328.

Example 22

5-Bromo-2-chloro-4-(5-nitrobenzo[b]thiophen-2-yl) pyrimidine $^1$H NMR δ (d$_6$-DMSO, 400 MHz) 8.18-8.23 (m, 1 H), 8.24-8.30 (m, 1 H), 8.94-9.00 (m, 2 H), 9.05 (s, 1 H).

Example 23

5-Bromo-2-chloro-4-(5-(2,5-dimethyl-1H-pyrrol-1-yl)benzo[b]thiophen-2-yl)pyrimidine $^1$H NMR: δ (CDCl$_3$, 400 MHz) 2.07 (s, 6 H), 5.95 (s, 2 H), 7.31 (dd, J=9, 2 Hz, 1 H), 7.75 (s, 1 H), 7.96 (d, J=9 Hz, 1 H), 8.75 (s, 1 H), 8.79 (s, 1H).

Example 24

1-[2-(4-Benzo[b]thiophen-2-yl-5-bromo-pyrimidin-2-ylamino)-ethyl]-1,3-diazaspiro[4.5]decane-2,4-dione A mixture of 4-benzo[b]thiophen-2-yl-5-bromo-2-chloropyrimidine (318 mg, 1.0 mmol) and 1-(2-aminoethyl)-1,3-diaza-spiro[4.5]decane-2,4-dione (214 mg, 1.01 equiv.) in isopropyl alcohol (4 mL) was treated with diisopropylethylamine (192 µL, 1.1 equiv.) and heated at 170° C. for 17 min in a Personal Chemistry microwave reactor. Upon cooling, the product was obtained by filtration and washing with isopropyl alcohol, recrystallizing from hot isopropyl alcohol. MS (M+H)$^+$ 500/502.

Examples 25-44 were prepared in an analogous manner to Example 24.

Example 25

1-[2-(4-Benzo[b]thiophen-2-yl-5-bromopyrimidin-2-ylamino)-ethyl]-8-methyl-1,3,8-triazaspiro[4.5]decane-2,4-dione Crude product purified by preparative HPLC. MS (M+H)$^+$ 515/517.

Example 26

1-[2-(4-Benzo[b]thiophen-2-yl-5-bromo-pyrimidin-2-ylamino)-ethyl]-1,3-diazaspiro[4.4]nonane-2,4-dione Crude product purified by preparative HPLC. MS (M+H)$^+$ 486/488.

Example 27

1-[2-(4-Benzo[b]thiophen-2-yl-5-bromo-pyrimidin-2-ylamino)-ethyl]-5-phenyl-imidazolidine-2,4-dione Crude product purified by preparative HPLC. MS (M+H)$^+$ 508/510.

Example 28

5-[2-(4-Benzo[b]thiophen-2-yl-5-bromo-pyrimidin-2-ylamino)-ethyl]-5,7-diazaspiro[3.4]octane-6,8-dione Crude product purified by preparative HPLC. MS (M+H)$^+$ 472/474.

Example 29

1-[2-(4-Benzo[b]thiophen-2-yl-5-bromo-pyrimidin-2-ylamino)-ethyl]-5-ethyl-5-methyl-imidazolidine-2,4-dione Crude product purified by preparative HPLC. MS (M+H)+ 474/476.

Example 30

1-[2-(4-Benzo[b]thiophen-2-yl-5-bromo-pyrimidin-2-ylamino)-ethyl]-5-benzyl-imidazolidine-2,4-dione Crude product purified by preparative HPLC. MS (M+H)+ 522/524.

Example 31

1-[2-(4-Benzo[b]thiophen-2-yl-5-bromo-pyrimidin-2-ylamino)-ethyl]-5-dimethylaminomethyl-5-methyl-imidazolidine-2,4-dione Crude product purified by preparative HPLC. MS (M+H)+ 503/505.

Example 32

1-[2-(4-Benzo[b]thiophen-2-yl-5-bromo-pyrimidin-2-ylamino)-ethyl]-5-methyl-imidazolidine-2,4-dione Crude product purified by preparative HPLC. MS (M+H)+ 446/448.

Example 33

1-[2-(4-Benzo[b]thiophen-2-yl-5-bromo-pyrimidin-2-ylamino)-ethyl]-5-benzyl-5-methyl-imidazolidine-2,4-dione Crude product purified by preparative HPLC. MS (M+H)+ 436/438.

Example 34

1-[2-(4-Benzo[b]thiophen-2-yl-5-bromo-pyrimidin-2-ylamino)-ethyl]-5,5-dimethylimidazolidine-2,4-dione Crude product recrystallized from hot ethanol. MS (M+H)+ 460/462.

Example 35

1-[2-(4-Benzo[b]thiophen-2-yl-5-bromo-pyrimidin-2-ylamino)-ethyl]-imidazolidin-2-one Crude product recrystallized from hot EtOAc. MS (M+H)+ 418/420.

Example 36

1-[2-(4-Benzo[b]thiophen-2-yl-5-bromo-pyrimidin-2-ylamino)-ethyl]-1,3-dihydro-imidazol-2-one The crude product was purified by flash chromatography (SiO$_2$/chloroform:methanol/98:2 to 95:5). MS (M+H)+ 416/418.

Example 37

1-[2-(4-Benzo[b]thiophen-2-yl-5-bromo-pyrimidin-2-ylamino)-ethyl]-5,5-dimethyl-imidazolidin-2-one Crude product purified by preparative HPLC. MS (M+H)+ 446/448.

Example 38

1-(2-(4-(Benzo[d]thiazol-2-yl)-5-bromopyrimidin-2-ylamino)ethyl)-5,5-dimethylimidazolidine-2,4-dione The crude solid was recrystallized from diethyl ether/methanol (20:1). MS (M+H)+ 461/463.

Example 39

3-(2-(4-(Benzo[d]thiazol-2-yl)-5-bromopyrimidin-2-ylamino)ethyl)-1H-imidazol-2(3H)-one The crude solid was purified by flash chromatography (chloroform/methanol 98:2 to 95:5). MS (M+H)+ 417/419.

Example 40

1-(2-(4-(Benzo[d]thiazol-2-yl)-5-bromopyrimidin-2-ylamino)ethyl)-imidazolidin-2-one The crude solid was purified by flash chromatography (chloroform/methanol 99.5:0.5 to 97:3). MS (M+H)+ 419/421.

Example 41

1-(2-(4-(benzo[d]thiazol-2-yl)-5-bromopyrimidin-2-ylamino)ethyl)-5,5-dimethylimidazolidin-2-one The crude solid was purified by flash chromatography (chloroform/methanol 99:1 to 96:4). MS (M+H)+ 447/449.

Example 42

1-(2-(5-bromo-4-(5-nitrobenzo[b]thiophen-2-yl)pyrimidin-2-ylamino)ethyl)-5,5-dimethylimidazolidine-2,4-dione

MS (M+H)+ 505/507.

Example 43

1-(2-(5-bromo-4-(5-(2,5-dimethyl-1H-pyrrol-1-yl)benzo[b]thiophen-2-yl)pyrimidin-2-ylamino)ethyl)-5,5-dimethylimidazolidine-2,4-dione The crude solid was purified by flash chromatography (ethyl acetate/hexane 25:75 to 60:40). MS (M+H)+ 553/555.

Example 44

N-(2-aminoethyl)-4-(5-(thiophen-2-yl)thiophen-2-yl)pyrimidin-2-amine

Prepared with a large excess of 1,2-diaminoethane. MS (M+H)+ 303.

Example 45

1-(2-(4-(5-Bromothiophen-2-yl)pyrimidin-2-ylamino)ethyl)imidazolidin-2-one

A mixture of 4-(5-bromothiophen-2-yl)-2-chloropyrimidine (1.0 g, 3.63 mmol), 1-(2-aminoethyl)imidazolidin-2-one (0.47 g, 3.63 mmol) and triethylame (0.44 g, 4.36 mmol) in isopropanol (25 mL) was refluxed for 30 h. After cooling down to rt the precipitate was filtered and washed with methanol (5 mL) and dried to give the title compound as a yellow solid (0.9 g, 68%). MS (M+H)+ 368/370.

Example 46

1-(2-(4-(5-(Thiophen-2-yl)thiophen-2-yl)pyrimidin-2-ylamino)ethyl)-1H-benzo[d]imidazol-2(3H)-one A mixture of 2-chloro-4-(5-(thiophen-2-yl)thiophen-2-yl)pyrimidine (20 mg, 0.072 mmol), 1-(2-aminoethyl)-1H-benzo[d]imidazol-2(3H)-one hydrochloride salt (15 mg, 0.072 mmol) and potassium carbonate (20 mg, excess) in N-methylpyrrolidine (1 mL) was heated at 160° C. for 35 min in a Personal Chemistry microwave reactor. The solvent was removed in vacuo and the product was purified by HPLC to give the title compound (trifluoroacetate salt) as a yellow solid. MS (M+H)+ 420.

Example 47

1-(2-(4-(5-(4-Methoxyphenyl)thiophen-2-yl)pyrimidin-2-ylamino)ethyl)imidazolidin-2-one A mixture of 1-(2-(4-(5-bromothiophen-2-yl)pyrimidin-2-ylamino)ethyl)imidazolidin-2-one (30 mg, 0.08 mmol), 4-ethylphenylboronic acid (16 mg, 0.1 mmol), tetrakis(triphenyl-phosphine)palladium (9 mg, 0.008 mmol) and 2 M sodium carbonate (0.08 mL, 0.16 mmol) in 1,2-dimethoxyethane (3 mL) was heated at 150° C. for 25 min in a Personal Chemistry microwave reactor. Upon cooling, the mixture was filtered through celite and washed with ethyl acetate. Solvent was removed under vacuum and the product was purified by column chromatography eluting with MeOH/CH$_2$Cl$_2$ (1:20) to yield a slight yellow solid (18, mg, 56%). MS (M+H)+ 396.

Examples 48-56 were prepared in an analogous manner to Example 47.

Example 48

1-(2-(4-(5-(Thiophen-2-yl)thiophen-2-yl)pyrimidin-2-ylamino)ethyl)-imidazolidin-2-one

MS (M+H)+ 372.

Example 49

1-(2-(4-(5-(3-Methoxyphenyl)thiophen-2-yl)pyrimidin-2-ylamino)ethyl)imidazolidin-2-one

MS (M+H)+ 396.

Example 50

1-{2-[4-(5'-Methyl-[2,2']bithiophenyl-5-yl)-pyrimidin-2-ylamino]-ethyl}-imidazolidin-2-one

MS (M+H)+ 386.

Example 51

1-(2-(4-(5-(Pyridin-4-yl)thiophen-2-yl)pyrimidin-2-ylamino)ethyl)imidazolidin-2-one

MS (M+H)+ 367.

Example 52

4-(5-(2-(2-(2-Oxoimidazolidin-1-yl)ethylamino)pyrimidin-4-yl)thiophen-2-yl)benzonitrile

MS (M+H)+ 391.

Example 53

1-(2-(4-(5-m-Tolylthiophen-2-yl)pyrimidin-2-ylamino)ethyl)imidazolidin-2-one

MS (M+H)+ 380.

Example 54

1-(2-(4-(5-(Pyridin-3-yl)thiophen-2-yl)pyrimidin-2-ylamino)ethyl)-imidazolidin-2-one

MS (M+H)+ 367.

Example 55

1-(2-(4-(5-(1H-Indol-5-yl)thiophen-2-yl)pyrimidin-2-ylamino)ethyl)imidazolidin-2-one

MS (M+H)+ 405.

Example 56

1-(2-(4-(5-(6-Methoxypyridin-3-yl)thiophen-2-yl)pyrimidin-2-ylamino)-ethyl)imidazolidin-2-one

MS (M+H)+ 397

Example 57

1-(2-Phenylsulfanyl-thiazol-5-yl)-ethanone (i) 1-(2-Chloro-thiazol-5-yl)-ethanone 2-Chloro-thiazole-5-carbaldehyde (1.00 g., 6.77 mmol) was dissolved in THF (10 mL) and cooled to −78° C. MeMgBr (2.26 mL of a 3.0 M solution in Et$_2$O, 6.78 mmol) was added dropwise. The mixture was stirred at −78° C. for 30 min and then allowed to slowly warm to −20° C. over a further 30 min. The reaction was quenched by the addition of EtOAc (2 mL), allowed to warm to 20° C., and 2 M hydrochloric acid (20 mL) was added. The mixture was poured into water (200 mL) and extracted into DCM (200 mL), dried (Na$_2$SO$_4$) and concentrated. The residue was dissolved in reagent grade acetone (20 mL), cooled in an ice bath, and Jones' reagent (3.0 mL of a 2.67 M solution) was added dropwise. The mixture was stirred for 16 h, allowing to warm to 20° C., and then quenched with IPA (5 mL), poured into saturated aqueous NaHCO$_3$ (200 mL) and extracted with EtOAc (2×100 mL). The EtOAc extracts were dried (Na$_2$SO$_4$) and concentrated to give pure product (800 mg, 73%) as a somewhat volatile white solid.

(ii) 1-(2-Phenylsulfanyl-thiazol-5-yl)-ethanone 1-(2-Chloro-thiazol-5-yl)-ethanone (221 mg, 1.37 mmol) and sodium benzenethiolate (226 mg, 1.71 mmol) were added to acetone (20 mL) and stirred for 3 h. The suspension was poured into water (100 mL) containing 2 M aqueous NaOH (10 mL) and extracted with DCM (3×50 mL). The combined organic extracts were dried (Na$_2$SO$_4$) and concentrated to give the product. Yield=314 mg, 97%.

Example 58

1-(4,5-Dichlorothiophen-2-yl)ethanone

Method A: n-Butyl lithium (2.51 g, 39.2 mmol, 24.5 mL) was added dropwise to a stirring solution of diisopropylamine (3.97 g, 39.2 mmol, 5.54 mL) in tetrahydrofuran (5 mL) at −78° C. and stirred for 45 min to generate lithium diisopropylamine (LDA) in situ. 2,3-Dichlorothiophene (5 g, 32.7 mmol) dissolved in tetrahydrofuran (5 mL) was added dropwise and the mixture was stirred at −78° C. for 30 min. Dimethylformamide (3.41 g, 39.2 mmol, 3.64 mL) dissolved in tetrahydrofuran (5 mL) was added dropwise and the mixture was stirred at −78° C. for 30 min. The cooling bath was removed and the reaction was allowed to warm to room temperature. The reaction was then cooled to −20° C., quenched with acetic acid/methanol (4 mL each), and stirred for 15 min at ambient temperature. The reaction was diluted with ethyl acetate (50 mL) and washed in turn with a saturated aqueous solution of sodium bicarbonate (25 mL), deionized water (25 mL), and a saturated aqueous solution of sodium chloride (25 mL). The organic layer was dried over sodium sulfate (500 mg), filtered through a coarse frit (to remove the sodium sulfate), and condensed in vacuo to give a white solid (9 g). The crude material was purified by flash chromatography (EtOAc/hexane) to yield the title compound as a white powder (6.34 g, 19%). MS (M+H)$^+$ 195.

Method B: Acetyl chloride (4.23 g, 53.9 mmol) was added to a solution of 2-chloro-3-methylthiophene (5.96 g, 44.9 mmol) in dichloromethane (65 mL). Anhydrous aluminum chloride (8.98 g, 67.3 mmol) was added in a slow steady stream, and then stirred at room temperature for 1.5 h. The reaction was poured into saturated aqueous solution of sodium bicarbonate solution (100 mL) in small portions accompanied by much effervescence. The color changed from deep purple to deep green, and a white precipitate formed. The reaction was diluted with dichloromethane (100 mL), washed in turn with saturated aqueous sodium bicarbonate (50 mL), deionized water (2×50 mL), and a saturated aqueous solution of sodium chloride (3×25 mL). The organic layer was dried over sodium sulfate (500 mg), filtered through a coarse frit (to remove the sodium sulfate), and condensed in vacuo to give a light brown oil (7.5 g). The crude material was purified by flash chromatography (EtOAc/hexane) to yield the title compound as an orange oil (5.96 g, 76%). MS (M+H)$^+$ 195.

Example 59

1-(5-Nitrobenzo[b]thiophen-2-yl)ethanone

A mixture of sulfur (90 mg, 2.96 mmol), sodium hydrosulfide hydrate (250 mg, 4.44 mmol) and sodium carbonate (330 mg, 2.37 mmol) in N-methylpyrrolidine (10 mL) was stirred at rt for 1 h. A solution of 2-fluoro-5-nitrobenzaldehyde (500 mg, 2.96 mmol) in N-methylpyrrolidine (2 mL) was added dropwise and the mixture was stirred at rt for 3 h. Chloroacetone (270 mg, 2.96 mmol) was added slowly with cooling and the resulting mixture was stirred at rt overnight. The reaction was quenched with 20 mL of water and sodium hydroxide (1 M) was added to adjust pH to 11. The mixture was extracted with diethyl ether (3×50 mL) and the combined organic layer was washed with brine (100 mL), dried over sodium sulfate and filtered. After removing the solvent in vacuo the product was recrystallized from methanol to give a yellow solid (400 mg, 62%). MS (M+H)$^+$ 222.

Example 60

1-(4-(Piperidin-1-ylsulfonyl)phenyl)ethanone

A mixture of 4-acetylbenzene-1-sulfonyl chloride (2 g, 9.2 mmol), piperidine (0.85 g, 10.0 mmol) and triethylamine (1.9 g, 18.4 mmol) in tetrahydrofuran (60 mL) was stirred at rt overnight. Brine (100 mL) was added and the mixture was extracted with ethyl acetate (3×100 mL). The combined organic layer was washed with brine (100 mL), dried over anhydrous sodium sulfate and filtered. Removal of solvent in vacuo gave the title compound as a white solid (2.3 g, 94%). MS (M+H)$^+$ 268.

Example 61

1-[2-(4-Thiophen-2-yl-pyrimidin-2-ylamino)-ethyl]-imidazolidin-2-one

1-Thiophen-2-yl-ethanone (100 mg, 0.79 mmol) was dissolved in DMF-DMA (1 mL) and heated at 100° C. for 16 h. The solution was concentrated to give a gum. This was treated with a solution of N-[2-(2-oxo-imidazolidin-1-yl)-ethyl]-guanidine hydrochloride (233 mg, 1.12 mmol) in NMP (1.5 mL), cesium carbonate (228 mg, 0.7 mmol) was added and the mixture was heated at 100° C. for 16 h. The mixture was cooled and filtered, concentrated, and purified by preparative HPLC to give the product (140 mg, 61%) as an amorphous off-white solid. MS (M+H)$^+$ 290.

Examples 62-89 were prepared in an analogous manner to Example 61.

Example 62

5,5-Dimethyl-1-{2-[4-(2-phenylsulfanyl-thiazol-5-yl)-pyrimidin-2-ylamino]-ethyl}-imidazolidine-2,4-dione

MS (M+H)$^+$ 441.

Example 63

1-(2-(4-(Benzo[b]thiophen-2-yl)pyrimidin-2-ylamino)ethyl)-5,5-dimethylimidazolidine-2,4-dione The crude product was purified by flash chromatography (methanol/chloroform 0.5:99.5 to 5:95) followed by a second column (ethyl acetate/hexane 65:35 to 80:20) to afford the title compound (54 mg, 16%) as a white amorphous solid. HRMS (M+H)$^+$ Calcd. $C_{19}H_{19}N_5O_2S$ 382.1337, found 382.1327.

Example 64

1-(2-(4-(Thiazol-2-yl)pyrimidin-2-ylamino)ethyl) imidazolidin-2-one

MS (M+H)$^+$ 291.

Example 65

1-(2-(4-(2,4-Dimethylthiazol-5-yl)pyrimidin-2-ylamino)ethyl)-imidazolidin-2-one

MS (M+H)$^+$ 321.

Example 66

1-(2-(4-(3-Methylthiophen-2-yl)pyrimidin-2-ylamino)ethyl) imidazolidin-2-one

MS (M+H)$^+$ 306.

Example 67

1-(2-(4-(5-Chlorothiophen-2-yl)pyrimidin-2-ylamino)ethyl) imidazolidin-2-one

MS (M+H)$^+$ 326.

Example 68

1-(2-(4-(5-Methylthiophen-2-yl)pyrimidin-2-ylamino)ethyl) imidazolidin-2-one

MS (M+H)$^+$ 306.

Example 69

1-(2-(4-(4-Phenyl-5-(trifluoromethyl)thiophen-2-yl)pyrimidin-2-ylamino)ethyl)imidazolidin-2-one

MS (M+H)$^+$ 436.

Example 70

1-(2-(4-(2,4-Dimethylthiophen-2-yl)pyrimidin-2-ylamino)ethyl)imidazolidin-2-one

MS (M+H)$^+$ 320.

Example 71

1-(2-(4-(3,5-Dimethylbenzothiophen-2-yl)pyrimidin-2-ylamino)ethyl)imidazolidin-2-one

MS (M+H)$^+$ 370.

Example 72

1-(2-(4-(5-(2-Phenylethylnyl)thiophen-2-yl)pyrimidin-2-ylamino)ethyl)imidazolidin-2-one

MS (M+H)$^+$ 392.

Example 73

1-(2-(4-(Benzothiazol-2-yl)pyrimidin-2-ylamino) ethyl) imidazolidin-2-one

MS (M+H)$^+$ 341.

Example 74

1-(2-(4-(2-Phenylthiazol-5-yl)pyrimidin-2-ylamino) ethyl) imidazolidin-2-one

MS (M+H)$^+$ 367.

Example 75

1-(2-(4-(4-Methyl-2-phenylthiazol-5-yl)pyrimidin-2-ylamino)ethyl)imidazolidin-2-one

MS (M+H)$^+$ 381.

Example 76

1-(2-(4-(2-(4-Chlorophenyl)-4-methylthiazol-5-yl)pyrimidin-2-ylamino)ethyl)imidazolidin-2-one

MS (M+H)$^+$ 415.

Example 77

1-(2-(4-(4-Methyl-2-(pyridin-3-yl)thiazol-5-yl)pyrimidin-2-ylamino)ethyl)imidazolidin-2-one

MS (M+H)$^+$ 382.

Example 78

1-(2-(4-(4-Methyl-2-(pyridin-2-yl)thiazol-5-yl)pyrimidin-2-ylamino)ethyl)imidazolidin-2-one

MS (M+H)$^+$ 382.

Example 79

1-(2-(4-(2-(2-Chlorophenyl)-4-methylthiazol-5-yl)pyrimidin-2-ylamino)ethyl)imidazolidin-2-one

MS (M+H)$^+$ 415.

Example 80

1-(2-(4-(2-(2-Chlorophenyl)thiazol-5-yl)pyrimidin-2-ylamino)ethyl)imidazolidin-2-one

MS (M+H)+ 401.

Example 81

1-(2-(4-(2-(3-Chlorophenyl)thiazol-5-yl)pyrimidin-2-ylamino)ethyl)imidazolidin-2-one

MS (M+H)+ 401.

Example 82

1-(2-(4-(2-(Pyridin-3-yl)thiazol-5-yl)pyrimidin-2-ylamino)ethyl)imidazolidin-2-one

MS (M+H)+ 368.

Example 83

1-(2-(4-(4,5-Dimethylthiazol-2-yl)pyrimidin-2-ylamino)ethyl)imidazolidin-2-one

MS (M+H)+ 319.

Example 84

1-(2-(4-(2-(Pyridin-2-yl)thiazol-5-yl)pyrimidin-2-ylamino)ethyl)imidazolidin-2-one

MS (M+H)+ 368.

Example 85

5-(2-(2-(2-Oxoimidazolidin-1-yl)ethylamino)pyrimidin-4-yl)thiophene-2-carbonitrile

MS (M+H)+ 315.

Example 86

1-(2-(4-(4,5-Dichlorothiophen-2-yl)pyrimidin-2-ylamino)ethyl)-5,5-dimethylimidazolidine-2,4-dione

MS (M+H)+ 400.

Example 87

1-(2-(4-(5-Chloro-4-methylthiophen-2-yl)pyrimidin-2-ylamino)ethyl)-5,5-dimethylimidazolidine-2,4-dione

MS (M+H)+ 380.

Example 88

1-(2-(4-(4-Bromo-5-chlorothiophen-2-yl)pyrimidin-2-ylamino)ethyl)-5,5-dimethylimidazolidine-2,4-dione

MS (M+H)+ 444/446.

Example 89

1-(2-(4-(3,5-dibromothiophen-2-yl)pyrimidin-2-ylamino)ethyl)-5,5-dimethylimidazolidine-2,4-dione

MS (M+H)+ 488/490/492.

Example 90

4-(Benzo[b]thiophen-2-yl)-2-(methylsulfonyl)pyrimidine

(i) (E)-1-(Benzo[b]thiophen-2-yl)-3-(dimethylamino)prop-2-en-1-one

A solution of 1-(benzo[b]thiophen-2-yl)ethanone (1 g) in dimethoxy-N,N-dimethyl-methanamine (10 mL) was refluxed for 6 h and then cooled to rt. The precipitate was filtered and washed with diethyl ether to afford the title compound (1.1 g, 84%).
MS (M+H)+ 232.

(ii) 4-(Benzo[b]thiophen-2-yl)-2-(methylsulfonyl)pyrimidine

Potassium tert-butoxide in THF (1.0 M, 8.7 mL) was added slowly at rt to a mixture of (E)-1-(benzo[b]thiophen-2-yl)-3-(dimethylamino)prop-2-en-1-one (2 g, 8.66 mmol) and thiourea (0.66 g, 8.66 mmol) in methoxyethanol (40 mL). The resulting mixture was refluxed for 5 h. After cooling to rt, iodomethane (2.5 g, 17.32 mmol) was added and the mixture stirred at rt overnight. The solvent was removed under vacuum and water (100 mL) was added to the residue. The mixture was extracted with ethyl acetate (3×100 mL). The combined organic layer was washed with brine (100 mL), dried over sodium sulfate and filtered. After removing solvent under vacuum, the residue was dissolved in 100 mL of acetone/water (1:1) and treated with Oxone (11.7 g). The resulting mixture was stirred at rt for 48 h and the precipitate filtered and washed with water to give the title compound (0.76 g, 30%). MS (M+H)+ 291.

Example 91

4-(3-Bromobenzo[b]thiophen-2-yl)-2-(methylsulfonyl)pyrimidine

Bromine (0.48 g, 3.02 mmol) was slowly added at rt to a mixture of 4-(benzo[b]thiophen-2-yl)-2-(methylsulfonyl)pyrimidine (0.73 g, 2.52 mmol) in acetic acid (20 mL). The resulting mixture was stirred at rt for 15 h and then heated at 60° C. for 5 h. After cooling to rt, acetic acid was removed in vacuo. 100 mL of saturated sodium bicarbonate was added and the mixture was extracted with dichloromethane (3×100 mL).). The combined organic layer was washed with brine (200 mL), dried over anhydrous sodium sulfate and filtered. The solvent was evaporated in vacuo and the solid treated with 20 mL of methanol, filtered and dried to give the title compound (0.75 g, 80%). MS (M+H)+ 369/371.

Example 92

2-(Methylsulfonyl)-4-(3-nitrobenzo[b]thiophen-2-yl)pyrimidine

Nitronium tetrafluoroborate (3.4 mL, 0.5 M in sulfolane, 1.72 mmol) was slowly added at 0° C. to a suspension of 4-(benzo[b]thiophen-2-yl)-2-(methylsulfonyl)pyrimidine (0.50 g, 1.72 mmol) in acetonitrile (10 mL). The resulting mixture was stirred at rt for 14 h and concentrated in vacuo. The product was purified by flash chromatography eluting with ethyl acetate/hexane (1:3) to afford the title compound (0.35 g, 57%). MS (M+H)$^+$ 336.

Example 93

1-(2-(4-(Benzo[b]thiophen-2-yl)pyrimidin-2-ylamino)ethyl)imidazolidin-2-one

A mixture of 4-(benzo[b]thiophen-2-yl)-2-(methylsulfonyl)pyrimidine (75 mg, 0.26 mmol)), 1-(2-aminoethyl)imidazolidin-2-one (33 mg, 0.26 mmol) and triethylamine (32 mg, 0.31 mmol) in methoxyethanol (3 mL) was heated at 100° C. overnight. After cooling to rt the solvent was removed in vacuo and the product was purified by chromatography eluting with methanol/dichloromethane (1:20) to give the title compound as a slightly yellow solid (56 mg, 64%). MS (M+H)$^+$ 340.

Examples 94-102 were prepared in an analogous manner to Example 93.

Example 94

1-(2-(4-(Benzofuran-2-yl)pyrimidin-2-ylamino)ethyl)imidazolidin-2-one

MS (M+H)$^+$ 324.

Example 95

1-(2-(5,6-Dihydrothieno[3,2-h]quinazolin-2-ylamino)ethyl)imidazolidin-2-one

MS (M+H)$^+$ 316.

Example 96

1-(2-(4-(8-Fluoro-4H-thieno[3,2-c]chromen-2-yl)pyrimidin-2-ylamino)-ethyl)imidazolidin-2-one

MS (M+H)$^+$ 412.

Example 97

1-(2-(4-(3-Nitrobenzo[b]thiophen-2-yl)pyrimidin-2-ylamino)-ethyl)-imidazolidin-2-one

MS (M+H)$^+$ 385.

Example 98

1-(2-(4-(3-Bromobenzo[b]thiophen-2-yl)pyrimidin-2-ylamino)ethyl)-imidazolidin-2-one

MS (M+H)$^+$ 418/420.

Example 99

1-(2-(4-(4-(Piperidin-1-ylsulfonyl)phenyl)pyrimidin-2-ylamino)ethyl)imidazolidin-2-one

MS (M+H)$^+$ 331.

Example 100

1-(2-(4-(5-Nitrobenzo[b]thiophen-2-yl)pyrimidin-2-ylamino)ethyl)-imidazolidin-2-one

MS (M+H)$^+$ 385.

Example 101

1-(2-(4-(5-(1-Methyl-5-(trifluoromethyl)-1H-pyrazol-3-yl)thiophen-2-yl)pyrimidin-2-ylamino)ethyl)imidazolidin-2-one

MS (M+H)$^+$ 438.

Example 102

2-(Methylsulfonyl)-5-(2-(2-(2-oxoimidazolidin-1-yl)ethylamino)pyrimidin-4-yl)-4-phenylthiophene-3-carbonitrile

MS (M+H)$^+$ 469.

Example 103

1-(2-(5-Bromo-4-(4,5-dichlorothiophen-2-yl)pyrimidin-2-ylamino)ethyl)-5,5-dimethylimidazolidine-2,4-dione 1-(2-(4-(4,5-Dichlorothiophen-2-yl)pyrimidin-2-ylamino)ethyl)-5,5-dimethyl imidazolidine-2,4-dione (300 mg, 0.75 mmol) was suspended in a 10% solution of methanol in dichloromethane (7 mL). Glacial acetic acid (1 mL) followed by bromine (120 mg, 0.75 mmol, 39 μL) [material immediately went into solution] were added, and the mixture was stirred at room temperature for 3 h. The reaction was concentrated in vacuo, diluted with deionized water (25 mL), stirred for 5 min, and then the product was collected by filtration to give a yellow solid (265 mg). The crude product was purified by flash chromatography (MeOH/DCM) to yield the title compound as a yellow powder (162 mg, 45%). MS (M+H)$^+$ 478/480.

Examples 104-106 were prepared in an analogous manner to Example 103.

Example 104

1-(2-(5-Bromo-4-(5-chloro-4-methylthiophen-2-yl)pyrimidin-2-ylamino)ethyl)-5,5-dimethylimidazolidine-2,4-dione

MS (M+H)$^+$ 458/460.

Example 105

1-(2-(5-Bromo-4-(4-bromo-5-chlorothiophen-2-yl)pyrimidin-2-ylamino)ethyl)-5,5-dimethylimidazolidine-2,4-dione

MS (M+H)$^+$ 522/524/526.

Example 106

1-(2-(5-Bromo-4-(3,5-dibromothiophen-2-yl)pyrimidin-2-ylamino)ethyl)-5,5-dimethylimidazolidine-2,4-dione

MS (M+H)$^+$ 566/568/570.

Example 107

1-(2-(4-(Benzo[b]thiophen-2-yl)-5-phenylpyrimidin-2-ylamino)ethyl)-5,5-dimethylimidazolidine-2,4-dione A 5 mL Personal Chemistry microwave tube was charged with 1-(2-(4-(benzo[b]thiophen-2-yl)-5-bromopyrimidin-2-ylamino)ethyl)-5,5-dimethylimidazolidine-2,4-dione (103 mg, 0.22 mmol), phenyl boronic acid (55 mg, 0.44 mmol), a 2 M aqueous solution of sodium carbonate (0.22 mL, 0.44 mmol), dioxane (2 mL) and tetrakis(triphenylphosphine)palladium (0) (52 mg, 0.044 mmol). The vessel was sealed and heated to 140° C. for 20 min with stirring. After cooling to r.t. the mixture was diluted with ethyl acetate (10 mL) and washed with a saturated aqueous solution of sodium hydrogen carbonate (10 mL). The organic layer was separated, dried over magnesium sulfate, filtered and the solvent evaporated in vacuo. The residue was purified by flash chromatography (chloroform/methanol 99:1 to 96:4 followed by a second column: ethyl acetate/hexane/methanol 50:48:2) to afford the title compound (17 mg, 17%). $^1$H NMR: δ (CDCl$_3$, 400 MHz) 1.47 (s, 6 H), 3.60-3.68 (m, 2 H), 3.81-3.92 (m, 2 H), 6.32 (br. s., 1 H), 6.92 (s, 1 H), 7.26 (t, J=7 Hz, 1 H), 7.32 (t, J=7 Hz, 1 H), 7.36 (dd, J=3 Hz, 2 H), 7.44-7.47 (m, 3 H), 7.50 (d, J=8 Hz, 1 H), 7.79 (d, J=8 Hz, 1 H), 8.22 (s, 1 H): HRMS (M+H)$^+$ Calcd. C$_{25}$H$_{23}$N$_5$O$_2$S 458.1650, found 458.1616

Examples 108-117 were prepared in an analogous manner to Example 107.

Example 108

1-(2-(4-(Benzo[b]thiophen-2-yl)-5-(3-(piperidin-1-yl)phenyl)pyrimidin-2-ylamino)ethyl)-5,5-dimethylimidazolidine-2,4-dione The crude product was purified by flash chromatography (SiO$_2$/ethyl acetate:hexane:methanol/5:94:1 to 20:70:5). HRMS (M+H)$^+$ Calcd. C$_{30}$H$_{32}$N$_6$O$_2$S 541.2385, found 541.2260.

Example 109

1-(2-(4-(Benzo[b]thiophen-2-yl)-5-(3-hydroxyphenyl)pyrimidin-2-ylamino)ethyl)-5,5-dimethylimidazolidine-2,4-dione The crude product was purified by flash chromatography (SiO$_2$/chloroform:methanol/99:5 to 97:3). HRMS (M+H)$^+$ Calcd. C$_{25}$H$_{23}$N$_5$O$_3$S 474.1600, found 474.1596.

Example 110

1-(2-(4-(Benzo[b]thiophen-2-yl)-5-(pyridin-3-yl)pyrimidin-2-ylamino)ethyl)-5,5-dimethylimidazolidine-2,4-dione The crude product was purified by flash chromatography (ethyl acetate/hexane/methanol 10:88:2 to 40:52:8). HRMS (M+H)$^+$ Calcd. C$_{24}$H$_{22}$N$_6$O$_2$S 459.1603, found 459.1595.

Example 111

1-(2-(4-(Benzo[b]thiophen-2-yl)-5-(naphthalen-2-yl)pyrimidin-2-ylamino)ethyl)-5,5-dimethylimidazolidine-2,4-dione The crude product was purified by flash chromatography (ethyl acetate/hexane/methanol 7:92:1 to 20:77:3). HRMS (M+H)$^+$ Calcd. C$_{29}$H$_{25}$N$_5$O$_2$S 508.1807, found 508.1785.

Example 112

1-(2-(4-(Benzo[b]thiophen-2-yl)-5-(3-chlorophenyl)pyrimidin-2-ylamino)ethyl)-5,5-dimethylimidazolidine-2,4-dione The crude product was purified by flash chromatography (chloroform/methanol 100:0 to 97:3). HRMS (M+H)$^+$ Calcd. C$_{25}$H$_{22}$ClN$_5$O$_2$S 492.1261, found 492.1254.

Example 113

1-(2-(4-(Benzo[b]thiophen-2-yl)-5-(3-(dimethylamino)phenyl)pyrimidin-2-ylamino)ethyl)-5,5-dimethylimidazolidine-2,4-dione The crude product was purified by flash chromatography (chloroform/methanol 100:0 to 95:5 followed by a second column: ethyl acetate/hexane/methanol 5:94:1 to 20:75:5). HRMS (M+H)$^+$ Calcd. C$_{27}$H$_{28}$N$_6$O$_2$S 501.2072, found 501.2059.

Example 114

1-(2-(4-(4,5-Dichlorothiophen-2-yl)-5-(3-hydroxyphenyl)pyrimidin-2-ylamino)ethyl)-5,5-dimethylimidazolidine-2,4-dione

MS (M+H)$^+$ 492.

Example 115

1-(2-(4-(5-Chloro-4-methylthiophen-2-yl)-5-(3-hydroxyphenyl)pyrimidin-2-ylamino)ethyl)-5,5-dimethylimidazolidine-2,4-dione

MS (M+H)$^+$ 472.

Example 116

1-(2-(5-(3-Hydroxyphenyl)-4-(5-(3-hydroxyphenyl)-4-methylthiophen-2-yl)pyrimidin-2-ylamino)ethyl)-5,5-dimethylimidazolidine-2,4-dione

MS (M+H)$^+$ 530.

Example 117

1-(2-(5-(3-Hydroxyphenyl)-4-(5-(3-hydroxyphenyl)-4-methylthiophen-2-yl)pyrimidin-2-ylamino)ethyl)-5,5-dimethylimidazolidine-2,4-dione

MS (M+H)$^+$ 673.

Example 118

1-(2-(4-(5-Aminobenzo[b]thiophen-2-yl)-5-bromopyrimidin-2-ylamino)ethyl)-5,5-dimethylimidazolidine-2,4-dione A mixture of 1-(2-(5-bromo-4-(5-nitrobenzo[b]thiophen-2-yl)pyrimidin-2-ylamino)ethyl)-5,5-dimethylimidazolidine-2,4-dione (996 mg, 1.97 mmol), ethanol (100 mL) and indium powder, 100 mesh (1.13 g, 9.85 mmol) was heated to reflux with stirring. After 1.5 h the reaction mixture was cooled to r.t., diluted with water (40 mL) and filtered through a pad of celite. The yellow precipitate (collected on the celite) was purified by reverse phase chromatography (0.1% TFA in AcCN:$H_2$O/10:90 to 95:5). The product fractions were combined, then passed through a 1 g SCX cartridge. The fully loaded cartridge was then washed with MeOH (4 mL) and 2 M ammonia in MeOH (8 mL). Elution of the desired compound was brought about by washing the cartridge finally with DMSO (4 mL). The solvent was removed in vacuo, employing a Genevac, to yield the title compound (142 mg, 15%) as a yellow amorphous solid. $^1$H NMR: δ ($d_6$-DMSO, 400 MHz) 1.29 (s, 6 H), 3.39-3.54 (m, 4 H), 5.20 (s, 2 H), 6.83 (d, J=8.61 Hz, 1 H), 7.02 (s, 1 H), 7.62 (d, J=8.61 Hz, 1 H), 7.68 (s, 1 H), 8.38 (s, 1 H), 8.48 (s, 1 H), 10.82 (s, 1 H).

Example 119

1-(2-(4-(5-Aminobenzothiophen-2-yl)pyrimidin-2-ylamino)ethyl)-5,5-dimethylimidazolidin-2,4-dione Method A: 5,5-Dimethyl-1-(2-(4-(5-nitrobenzothiophen-2-yl)pyrimidin-2-ylamino)ethyl)imidazolidine-2,4-dione (1.2 g, 2.82 mmol) was suspended in methanol (120 mL) (or in ethanol), 20% palladium on carbon (120 mg) was added, and the mixture placed on a Parr shaker under 50 psi of hydrogen gas for a total of 7 days. The reaction mixture was filtered through a thick bed of celite and washed with methanol (5×50 mL) to give a bright yellow solution. The crude material was purified by flash chromatography (MeOH/DCM) to give the title compound as a bright yellow powder (400 mg, 36%). MS (M+H)$^+$ 397.

Method B: 5,5-Dimethyl-1-(2-(4-(5-nitrobenzothiophen-2-yl)pyrimidin-2-ylamino)ethyl)imidazolidine-2,4-dione (500 mg, 1.17 mmol) was suspended in ethanol (12 mL) and a saturated aqueous solution of ammonium chloride (4 mL). Indium powder (940 mg, 8.19 mmol) was added in one portion and the mixture was heated to 80° C. in an oil bath for 6 h. The reaction was cooled to room temperature and the pure product collected by filtration, washed with deionized water (3×25 mL) to remove salts, indium beads were removed with a spatula, and the solid was dried under vacuum at 40° C. for 48 h to yield the title compound as a tan amorphous solid (280 mg). The filtrate was concentrated, washed with deionized water (3×25 mL) to remove salts, and dried under vacuum at 40° C. for 48 h to yield an additional amount of the title compound as a bright yellow orange crystalline solid. Total yield=360 mg, 78%. MS (M+H)$^+$ 397.

Example 120

5,5-Dimethyl-1-(2-(4-(5-aminobenzothiophen-2-yl)pyrimidin-2-ylamino)ethyl)imidazolidine-2,4-dione 5,5-Dimethyl-1-(2-(4-(5-nitrobenzothiophen-2-yl)pyrimidin-2-ylamino)ethyl)imidazolidine-2,4-dione (1.2 g, 2.82 mmol) was suspended in methanol (120 mL), 20% palladium on carbon (120 mg) was added, and the mixture placed on a Parr shaker under 50 psi of hydrogen gas for a total of 7 days. The reaction mixture was filtered through a thick bed of celite and washed with methanol (5×50 mL) to give a bright yellow solution. The crude material was purified by flash chromatography (MeOH/DCM) to give the title compound as a light yellow powder (300 mg, 63%). MS (M+H)$^+$ 411.

Example 121

1-(2-(4-(5-Aminobenzo[b]thiophen-2-yl)pyrimidin-2-ylamino)ethyl)-imidazolidin-2-one A mixture of 1-(2-(4-(5-nitrobenzo[b]thiophen-2-yl)pyrimidin-2-ylamino)ethyl)imidazol-idin-2-one (50 mg) and palladium (10% on activated carbon, 10 mg) in ethanol (10 mL) was stirred under hydrogen (1 atm) for 5 h. The mixture was filtered through Celite and washed with methanol/dichloromethane. The solvent was removed in vacuo and the product was purified by flash chromatography eluting with $NH_3$ in methanol (1 M)/DCM (1:20) to give the title compound as a slightly yellow solid (32 mg, 69%). MS (M+H)$^+$ 355.

Example 122

1-(2-(4-(5-(Ethylamino)benzothiophen-2-yl)pyrimidin-2-ylamino)ethyl)-5,5-dimethylimidazolidine-2,4-dione Prepared in an analogous manner to Example 120, with the reaction being carried out in ethanol rather than methanol. MS (M+H)$^+$ 425.

Example 123

5,5-Dimethyl-1-(2-(4-(5-(pyridine-4-ylmethylamino)benzothiophen-2-yl)pyrimidin-2-ylamino)ethyl)imidazolidine-2,4-dione 1-(2-(4-(5-aminobenzothiophen-2-yl)pyrimidin-2-ylamino)ethyl)-5,5-dimethyl imidazo-lidin-2,4-dione (300 mg, 0.758 mmol) was suspended in dichloromethane (10 mL). Isonicotinaldehyde (97.4 mg, 0.910 mmol), acetic acid (4-5 drops), and sodium triacetoxy-borohydride (321 mg, 1.516 mmol) were added, and the mixture was heated to 60° C. for 16 h. The reaction was cooled to room temperature, diluted with a saturated aqueous solution of sodium bicarbonate (15 mL), and extracted with dichloromethane (4×15 mL). The organic layers were combined and then washed in turn with a saturated aqueous solution of sodium bicarbonate (10 mL), deionized water (15 mL), and a saturated aqueous solution of sodium chloride (15 mL). The organic layer was separated, dried over sodium sulfate (200 mg), filtered through a coarse frit (to remove the sodium sulfate), and concentrated in vacuo to give a white solid (100 mg). The crude material was purified by flash chromatography (MeOH/DCM) to yield the title compound as a white powder (20 mg). MS (M+H)$^+$ 488.

Example 124

N-(2-(2-(2-(5,5-Dimethyl-2,4-dioxoimidazolidin-1-yl)ethylamino)pyrimidin-4-yl)benzothiophen-5-yl)acetamide Acetic acid (sodium salt) (4.6 mg, 0.056 mmol) in dimethylformamide (3 mL) was treated with triethylamine (5.7 mg, 0.056 mmol), and O-(7-azabenzotriazol-1-yl)-N,N,N',N'-tetramethyluronium hexafluorophosphate (HATU) (22 mg, 0.056 mmol). 1-(2-(4-(5-Aminobenzothiophen-2-yl)pyrimidin-2-ylamino)ethyl)-5,5-dimethylimidazolidin-2,4-dione (20 mg, 0.051 mmol) in DMF (2 mL) was added dropwise and the mixture was stirred at room temperature for 18 h. The reaction was diluted with ethyl acetate (5 mL) and washed in turn with a saturated aqueous solution of sodium bicarbonate (5 mL), deionized water (5 mL), and a saturated aqueous solution of sodium chloride (5 mL). The organic layer was dried over sodium sulfate (20 mg), filtered through a coarse frit (to remove the sodium sulfate), and condensed in vacuo to give a red brown powder (12.0 mg). The crude material was dissolved in dimethyl sulfoxide (1.0 mL) and then purified by mass-directed preparative HPLC to yield the title compound as a TFA salt (10.2 mg).

MS (M+H)$^+$ 439.

Examples 125-162 were prepared in an analogous manner to Example 124.

Example 125

N-(2-(2-(2-(5,5-Dimethyl-2,4-dioxoimidazolidin-1-yl)ethylamino)pyrimidin-4-yl)benzothiophen-5-yl) benzamide

MS (M+H)$^+$ 501.

Example 126

N-(2-(2-(2-(5,5-Dimethyl-2,4-dioxoimidazolidin-1-yl)ethylamino)pyrimidin-4-yl)benzothiophen-5-yl) cyclohexanecarboxamide

MS (M+H)$^+$ 507.

Example 127

N-(2-(2-(2-(5,5-Dimethyl-2,4-dioxoimidazolidin-1-yl)ethylamino)pyrimidin-4-yl)benzothiophen-5-yl)-1-methylcyclohexanecarboxamide

MS (M+H)$^+$ 521.

Example 128

4-Cyclohexyl-N-(2-(2-(2-(5,5-dimethyl-2,4-dioxoimidazolidin-1-yl)ethylamino)pyrimidin-4-yl)benzothiophen-5-yl)butanamide

MS (M+H)$^+$ 549.

Example 129

N-(2-(2-(2-(5,5-Dimethyl-2,4-dioxoimidazolidin-1-yl)ethylamino)pyrimidin-4-yl)benzothiophen-5-yl) cyclohex-1-enecarboxamide

MS (M+H)$^+$ 505.

Example 130

N-(2-(2-(2-(5,5-Dimethyl-2,4-dioxoimidazolidin-1-yl)ethylamino)pyrimidin-4-yl)benzothiophen-5-yl)-2-fluorobenzamide

MS (M+H)$^+$ 519.

Example 131

N-(2-(2-(2-(5,5-Dimethyl-2,4-dioxoimidazolidin-1-yl)ethylamino)pyrimidin-4-yl)benzothiophen-5-yl) isobutyramide

MS (M+H)$^+$ 467.

Example 132

N-(2-(2-(2-(5,5-Dimethyl-2,4-dioxoimidazolidin-1-yl)ethylamino)pyrimidin-4-yl)benzothiophen-5-yl)-3-methylbutanamide

MS (M+H)$^+$ 481.

Example 133

2,2,2-Trichloro-N-(2-(2-(2-(5,5-dimethyl-2,4-dioxoimidazolidin-1-yl)ethylamino)pyrimidin-4-yl)benzothiophen-5-yl)acetamide

MS (M+H)$^+$ 541/543.

Example 134

N-(2-(2-(2-(5,5-Dimethyl-2,4-dioxoimidazolidin-1-yl)ethyl-amino)pyrimidin-4-yl)benzothiophen-5-yl) pivalamide

MS (M+H)$^+$ 481.

Example 135

N-(2-(2-(2-(5,5-Dimethyl-2,4-dioxoimidazolidin-1-yl)ethylamino)pyrimidin-4-yl)benzothiophen-5-yl)-2-phenylacetamide

MS (M+H)$^+$ 515.

Example 136

N-(2-(2-(2-(5,5-Dimethyl-2,4-dioxoimidazolidin-1-yl)ethylamino)pyrimidin-4-yl)benzothiophen-5-yl) pent-4-enamide

MS (M+H)$^+$ 479.

Example 137

N-(2-(2-(2-(5,5-Dimethyl-2,4-dioxoimidazolidin-1-yl)ethylamino)pyrimidin-4-yl)benzothiophen-5-yl)-3-(1H-imidazol-4-yl)acrylamide

MS (M+H)$^+$ 517.

Example 138

N-(2-(2-(2-(5,5-Dimethyl-2,4-dioxoimidazolidin-1-yl)ethylamino)pyrimidin-4-yl)benzothiophen-5-yl) picolinamide

MS (M+H)$^+$ 502.

Example 139

N-(2-(2-(2-(5,5-Dimethyl-2,4-dioxoimidazolidin-1-yl)ethylamino)pyrimidin-4-yl)benzothiophen-5-yl)nicotinamide

MS (M+H)+ 502.

Example 140

N-(2-(2-(2-(5,5-Dimethyl-2,4-dioxoimidazolidin-1-yl)ethylamino)pyrimidin-4-yl)benzothiophen-5-yl)-3-(pyridin-3-yl)acrylamide

MS (M+H)+ 528.

Example 141

N-(2-(2-(2-(5,5-Dimethyl-2,4-dioxoimidazolidin-1-yl)ethylamino)pyrimidin-4-yl)benzothiophen-5-yl)isonicotinamide

MS (M+H)+ 502.

Example 142

N-(2-(2-(2-(5,5-Dimethyl-2,4-dioxoimidazolidin-1-yl)ethylamino)pyrimidin-4-yl)benzothiophen-5-yl)-3-(piperidine-1-yl)propanamide

MS (M+H)+ 536.

Example 143

N-(2-(2-(2-(5,5-Dimethyl-2,4-dioxoimidazolidin-1-yl)ethylamino)pyrimidin-4-yl)benzothiophen-5-yl)-2-(pyridin-4-yl)acetamid

MS (M+H)+ 516.

Example 144

N-(2-(2-(2-(5,5-Dimethyl-2,4-dioxoimidazolidin-1-yl)ethylamino)pyrimidin-4-yl)benzothiophen-5-yl)-2-methylnicotinamide

MS (M+H)+ 516.

Example 145

N-(2-(2-(2-(5,5-Dimethyl-2,4-dioxoimidazolidin-1-yl)ethylamino)pyrimidin-4-yl)benzothiophen-5-yl)cyclohex-3-enecarboxamide

MS (M+H)+ 505.

Example 146

N-(2-(2-(2-(5,5-Dimethyl-2,4-dioxoimidazolidin-1-yl)ethylamino)pyrimidin-4-yl)benzothiophen-5-yl)-N-methylmaleamide

MS (M+H)+ 508.

Example 147

N-(2-(2-(2-(5,5-Dimethyl-2,4-dioxoimidazolidin-1-yl)ethylamino)pyrimidin-4-yl)benzothiophen-5-yl)-3-(pyridin-4-yl)acrylamide

MS (M+H)+ 528.

Example 148

2-Cyano-N-(2-(2-(2-(5,5-dimethyl-2,4-dioxoimidazolidin-1-yl)ethylamino)pyrimidin-4-yl)benzothiophen-5-yl)benzamide

MS (M+H)+ 526.

Example 149

N-(2-(2-(2-(5,5-Dimethyl-2,4-dioxoimidazolidin-1-yl)ethylamino)pyrimidin-4-yl)benzothiophen-5-yl)-2-(methylsulfonyl)acetamide

MS (M+H)+ 517.

Example 150

N-(2-(2-(2-(5,5-Dimethyl-2,4-dioxoimidazolidin-1-yl)ethylamino)pyrimidin-4-yl)benzothiophen-5-yl)-2-(pyridin-3-yl)acetamide

MS (M+H)+ 516.

Example 151

N-(2-(2-(2-(5,5-Dimethyl-2,4-dioxoimidazolidin-1-yl)ethylamino)pyrimidin-4-yl)benzothiophen-5-yl)-4-methylcyclohexanecarboxamide

MS (M+H)+ 521.

Example 152

N-(2-(2-(2-(5,5-Dimethyl-2,4-dioxoimidazolidin-1-yl)ethylamino)pyrimidin-4-yl)benzothiophen-5-yl)-4-methylisonicotinamide

MS (M+H)+ 516.

Example 153

N-(2-(2-(2-(5,5-Dimethyl-2,4-dioxoimidazolidin-1-yl)ethylamino)pyrimidin-4-yl)benzothiophen-5-yl)-3-(pyridin-2-yl)acrylamide

MS (M+H)+ 528.

Example 154

N-(2-(2-(2-(5,5-Dimethyl-2,4-dioxoimidazolidin-1-yl)ethylamino)pyrimidin-4-yl)benzothiophen-5-yl)-1-methylpiperidine-4-carboxamide

MS (M+H)+ 522.

Example 155

N-(2-(2-(2-(5,5-Dimethyl-2,4-dioxoimidazolidin-1-yl)ethylamino)pyrimidin-4-yl)benzothiophen-5-yl)-2-morpholinoacetamide

MS (M+H)$^+$ 524.

Example 156

N-(2-(2-(2-(5,5-Dimethyl-2,4-dioxoimidazolidin-1-yl)ethylamino)pyrimidin-4-yl)benzothiophen-5-yl)-2,3-dihydrobenzfuran-7-carboxamide

MS (M+H)$^+$ 543.

Example 157

N-(2-(2-(2-(5,5-Dimethyl-2,4-dioxoimidazolidin-1-yl)ethylamino)pyrimidin-4-yl)benzothiophen-5-yl)-2-(5-oxopyrrolidin-2-ylthio)acetamide

MS (M+H)$^+$ 554.

Example 158

N-(2-(2-(2-(5,5-Dimethyl-2,4-dioxoimidazolidin-1-yl)ethylamino)pyrimidin-4-yl)benzothiophen-5-yl)-5-methylnicotinamide

MS (M+H)$^+$ 516.

Example 159

N-(2-(2-(2-(5,5-Dimethyl-2,4-dioxoimidazolidin-1-yl)ethylamino)pyrimidin-4-yl)benzothiophen-5-yl)-2-(tetrahydro-2H-pyran-4-yl)acetamide

MS (M+H)$^+$ 523.

Example 160

N-(2-(2-(2-(5,5-Dimethyl-2,4-dioxoimidazolidin-1-yl)ethylamino)pyrimidin-4-yl)benzothiophen-5-yl)-3-morpholinopropanamide

MS (M+H)$^+$ 538.

Example 161

3-Chloro-N-(2-(2-(2-(5,5-dimethyl-2,4-dioxoimidazolidin-1-yl)ethylamino)pyrimidin-4-yl)benzothiophen-5-yl)benzamide

MS (M+H)$^+$ 535.

Example 162

N-(2-(2-(2-(5,5-Dimethyl-2,4-dioxoimidazolidin-1-yl)ethylamino)pyrimidin-4-yl)benzothiophen-5-yl)-1H-indole-7-carboxamide

MS (M+H)$^+$ 540.

Example 163

N-(2-(2-(2-(2-Oxoimidazolidin-1-yl)ethylamino)pyrimidin-4-yl)benzo[b]-thiophen-5-yl)acetamide Acetyl chloride (61 mg, 0.78 mmol) was added to a mixture of 1-(2-(4-(5-aminobenzo[b]-thiophen-2-yl)pyrimidin-2-ylamino)ethyl)imidazolidin-2-one (230 mg, 0.65 mmol) and triethylamine (131 mg, 1.30 mmol) in dichloromethane (10 mL) at 0° C. and stirred at rt for 6 h. Water (50 mL) was added and the mixture was extracted with dichloromethane (3×50 mL). The combined organic layer was washed with brine (50 mL), dried over sodium sulfate and filtered. After removing the solvent in vacuo the product was purified by column chromatography eluting with methanol/dichloromethane (1:20) to give the title compound as a slightly yellow solid (39 mg, 15%). MS (M+H)$^+$ 397.

Example 164

1-(2-(5-Bromo-4-(thiazolo[5,4-c]pyridin-2-yl)pyrimidin-2-ylamino)ethyl)-5,5-dimethylimidazolidine-2,4-dione

(i) N-(Pyridin-4-yl)pivalamide

A solution of trimethylacetyl chloride (32.5 mL, 0.264 mol) in dry dichloromethane (50 mL) was added dropwise over 1 h to a stirred suspension of 4-aminopyridine (22.60 g, 0.240 mol) and triethylamine (41.8 mL, 0.300 mol) in dry dichloromethane (360 mL) at 0° C. under nitrogen. The ice bath was removed and the reaction allowed to warm to r.t. overnight. After 17 h, the pale brown mixture was poured into water (500 mL). The organic layer was separated and washed with a dilute aqueous solution of sodium hydrogen carbonate (400 mL). The organic layer was separated, dried over sodium sulfate, filtered and the solvent evaporated in vacuo. The crude solid was recrystallized from ethyl acetate (75 mL)/hexane (50 mL), washed with diethyl ether (2×10 mL) and air dried to yield N-(pyridin-4-yl)pivalamide (29.11 g, 68%) as colourless plate like crystals. $^1$H NMR: δ (CDCl$_3$, 400 MHz) 1.33 (s, 9 H), 7.50 (d, J=6 Hz, 2 H), 7.56 (br. s., 1 H), 8.49 (d, J=6 Hz, 2 H).

(ii) 4-Pivalamidopyridin-3-yl diethylcarbamodithioate

A 2.5 M solution of n-butyllithium (67.3 mL) in hexanes was added dropwise over 2 h to a stirred solution of N-(pyridin-4-yl)pivalamide (12.0 g, 0.067 mol) in tetrahydrofuran (268 mL) at −10° C. (acetone/ice 1:1) under nitrogen. The temperature was kept between −10° C. and 1° C. Upon complete addition, the temperature returned to −10° C. and a solution of tetraethylthiuram disulfide (59.9 g, 0.202 mol) in tetrahydrofuran (180 mL) was added dropwise, rapidly. The mixture was allowed to warm to r.t., poured into water (500 mL) and extracted with diethyl ether (2×400 mL). The organic layers were combined, washed with brine (300 mL), then separated, dried over sodium sulfate, filtered and the solvent evaporated in vacuo to yield 4-pivalamidopyridin-3-yl diethylcarbamodithioate (21.9 g, 100%) as an orange oil. $^1$H NMR: δ (CDCl$_3$, 400 MHz) 1.28 (s, 9 H), 1.31 (t, J=7 Hz, 3 H), 1.46 (t, J=7 Hz, 3 H), 3.93 (q, J=7 Hz, 2 H), 4.03 (q, J=7 Hz, 2 H), 8.39 (d, J=5 Hz, 1 H), 8.45 (br. s., 1H), 8.52 (s, 1 H), 8.61 (d, J=5 Hz, 1 H).

(iii) 4-Aminopyridin-3-yl diethylcarbamodithioate

An opaque solution of 4-pivalamidopyridin-3-yl diethylcarbamodithioate (21.9 g, 67 mmol) in methanol (220 mL) and 1 N sodium hydroxide (220 mL) was stirred at r.t. for 20 h. Tlc showed consumption of starting material. The clear yellow solution was diluted with water (500 mL). After letting the turbid solution stand for 5 min, crystals precipitated out. The solid was filtered off, washed with water (2×50 mL) and diethyl ether (3×50 mL), and air dried to afford 4-aminopyridin-3-yl diethylcarbamodithioate (10.05 g, 62%) as colorless plate like crystals. $^1$H NMR: δ (CDCl$_3$, 400 MHz) 1.30 (t, J=7 Hz, 3 H), 1.44 (t, J=7 Hz, 3 H), 3.90 (q, J=7 Hz, 2 H), 4.03 (q, J=7 Hz, 2 H), 4.68 (br. s., 2 H), 6.65 (d, J=5.5 Hz, 1 H), 8.25-8.30 (m, 2 H).

(iv) 5-Bromo-2-(methylthio)pyrimidine-4-carboxylic acid

Mucobromic acid (58.05 g, 0.225 mol) was added to a stirred solution of 2-methyl-2-thio-pseudourea sulfate (62.66 g, 0.225 mol) in water (500 mL) at r.t. The suspension was cooled to 10° C. (ice bath) and triethylamine (94.1 mL, 0.675 mol) was added dropwise over 4 h. The reaction mixture was then left to stand at r.t. for 24 h. Activated carbon (Darco G-60) was added to the now dark red/brown solution and after stirring for 10 min the charcoal was filtered off. The filtrate was acidified with concentrated hydrochloric acid (50 mL) and the yellow precipitate was filtered off, washed with water (2×80 mL) and diethyl ether (2×100 mL), and then placed in a vacuum oven at 50° C. for 2 days to yield 5-bromo-2-(methylthio)pyrimidine-4-carboxylic acid (33.13 g, 59%) as a yellow amorphous solid. $^1$H NMR δ (d$_6$-DMSO, 400 MHz) 2.75 (s, 3 H), 9.20 (s, 1 H).

(v) 4-(5-Bromo-2-(methylthio)pyrimidine-6-carboxamido)pyridin-3-yl diethylcarbamodithioate A catalytic amount of N,N-dimethylformamide (2 drops) was added to a stirred suspension of 5-bromo-2-(methylthio)pyrimidine-4-carboxylic acid (2.07 g, 8.33 mmol) and a 2 M solution of oxalyl chloride (21 mL, 0.042 mol) in dichloromethane under nitrogen at r.t. Vigorous effervescence was observed. After 30 min everything had dissolved and the solvent was then evaporated in vacuo. The residue was dissolved in dichloromethane (20 mL) and placed under nitrogen. Triethylamine (2.32 mL, 16.66 mmol) was added to this stirred solution at r.t. followed by 4-aminopyridin-3-yl diethylcarbamodithioate (2.01 g, 8.33 mmol). Everything quickly dissolved with a noticeable exotherm. After 3 h at r.t. tlc showed a new major product. The reaction was diluted with dichloromethane (20 mL) and washed with a saturated aqueous solution of sodium hydrogen carbonate (40 mL). The organic layer was separated, dried over sodium sulfate, filtered and the solvent evaporated in vacuo. The residue was purified by flash chromatography (ethyl acetate/hexane 15:85 to 60:40) to yield 4-(5-bromo-2-(methylthio)pyrimidine-6-carboxamido)pyridin-3-yl diethylcarbamodithioate (1.99 g, 51%) as a pale yellow amorphous solid. $^1$H NMR: δ (CDCl$_3$, 400 MHz) 1.30 (t, J=7 Hz, 3 H), 1.51 (t, J=7 Hz, 3 H), 2.60 (s, 3 H), 3.93-4.08 (m, 4 H), 8.57-8.62 (m, 2 H), 8.69 (d, J=6 Hz, 1 H), 8.85 (s, 1 H), 10.67 (s, 1 H).

(vi) 2-(5-Bromo-2-(methylthio)pyrimidin-4-yl)thiazolo[5,4-c]pyridine

A stirred solution of 4-(5-bromo-2-(methylthio)pyrimidine-6-carboxamido)pyridin-3-yl diethylcarbamodithioate (1.99 g, 4.21 mmol) in 96% formic acid (40 mL) was heated to reflux for 4 h. After cooling to r.t. the reaction mixture was poured into ice/water (400 mL), then basified with 5 N aqueous sodium hydroxide and extracted with ethyl acetate (3×150 mL). The organic layers were combined, dried over sodium sulfate, filtered and the solvent evaporated in vacuo to yield 2-(5-bromo-2-(methylthio)pyrimidin-4-yl)thiazolo[5,4-c]pyridine (1.34 g, 94%) as a yellow amorphous solid. $^1$H NMR: δ (CDCl$_3$, 400 MHz) 2.67 (s, 3 H), 8.09 (d, J=5.5 Hz, 1 H), 8.74 (d, J=5.5 Hz, 1 H), 8.86 (s, 1 H), 9.34 (s, 1 H).

(vii) 2-(5-Bromo-2-(methylsulfonyl)pyrimidin-4-yl)thiazolo[5,4-c]pyridine

A solution of oxone (179 mg, 0.29 mmol) in water (10 mL) was added dropwise to a stirred solution of 2-(5-bromo-2-(methylthio)pyrimidin-4-yl)thiazolo[5,4-c]pyridine (66 mg, 0.19 mmol) in dichloromethane (12 mL) at 0° C. The bright yellow suspension was allowed to warm to r.t. overnight. After 14 h the organic layer was separated, dried over sodium sulfate, filtered and the solvent evaporated in vacuo. The residue was purified by flash chromatography (ethyl acetate/hexane 25:75 to 50:50) to yield 2-(5-bromo-2-(methylsulfonyl)pyrimidin-4-yl)thiazolo[5,4-c]pyridine (59 mg, 82%) as a white amorphous solid. $^1$H NMR: δ (CDCl$_3$, 400 MHz) 3.47 (s, 3 H), 8.13 (d, J=5.5 Hz, 1 H), 8.79 (d, J=5.5 Hz, 1 H), 9.29 (s, 1 H), 9.39 (s, 1 H).

(viii) 1-(2-(5-Bromo-4-(thiazolo[5,4-c]pyridin-2-yl)pyrimidin-2-ylamino)ethyl)-5,5-dimethylimidazolidine-2,4-dione A microwave tube was charged with 2-(5-bromo-2-(methylsulfonyl)pyrimidin-4-yl)thiazolo[5,4-c]pyridine (300 mg, 0.81 mmol), 1-(2-Aminoethyl)-5,5-dimethyl-imidazolidine-2,4-dione (138 mg, 0.81 mmol), isopropanol (3 mL) and N,N-diisopropylethylamine (0.21 mL, 1.21 mmol). The vessel was sealed and heated in a microwave reactor at 160° C. for 1000 seconds. The resulting solid was filtered off and washed with methanol (4×10 mL). The solid was then dissolved in dimethylsulfoxide (4 mL) and purified by reverse phase HPLC. Product fractions were combined and loaded onto an SCX cartridge, washed with methanol (4 mL), then free based and eluted with 2 M ammonia in methanol (4 mL). The solvent was evaporated in vacuo to yield 1-(2-(5-bromo-4-(thiazolo[5,4-c]pyridin-2-yl)pyrimidin-2-ylamino)ethyl)-5,5-dimethylimidazolidine-2,4-dione (17 mg, 5%) as a yellow amorphous solid. $^1$H NMR δ (d$_6$-DMSO, 400 MHz) 1.50 (s, 6 H), 3.67 (br. s., 2 H), 3.75 (br. s., 2 H), 4.32 (br. s., 1 H), 6.89 (s, 1 H), 7.49 (s, 1 H), 8.33 (d, J=5.5 Hz, 1 H), 8.91 (d, J=5.1 Hz, 1 H), 9.71 (s, 1 H): HRMS (M+H)$^+$ Calcd. C$_{17}$H$_{16}$BrN$_7$O$_2$S 462.0348, found 462.0339.

Example 165

(2S)-tert-Butyl 2-((2-(5-bromo-2-(2-(5,5-dimethyl-2,4-dioxoimidazolidin-1-yl)ethylamino)pyrimidin-4-yl)benzo[b]thiophen-5-yloxy)methyl)pyrrolidine-1-carboxylate

(i) tert-Butyl 1-((benzo[b]thiophen-5-yloxy)methyl)pyrrolidine-2-carboxylate Polymer supported triphenyl phosphine (5.12 g, 13.32 mmol, 2.6 mmol/g loading) was suspended in dichloromethane (15 mL) cooled to 0° C. in an ice/water bath. Diisopropyl azodicarboxylate (2.69 g, 13.3 mmol, 2.6 mL) was added dropwise and the mixture was stirred for 10 min. A solution of benzo[b]thiophen-5-ol (1.20 g, 7.99 mmol) and (S)-tert-butyl-2-(hydroxymethyl)pyrrolidine-1-carboxylate (1.34 g, 6.66 mmol) dissolved in dichloromethane (20 mL) was added dropwise at 0° C. The cooling bath was removed, triethylamine (1.35 g, 13.3 mmol) was added, and the mixture was stirred for 16 h. The polymer bound triphenylphosphine was removed by filtration and washed with dichloromethane (3×10 mL). The organic layer was separated, dried over sodium sulfate (200 mg), filtered through a coarse frit (to remove the sodium sulfate), and condensed in vacuo to give a white solid (2.3 g). The crude product was purified by flash chromatography (EtOAc/hexane 1:1) to yield the title compound as a white solid (1.95 g, 55%). MS (M+H)$^+$ 334.

(ii) (2S)-tert-Butyl 2-((2-(5-bromo-2-chloropyrimidin-4-yl)benzo[b]thiophen-5-yloxy)methyl)pyrrolidine-1-carboxylate tert-Butyl 1-((benzo[b]thiophen-5-yloxy)methyl)pyrrolidine-2-carboxylate (1.07 g, 3.21 mmol) in tetrahydrofuran (10 mL) was cooled to –78° C., n-butyl lithium (2.41 mL, 3.85 mmol) was added dropwise, and the mixture was stirred for 45 min. 5-Bromo-2-chloropyrimidine (746 mg, 3.85 mmol) dissolved in tetrahydrofuran (5 mL) was added dropwise and the mixture was stirred at –78° C. for 2 h. The reaction mixture was carefully quenched with acetic acid/methanol (2 mL each) and stirred for 15 min. The reaction was then warmed to –40° C. and 2,3-dichloro-5,6-dicyano-1,4-benzoquinone (874 mg, 3.85 mmol) dissolved in tetrahydrofuran (5 mL) was added dropwise. The mixture was stirred for 1 h. A 1.0 M aqueous solution of sodium hydroxide (3.1 mL) was added, the cooling bath was removed, and the reaction mixture was allowed to slowly warm to room temperature. The reaction was diluted with ethyl acetate (25 mL), washed in turn with a saturated aqueous solution of sodium bicarbonate (25 mL), deionized water (25 mL), and a saturated aqueous solution of sodium chloride (15 mL). The organic layer was separated and then dried over sodium sulfate (200 mg), filtered through a coarse frit (to remove the sodium sulfate), and condensed in vacuo to give a white solid (1.15 g). The material was purified by flash chromatography (EtOAc/hexane v/v) to yield the title compound as a white solid (902 mg, 58%). MS (M+H)$^+$ 524/526.

(iii) (2S)-tert-Butyl 2-((2-(5-bromo-2-(2-(5,5-dimethyl-2,4-dioxoimidazolidin-1-yl)ethylamino)pyrimidin-4-yl)benzo[b]thiophen-5-yloxy)methyl)pyrrolidine-1-carboxylate A mixture of (2S)-tert-butyl 2-((2-(5-bromo-2-chloropyrimidin-4-yl)benzo[b]thiophen-5-yloxy)methyl)pyrrolidine-1-carboxylate (524 mg, 1.00 mmol) in toluene (25 mL) was treated with 1-(2-aminoethyl)-5,5-dimethylimidazolidine-2,4-dione (205 mg, 1.20 mmol) and triethylamine (121 mg, 1.2 mmol) and then heated to reflux in an oil bath for 3 h. The reaction was cooled to room temperature, diluted with ethyl acetate (25 mL) and washed in turn with a saturated aqueous solution of sodium bicarbonate (15 mL), deionized water (15 mL), and a saturated aqueous solution of sodium chloride (15 mL). The organic layer was separated, dried over sodium sulfate (300 mg), filtered through a coarse frit (to remove the sodium sulfate), and condensed in vacuo to give a white solid (450 mg). The crude material was purified by flash chromatography (EtOAc/hexane v/v) to yield the title compound as a white solid (325 mg, 50%). MS (M+H)$^+$ 659/661.

Example 166

1-(2-(5-Bromo-4-(5-((S)-pyrrolidin-2-ylmethoxy) benzo[b]thiophen-2-yl)pyrimidin-2-ylamino)ethyl)- 5,5-dimethylimidazolidine-2,4-dione trifluoroacetate A solution of (2S)-tert-butyl 2-((2-(5-bromo-2-(2-(5,5-dimethyl-2,4-dioxoimidazolidin-1-yl)ethylamino)pyrimidin-4-yl)benzo[b]thiophen-5-yloxy)methyl)pyrrolidine-1-carboxylate (146 mg, 0.222 mmol) in dichloromethane (5 mL) was treated with trifloroacetic acid (1 mL) and stirred at room temperature for 30 min. The reaction was concentrated in vacuo to yield the title compound as a bright yellow solid (213 mg, quantitative yield). MS (M+H)$^+$ 559/561.

Example 167

1-(2-(4-(5-(Morpholinosulfonyl)thiophen-2-yl)pyrimidin-2-ylamino)-ethyl)imidazolidin-2-one (i) 2-(Methylsulfonyl)-4-(5-(morpholinosulfonyl) thiophen-2-yl)pyrimidine A mixture of 5-(2-(methylthio)pyrimidin-4-yl)thiophene-2-sulfonyl chloride (200 mg, 0.65 mmol), morpholine (62 mg, 0.72 mmol) and triethylamine (78 mg, 0.78 mmol) in tetrahydrofuran (5 mL) was stirred at rt for 2 days. Water (50 mL) was added and the mixture was extracted with ethyl acetate (3×50 mL). The combined organic layer was washed with brine (50 mL), dried over anhydrous sodium sulfate and filtered. The solvent was evaporated in vacuo and the residue was washed with diethyl ether (2 mL) to give a white solid. The solid was dissolved in 30 mL of acetone-water (1:1) and then oxone (2 g) was added. After stirring at rt for 20 h the mixture was concentrated in vacuo to remove the acetone. The white precipitate was filtered off, washed with water and dried to afford the title compound (186 mg, 73%). MS (M+H)$^+$ 390.

(ii) 1-(2-(4-(5-(Morpholinosulfonyl)thiophen-2-yl) pyrimidin-2-ylamino)ethyl)imidazolidin-2-one A mixture of 2-(methylsulfonyl)-4-(5-(morpholinosulfonyl)thiophen-2-yl)pyrimidine (100 mg, 0.26 mmol), 1-(2-aminoethyl)imidazolidin-2-one (36 mg, 0.28 mmol) and triethylamine (56 mg, 0.52 mmol) in toluene (3 mL) was refluxed for 6 h. After cooling to rt, the solvent was evaporated in vacuo and then methanol (5 mL) was added. After stirring for 15 min the solid was filtered and dried to give the title compound with a light yellow color (81 mg, 72%). MS (M+H)$^+$ 439.

Examples 168-201 were prepared in an analogous manner to Example 167.

Example 168

N-(3,5-Bis(trifluoromethyl)phenyl)-5-(2-(2-(2-oxoimidazolidin-1-yl)-ethylamino)pyrimidin-4-yl) thiophene-2-sulfonamide

MS (M+H)$^+$ 581.

Example 169

5-(2-(2-(2-Oxoimidazolidin-1-yl)ethylamino)pyrimidin-4-yl)-N-(3-(trifluoromethyl)phenyl)thiophene-2-sulfonamide

MS (M+H)$^+$ 513.

Example 170

N,N-Dimethyl-5-(2-(2-(2-oxoimidazolidin-1-yl)ethylamino)pyrimidin-4-yl)thiophene-2-sulfonamide

MS (M+H)$^+$ 397.

Example 171

1-(2-(4-(5-(Piperidin-1-ylsulfonyl)thiophen-2-yl)pyrimidin-2-ylamino)-ethyl)imidazolidin-2-one

MS (M+H)$^+$ 437.

Example 172

1-(2-(4-(5-(Pyrrolidin-1-ylsulfonyl)thiophen-2-yl)pyrimidin-2-ylamino)-ethyl)imidazolidin-2-one

MS (M+H)$^+$ 423.

Example 173

1-(2-(4-(5-(4-Methylpiperazin-1-ylsulfonyl)thiophen-2-yl)pyrimidin-2-ylamino)ethyl)imidazolidin-2-one

MS (M+H)$^+$ 452.

Example 174

5-(2-(2-(2-Oxoimidazolidin-1-yl)ethylamino)pyrimidin-4-yl)thiophene-2-sulfonamide

MS (M+H)$^+$ 369.

Example 175

1-(2-(4-(5-(Azetidin-1-ylsulfonyl)thiophen-2-yl)pyrimidin-2-ylamino)-ethyl)imidazolidin-2-one

MS (M+H)$^+$ 409.

Example 176

1-(2-(4-(5-(2-Methylpiperidin-1-ylsulfonyl)thiophen-2-yl)pyrimidin-2-ylamino)ethyl)imidazolidin-2-one

MS (M+H)$^+$ 451.

Example 177

1-(2-(4-(5-(3-Methylpiperidin-1-ylsulfonyl)thiophen-2-yl)pyrimidin-2-ylamino)ethyl)imidazolidin-2-one

MS (M+H)$^+$ 451.

Example 178

1-(2-(4-(5-(Azepan-1-ylsulfonyl)thiophen-2-yl)pyrimidin-2-ylamino)-ethyl)imidazolidin-2-one

MS (M+H)$^+$ 451.

Example 179

1-(2-(4-(5-(4-Methylpiperidin-1-ylsulfonyl)thiophen-2-yl)pyrimidin-2-ylamino)ethyl)imidazolidin-2-one

MS (M+H)$^+$ 451.

Example 180

1-(2-(4-(5-(2-Ethylpiperidin-1-ylsulfonyl)thiophen-2-yl)pyrimidin-2-ylamino)ethyl)imidazolidin-2-one

MS (M+H)$^+$ 465.

Example 181

1-(2-(4-(5-((2R,6S)-2,6-Dimethylpiperidin-1-ylsulfonyl)thiophen-2-yl)pyrimidin-2-ylamino)ethyl)imidazolidin-2-one

MS (M+H)$^+$ 465

Example 182

1-(2-(4-(5-(2-Methylpiperidin-1-ylsulfonyl)thiophen-2-yl)pyrimidin-2-ylamino)ethyl)-1H-benzo[d]imidazol-2(3H)-one

MS (M+H)$^+$ 499.

Example 183

1-(2-(4-(5-(3,4-Dihydroisoquinolin-2(1H)-ylsulfonyl)thiophen-2-yl)-pyrimidin-2-ylamino)ethyl)imidazolidin-2-one

MS (M+H)$^+$ 485.

Example 184

1-(2-(4-(5-(3,4-Dihydroquinolin-1(2H)-ylsulfonyl)thiophen-2-yl)-pyrimidin-2-ylamino)ethyl)imidazolidin-2-one

MS (M+H)$^+$ 485.

Example 185

1-(2-(4-(5-(Octahydroquinolin-1(2H)-ylsulfonyl)thiophen-2-yl)-pyrimidin-2-ylamino)ethyl)imidazolidin-2-one

MS (M+H)+ 491.

Example 186

1-(2-(4-(5-(1,3,3-Trimethyl-6-aza-bicyclo [3.2.1]octan-6-ylsulfonyl)-thiophen-2-yl)pyrimidin-2-ylamino)ethyl)imidazolidin-2-one

MS (M+H)+ 505.

Example 187

N-Methyl-5-(2-(2-(2-oxoimidazolidin-1-yl)ethylamino)pyrimidin-4-yl)-N-phenylthiophene-2-sulfonamide

MS (M+H)+ 459.

Example 188

1-(2-(4-(5-(3,3-Dimethylpiperidin-1-ylsulfonyl)thiophen-2-yl)pyrimidin-2-ylamino)ethyl)imidazolidin-2-one

MS (M+H)+ 465.

Example 189

1-(2-(4-(5-(6-Methyl-3,4-dihydroquinolin-1(2H)-ylsulfonyl)thiophen-2-yl)pyrimidin-2-ylamino)ethyl)imidazolidin-2-one

MS (M+H)+ 499.

Example 190

1-(2-(4-(5-(6-Methoxy-3,4-dihydroquinolin-1(2H)-ylsulfonyl)thiophen-2-yl)pyrimidin-2-ylamino)ethyl)imidazolidin-2-one

MS (M+H)+ 515.

Example 191

1-(2-(4-(5-(1H-Indol-1-ylsulfonyl)thiophen-2-yl)pyrimidin-2-ylamino)-ethyl)imidazolidin-2-one

MS (M+H)+ 469.

Example 192

1-(2-(4-(5-(2,3-Dihydrobenzo[b][1,4]oxazin-4-ylsulfonyl)thiophen-2-yl)-pyrimidin-2-ylamino)ethyl)imidazolidin-2-one

MS (M+H)+ 487

Example 193

1-(2-(4-(5-(4,4-Dimethyl-3,4-dihydroquinolin-1(2H)-ylsulfonyl)thiophen-2-yl)pyrimidin-2-ylamino)ethyl)imidazolidin-2-one

MS (M+H)+ 513.

Example 194

1-(2-(4-(5-(6-Bromo-3,4-dihydroquinolin-1(2H)-ylsulfonyl)thiophen-2-yl)pyrimidin-2-ylamino)ethyl)imidazolidin-2-one

MS (M+H)+ 563/565.

Example 195

5,5-Dimethyl-1-(2-(4-(5-(3-methylpiperidin-1-ylsulfonyl)thiophen-2-yl)-pyrimidin-2-ylamino)ethyl)imidazolidine-2,4-dione

MS (M+H)+ 493.

Example 196

5,5-Dimethyl-1-(2-(4-(5-(2-methylpiperidin-1-ylsulfonyl)thiophen-2-yl)-pyrimidin-2-ylamino)ethyl)imidazolidine-2,4-dione

MS (M+H)+ 493.

Example 197

1-(2-(4-(5-(3,4-Dihydroquinolin-1(2H)-ylsulfonyl)thiophen-2-yl)pyrimidin-2-ylamino)ethyl)-5,5-dimethylimidazolidine-2,4-dione

MS (M+H)+ 527.

Example 198

1-(2-(4-(5-(1H-Indol-1-ylsulfonyl)thiophen-2-yl)pyrimidin-2-ylamino)-ethyl)-5,5-dimethylimidazolidine-2,4-dione

MS (M+H)+ 511.

Example 199

1-(2-(4-(5-(2,3-Dihydrobenzo[b][1,4]oxazin-4-ylsulfonyl)thiophen-2-yl)-pyrimidin-2-ylamino)ethyl)-5,5-dimethylimidazolidine-2,4-dione

MS (M+H)+ 529.

Example 200

N-(2-Chloroethyl)-5-(2-(2-(5,5-dimethyl-2,4-dioxoimidazolidin-1-yl)-ethylamino)pyrimidin-4-yl)-N-methylthiophene-2-sulfonamide

MS (M+H)+ 486/489.

Example 201

N-(2-Chloroethyl)-5-(2-(2-(5,5-dimethyl-2,4-diox-oimidazolidin-1-yl)-ethylamino)pyrimidin-4-yl)thiophene-2-sulfonamide

MS (M+H)+ 473/475.

Example 202

1-(2-(5-bromo-4-(5-(piperidin-1-ylsulfonyl)thiophen-2-yl)pyrimidin-2-ylamino)ethyl)imidazolidin-2-one

(i) 1-(5-Bromothiophen-2-ylsulfonyl)piperidine

Piperidine (0.72 g, 8.41 mmol) was added to a solution of 5-bromothiophene-2-sulfonyl chloride (2 g, 7.65 mmol) in tetrahydrofuran (100 mL) at 0° C. followed by triethylamine (0.93 g, 9.18 mmol) added slowly. The resulting mixture was stirred at rt overnight and 100 mL of brine was added. The mixture was extracted with ethyl acetate (3×100 mL). The combined organic layer was washed with brine (100 mL), dried over anhydrous sodium sulfate and filtered. Removal of the solvent gave the title compound as a slightly yellow solid (quantitative yield).

(ii) 5-Bromo-2-chloro-4-(5-(piperidin-1-ylsulfonyl)thiophen-2-yl)pyrimidine

Prepared in an analogous manner to Example 20.

(iii) 1-(2-(5-Bromo-4-(5-(piperidin-1-ylsulfonyl)thiophen-2-yl)pyrimidin-2-ylamino)ethyl)imidazolidin-2-one Prepared in an analogous manner to Example 24. MS (M+H)+ 515/517.

Example 203

1-(2-(5-Bromo-4-(5-(3,4-dihydroquinolin-1(2H)-ylsulfonyl)thiophen-2-yl)pyrimidin-2-ylamino)ethyl)imidazolidin-2-one Prepared in an analogous manner to Example 202. MS (M+H)+ 563/565.

Example 204

5,5-Dimethyl-1-(2-(4-(5-(thiophen-2-yl)thiophen-2-yl)pyrimidin-2-ylamino)ethyl)imidazolidine-2,4-dione Prepared in an analogous manner to Example 24. MS (M+H)+ 414.

Example 205

3-(4-(5-(2-Methylpiperidin-1-ylsulfonyl)thiophen-2-yl)pyrimidin-2-ylamino)propanenitrile A mixture of 4-(5-(2-methylpiperidin-1-ylsulfonyl)thiophen-2-yl)-2-(methylsulfonyl)pyrimidine (20 mg) and 1.5 mL of 3-aminopropanenitrile (0.3 M in toluene) was heated at 160° C. for 25 min in a Personal Chemistry microwave reactor. Upon cooling, toluene was removed in vacuo and 1 mL of methyl sulfoxide was added. The product was purified by HPLC to give the product as the yellow trifluoroacetate salt.

MS (M+H)+ 392.

Example 206

3-(4-(5-(Azepan-1-ylsulfonyl)thiophen-2-yl)pyrimidin-2-ylamino)propanenitrile

Prepared in an analogous manner to Example 205. MS (M+H)+ 392.

Example 207

1-(2-(4-(5-(Morpholine-4-carbonyl)thiophen-2-yl)pyrimidin-2-yl-amino)ethyl)imidazolidin-2-one

(i) (E)-Methyl 5-(3-(dimethylamino)acryloyl)thiophene-2-carboxylate

A solution of 5-acetylthiophene-2-carboxylic acid (1 g) in dimethoxy-N,N-dimethylmethanamine (20 mL) was refluxed 6 h and then cooled to rt. The precipitate was filtered and put into 10 mL of acetone. The suspension was stirred for 10 min and the solid was filtered and used for next step. MS (M+H)+ 240.

(ii) 5-(2-(Methylthio)pyrimidin-4-yl)thiophene-2-carboxylic acid

A mixture of (E)-methyl 5-(3-(dimethylamino)acryloyl)thiophene-2-carboxylate (1.2 g, 5.02 mmol) and thiourea (0.38 g, 5.02 mmol) in methoxyethanol (20 mL) was treated slowly with 1.0 M potassium tert-butoxide in THF (5 mL, 5.02 mmol) at rt. The resulting mixture refluxed for 6 h. After cooling to rt, iodomethane (1.4 g, 10.04 mmol) was added and the mixture was stirred at rt for 15 h. The solvent was removed under vacuum and water (150 mL) was added to the residue. The mixture was extracted with ethyl acetate (3×100 mL). The combined organic layer was washed with brine (100 mL), dried over anhydrous sodium sulfate and filtered. The solvent was evaporated in vacuo and the solid was treated with methanol (10 mL) and filtered. The solid was suspended in 2.5 M sodium hydroxide (100 mL), stirred at rt for 24 h and extracted with ethyl acetate (50 mL). The aqueous layer was acidified with hydrochloric acid (6 N) and acetic acid to pH 5 and then extracted with ethyl acetate (3×70 mL). The combined organic layer was washed with brine (100 mL), dried over anhydrous sodium sulfate and filtered. The solvent was removed in vacuo and the solid treated with methanol (10 mL) and filtered to give the title compound (0.58 g, 48%). MS (M+H)+ 253.

(iii) (5-(2-(Methylthio)pyrimidin-4-yl)thiophen-2-yl)(morpholino)methanone

A mixture of 5-(2-(methylthio)pyrimidin-4-yl)thiophene-2-carboxylic acid (200 mg, 0.79 mmol), morpholine (69 mg, 0.79 mmol), EDCI (182 mg, 0.95 mmol), HOAt (21 mg, 0.16 mmol) and triethylamine (159 mg, 1.58 mmol) in dichloromethane (20 mL) was stirred at rt for 24 h. Water (50 mL) was added and the mixture was extracted with dichloromethane (3×50 mL). The combined organic layers were washed with brine (100 mL), dried over anhydrous sodium sulfate and filtered. The solvent was removed in vacuo and the residue purified by flash chromatography eluting with ethyl acetate/hexane (1:1) to give the intermediate (5-(2-(methylthio)pyrimidin-4-yl)thiophen-2-yl)(morpholino)methanone as a white solid (200 mg, 78%). MS (M+H)$^+$ 322.

(iv) (5-(2-(Methylsulfonyl)pyrimidin-4-yl)thiophen-2-yl)(morpholino)methanone A mixture of (5-(2-(methylthio)pyrimidin-4-yl)thiophen-2-yl)(morpholino)methanone (200 mg) and oxone (2 g) in 60 mL of acetone-water (1:1) was stirred at rt for 24 h. The mixture was concentrated in vacuo to remove the acetone. The white precipitate was filtered, washed with water and dried to give the title compound (183 mg, 83%). MS (M+H)$^+$ 354.

(v) 1-(2-(4-(5-(Morpholine-4-carbonyl)thiophen-2-yl)pyrimidin-2-ylamino)ethyl)-imidazolidin-2-one A mixture of (5-(2-(methylsulfonyl)pyrimidin-4-yl)thiophen-2-yl)(morpholino)methanone (100 mg, 0.26 mmol), 1-(2-aminoethyl)imidazolidin-2-one (36 mg, 0.28 mmol) and triethylamine (56 mg, 0.52 mmol) in toluene (3 mL) was refluxed for 6 h. After cooling to rt, the solvent was evaporated in vacuo and then methanol (5 mL) was added. After stirring for 15 min the solid was filtered and dried to give title compound as a light yellow solid. MS (M+H)$^+$ 403.

Example 208

1-(2-(4-(5-(Piperidine-1-carbonyl)thiophen-2-yl)pyrimidin-2-ylamino)ethyl)imidazolidin-2-one Prepared in an analogous manner to Example 207. MS (M+H)$^+$ 401.

Example 209

1-(2-(4-(3-Vinylbenzo[b]thiophen-2-yl)pyrimidin-2-ylamino)ethyl)imidazolidin-2-one A mixture of 1-(2-(4-(3-bromobenzo[b]thiophen-2-yl)pyrimidin-2-ylamino)ethyl)imidazolidin-2-one (20 mg, 0.048 mmol), potassium vinyltrifluoroborate (8 mg, 0.057 mmol), tetrakis(triphenylphosphine)palladium (5 mg, 0.0048 mmol) and 0.05 mL of sodium carbonate (2 M. 0.096 mmol) in isopropanol (1.5 mL) was heated at 150° C. for 35 min in a Personal Chemistry microwave reactor. Upon cooling, the mixture was filtered through Celite and washed with methanol/dichloromethane (1:1). After evaporating solvent in vacuo the product was purified by HPLC to afford the title compound as the yellow trifluoroacetate salt. MS (M+H)$^+$ 366.

Example 210-212 were prepared in an analogous manner to Example 209.

Example 210

1-(2-(4-(3-Methylbenzo[b]thiophen-2-yl)pyrimidin-2-ylamino)ethyl)imidazolidin-2-one

MS (M+H)$^+$ 354.

Example 211

1-(2-(4-(5-Vinylthiophen-2-yl)pyrimidin-2-ylamino)ethyl)imidazolidin-2-one

MS (M+H)$^+$ 316.

Example 212

1-(2-(4-(3-Phenylbenzo[b]thiophen-2-yl)pyrimidin-2-ylamino)ethyl)imidazolidin-2-one

MS (M+H)$^+$ 416.

Example 213

5,5-Dimethyl-1-(2-(4-(5-tosylthiophen-2-yl)pyrimidin-2-ylamino)ethyl)imidazolidine-2,4-dione

(i) 2-Tosylthiophene

A mixture of p-toluenesulfonyl chloride (3 g, 15.7 mmol) and zinc chloride (3 g, 21.3 mmol) in acetonitrile (30 mL) was heated to reflux and thiophene (2.4 g, 28.5 mmol) was added dropwise. After refluxing for 4 h the mixture was cooled to rt and filtered through Celite. The filtrate was concentrated in vacuo and then 100 mL of sodium hydroxide (2 N) was added. The mixture was extracted with ethyl acetate (3×60 mL) and the combined organic layers were washed with hydrochloric acid (10%, 50 mL) and brine (100 mL), dried over anhydrous magnesium sulfate and filtered. The solvent was evaporated in vacuo and the product was purified by flash chromatography eluting with dichloromethane/hexane (2:3) to give the title compound (0.54 g, 15 mmol).

(ii) 2-Chloro-4-(5-tosylthiophen-2-yl)pyrimidine n-Butyllithium in hexanes (0.92 mL, 2.5 M, 2.30 mmol) was added dropwise to a solution of 2-tosylthiophene (0.5 g, 2.09 mmol) in anhydrous tetrahydrofuran (30 mL) at −78° C. The resulting mixture was stirred at −78° C. for 1 h and a solution of 2-chloropyrimidine (0.26 g, 2.30 mmol) in 3 mL of tetrahydrofuran was added slowly. The mixture was stirred at −78° C. for 1 h and then at −40° C. for 2 h. The reaction was quenched with a solution (0.22 mL) of acetic acid and methanol (1:1) at −40° C. and a solution of 2,3-dichloro-5,6-dicyano-1,4-benzoquinone (0.57 g, 2.51 mmol) was added. After complete addition the reaction was stirred for 1 h, and then warmed to rt and stirred for an additional 15 h. 20 mL of aqueous sodium hydroxide (2 M) was added and the mixture was extracted with ethyl acetate (3×50 mL). The combined organic layer was washed with brine (80 mL), dried over anhydrous sodium sulfate and filtered. The solvent was evaporated in vacuo and the product was purified by flash chromatography eluting with ethyl acetate/hexane (1:3) to afford the title compound as a white solid (0.36 g, 49%).

MS (M+H)$^+$ 351/353.

(iii) 5,5-Dimethyl-1-(2-(4-(5-tosylthiophen-2-yl)pyrimidin-2-ylamino)ethyl)imidazol-idine-2,4-dione A mixture of 2-chloro-4-(5-tosylthiophen-2-yl)pyrimidine (100 mg, 0.23 mmol), 1-(2-aminoethyl)-5,5-dimethylimidazolidine-2,4-dione (33 mg, 0.26 mmol) and triethylamine (28 mg, 0.27 mmol) in toluene (3 mL) was heated at 160° C. for 35 min in a Personal Chemistry microwave reactor. Upon cooling to rt the precipitate was filtered and washed with diethyl ether. The solid was put into 2 mL of methanol and the suspension was stirred for about 15 min and filtered to afford the title compound as pale yellow crystals (56 mg, 50%). MS (M+H)$^+$ 486.

Examples 214-228 were prepared in an analogous manner to Example 213.

Example 214

1-(2-(4-(5-Tosylthiophen-2-yl)pyrimidin-2-ylamino) ethyl)imidazolidin-2-one

MS (M+H)$^+$ 444.

Example 215

5,5-Dimethyl-1-(2-(4-(5-(phenylsulfonyl)thiophen-2-yl)pyrimidin-2-ylamino)ethyl)imidazolidine-2,4-dione

MS (M+H)$^+$ 472.

Example 216

1-(2-(5-Bromo-4-(5-(phenylsulfonyl)thiophen-2-yl) pyrimidin-2-ylamino)ethyl)-5,5-dimethylimidazolidine-2,4-dione

MS (M+H)$^+$ 450/452.

Example 217

1-(2-(4-(5-(4-Fluorophenylsulfonyl)thiophen-2-yl) pyrimidin-2-ylamino)ethyl)-5,5-dimethylimidazolidine-2,4-dione

MS (M+H)$^+$ 490.

Example 218

1-(2-(4-(5-(4-Methoxyphenylsulfonyl)thiophen-2-yl) pyrimidin-2-ylamino)ethyl)-5,5-dimethylimidazolidine-2,4-dione

MS (M+H)$^+$ 502.

Example 219

1-(2-(5-Bromo-4-(5-(4-fluorophenylsulfonyl) thiophen-2-yl)pyrimidin-2-ylamino)ethyl)-5,5-dimethylimidazolidine-2,4-dione

MS (M+H)$^+$ 568/570.

Example 220

1-(2-(5-Bromo-4-(5-(4-chlorophenylsulfonyl) thiophen-2-yl)pyrimidin-2-ylamino)ethyl)-5,5-dimethylimidazolidine-2,4-dione

MS (M+H)$^+$ 584/586.

Example 221

1-(2-(5-Bromo-4-(5-(3-fluorophenylsulfonyl) thiophen-2-yl)pyrimidin-2-ylamino)ethyl)-5,5-dimethylimidazolidine-2,4-dione

MS (M+H)$^+$ 568/570.

Example 222

1-(2-(5-Bromo-4-(5-(phenylsulfonyl)thiophen-2-yl) pyrimidin-2-ylamino)ethyl)imidazolidin-2-one

MS (M+H)$^+$ 508/510.

Example 223

1-(2-(5-Bromo-4-(5-(4-fluorophenylsulfonyl) thiophen-2-yl)pyrimidin-2-ylamino)ethyl)imidazolidin-2-one

MS (M+H)$^+$ 526/528.

Example 224

1-(2-(5-Bromo-4-(5-(pyridin-2-ylsulfonyl)thiophen-2-yl)pyrimidin-2-ylamino)ethyl)-5,5-dimethylimidazolidine-2,4-dione

MS (M+H)$^+$ 551/553.

Example 225

1-(2-(4-(5-(Phenylsulfonyl)thiophen-2-yl)pyrimidin-2-ylamino)ethyl)imidazolidin-2-one

MS (M+H)$^+$ 430.

Example 226

1-(2-(4-(5-(Naphthalen-1-ylsulfonyl)thiophen-2-yl) pyrimidin-2-ylamino)ethyl)imidazolidin-2-one

MS (M+H)$^+$ 480.

Example 227

1-(2-(4-(5-(Naphthalen-2-ylsulfonyl)thiophen-2-yl) pyrimidin-2-ylamino)ethyl)imidazolidin-2-one

MS (M+H)$^+$ 480.

Example 228

1-(2-(4-(5-(4-Fluorophenylsulfonyl)thiophen-2-yl) pyrimidin-2-ylamino)ethyl)imidazolidin-2-one

MS (M+H)$^+$ 448.

Example 229

5-Methyl-3-(2-(4-(5-(thiophen-2-yl)thiophen-2-yl) pyrimidin-2-ylamino)ethyl)imidazolidine-2,4-dione Ethyl 2-isocyanatopropanoate (104 mg, 0.73 mmol) was added to a suspension of N-(2-aminoethyl)-4-(5-(thiophen-2-yl)thiophen-2-yl)pyrimidin-2-amine (200 mg, 0.66 mmol) in dichloromethane (10 mL) at rt and stirred for 8 h. The solid was filtered off and added to 15 mL of hydrochloric acid (5 M). After refluxing for 6 h, the mixture was cooled to rt and the precipitate was filtered off, washed with water and then dissolved in 10 mL of methanol. 50 mg of potassium carbonate was added and the mixture was stirred for 10 min. 20 mL of dichloromethane was added and the mixture was filtered through Celite. The filtrate was concentrated to give the title compound (180 mg, 68%). MS (M+H)+ 400.

Example 230

4-Methyl-1-(2-(4-(5-(thiophen-2-yl)thiophen-2-yl)pyrimidin-2-ylamino)ethyl)-1H-imidazol-2(3H)-one Lithium aluminum hydride (0.48 mL, 1 M in THF) was added to a suspension of 5-methyl-3-(2-(4-(5-(thiophen-2-yl)thiophen-2-yl)pyrimidin-2-ylamino)ethyl)imidazolidine-2,4-dione (176 mg, 0.44 mmol) in tetrahydrofuran (15 mL) at 0° C. After the stirring at rt for 5 h, water (5 mL) was added slowly followed by sodium hydroxide (1 M, 10 mL). The mixture was extracted with ethyl acetate (3×50 mL). The combined organic layers were washed with brine (50 mL), dried over anhydrous sodium sulfate and filtered. The solvent was removed in vacuo and the solid was purified by flash chromatography eluting with methanol/dichloromethane (1:20). After evaporating solvent, the solid and a catalytic amount of p-toluenesulfonic acid monohydrate were treated with 10 mL of toluene and refluxed for 5 h. The solvent was removed in vacuo and the product purified by HPLC to afford the title compound as the yellow trifluoroacetate salt. MS (M+H)+ 384.

Example 231

3-(2-(4-(5-(thiophen-2-yl)thiophen-2-yl)pyrimidin-2-ylamino)ethyl)imidazolidine-2,4-dione Prepared in an analogous manner to Example 229. MS (M+H)+ 386.

Example 232

1-(2-(4-(5-(thiophen-2-yl)thiophen-2-yl)pyrimidin-2-ylamino)ethyl)-1H-imidazol-2(3H)-one Prepared in an analogous manner to Example 230. MS (M+H)+ 370.

Example 233

5-Methyl-1-(2-(4-(5-(thiophen-2-yl)thiophen-2-yl)pyrimidin-2-ylamino)ethyl)imidazolidine-2,4-dione (i) Methyl 2-(2-(4-(5-(thiophen-2-yl)thiophen-2-yl)pyrimidin-2-ylamino)ethylamino)propanoate Methyl 2-bromopropanoate (182 mg, 1.09 mmol) was added to a mixture of N-(2-amino-ethyl)-4-(5-(thiophen-2-yl)thiophen-2-yl)pyrimidin-2-amine (300 mg, 0.99 mmol) and N,N-diisopropylethylamine (153 mg, 1.19 mmol) in 1-methylpyrrolidine (8 mL) at rt. After stirring at rt for 24 h, water (50 mL) was added and the mixture extracted with ethyl acetate (3×50 mL). The combined organic layers were washed with brine (3×50 mL), dried over anhydrous sodium sulfate, filtered and concentrated to give the title compound. MS (M+H)+ 389.

(ii) 5-Methyl-1-(2-(4-(5-(thiophen-2-yl)thiophen-2-yl)pyrimidin-2-ylamino)ethyl)imidazolidine-2,4-dione 100 mg of the intermediate from Step 1 was dissolved in 1,2-dichloroethane (8 mL) and the solution was treated with trimethylsilyl isocyanate (60 mg) at rt. The mixture was refluxed for 20 h and then cooled to rt. The solvent was evaporated in vacuo and the product was purified by flash chromatography eluting with methanol(NH₃)/dichloromethane (1:20) to give a solid. The solid was suspended in toluene (3 mL) and the suspension was heated at 160° C. for 35 min in a Personal Chemistry microwave reactor. After cooling to rt the precipitate was filtered and washed with methanol (2 mL) to give the title compound with a slight yellow color (84 mg, 68%). MS (M+H)+ 400.

Example 234

1-(2-(4-(5-(Thiophen-2-yl)thiophen-2-yl)pyrimidin-2-ylamino)ethyl)imidazolidine-2,4-dione Prepared in an analogous manner to Example 233. MS (M+H)+ 386.

Example 235

5,5-Dimethyl-1-(2-(4-(5-(thiophen-2-yl)thiophen-2-yl)pyrimidin-2-ylamino)ethyl)imidazolidin-2-one Lithium aluminum hydride (0.88 mL, 1 M in THF) was added to a suspension of 5,5-dimethyl-1-(2-(4-(5-(thiophen-2-yl)thiophen-2-yl)pyrimidin-2-ylamino)ethyl)imidazolidine-2,4-dione (120 mg) in tetrahydrofuran (15 mL) at 0° C. After stirring at rt for 30 h, water (5 mL) was added followed by sodium hydroxide (1 M, 10 mL). The mixture was extracted with ethyl acetate (3×50 mL). The combined organic layers were washed with brine (50 mL), dried over anhydrous sodium sulfate and filtered. The solvent was evaporated in vacuo and the product purified by HPLC to give the title compound as the yellow trifluoroacetate salt (13 mg, 10%). MS (M+H)+ 400.

Example 236

1-(2-(5-(3-(1H-Tetrazol-5-yl)phenyl)-4-(5-(4-azidophenyl-sulfonyl)thiophen-2-yl)pyrimidin-2-ylamino)ethyl)-5,5-dimethylimidazolidine-2,4-dione and 1-(2-(5-(3-(1H-tetrazol-5-yl)phenyl)-4-(5-(4-aminophenylsulfonyl)thiophen-2-yl)pyrimidin-2-ylamino)ethyl)-5,5-dimethylimidazolidine-2,4-dione A mixture of 3-(2-(2-(5,5-dimethyl-2,4-dioxoimidazolidin-1-yl)ethylamino)-4-(5-(4-fluorophenylsulfonyl)thiophen-2-yl)pyrimidin-5-yl)benzonitrile (50 mg, 0.10 mmol), sodium azide (33 mg, 0.50 mmol) and ammonium chloride (27 mL, 0.50 mmol) in N,N-dimethylformamide (3 mL) was heated at 100° C. for 8 h. After cooling to rt water (25 mL) was added and the mixture was extracted with ethyl acetate (3×25 mL). The combined organic layers were washed with brine (3×50 mL), dried over anhydrous sodium sulfate and filtered. After evaporating solvent in vacuo, the products were purified by HPLC to give two compounds as yellow trifluoroacetate salts. Minor compound: 1-(2-(5-(3-(1H-tetrazol-5-yl)phenyl)-4-(5-(4-aminophenylsulfonyl)thiophen-2-yl)pyrimidin-2-ylamino)ethyl)-5,5-dimethylimidazolidine-2,4-dione. MS (M+H)+ 631; Major compound: 1-(2-(5-(3-(1H-tetrazol-5-yl)phenyl)-4-(5-(4-azidophenylsulfonyl)thiophen-2-yl)pyrimidin-2-ylamino)ethyl)-5,5-dimethylimidazolidine-2,4-dione. MS (M+H)+ 657.

Example 237

1-(2-(5-(3-(1H-Tetrazol-5-yl)phenyl)-4-(5-(4-fluorophenylsulfonyl)thiophen-2-yl)pyrimidin-2-ylamino)ethyl)-5,5-dimethylimidazolidine-2,4-dione A mixture of 3-(2-(2-(5,5-dimethyl-2,4-dioxoimidazolidin-1-yl)ethylamino)-4-(5-(4-fluorophenylsulfonyl)thiophen-2-yl)pyrimidin-5-yl)benzonitrile (110 mg, 0.19 mmol), trimethylsilyl azide (178 mg, 1.52 mmol) and dibutyltin oxide (47 mg, 0.19 mmol) in N,N-dimethylformamide (5 mL) was heated at 120° C. for 24 h. After cooling to rt, 10 mL of aqueous hydrochloric acid (10%) was added and the resulting mixture was stirred for 30 min. Saturated sodium bicarbonate was added to adjust to pH 5 and the mixture was extracted with ethyl acetate (3×50 mL). The combined organic layers were washed with brine (3×50 mL), dried over anhydrous sodium sulfate and filtered. The solvent was removed in vacuo and the product purified by flash chromatography eluting with methanol (containing 10% acetic acid)/dichloromethane (1:20). MS (M+H)$^+$ 634.

Example 238

1-(2-(5-(3-(1H-Tetrazol-5-yl)phenyl)-4-(benzo[b]thiophen-2-yl)pyrimidin-2-ylamino)ethyl)-5,5-dimethylimidazolidine-2,4-dione Prepared in an analogous manner to Example 237. MS (M+H)$^+$ 526.

Example 239

5-(2-(2-(5,5-Dimethyl-2,4-dioxoimidazolidin-1-yl)ethylamino)pyrimidin-4-yl)-N-methyl-N-(2-(pyrrolidin-1-yl)ethyl)thiophene-2-sulfonamide A mixture of N-(2-chloroethyl)-5-(2-(2-(5,5-dimethyl-2,4-dioxoimidazolidin-1-yl)ethylamino)pyrimidin-4-yl)-N-methylthiophene-2-sulfonamide (200 mg, 0.41 mmol), pyrrolidine (59 mg, 0.82 mmol) and a catalytic amount of sodium iodide in N-methyl-pyrrolidine (5 mL) was heated at 90° C. overnight. After cooling to rt, 50 mL of brine was added and the mixture was extracted with ethyl acetate (3×50 mL). The combined organic layers were washed with brine (3×80 mL), dried over anhydrous sodium sulfate and filtered. The solvent was removed in vacuo and the product purified by flash chromatography eluting with methanol (1 M, ammonia)/dichloromethane (1:20) to afford the title compound as a slightly yellow solid (98 mg, 46%). MS (M+H)$^+$ 522.

Example 240

1-(2-(4-(5-(4-fluorobenzyl)-4-(2-(tert-butyldimethylsilyloxy)ethyl)thiophen-2-yl)-5-bromopyrimidin-2-ylamino)ethyl)-5,5-dimethylimidazolidine-2,4-dione

(i) 2-(2-Bromothiophen-3-yl)ethanol

N-bromosuccinimide (33.8 g, 0.19 mmol) followed by perchloric acid (0.19 g, 0.002 mol) were added to a solution of 2-(thiophen-3-yl)ethanol)24.3 g, 0.19 mol) in carbon tetrachloride (250 mL) in a flask wrapped with aluminum foil at rt. The mixture was stirred in the dark at rt overnight and then potassium carbonate (40 g) was added. After stirring at rt for 1 h the mixture was filtered through Celite and washed with diethyl ether. The solvent was removed in vacuo and the product purified by flash chromatography eluting with ethyl acetate/hexane ((1:3) to give the title compound as an oil (25 g, 64%). MS (M+H)$^+$ 207/209.

(ii) (2-(2-Bromothiophen-3-yl)ethoxy)(tert-butyl)dimethylsilane

A mixture of 2-(2-bromothiophen-3-yl)ethanol (4.5 g, 21.8 mmol), tert-butylchloro-dimethylsilane (3.16 g, 24.0 mmol) and imidazole (1.63 g, 24.0 mmol) in N,N-dimethylformamide (40 mL) was stirred at rt for 24 h. 100 mL of water was added and the mixture was extracted with diethyl ether (3×00 mL). The combined organic layers were washed with brine (3×100 mL), dried over anhydrous sodium sulfate and filtered. The solvent was removed in vacuo and the product purified by flash chromatography eluting with ethyl acetate/hexane (1:20) to give the title compound as an oil (5.9 g, 84%).

(iii) (3-(2-(tert-Butyldimethylsilyloxy)ethyl)thiophen-2-yl)(4-fluorophenyl)methanol n-Butyllithium in hexanes (12.7 mL, 1.6 M, 20.3 mmol) was added dropwise to a solution of (2-(2-bromothiophen-3-yl)ethoxy)(tert-butyl)dimethylsilane (5.9 g, 18.4 mmol) in anhydrous THF (15 mL) at −78° C. The resulting mixture was stirred at −78° C. for 30 min and 4-fluorobenzaldehyde (2.5 g, 20.3 mmol) in THF was added slowly. The mixture was stirred at −78° C. for 2 h and then warmed up to rt. After cooling again to 0° C. 50 mL of aqueous saturated ammonium chloride was added and the mixture was extracted with ethyl acetate (3×80 mL). The combined organic layers were washed with brine (100 mL), dried over anhydrous sodium sulfate and filtered. The solvent was evaporated in vacuo and the product was purified by flash chromatography eluting with ethyl acetate/hexane (1:3) to afford the title compound as a solid (3.8 g, 59%).

(iv) 2-(2-(4-Fluorobenzyl)thiophen-3-yl)ethanol

Chlorotrimethylsilane (5.56 g, 51.2 mmol) was added slowly to a solution of sodium iodide (7.7 g, 51.2 mmol) in acetonitrile (80 mL) at rt. After stirring for 15 min the mixture was cooled to 0° C. and a solution of (3-(2-(tert-butyldimethylsilyloxy)ethyl)thiophen-2-yl)(4-fluorophenyl)methanol (3.75 g, 10.2 mmol) in acetonitrile (10 mL) was added dropwise. The resulting mixture was stirred at 0° C. for 1 h and then at rt for 2 h. After cooling down to 0° C., 2 N sodium hydroxide (30 mL) was added slowly and the mixture stirred for 30 min. 100 mL of water was added and the mixture was extracted with ethyl acetate (3×80 mL). The combined organic layers were washed with brine (100 mL), dried over anhydrous sodium sulfate and filtered. The solvent was evaporated in vacuo and the product purified by flash chromatography eluting with ethyl acetate/hexane (1:20) to afford the title compound as a solid (1.8 g, 75%). MS (M+H)$^+$ 237.

(v) (2-(2-(4-Fluorobenzyl)thiophen-3-yl)ethoxy)(tert-butyl)dimethylsilane

Prepared in an analogous manner to Example 240, Step 2.

(vi) 4-(5-(4-Fluorobenzyl)-4-(2-(tert-butyldimethylsilyloxy)ethyl)thiophen-2-yl)-5-bromo-2-chloropyrimidine Prepared in an analogous manner to Example 20, MS (M+H)$^+$ 541/543.

(vii) 1-(2-(4-(5-(4-Fluorobenzyl)-4-(2-(tert-butyldimethylsilyloxy)ethyl)thiophen-2-yl)-5-bromopyrimidin-2-ylamino)ethyl)-5,5-dimethylimidazolidine-2,4-dione:

Prepared in an analogous manner to Example 24. MS (M+H)$^+$ 676/678

Example 241

1-(2-(4-(5-(4-Fluorobenzyl)-4-(2-hydroxyethyl)thiophen-2-yl)-5-bromopyrimidin-2-ylamino)ethyl)-5,5-dimethylimidazolidine-2,4-dione Tetrabutylammonium fluoride (5 mL, 1M in tetrahydrofuran, 5.00 mmol) was added slowly to a solution of 1-(2-(4-(5-(4-fluorobenzyl)-4-(2-(tert-butyldimethylsilyloxy)ethyl)thiophen-2-yl)-5-bromopyrimidin-2-ylamino)ethyl)-5,5-dimethylimidazolidine-2,4-dione (1.8 g, 2.66 mmol) in tetrahydrofuran (40 mL) at rt. After stirring at rt for 4 h, 100 mL of water was added. The mixture was extracted with ethyl acetate (3×100 mL). The combined organic layers were washed with brine (100 mL), dried over anhydrous sodium sulfate and filtered. The solvent was removed in vacuo and the product purified by flash chromatography eluting with methanol/dichloromethane (1:30) to give the title compound as a slightly yellow solid (1.2 g, 80%). MS (M+H)$^+$ 562/564.

Example 242

1-(2-(4-(5-(4-Fluorobenzyl)-4-(2-((S)-2-(hydroxymethyl)pyrrolidin-1-yl)ethyl)thiophen-2-yl)-5-bromopyrimidin-2-ylamino)ethyl)-5,5-dimethylimidazolidine-2,4-dione Methanesulfonyl chloride (82 mg, 0.72 mmol) was added to a mixture of 1-(2-(4-(5-(4-fluorobenzyl)-4-(2-hydroxyethyl)thiophen-2-yl)-5-bromopyrimidin-2-ylamino)ethyl)-5,5-dimethylimidazolidine-2,4-dione (200 mg, 0.36 mmol) and diisopropylethylamine (93 mg, 0.72 mmol) in dichloromethane (10 mL) at 0° C. After stirring at 0° C. for 5 h, the solvent was removed in vacuo and 5 mL of N-methylpyrrolidine, a catalytic amount of sodium iodide and (S)-pyrrolidin-2-ylmethanol (0.3 g, 2.97 mmol) were added. The mixture was heated at 100° C. for 15 h and then cooled to rt. 50 mL of water was added and the mixture extracted with ethyl acetate (3×50 mL). The combined organic layers were washed with brine (3×50 mL), dried over anhydrous sodium sulfate and filtered. The solvent was removed in vacuo and the product purified by flash chromatography eluting with methanol (1M, ammonia)/dichloromethane (1:20) to give the title compound as a slightly yellow solid (105 mg, 46%). MS (M+H)$^+$ 645/647.

Examples 243-247 were prepared in an analogous manner to Example 242.

Example 243

1-(2-(4-(5-(4-Fluorobenzyl)-4-(2-(4-methylpiperazin-1-yl)ethyl)thiophen-2-yl)-5-bromopyrimidin-2-ylamino)ethyl)-5,5-dimethylimidazolidine-2,4-dione

MS (M+H)$^+$ 644/646.

Example 244

1-(2-(4-(5-(4-Fluorobenzyl)-4-(2-(isopropylamino)ethyl)thiophen-2-yl)-5-bromopyrimidin-2-ylamino)ethyl)-5,5-dimethylimidazolidine-2,4-dione

MS (M+H)$^+$ 603/605.

Example 245

1-(2-(4-(5-(4-Fluorobenzyl)-4-(2-(piperazin-1-yl)ethyl)thiophen-2-yl)-5-bromopyrimidin-2-ylamino)ethyl)-5,5-dimethylimidazolidine-2,4-dione

MS (M+H)$^+$ 630/632.

Example 246

1-(2-(4-(5-(4-Fluorobenzyl)-4-(2-(2-((isopropylamino)methyl)pyrrolidin-1-yl)ethyl)thiophen-2-yl)-5-bromopyrimidin-2-ylamino)ethyl)-5,5-dimethylimidazolidine-2,4-dione

MS (M+H)$^+$ 686/688.

Example 247

1-(2-(4-(5-(4-Fluorobenzyl)-4-(2-(piperidin-1-yl)ethyl)thiophen-2-yl)-5-bromopyrimidin-2-ylamino)ethyl)-5,5-dimethylimidazolidine-2,4-dione

MS (M+H)$^+$ 629/631.

Example 248

1-(2-(4-(5-(4-Fluorobenzyl)-4-(2-morpholinoethyl)thiophen-2-yl)-5-chloropyrimidin-2-ylamino)ethyl)-5,5-dimethylimidazolidine-2,4-dione and 1-(2-(4-(5-(4-fluorobenzyl)-4-vinylthiophen-2-yl)-5-chloropyrimidin-2-ylamino)ethyl)-5,5-dimethylimidazolidine-2,4-dione (i) 2-(2-(4-Fluorobenzyl)-5-(5-chloro-2-(methylthio)pyrimidin-4-yl)thiophen-3-yl)ethanol n-Butyllithium (5.4 mL, 1.6 M in hexanes, 8.63 mmol) was added dropwise to a solution of 2-(2-(4-fluorobenzyl)thiophen-3-yl)ethanol (0.97 g, 4.11 mmol) in anhydrous tetrahydrofuran (15 mL) at −78° C. The resulting mixture was stirred at −78° C. for 1 h and then a solution of 5-chloro-2-(methylthio)pyrimidine (0.79 g, 4.93 mmol) in 1 mL of tetrahydrofuran was added slowly. The mixture was stirred at −78° C. for 1 h and then at −40° C. for 2 h. The reaction was quenched with a solution (1.1 mL) of acetic acid and methanol (1:1) at −40° C. and then a solution of 2,3-dichloro-5,6-dicyano-1,4-benzoquinone (0.1.1 g, 4.93 mmol) in tetrahydrofuran (1 mL) was added. After complete addition the reaction was stirred at −40° C. for 1 h, then warmed to rt. 10 mL of aqueous sodium hydroxide (2 M) and 50 mL of water were added and the mixture was extracted with ethyl acetate (3×50 mL). The combined organic layers were washed with brine (80 mL), dried over anhydrous sodium sulfate and filtered. The solvent was evaporated in vacuo and the product purified by flash chromatography eluting with ethyl acetate/hexane (1:4) to afford the title compound (0.45 g, 28%). MS (M+H)+ 395/397.

(ii) 4-(5-(4-Fluorobenzyl)-4-(2-morpholinoethyl) thiophen-2-yl)-5-chloro-2-(methylthio)pyrimidine Methanesulfonyl chloride (59 mg, 0.52 mmol) was added to a mixture of 2-(2-(4-fluoro-benzyl)-5-(5-chloro-2-(methylthio)pyrimidin-4-yl)thiophen-3-yl)ethanol (170 mg, 0.43 mmol) and diisopropylethylamine (72 mg, 0.55 mmol) in dichloromethane (8 mL) at 0° C. After stirring at 0° C. for 1 h, the solvent was removed in vacuo. Acetonitrile (5 mL) and morpholine (112 mg, 1.29 mmol) were added to the residue and the mixture was heated to 70° C. overnight. After cooling to rt solvent was evaporated in vacuo and the product was purified by flash chromatography eluting with methanol (1 M ammonia)/dichloromethane (1:20) to afford the title compound (148 mg, 74%). MS (M+H)+ 464/466.

(iii) 1-(2-(4-(5-(4-Fluorobenzyl)-4-(2-morpholinoethyl)thiophen-2-yl)-5-chloropyrimidin-2-ylamino) ethyl)-5,5-dimethylimidazolidine-2,4-dione and 1-(2-(4-(5-(4-fluorobenzyl)-4-vinylthiophen-2-yl)-5-chloropyrimidin-2-ylamino)ethyl)-5,5-dimethyl-imidazolidine-2,4-dione A mixture of 4-(5-(4-fluorobenzyl)-4-(2-morpholinoethyl)thiophen-2-yl)-5-chloro-2-(methylthio)pyrimidine (300 mg) and oxone (2 g) in 100 mL of acetone/water (1:1) was stirred at rt for 24 h. The mixture was concentrated in vacuo to remove the acetone and extracted with ethyl acetate (3×50 mL). The combined organic layers were washed with brine (50 mL), dried over anhydrous sodium sulfate and filtered. After evaporating the solvent in vacuo the solid was put into 4 mL of toluene and treated with 1-(2-aminoethyl)-5,5-dimethylimidazolidine-2,4-dione (140 mg) and triethylamine (7 mg). The resulting mixture was heated at 150° C. for 35 min in a Personal Chemistry microwave reactor. After removal of solvent, the solid was purified by flash chromatography eluting with methanol (1 M ammonia)/dichloromethane (1:20) to give two compounds. Major product: 1-(2-(4-(5-(4-fluorobenzyl)-4-vinylthiophen-2-yl)-5-chloropyrimidin-2-ylamino)ethyl)-5,5-dimethylimidazolidine-2,4-dione (84 mg, 26%), MS (M+H)+ 500/502; Minor product: 1-(2-(4-(5-(4-fluorobenzyl)-4-(2-morpholinoethyl)thiophen-2-yl)-5-chloropyrimidin-2-ylamino)ethyl)-5,5-dimethylimidazolidine-2,4-dione (42 mg, 11%). MS (M+H)+ 587/589.

Example 249

1-{2-[4-(5-Iodothiophen-2-yl)pyrimidin-2-ylamino] ethyl}-5,5-dimethylimidazolidine-2,4-dione (i) 2-Chloro-4-(5-iodothiophen-2-yl)pyrimidine nBuLi (16 mL, 1.6 M solution in hexane, 25 mmol) was added to a stirred solution of 2,5-diiodothiophene (7.0 g, 21 mmol) in THF (80 mL) at −50° C. The solution was stirred for 10 min at −50° C. before 2.9 g (25 mmol) of 2-chloropyrimidine was added. The reaction solution was stirred for 1 h at −20° C., then cooled to −50° C. and quenched by addition of 2 mL of AcOH in 10 mL of MeOH. Solid 2,3-dichloro-5,6-dicyano-1,4-benzoquinone (10.4 g, 46 mmol) was added and the reaction solution was warmed to 0° C. and stirred for 1 h. The reaction mixture was then poured into 100 mL of a 0.5 M solution of sodium ascorbate, diluted with 250 mL of 1 M aqueous Na2CO3 and the crude product removed by filtration and washed repeatedly with water. The residue was azeotroped with toluene to give the product. MS (M+H)+ 323.

(ii) 1-{2-[4-(5-Iodothiophen-2-yl)pyrimidin-2-ylamino]ethyl}-5,5-dimethylimidazolidine-2,4-dione A solution of 205 mg (0.64 mmol) of 2-chloro-4-(5-iodothiophen-2-yl)pyrimidine, 186 mg (1.1 mmol) of 1-(2-aminoethyl)-5,5-dimethylimidazolidine-2,4-dione and 0.15 mL (1.1 mmol) of triethylamine in 5 mL of iPrOH was heated in a microwave to 180° C. for 10 min then concentrated in vacuo. The crude solid product was purified by flash chromatography eluting with a linear gradient of 40% EtOAc in hexane to 100% EtOAc to deliver the title compound. MS (M+H)+ 458.

Example 250

1-(2-{4-[5-(Trimethylsilyl)thiophen-2-yl]pyrimidin-2-ylamino}ethyl)-5,5-dimethylimidazolidine-2,4-dione (i) 2-Chloro-4-[5-(trimethylsilyl)thiophen-2-yl]pyrimidine nBuLi (1.9 mL, 1.6 M solution in hexane, 3.0 mmol) was added to a stirred solution of 0.50 mL (3.0 mmol) of 2-(trimethylsilyl)thiophene in 7 mL of THF at −78° C. The solution was stirred for 30 min at −78° C., then warmed to 0° C. and stirred 30 min, before 6.1 mL (3.0 mmol) of a 0.5 M solution of ZnCl2 in THF was added. The reaction solution was stirred for 30 min at 0° C., then transferred via syringe to a microwave vessel containing 315 mg (2.8 mmol) of 2,4-dichloropyrimidine and 158 mg (0.14 mmol) of tetrakis(triphenylphosphine)palladium(0) in 2 mL of THF. The vessel was sealed and heated in a microwave for 10 min at 160° C., then cooled to rt, diluted with 100 mL of Et2O, dried over MgSO4, filtered, concentrated in vacuo, and purified by flash chromatography eluting with a linear gradient of 20% EtOAc in hexane to 50% EtOAc to deliver the title compound. MS (M+H)+ 269.

(ii) 1-(2-{4-[5-(Trimethylsilyl)thiophen-2-yl]pyrimidin-2-ylamino}ethyl)-5,5-dimethylimidazolidine-2, 4-dione The title compound was prepared from 2-chloro-4-[5-(trimethylsilyl)thiophen-2-yl]-pyrimidine in a manner analogous to Example 249, Step 2. MS (M+H)+ 404.

Example 251

5,5-Dimethyl-1-{2-[4-(thiophen-2-yl)pyrimidin-2-ylamino]ethyl}imidazolidine-2,4-dione (i) 2-Chloro-4-(thiophen-2-yl)pyrimidine A solution of 2.0 g (15.6 mmol) of 2-thiopheneboronic acid in 80 mL of a 5% (w/v) Na2CO3 aqueous solution was added drop wise to a refluxing solution of 4.7 g (31 mmol) of 2,4-dichloropyrimidine and 0.55 g (0.78 mmol) of bis(triphenylphosphine)palladium(II) chloride in 80 mL of MeCN. The reaction solution was heated at reflux for 6 h, then cooled to rt, the organic solvent removed in vacuo, and the resulting purple solid filtered and washed with water. The crude product was purified by flash chromatography eluting with a linear gradient of neat hexane to neat EtOAc to deliver the title compound. MS (M+H)+ 197.

(ii) 5,5-Dimethyl-1-{2-[4-(thiophen-2-yl)pyrimidin-2-ylamino]ethyl}imidazolidine-2,4-dione The title compound was prepared from 2-chloro-4-(thiophen-2-yl)pyrimidine in a manner analogous to Example 249, Step 2. MS (M+H)+ 332.

Example 252

1-{2-[4-(5-Bromothiophen-2-yl)pyrimidin-2-ylamino]ethyl}-5,5-dimethylimidazolidine-2,4-dione 1.22 mL (0.71 mmol) of a 10% (w/v) solution of 1-(2-aminoethyl)-5,5-dimethylimidazol-idine-2,4-dione in MeOH was added to a 10 mL microwave vessel. The MeOH was evaporated with a stream of $N_2$, to leave an oily solid which was dissolved in 0.34 mL (2.0 mmol) of N,N-diisopropylethylamine, 0.5 mL of N-methylpyrrolidinone and 3.5 mL of toluene, to which was added 0.15 g (0.65 mmol) of 4-(5-bromothiophen-2-yl)-2-chloropyrimidine. The reaction solution was heated in a microwave to 180° C. for 20 min then concentrated in vacuo and purified by flash chromatography eluting with a linear gradient of 75% EtOAc in hexane to neat EtOAc to deliver The title compound. MS (M+H)+ 410.

Example 253

1-{2-[4-(5-Chlorothiophen-2-yl)pyrimidin-2-ylamino]ethyl}-5,5-dimethylimidazolidine-2,4-dione (i) 2-Chloro-4-(5-chlorothiophen-2-yl)pyrimidine The title compound was prepared from 2-chlorothiophene and 2-chloropyrimidine in a manner analogous to Example 249, Step 1. MS (M+H)+ 231.

(ii) 1-{2-[4-(5-Chlorothiophen-2-yl)pyrimidin-2-ylamino]ethyl}-5,5-dimethylimidazolidine-2,4-dione The title compound was prepared from 2-chloro-4-(5-chlorothiophen-2-yl)pyrimidine in a manner analogous to Example 252. MS (M+H)+ 366.

Example 254

1-{2-[5-Bromo-4-(5-chlorothiophen-2-yl)pyrimidin-2-ylamino]ethyl}-5,5-dimethylimidazolidine-2,4-dione (i) 5-Bromo-2-chloro-4-(5-chlorothiophen-2-yl)pyrimidine The title compound was prepared from 2-chlorothiophene and 5-bromo-2-chloropyrimidine in a manner analogous to Example 249, Step 1. MS (M+H)+ 311.

(ii) 1-{2-[5-Bromo-4-(5-chlorothiophen-2-yl)pyrimidin-2-ylamino]ethyl}-5,5-dimethylimidazolidine-2, 4-dione The title compound was prepared from 5-bromo-2-chloro-4-(5-chlorothiophen-2-yl)pyrimidine in a manner analogous to Example 252. MS (M+H)+ 446.

Example 255

1-{2-[5-Bromo-4-(3-bromo-5-chlorothiophen-2-yl)pyrimidin-2-ylamino]ethyl}-5,5-dimethylimidazolidine-2,4-dione (i) 5-Bromo-4-(3-bromo-5-chlorothiophen-2-yl)-2-chloropyrimidine nBuLi (1.1 mL, 1.6 M solution in hexane, 1.8 mmol) was added to a stirred solution of 2,3-dibromo-5-chlorothiophene (0.50 g, 1.8 mmol) in 10 mL of THF at −78° C. The solution was stirred for 10 min at −78° C. before 0.35 g (1.8 mmol) of 5-bromo-2-chloropyrimidine was added. The reaction solution was stirred for 30 min at −78° C., then quenched by addition of 1 mL of AcOH in 4 mL of MeOH. Solid 2,3-dichloro-5,6-dicyano-1,4-benzoquinone (0.82 g, 3.6 mmol) was added and the reaction mixture warmed to 0° C. and stirred for 10 min. The reaction mixture was then poured into 50 mL of a 0.5 M solution of sodium ascorbate and diluted with 100 mL of a 1 M aqueous solution of $Na_2CO_3$. The aqueous solution was extracted four times with $CH_2Cl_2$ and the combined organic extracts dried over $MgSO_4$, filtered and concentrated to give the crude product which was purified by flash chromatography eluting with a linear gradient of 50% EtOAc in hexane to neat EtOAc, then to 20% MeOH in EtOAc to deliver the title compound. MS (M+H)+ 389.

(ii) 1-{2-[5-Bromo-4-(3-bromo-5-chlorothiophen-2-yl)pyrimidin-2-ylamino]ethyl}-5,5-dimethylimidazolidine-2,4-dione A 10% (w/v) solution of 1-(2-aminoethyl)-5,5-dimethylimidazolidine-2,4-dione in MeOH (4.3 mL, 2.5 mmol) was added to a 10 mL microwave vessel. The MeOH was evaporated with a stream of $N_2$, to leave an oily solid which was dissolved in 0.58 mL (3.3 mmol) of N,N-diisopropylethylamine and 5 mL of iPrOH, to which was added 0.65 g (1.7 mmol) of 5-bromo-4-(3-bromo-5-chlorothiophen-2-yl)-2-chloropyrimidine. The reaction mixture was heated in a microwave to 170° C. for 20 min then concentrated in vacuo and purified by flash chromatography eluting with a linear gradient of 60% EtOAc in hexane to neat EtOAc to deliver the title compound. MS (M+H)+ 524.

Example 256

5,5-Dimethyl-1-{2-[4-(5-methylthiophen-2-yl)pyrimidin-2-ylamino]ethyl}imidazolidine-2,4-dione (i) 2-Chloro-4-(5-methylthiophen-2-yl)pyrimidine A solution of 0.20 g (1.4 mmol) of 5-methyl-2-thiopheneboronic acid, 0.21 g (1.4 mmol) of 2,4-dichloropyrimidine and 49 mg (0.070 mmol) of bis(triphenylphosphine)palladium(II) chloride in 2 mL of a 2 M $Na_2CO_3$ aqueous solution and 5 mL of MeCN was heated in a microwave for 10 min at 160° C., then cooled to rt, diluted with $CH_2Cl_2$ and MeOH, and dried over $MgSO_4$. The organic solvent was (ii) 5,5-Dimethyl-1-{2-[4-(5-methylthiophen-2-yl)pyrimidin-2-ylamino]ethyl}imidazolidine-2,4-dione removed in vacuo, and the resulting solid was purified by flash chromatography eluting with a linear gradient of 50% EtOAc in hexane to neat EtOAc to deliver the title compound. MS (M+H)$^+$ 211.

(ii) 5,5-Dimethyl-1-{2-[4-(5-methylthiophen-2-yl)pyrimidin-2-ylamino]ethyl}imidazolidine-2,4-dione The title compound was prepared from 2-chloro-4-(5-methylthiophen-2-yl)pyrimidine in a manner analogous to Example 252. MS (M+H)$^+$ 346.

Example 257

5-{2-[2-(5,5-Dimethyl-2,4-dioxoimidazolidin-1-yl)ethylamino]pyrimidin-4-yl}thiophene-2-carbonitrile (i) 5-(2-Chloropyrimidin-4-yl)thiophene-2-carbonitrile A solution of 0.22 g (1.4 mmol) of 5-cyanothiophen-2-ylboronic acid, 0.21 g (1.4 mmol) of 2,4-dichloropyrimidine and 49 mg (0.070 mmol) of bis(triphenylphosphine)palladium(II) chloride in 2 mL of a 2 M Na$_2$CO$_3$ aqueous solution and 5 mL of 1,4-dioxane was as heated in a microwave for 30 min at 140° C., then cooled to rt, diluted with CH$_2$Cl$_2$ and MeOH, and dried over MgSO$_4$. The organic solvent was removed in vacuo, and the resulting solid was purified by flash chromatography eluting with a linear gradient of 50% EtOAc in hexane to neat EtOAc to deliver the title compound. MS (M+H)$^+$ 222.

(ii) 5-{2-[2-(5,5-Dimethyl-2,4-dioxoimidazolidin-1-yl)ethylamino]pyrimidin-4-yl}thiophene-2-carbonitrile The title compound was prepared from 5-(2-chloropyrimidin-4-yl)thiophene-2-carbonitrile in a manner analogous to Example 252. MS (M+H)$^+$ 357.

Example 258

1-(2-{4-[5-(Hydroxymethyl)thiophen-2-yl]pyrimidin-2-ylamino}ethyl)-5,5-dimethylimidazolidine-2,4-dione The title compound was prepared from 5-(hydroxymethyl)thiophen-2-ylboronic acid in a manner analogous to Example 257. MS (M+H)$^+$ 362.

Example 259

1-(2-{4-[5-(2-Ethylphenylthio)thiophen-2-yl]pyrimidin-2-ylamino}ethyl)-5,5-dimethylimidazolidine-2,4-dione A solution of 1-{2-[4-(5-iodothiophen-2-yl)pyrimidin-2-ylamino]ethyl}-5,5-dimethyl-imidazolidine-2,4-dione (50 mg, 0.109 mmol) and 0.060 mL (0.44 mmol) of 2-ethylthiophenol in 2 mL toluene was treated with 3 mg of Pd$_2$ dba$_3$ (0.003 mmol), 3 mg of Xantphos (0.005 mmol) and 0.22 mL of a 1 M solution of tBuOK in t-butanol. The reaction vial was sealed and heated at 110° C. in a microwave for 10 min. The crude solution was concentrated onto 5 g of silica gel and then purified by flash chromatography to give the title compound. MS (M+H)$^+$ 468.

Example 260

1-(2-{4-[5-(2-Ethylphenylsulfinyl)thiophen-2-yl]pyrimidin-2-ylamino}ethyl)-5,5-dimethylimidazolidine-2,4-dione and 1-(2-{4-[5-(2-ethylphenylsulfonyl)thiophen-2-yl]pyrimidin-2-ylamino}ethyl)-5,5-dimethylimidazolidine-2,4-dione A solution of 1-(2-{4-[5-(2-ethylphenylthio)thiophen-2-yl]pyrimidin-2-ylamino}ethyl)-5,5-dimethylimidazolidine-2,4-dione (80 mg, 0.171 mmol) in 20 mL of acetone and 15 mL of water was treated with 0.5 g of Oxone (0.8 mmol) and stirred for 3 h at rt. The reaction suspension was diluted with 75 mL of water and extracted twice with CH$_2$Cl$_2$ and once with CHCl$_3$. The combined organic extracts were treated with solid Na$_2$SO$_4$ and Na$_2$S$_2$O$_3$, filtered and then concentrated in vacuo. The crude mixture of sulfoxide and sulfone was purified by C-8 prep HPLC to give the title compounds as pure solids. Sulfoxide: MS (M+H)$^+$ 484. Sulfone: MS (M+H)$^+$ 500.

Example 261

5,5-Dimethyl-1-(2-{4-[5-(phenylthio)thiophen-2-yl]pyrimidin-2-ylamino}ethyl)imidazolidine-2,4-dione The title compound was prepared from 1-{2-[4-(5-iodothiophen-2-yl)pyrimidin-2-ylamino]ethyl}-5,5-dimethylimidazolidine-2,4-dione and thiophenol in a manner analogous to Example 259. MS (M+H)$^+$ 440.

Example 262

5,5-dimethyl-1-(2-{4-[5-(m-tolylthio)thiophen-2-yl]pyrimidin-2-ylamino}ethyl)imidazolidine-2,4-dione The title compound was prepared from 1-{2-[4-(5-iodothiophen-2-yl)pyrimidin-2-ylamino]ethyl}-5,5-dimethylimidazolidine-2,4-dione and 3-methylthiophenol in a manner analogous to Example 259. MS (M+H)$^+$ 454.

Example 263

5,5-Dimethyl-1-(2-{4-[5-(m-tolylsulfonyl)thiophen-2-yl]pyrimidin-2-ylamino}ethyl)imidazolidine-2,4-dione The title compound was prepared from 5,5-dimethyl-1-(2-{4-[5-(m-tolylthio)thiophen-2-yl]pyrimidin-2-ylamino}ethyl)imidazolidine-2,4-dione in a manner analogous to Example 261. MS (M+H)$^+$ 486.

Example 264

5,5-Dimethyl-1-(2-{4-[5-(o-tolylsulfonyl)thiophen-2-yl]pyrimidin-2-ylamino}ethyl)imidazolidine-2,4-dione (i) 5,5-Dimethyl-1-(2-{4-[5-(o-tolylthio)thiophen-2-yl]pyrimidin-2-ylamino}ethyl)imidazolidine-2,4-dione The title compound was prepared from 1-{2-[4-(5-iodothiophen-2-yl)pyrimidin-2-ylamino]ethyl}-5,5-dimethylimidazolidine-2,4-dione and 2-methylthiophenol in a manner analogous to Example 259. MS (M+H)$^+$ 454.

(ii) 5,5-Dimethyl-1-(2-{4-[5-(o-tolylsulfonyl) thiophen-2-yl]pyrimidin-2-ylamino}ethyl)imidazolidine-2,4-dione The title compound was prepared from 5,5-dimethyl-1-(2-{4-[5-(o-tolylthio)thiophen-2-yl]pyrimidin-2-ylamino}ethyl)imidazolidine-2,4-dione in a manner analogous to Example 261. MS (M+H)$^+$ 486.

Example 265

1-(2-{4-[5-(3,4-Dimethylphenylsulfonyl)thiophen-2-yl]pyrimidin-2-ylamino}ethyl)-5,5-dimethylimidazolidine-2,4-dione The title compound was prepared from 1-{2-[4-(5-iodothiophen-2-yl)pyrimidin-2-ylamino]ethyl}-5,5-dimethylimidazolidine-2,4-dione and 3,4-dimethylthiophenol in a manner analogous to Example 264. MS (M+H)$^+$ 500.

Example 266

1-(2-{4-[5-(Cyclopentylsulfonyl)thiophen-2-yl]pyrimidin-2-ylamino}ethyl)-5,5-dimethylimidazolidine-2,4-dione The title compound was prepared from 1-{2-[4-(5-iodothiophen-2-yl)pyrimidin-2-ylamino]ethyl}-5,5-dimethylimidazolidine-2,4-dione and cyclopentanethiol in a manner analogous to Example 264. MS (M+H)$^+$ 464.

Example 267

5,5-Dimethyl-1-(2-{4-[5-(pentan-2-ylsulfonyl) thiophen-2-yl]pyrimidin-2-ylamino}ethyl)imidazolidine-2,4-dione The title compound was prepared from 1-{2-[4-(5-iodothiophen-2-yl)pyrimidin-2-ylamino]ethyl}-5,5-dimethylimidazolidine-2,4-dione and pentane-2-thiol in a manner analogous to Example 264. MS (M+H)$^+$ 466.

Example 268

1-(2-{4-[5-(Cyclohexylsulfonyl)thiophen-2-yl]pyrimidin-2-ylamino}ethyl)-5,5-dimethylimidazolidine-2,4-dione The title compound was prepared from 1-{2-[4-(5-iodothiophen-2-yl)pyrimidin-2-ylamino]ethyl}-5,5-dimethylimidazolidine-2,4-dione and cyclohexanethiol in a manner analogous to Example 264. MS (M+H)$^+$ 478.

Example 269

1-{2-[4-(5-Chlorothiophen-2-yl)-5-phenylpyrimidin-2-ylamino]ethyl}-5,5-dimethylimidazolidine-2,4-dione and 5,5-Dimethyl-1-{2-[5-phenyl-4-(5-phenylthiophen-2-yl)pyrimidin-2-ylamino] ethyl}imidazolidine-2,4-dione A biphasic mixture of 30 mg (0.068 mmol) of 1-{2-[5-bromo-4-(5-chlorothiophen-2-yl)pyrimidin-2-ylamino] ethyl}-5,5-dimethylimidazolidine-2,4-dione, 10 mg (0.081 mmol) of phenylboronic acid, 4.0 mg (0.0034 mmol) of tetrakis(triphenylphosphine)palladium(0) in 2 mL of 1,4-dioxane and 0.5 mL of 2 M aqueous Na$_2$CO$_3$ was heated in a microwave at 140° C. for 20 min. The reaction mixture was cooled to rt, diluted with 5 mL of water and extracted twice with CH$_2$Cl$_2$ and twice with a 3:1 mixture of CHCl$_3$ and iPrOH. The combined organic extracts were concentrated and the crude products separated by C-18 prep HPLC to give 1-{2-[4-(5-chlorothiophen-2-yl)-5-phenylpyrimidin-2-ylamino]ethyl}-5,5-dimethylimidazolidine-2,4-dione: MS (M+H)$^+$ 442; and 5,5-dimethyl-1-{2-[5-phenyl-4-(5-phenylthiophen-2-yl)pyrimidin-2-ylamino] ethyl}imidazolidine-2,4-dione: MS (M+H)$^+$ 484.

Example 270

3-{4-(5-Chlorothiophen-2-yl)-2-[2-(5,5-dimethyl-2, 4-dioxoimidazolidin-1-yl)ethylamino]pyrimidin-5-yl}benzamide The title compound was prepared from 1-{2-[5-bromo-4-(5-chlorothiophen-2-yl)pyrimidin-2-ylamino]ethyl}-5,5-dimethylimidazolidine-2,4-dione and 3-carbamoylphenylboronic acid in a manner analogous to Example 269. MS (M+H)$^+$ 485.

Example 271

3-{4-(5-Chlorothiophen-2-yl)-2-[2-(5,5-dimethyl-2, 4-dioxoimidazolidin-1-yl)ethylamino]pyrimidin-5-yl}-N-methylbenzamide The title compound was prepared from 1-{2-[5-bromo-4-(5-chlorothiophen-2-yl)pyrimidin-2-ylamino]ethyl}-5,5-dimethylimidazolidine-2,4-dione and 3-(methyl-carbamoyl)phenylboronic acid in a manner analogous to Example 269. MS (M+H)$^+$ 499.

Example 272

N-(3-{4-(5-Chlorothiophen-2-yl)-2-[2-(5,5-dimethyl-2,4-dioxoimidazolidin-1-yl)ethylamino]pyrimidin-5-yl}phenyl)acetamide The title compound was prepared from 1-{2-[5-bromo-4-(5-chlorothiophen-2-yl)pyrimidin-2-ylamino]ethyl}-5,5-dimethylimidazolidine-2,4-dione and 3-acetamidophenylboronic acid in a manner analogous to Example 269. MS (M+H)$^+$ 499.

Example 273

1-{2-[4-(5-Chlorothiophen-2-yl)-5-(3-hydroxyphenyl)pyrimidin-2-ylamino]ethyl}-5,5-dimethylimidazolidine-2,4-dione The title compound was prepared from 1-{2-[5-bromo-4-(5-chlorothiophen-2-yl)pyrimidin-2-ylamino]ethyl}-5,5-dimethylimidazolidine-2,4-dione and 3-hydroxyphenylboronic acid in a manner analogous to Example 269. MS (M+H)$^+$ 458.

Example 274

1-(2-{4-(5-Chlorothiophen-2-yl)-5-[3-(hydroxymethyl)phenyl]pyrimidin-2-ylamino}ethyl)-5,5-dimethylimidazolidine-2,4-dione The title compound was prepared from 1-{2-[5-bromo-4-(5-chlorothiophen-2-yl)pyrimidin-2-ylamino]ethyl}-5,5- dimethylimidazolidine-2,4-dione and 3-(hydroxymethyl) phenylboronic acid in a manner analogous to Example 269. MS (M+H)+ 472.

Example 275

1-{2-[4-(5-Chlorothiophen-2-yl)-5-(2-oxoindolin-6-yl)pyrimidin-2-ylamino]ethyl}-5,5-dimethylimidazolidine-2,4-dione (i) 6-(4,4,5,5-Tetramethyl-1,3,2-dioxaborolan-2-yl)indolin-2-one A solution of 0.17 g (0.82 mmol) of 6-bromoindolin-2-one, 0.25 g of bis(pinacolato)diboron and 0.20 g (0.98 mmol) of KOAc in 5 mL of DMSO was degassed with Ar sparging for 5 min, then 33 mg (0.041 mmol) of 1,1'-bis(diphenylphosphino)ferrocene-palladium(II) dichloride was added and the reaction solution was stirred at 85° C. for 18 h. The reaction solution was poured into 250 mL of EtOAc, washed twice with a 1 M aqueous solution of MgSO$_4$, once with brine, then concentrated in vacuo, and purified by flash chromatography eluting with a linear gradient of 20% EtOAc in hexane to neat EtOAc to yield the title compound. MS (M+H)+ 260.

(ii) 1-{2-[4-(5-Chlorothiophen-2-yl)-5-(2-oxoindolin-6-yl)pyrimidin-2-ylamino]ethyl}-5,5-dimethylimidazolidine-2,4-dione The title compound was prepared from 1-{2-[5-bromo-4-(5-chlorothiophen-2-yl)pyrimidin-2-ylamino]ethyl}-5,5-dimethylimidazolidine-2,4-dione and 6-(4,4,5,5-tetramethyl-1,3,2-dioxaborolan-2-yl)indolin-2-one in a manner analogous to Example 269. MS (M+H)+ 497.

Example 276

1-{2-[5-(3-Aminophenyl)-4-(5-chlorothiophen-2-yl)pyrimidin-2-ylamino]ethyl}-5,5-dimethylimidazolidine-2,4-dione The title compound was prepared from 1-{2-[5-bromo-4-(5-chlorothiophen-2-yl)pyrimidin-2-ylamino]ethyl}-5,5-dimethylimidazolidine-2,4-dione and 3-aminophenylboronic acid, hemihydrosulfate in a manner analogous to Example 269. MS (M+H)+ 457.

Example 277 tert-Butyl 2-(3-{4-(5-Chlorothiophen-2-yl)-2-[2-(5,5-dimethyl-2,4-dioxoimidazolidin-1-yl)ethylamino]pyrimidin-5-yl}phenylamino)-2-oxoethyl(methyl)carbamate A solution of 50 mg (0.11 mmol) of 1-{2-[5-(3-aminophenyl)-4-(5-chlorothiophen-2-yl)pyrimidin-2-ylamino]ethyl}-5,5-dimethylimidazolidine-2,4-dione, 31 mg (0.16 mmol) of N-Boc-sarcosine, 31 mg (0.16 mmol) of 1-ethyl-3-(3-dimethylaminopropyl)carbodiimide hydrochloride, 0.1 mg (0.01 mmol) of 4-dimethylaminopyridine and 0.057 mL (0.33 mmol) of N,N-diisopropylethylamine in 1 mL of CH$_2$Cl$_2$ was stirred for 18 h at rt. The reaction solution was poured into 75 mL of EtOAc and washed thrice with 2% (w/v) aqueous HCl, once with a saturated aqueous solution of NaHCO$_3$, then with brine, dried over MgSO$_4$, filtered and concentrated in vacuo. The crude product was purified by flash chromatography eluting with a linear gradient of neat EtOAc to 10% MeOH in EtOAc to yield the title compound. MS (M+H)+ 628.

Example 278

N-(3-{4-(5-Chlorothiophen-2-yl)-2-[2-(5,5-dimethyl-2,4-dioxoimidazolidin-1-yl)ethylamino]pyrimidin-5-yl}phenyl)-2-(methylamino)acetamide A solution of 15 mg (0.024 mmol) of tert-Butyl 2-(3-{4-(5-chlorothiophen-2-yl)-2-[2-(5,5-dimethyl-2,4-dioxoimidazolidin-1-yl)ethylamino]pyrimidin-5-yl}phenylamino)-2-oxoethyl(methyl)carbamate in 1 mL of 1,4-dioxane was treated with 2 mL of a 4 M solution of HCl in 1,4-dioxane and stirred 1 h at rt, then concentrated in vacuo to give the desired product as the hydrochloride salt. MS (M+H)+ 528.

Example 279 tert-Butyl 4-{4-(5-Chlorothiophen-2-yl)-2-[2-(5,5-dimethyl-2,4-dioxoimidazolidin-1-yl)ethylamino]pyrimidin-5-yl}-1H-indole-1-carboxylate and 1-{2-[4-(5-Chlorothiophen-2-yl)-5-(1H-indol-4-yl)pyrimidin-2-ylamino]ethyl}-5,5-dimethylimidazolidine-2,4-dione (i) tert-Butyl 4-Bromo-1H-indole-1-carboxylate A solution of 0.48 mL (3.8 mmol) of 4-bromo-1H-indole in 1 mL of THF was added to a suspension of 0.15 g (6.3 mmol) of NaH in 5 mL of THF, followed by 1.2 mL (6.3 mmol) of tert-butyl phenylcarbonate. The reaction solution was stirred 18 h, then quenched with 1 mL of iPrOH, poured into 100 mL of Et$_2$O and washed twice with a saturated aqueous solution of NH$_4$Cl and thrice with water. The organic solvent was removed in vacuo and the residue was purified by flash chromatography eluting with neat hexane to yield the title compound. MS (M-BOC+2H)+ 196.

(ii) tert-Butyl 4-(4,4,5,5-Tetramethyl-1,3,2-dioxaborolan-2-yl)-1H-indole-1-carboxylate The title compound was prepared from tert-butyl 4-bromo-1H-indole-1-carboxylate in a manner analogous to Example 275, Step 1. MS (M+H)+ 344.

(iii) tert-Butyl 4-{4-(5-Chlorothiophen-2-yl)-2-[2-(5,5-dimethyl-2,4-dioxoimidazolidin-1-yl)ethylamino]pyrimidin-5-yl}-1H-indole-1-carboxylate and 1-{2-[4-(5-chlorothiophen-2-yl)-5-(1H-indol-4-yl)pyrimidin-2-ylamino]ethyl}-5,5-dimethylimidazolidine-2,4-dione The title compounds were prepared from 1-{2-[5-bromo-4-(5-chlorothiophen-2-yl)pyrim-idin-2-ylamino]ethyl}-5,5-dimethylimidazolidine-2,4-dione and tert-butyl 4-(4,4,5,5-tetra-methyl-1,3,2-dioxaborolan-2-yl)-1H-indole-1-carboxylate in a manner analogous to Example 269, then purified and separated by C-8 prep HPLC to give tert-butyl 4-{4-(5-chlorothiophen-2-yl)-2-[2-(5,5-dimethyl-2,4-dioxoimidazolidin-1-yl)ethylamino]pyrimidin-5-yl}-1H-indole-1-carboxylate: MS (M+H)+ 581; and 1-{2-[4-(5-chlorothiophen-2-yl)-5-(1H-indol-4-yl)pyrimidin-2-ylamino]ethyl}-5,5-dimethylimidazolidine-2,4-dione: MS (M+H)+ 481.

Example 280

1-{2-[4-(5-Benzyl-thiophen-2-yl)-pyrimidin-2-ylamino]-ethyl}-5,5-dimethyl-imidazolidine-2,4-dione (i) 2-Benzylthiophene A solution of 7.8 g (52 mmol) of NaI and 5 mL (43 mmol) of benzyl chloride in THF was heated at reflux for 2 h to form benzyl iodide in situ and then the reaction was cooled to rt. In a separate flask, 37 mg (0.87 mmol) of LiCl and 58 mg (0.43 mmol) of copper(II) chloride were dissolved in 5 mL of THF and stirred at rt for 5 min to form $Li_2CuCl_4$ in situ. The benzyl iodide reaction flask was fitted with an addition funnel and 3 mL (3 mmol) of a 1 M solution of 2-thienylmagnesium bromide in THF was added dropwise, followed by addition of the $Li_2CuCl_4$ solution, and then the remaining 2-thienylmagnesium bromide solution (49 mL, 49 mmol) was added at such a rate as to maintain the reaction temperature ≦40° C. and the reaction solution was stirred for 2 h at rt. The THF was removed in vacuo, and the residue was partitioned between 250 mL of $Et_2O$ and 150 mL of $NH_4Cl$ and separated. The organic layer was treated with 15 mL of piperidine and stirred for 18 h, then washed twice with 10% (w/v) aqueous HCl, filtered, concentrated and the dark red residue was purified by flash chromatography eluting with neat hexane to yield the title compound. GC-MS (M)+ 174.

(ii) 4-(5-Benzylthiophen-2-yl)-2-chloro-pyrimidine

The title compound was prepared from 2-benzylthiophene and 2-chloropyrimidine in a manner analogous to Example 255, Step 1. MS (M+H)+ 287.

(iii) 1-{2-[4-(5-Benzyl-thiophen-2-yl)-pyrimidin-2-ylamino]-ethyl}-5,5-dimethyl-imidazolidine-2,4-dione A 10% (w/v) solution of 1-(2-aminoethyl)-5,5-dimethylimidazolidine-2,4-dione in MeOH (0.93 mL, 0.54 mmol) was added to a 5 mL microwave vessel. The MeOH was evaporated with a stream of $N_2$ to leave an oily solid which was dissolved in 94 μl (0.54 mmol) of N,N-diisopropylethylamine and 2 mL of iPrOH, to which was added 0.15 g (0.54 mmol) of 4-(5-benzylthiophen-2-yl)-2-chloropyrimidine. The reaction solution was heated in a microwave to 170° C. for 20 min and then allowed to stand at rt for 2 h to give a precipitate which was collected by filtration and purified by C-8 prep HPLC to give the title compound. MS (M+H)+ 422.

Example 281

1-{2-[4-(5-Benzyl-thiophen-2-yl)-pyrimidin-2-ylamino]-ethyl}-5,5-dimethyl-imidazolidine-2,4-dione (i) 4-(5-Benzylthiophen-2-yl)-5-bromo-2-chloro-pyrimidine The title compound was prepared from 2-benzylthiophene and 5-bromo-2-chloropyrimidine in a manner analogous to Example 255, Step 1. MS (M+H)+ 365.

(ii) 1-{2-[4-(5-Benzyl-thiophen-2-yl)-pyrimidin-2-ylamino]-ethyl}-5,5-dimethyl-imidazolidine-2,4-dione The title compound was prepared from 4-(5-benzylthiophen-2-yl)-5-bromo-2-chloro-pyrimidine in a manner analogous to Example 280, Step 3. MS (M+H)+ 500.

Example 282

5,5-Dimethyl-1-(2-{4-[5-(E,Z-β-styryl)thiophen-2-yl]-pyrimidin-2-ylamino}ethyl)imidazolidine-2,4-dione (i) 2-(E,Z-β-Styryl)thiophene A solid mixture of $NaNH_2$ and benzyltriphenylphosphonium bromide (5.0 g, 10 mmol) was suspended in 10 mL of THF and cooled in a tepid water bath before 0.75 mL (8.0 mmol) of 2-thiophenecarboxaldehyde was added to the reaction mixture. After 30 min of stirring, the reaction was quenched with 1 mL of 40% (w/v) aqueous NaOH and stirred for 10 min, then poured into 350 mL of hexane, filtered to remove the resulting precipitated triphenylphosphine oxide and the hexane removed in vacuo to give the title compound as a 7:2 mixture of E,Z-isomers. GC-MS (M)+ 186.

(ii) 2-Chloro-4-[5-(E,Z-β-styryl)thiophen-2-yl]pyrimidine

The title compounds were prepared from 2-(E,Z-β-styryl)thiophene and 2-chloropyrimidine in a manner analogous to Example 255, Step 1. MS (M+H)+ 299.

(iii) 5,5-Dimethyl-1-(2-{4-[5-(E,Z-β-styryl)thiophen-2-yl]-pyrimidin-2-ylamino}ethyl)imidazolidine-2,4-dione The title compounds were prepared from 2-chloro-4-[5-(E,Z-β-styryl)thiophen-2-yl]pyrimidine in a manner analogous to Example 280, Step 3 to give the pure E-isomer: 5,5-dimethyl-1-(2-{4-[5-(E-β-styryl)thiophen-2-yl]-pyrimidin-2-ylamino}ethyl)imidazolidine-2,4-dione: MS (M+H)+ 434; and a 4:1 mixture of E,Z-isomers: 5,5-dimethyl-1-(2-{4-[5-(E,Z-β-styryl)thiophen-2-yl]-pyrimidin-2-ylamino}ethyl)imidazolidine-2,4-dione: MS (M+H)+ 434.

Example 283

5,5-Dimethyl-1-{2-[4-(5-phenethyl-thiophen-2-yl)-pyrimidin-2-ylamino]-ethyl}-imidazolidine-2,4-dione (i) 2-Phenethyl-thiophene A solution of 0.50 g (2.7 mmol) of 2-(E,Z-β-styryl)thiophene and 0.51 g (2.0 mmol) of iodine in 25 mL of AcOH under Ar was treated with 0.97 mL (9.3 mmol) of a 50% (w/v) aqueous solution of $H_3PO_2$ and heated at 110° C. for 3 h. The reaction solution was cooled to rt, diluted with 200 mL $Et_2O$ and washed with water, saturated aqueous $NaHCO_3$, saturated aqueous $Na_2S_2O_3$ and brine. The organic layer was dried over $MgSO_4$, filtered and concentrated in vacuo to give the title compound. GC-MS (M)+ 188.

(ii) 2-Chloro-4-(5-phenethyl-thiophen-2-yl)-pyrimidine

The title compound was prepared from 2-phenethyl-thiophene and 2-chloropyrimidine in a manner analogous to Example 255, Step 1. MS (M+H)+ 301.

(iii) 5,5-Dimethyl-1-{2-[4-(5-phenethyl-thiophen-2-yl)-pyrimidin-2-ylamino]-ethyl}-imidazolidine-2,4-dione The title compound was prepared from 2-chloro-4-(5-phenethyl-thiophen-2-yl)-pyrimidine in a manner analogous to Example 280, Step 3. MS (M+H)+ 436.

Example 284

1-(2-{5-Bromo-4-[2-(phenylthio)thiazol-5-yl)pyrimidin-2-ylamino]ethyl}-5,5-dimethylimidazolidine-2,4-dione (i) 2-Phenylthiothiazole A solution of sodium thiophenolate (0.61 g, 4.62 mmol) and 2-bromothiazole (0.38 mL, 4.2 mmol) in 20 mL of toluene was treated with 0.19 g (0.21 mmol) of $Pd_2 dba_3$ and 0.12 g (0.21 mmol) of Xantphos and heated at reflux for 10 min. The crude solution was concentrated onto 5 g of silica gel and then purified by flash chromatography to give the title compound. MS (M+H)+ 194.

(ii) 5-Bromo-2-chloro-4-[2-(phenylthio)thiazol-5-yl]pyrimidine

The title compound was prepared from 2-Phenylthiothiazole and 5-bromo-2-chloro-pyrimidine in a manner analogous to Example 249, Step 1. MS (M+H)+ 386.

(iii) 1-(2-{5-Bromo-4-[2-(phenylthio)thiazol-5-yl)pyrimidin-2-ylamino]ethyl}-5,5-dimethylimidazolidine-2,4-dione The title compound was prepared from 5-bromo-2-chloro-4-[2-(phenylthio)thiazol-5-yl]pyrimidine in a manner analogous to Example 280, Step 3. MS (M+H)+ 521.

Example 285

1-[2-(5-Bromo-4-{2-[hydroxy(phenyl)methyl]thiazol-5-yl}pyrimidin-2-ylamino)ethyl]-5,5-dimethylimidazolidine-2,4-dione (i) 2-[Phenyl(trimethylsilyloxy)methyl]thiazole A neat solution of 1.0 mL (6.2 mmol) of 2-(trimethylsilyl) thiazole and 0.63 mL (6.2 mmol) of benzaldehyde was stirred at rt for 4 h to give the title compound. GC-MS (M)+ 263.

(ii) 5-Bromo-2-chloro-4-{2-[phenyl(trimethylsilyloxy)methyl]-thiazol-5-yl}pyrimidine A 1.7 M solution of tBuLi in pentane (1.8 mL, 3.0 mmol) was added to a stirred solution of 0.80 g (3.0 mmol) of 2-[phenyl(trimethylsilyloxy)methyl]thiazole in 25 mL of THF at −78° C. The solution was stirred for 10 min at −78° C. before 0.59 g (3.0 mmol) of 5-bromo-2-chloropyrimidine was added. The reaction solution was stirred for 30 min at −78° C., then quenched by addition of 1 mL of AcOH in 4 mL of MeOH. Solid 2,3-dichloro-5,6-dicyano-1,4-benzoquinone (1.4 g, 6.1 mmol) was added and the reaction solution was warmed to 0° C. and stirred for 10 min. The reaction solution was then poured into 50 mL of a 0.5 M solution of sodium ascorbate, diluted with 100 mL of a 1 M aqueous solution of $Na_2CO_3$. The aqueous solution was extracted four times with $CHCl_3$ and the combined organic extracts dried over $MgSO_4$, filtered and concentrated to give the crude product which was purified by flash chromatography eluting with a linear gradient of 30% EtOAc in hexane to neat EtOAc to deliver the title compound. MS (M+H)+ 456.

(iii) 1-[2-(5-Bromo-4-{2-[hydroxy(phenyl)methyl]thiazol-5-yl}pyrimidin-2-ylamino)ethyl]-5,5-dimethylimidazolidine-2,4-dione A solution of 150 mg (0.33 mmol) of 5-bromo-2-chloro-4-{2-[phenyl(trimethylsilyloxy)-methyl]-thiazol-5-yl}pyrimidine, 85 mg (0.50 mmol) of 1-(2-aminoethyl)-5,5-dimethylimidazolidine-2,4-dione and N,N-diisopropylethylamine (0.17 mL, 0.99 mmol) in 4 mL of iPrOH and 1 mol of $CHCl_3$ was heated in a microwave to 170° C. for 20 min and then treated with 0.75 mL of a 1 M solution of tetra-n-butylammonium fluoride in THF for 10 min at rt. The reaction solution was concentrated in vacuo and the crude solid product was purified by flash chromatography eluting with a linear gradient of 75% EtOAc in hexane to 100% EtOAc to deliver the title compound. MS (M+H)+ 519.

Example 286

1-[2-(5-Bromo-4-{2-[methyl(phenyl)amino]thiazol-5-yl}pyrimidin-2-ylamino)ethyl]-5,5-dimethylimidazolidine-2,4-dione (i) 2-(N-Methyl-N-phenylamino)thiazole A solution of 10 g (60 mmol) of N-methyl-N-phenylthiourea in 100 mL of toluene was treated with 7.2 mL (63 mmol) of chloroacetaldehyde dimethylacetal and heated at reflux for 12 h. The solvent was removed in vacuo and the residue purified by flash chromatography eluting with a linear gradient of 30% EtOAc in hexane to 80% EtOAc in hexane to deliver the title compound. MS (M+H)+ 191.

(ii) 5-(5-Bromo-2-chloropyrimidin-4-yl)-N-methyl-N-phenylthiazol-2-amine tBuLi (2.9 mL, 1.1 M solution in pentane, 3.0 mmol) was added to a stirred solution of 0.52 g (2.8 mmol) of 2-(N-Methyl-N-phenylamino)thiazole in 10 mL of $Et_2O$ at −78° C. The solution was stirred for 30 min at −78° C. before 0.59 g (3.0 mmol) of 5-bromo-2-chloropyrimidine and 10 mL of THF were added. The reaction solution was stirred for 30 min at −78° C., and then quenched by the addition of 5 mL of AcOH in 15 mL of MeOH. Solid 2,3-dichloro-5,6-dicyano-1,4-benzoquinone (1.4 g, 6.1 mmol) was added and the reaction solution was warmed to 0° C. and stirred for 10 min, then poured into 100 mL of a 0.5 M solution of sodium ascorbate, diluted with 300 mL of water and the crude product removed by filtration and washed repeatedly with water. The residue was azeotroped with toluene and purified by flash chromatography eluting with a linear gradient of 10% EtOAc in hexane to 100% EtOAc to deliver the title compound. MS (M+H)+ 383.

(iii) 1-[2-(5-Bromo-4-{2-[methyl(phenyl)amino]thiazol-5-yl}pyrimidin-2-ylamino)ethyl]-5,5-dimethylimidazolidine-2,4-dione The title compound was prepared from 5-(5-bromo-2-chloropyrimidin-4-yl)-N-methyl-N-phenylthiazol-2-amine in a manner analogous to Example 280, Step 3. MS (M+H)$^+$ 518.

Example 287

Sodium 1-[2-(5-Bromo-4-{2-[methyl(phenyl)amino]thiazol-5-yl}pyrimidin-2-ylamino)ethyl]-5,5-dimethyl-2-oxo-2,5-dihydro-1H-imidazololate A suspension of 0.14 g (0.27 mmol) of 1-[2-(5-bromo-4-{2-[methyl(phenyl)amino]thiazol-5-yl}pyrimidin-2-ylamino)ethyl]-5,5-dimethylimidazolidine-2,4-dione in 5 mL of MeOH was treated with 0.54 mL (0.27 mmol) of a 0.5 M solution of NaOMe in MeOH, placed in a sonicating bath for 5 min, then concentrated in vacuo and co-evaporated with hexane and dried under vacuum at 60° C. for 12 h to give the title compound. $^1$H NMR (d$_6$-DMSO, 400 MHz) showed the expected loss of NH; MS (M-Na+2H)$^+$ 518.

Example 288

1-[2-(5-Fluoro-4-{2-[methyl(phenyl)amino]thiazol-5-yl}pyrimidin-2-ylamino)ethyl]-5,5-dimethylimidazolidine-2,4-dione

(i) 5-(2-Chloro-5-fluoropyrimidin-4-yl)-N-methyl-N-phenylthiazol-2-amine

A 1.6 M solution of tBuLi in heptane (1.6 mL, 2.6 mmol) was added to a stirred solution of 0.44 g (2.3 mmol) of 2-(N-Methyl-N-phenylamino)thiazole in 8 mL of THF at −78° C. The solution was stirred for 15 min at −78° C. before 0.24 mL (2.6 mmol) of 2-chloro-5-fluoropyrimidine and 2 mL of THF were added. The reaction solution was stirred for 10 min at −78° C., then quenched by addition of 1 mL of AcOH in 1 mL of MeOH. Solid 2,3-dichloro-5,6-dicyano-1,4-benzoquinone (1.1 g, 4.6 mmol) was added and the reaction solution was warmed to 0° C. and stirred for 30 min, poured into 50 mL of a 0.5 M solution of sodium ascorbate, diluted with 200 mL of water and the crude product removed by filtration and washed repeatedly with water. The residue was dried by toluene co-evaporation to deliver the title compound. MS (M+H)$^+$ 321.

(ii) 1-[2-(5-Fluoro-4-{2-[methyl(phenyl)amino]thiazol-5-yl}pyrimidin-2-ylamino)ethyl]-5,5-dimethylimidazolidine-2,4-dione The title compound was prepared from 5-(2-chloro-5-fluoropyrimidin-4-yl)-N-methyl-N-phenylthiazol-2-amine in a manner analogous to Example 280, Step 3. MS (M+H)$^+$ 456.

Example 289

1-[2-(5-Fluoro-4-{2-[(4-fluorophenyl)(methyl)amino]thiazol-5-yl}pyrimidin-2-ylamino)ethyl]-5,5-dimethylimidazolidine-2,4-dione

(i) 1-(4-Fluorophenyl)-1-methylthiourea

A solution of 3.8 g (50 mmol) of ammonium thiocyanate in 100 mL of acetone was treated with a solution of 8.4 g (45 mmol) of 4-nitrobenzoyl chloride in 50 mL of acetone and the reaction solution was heated at reflux for 15 min. The reaction solution was removed from heating and 5.2 g (41 mmol) of 4-fluoro-N-methylaniline was added at such a rate as to maintain reflux, then heating was renewed for 15 min. The reaction mixture was poured onto 400 g of ice to give an orange oil that separated and solidified on standing. The solid was collected by filtration, washed with water and dried to give 1-(4-fluorophenyl)-1-methyl-3-(4-nitrobenzoyl)thiourea which was suspended in 500 mL of MeOH and treated with 2 mL (64 mmol) of hydrazine for 18 h. The byproduct 4-nitrobenzohydrazide was removed by filtration and the organic solvent was removed from the product in vacuo. The residue was dissolved in 500 mL of 8:1:1 (v/v/v) EtOAc/CHCl$_3$/MeOH, washed thrice with 10% (w/v) aqueous HCl, then dried over a mixture of solid MgSO$_4$ and solid Na$_2$CO$_3$, filtered and concentrated to give the desired compound. MS (M+H)$^+$ 185.

(ii) N-(4-Fluorophenyl)-N-methylthiazol-2-amine

A solution of 2.0 g (11 mmol) of 1-(4-fluorophenyl)-1-methylthiourea in 20 mL of EtOH was treated with 4.1 mL (33 mmol) of a 50% (w/v) aqueous solution of chloroacetaldehyde and heated at reflux for 18 h. The solvent was removed in vacuo and the residue purified by flash chromatography eluting with a linear gradient of 10% EtOAc in hexane to 100% EtOAc to deliver the title compound. MS (M+H)$^+$ 209.

(iii) 5-(2-Chloro-5-fluoropyrimidin-4-yl)-N-(4-fluorophenyl)-N-methylthiazol-2-amine 8.4 mL (13 mmol) of a 1.6 M solution of tBuLi in heptane was added to a rapidly stirred suspension of 2.5 g (12 mmol) of N-(4-fluorophenyl)-N-methylthiazol-2-amine in 50 mL of THF at −78° C. The solution was stirred for 1 min at −78° C. before 1.3 mL (13 mmol) of 2-chloro-5-fluoropyrimidine was added. The reaction solution was stirred for 1 h at −78° C., then quenched by addition of 2 mL of MeOH. Solid 2,3-dichloro-5,6-dicyano-1,4-benzoquinone (5.5 g, 24 mmol) was added and the reaction solution was stirred for 1 h and then 25 mL of 10% (w/v) aqueous NaOH was added. The reaction solution was warmed to rt and stirred 2 h, then poured into 500 mL of EtOAc and 200 mL of water, separated and the organic layer washed twice with saturated aqueous NaHCO$_3$, once with brine, dried over MgSO$_4$, filtered and concentrated. The residue was purified by C-18 prep MPLC to give the title compound. MS (M+H)$^+$ 339.

(iv) 1-[2-(5-Fluoro-4-{2-[(4-fluorophenyl)(methyl)amino]thiazol-5-yl}pyrimidin-2-ylamino)ethyl]-5,5-dimethylimidazolidine-2,4-dione The title compound was prepared from 5-(2-chloro-5-fluoropyrimidin-4-yl)-N-(4-fluoro-phenyl)-N-methylthiazol-2-amine in a manner analogous to Example 280, Step 3. MS (M+H)$^+$ 474.

Example 290

1-(2-[5-Fluoro-4-{5-[(4-fluorophenyl)(methyl)amino]thiazol-2-yl}pyrimidin-2-ylamino)ethyl]-5,5-dimethylimidazolidine-2,4-dione

(i) N-(4-Fluorophenyl)-N-methylthiazol-5-amine 5.0 g (40 mmol) of 4-fluoro-N-methylaniline and 3.6 mL (40 mmol) of 2-bromothiazole were added to a suspension of 1.9 g (81 mmol) of NaH in 100 mL of DMF, and the suspension was stirred overnight at rt. The reaction mixture was concentrated onto 20 g of silica in vacuo and the residue purified by flash chromatography eluting with a linear gradient of 20% EtOAc in hexane to 100% EtOAc to deliver the desired compound. MS (M+H)$^+$ 209.

(ii) 2-(2-Chloro-5-fluoropyrimidin-4-yl)-N-(4-fluorophenyl)-N-methylthiazol-5-amine 2.1 mL (5.3 mmol) of a 2.5 M solution of nBuLi in hexane was added to a stirred solution of 1.0 g (4.8 mmol) of N-(4-fluorophenyl)-N-methylthiazol-5-amine in 30 mL of THF at −78° C. The solution was stirred for 30 min at −78° C. before 0.61 mL (5.3 mmol) of 2-chloro-5-fluoropyrimidine was added. The reaction solution was stirred for 1 h at −78° C., then quenched by addition of 0.83 mL (14 mmol) of AcOH. A solution of 2,3-dichloro-5,6-dicyano-1,4-benzoquinone (1.1 g, 4.8 mmol) in 5 mL of THF was added and the reaction solution was warmed to 0° C. and stirred for 10 min then poured into 600 mL of water and the solid product was collected by filtration, washed with water and dried in vacuo. MS (M+H)$^+$ 339.

(iii) 1-(2-[5-Fluoro-4-{5-[(4-fluorophenyl)(methyl)amino]thiazol-2-yl}pyrimidin-2-ylamino)ethyl]-5,5-dimethylimidazolidine-2,4-dione The title compound was prepared from 2-(2-chloro-5-fluoropyrimidin-4-yl)-N-(4-fluoro-phenyl)-N-methylthiazol-5-amine in a manner analogous to Example 280, Step 3. MS (M+H)$^+$ 474.

Example 291

1-(2-{5-Bromo-4-[2-(4-fluorophenylamino)thiazol-5-yl]pyrimidin-2-ylamino}ethyl)-5,5-dimethylimidazolidine-2,4-dione

(i) N-(4-Fluorophenyl)thiazol-2-amine

The title compound was prepared from 1-(4-fluorophenyl)thiourea in a manner analogous to Example 286, Step 1. MS (M+H)$^+$ 195.

(ii) 5-(5-Bromo-2-chloropyrimidin-4-yl)-N-(4-fluorophenyl)thiazol-2-amine 8.1 mL (12 mmol) of a 1.5 M solution of tBuLi in heptane was added to a stirred solution of 1.1 g (5.5 mmol) of N-(4-fluorophenyl)thiazol-2-amine in 20 mL of THF at −20° C. The solution was stirred for 30 min and then cooled to −78° C. before 1.3 g (6.6 mmol) of 5-bromo-2-chloropyrimidine was added. The reaction solution was stirred for 30 min at −78° C., then quenched by addition of 0.2 mL of AcOH in 1 mL of MeOH. Solid 2,3-dichloro-5,6-dicyano-1,4-benzoquinone (10.4 g, 46 mmol) and 5 mL of MeOH were added and the reaction solution was warmed to 0° C. and stirred for 30 min, poured into 50 mL of a 0.5 M solution of sodium ascorbate, diluted with 200 mL of water and the crude product removed by filtration and washed repeatedly with water. The crude product was purified by flash chromatography eluting with a linear gradient of 10% EtOAc in hexane to 80% EtOAc in hexane to deliver the desired compound. MS (M+H)$^+$ 387.

(iii) 1-(2-{5-Bromo-4-[2-(4-fluorophenylamino)thiazol-5-yl]pyrimid-in-2-ylamino}ethyl)-5,5-dimethylimidazolidine-2,4-dione The title compound was prepared from 5-(5-bromo-2-chloropyrimidin-4-yl)-N-(4-fluoro-phenyl)thiazol-2-amine in a manner analogous to Example 280, Step 3. MS (M+H)$^+$ 522/524.

Example 292

1-(2-{5-Fluoro-4-[2-(4-fluorophenylamino)thiazol-5-yl]pyrimidin-2-ylamino}ethyl)-5,5-dimethylimidazolidine-2,4-dione The title compound was prepared from N-(4-fluorophenyl)thiazol-2-amine and 2-chloro-5-fluoropyrimidine in a manner analogous to Example 291. MS (M+H)$^+$ 460.

Example 293

1-[2-(5-Bromo-4-{2-[3-(trifluoromethyl)phenylamino]thiazol-5-yl}pyrimidin-2-ylamino)ethyl]-5,5-dimethylimidazolidine-2,4-dione

(i) N-[3-(Trifluoromethyl)phenyl]thiazol-2-amine

The title compound was prepared from 1-[3-(trifluoromethyl)phenyl]thiourea in a manner analogous to Example 286, Step 1. MS (M+H)$^+$ 245.

(ii) 5-(5-Bromo-2-chloropyrimidin-4-yl)-N-(4-fluorophenyl)thiazol-2-amine 6.0 mL (6.3 mmol) of a 1.1 M solution of tBuLi in heptane was added to a stirred solution of 0.73 g (3.0 mmol) of N-[3-(trifluoromethyl)phenyl]thiazol-2-amine in 10 mL of THF at −78° C. The solution was stirred for 30 min and then 0.64 g (3.3 mmol) of 5-bromo-2-chloropyrimidine was added. The reaction solution was stirred for 30 min at −78° C., then quenched by addition of 1 mL of AcOH in 5 mL of MeOH. After warming to 0° C., solid 2,3-dichloro-5,6-dicyano-1,4-benzoquinone (1.4 g, 6 mmol) was added and the reaction mixture was stirred for 30 min. The reaction solution was then poured into 100 mL of a 0.5 M solution of sodium ascorbate, diluted with 300 mL of water and the crude product removed by filtration and washed repeatedly with water. The crude product was purified by flash chromatography eluting with a linear gradient of 30% EtOAc in hexane to 100% EtOAc to deliver the desired compound. MS (M+H)$^+$ 437.

(iii) 1-[2-(5-Bromo-4-{2-[3-(trifluoromethyl)phenylamino]thiazol-5-yl}pyrimidin-2-ylamino)ethyl]-5,5-dimethylimidazolidine-2,4-dione The title compound was prepared from 5-(5-bromo-2-chloropyrimidin-4-yl)-N-(4-fluoro-phenyl)thiazol-2-amine in a manner analogous to Example 280, Step 3. MS (M+H)$^+$ 572.

Example 294

1-{2-[5-Fluoro-4-(2-{(4-fluorophenyl)[2-(pyrrolidin-1-yl)ethyl]amino}thiazol-5-yl)pyrimidin-2-ylamino]ethyl}-5,5-dimethylimidazolidine-2,4-dione (i) N-(4-Fluorophenyl)-N-[2-(pyrrolidin-1-yl)ethyl]thiazol-2-amine A solution of 1.0 g (5.2 mmol) of N-(4-fluorophenyl)thiazol-2-amine in 25 mL of THF was treated with 10.3 mL (10.3 mmol) of a 1.0 M solution of NaHMDS in THF and 0.88 g (5.2 mmol) of 1-(2-chloroethyl)pyrrolidine hydrochloride and heated at reflux for 18 h. The reaction mixture was poured into 250 mL of EtOAc and extracted thrice with 1 M aqueous HCl. The combined acidic extracts were brought to pH 12 with a 10% (w/v) solution of $Na_2CO_3$ and extracted five times with $CHCl_3$. The combined organic extracts were dried over $MgSO_4$, filtered and concentrated in vacuo, and the crude product was purified by flash chromatography eluting with a linear gradient of neat EtOAc to 20% MeOH in EtOAc to deliver the desired compound. MS $(M+H)^+$ 292.

(ii) 5-(2-Chloro-5-fluoropyrimidin-4-yl)-N-(4-fluorophenyl)-N-[2-(pyrrolidin-1-yl)ethyl]thiazol-2-amine The title compound was prepared from N-(4-fluorophenyl)-N-[2-(pyrrolidin-1-yl)ethyl]-thiazol-2-amine in a manner analogous to Example 289, Step 3. MS $(M+H)^+$ 422.

(iii) 1-{2-[5-Fluoro-4-(2-{(4-fluorophenyl) [2-(pyrrolidin-1-yl)ethyl]amino}thiazol-5-yl)pyrimidin-2-ylamino]ethyl}-5,5-dimethylimidazolidine-2,4-dione The title compound was prepared from 5-(2-chloro-5-fluoropyrimidin-4-yl)-N-(4-fluoro-phenyl)-N-[2-(pyrrolidin-1-yl)ethyl]thiazol-2-amine in a manner analogous to Example 280, Step 3. MS $(M+H)^+$ 557.

Example 295

3-Benzyl-1-{2-[4-(5-iodothiophen-2-yl)pyrimidin-2-ylamino]ethyl)-5,5-dimethylimidazolidine-2,4-dione A suspension of 50 mg (0.11 mmol) of 1-{2-[4-(5-iodothiophen-2-yl)pyrimidin-2-ylamino]ethyl}-5,5-dimethylimidazolidine-2,4-dione, 22 mg (0.13 mmol) of sodium benzenesulfinate, 3 mg (0.0027 mmol) of $Pd_2$ $dba_3$, 3.5 mg (0.00547 mmol) of Xantphos, 71 mg (0.22 mmol) of cesium carbonate, 34 mg (0.109 mmol) of N-benzyl-tri-n-butylammonium chloride and 0.22 mL of a 1 M solution of tBuOK in tBuOH in 3 mL of toluene was heated to 110° C. in a microwave for 10 min. The toluene was removed in vacuo and the residue purified by C-8 prep HPLC to deliver the title compound. MS $(M+H)^+$ 548.

Example 296

(4-Fluorophenyl)(thiazol-2-yl)methanone 4-fluorobenzoyl chloride (3 mL, 25.4 mmol) was added to 2-(trimethylsilyl)thiazole (2 mL, 12.7 mmol) in dichloromethane (70 mL). The reaction mixture was stirred over night at rt. Dichloromethane was evaporated under reduced pressure, and the crude product purified on a normal phase silica-gel column with 0-40% ethyl acetate in hexane to afford the title compound as white amorphous solid (2.050 g, 77% yield); MS $(M+H)^+$ 208.

Example 297

1-(4-Fluorophenyl)-1-(thiazol-2-yl)ethanol

A solution of (4-fluorophenyl)(thiazol-2-yl)methanone (1.05 g, 5.07 mmol) in diethyl ether (50 mL) and was cooled to 0° C., treated with methylmagnesium bromide (1.85 mL, 3.0 M in $Et_2O$, 5.57 mmol) and stirred overnight at room temperature. The reaction was quenched with saturated ammonium chloride solution, extracted with diethyl ether (2×30 mL), washed with brine, dried over anhydrous magnesium sulfate, filtered and concentrated in vacuo to afford the title compound as an oily brown residue (1.052 g, 93% yield). MS $(M+H)^+$ 224.

Example 298

2-(1-(4-Fluorophenyl)ethyl)thiazole

A mixture of iodine (856 mg, 3.37 mmol), hypophosphorous acid (3.152 mL, 20.22 mmol) and acetic acid (40 mL) was heated to 60° C. until the reaction mixture became clear. 1-(4-fluorophenyl)-1-(thiazol-2-yl)ethanol (1.05 g, 5.07 mmol) was added to the solution and the reaction mixture was heated to 80° C. overnight. After cooling to rt, the reaction mixture was neutralized with concentrated sodium hydroxide and the crude product was extracted with chloroform, washed with brine, dried over anhydrous sodium sulfate, filtered and concentrated in vacuo. The crude product was purified by flash chromatography with 0-40% ethyl acetate in hexane to afford the title compound as an oily brown residue (351 mg, 50% yield). MS $(M+H)^+$ 208.

Example 299

5-Bromo-2-chloro-4-(2-(1-(4-fluorophenyl)ethyl)thiazole-5-yl)-pyrimidine

A solution of 2-(1-(4-fluorophenyl)ethyl)thiazole (200 mg, 0.966 mmol) in 5 mL of tetrahydrofuran was cooled to −78° C. and treated with tert-butyllithium (0.622 mL, 1.7 M solution in pentane, 1.06 mmol) added dropwise. 5-Bromo-2-chloropyrimidine (205.5 mg, 1.06 mmol) was added to the reaction mixture and stirred for another 30 min before quenching with 1 mL of acetic acid in 5 mL of methanol. 2,3-Dichloro-5,6-dicyano-1,4-benzoquinone (468 mg, 2.06 mmol) was added to the reaction after cooling to 0° C., stirred for 20 min, diluted with sodium ascorbate (0.5M, 100 mL) and water (300 mL). The crude product was extracted from the aqueous layer with chloroform (3×75 mL), dried over anhydrous sodium sulfate, filtered, and concentrated in vacuo. The crude product was purified by flash chromatography with 0-40% ethyl acetate in hexane to afford the title compound as a yellow amorphous solid (177 mg,). MS $(M+H)^+$ 398/400.

Example 300

1-(2-(1-(4-Fluorophenyl)ethyl)thiazol-5-yl)pyrimidin-2-ylamino)ethyl)-5,5-dimethylimidazolidine-2,4-dione Prepared in an analogous manner to Example 24. MS (M+H)+ 533/535.

Example 301

2-(4-Fluorobenzyl)thiazole

Prepared in an analogous manner to Example 298. MS (M+H)+ 194.

Example 302

5-Bromo-2-chloro-4-((4-fluorophenyl)thiazol-2-yl) methyl)pyrimidine

Prepared in an analogous manner to Example 299. MS (M+H)+ 384/386.

Example 303

1-(2-(5-Bromo-4-((4-fluorophenyl(thiazol-2-yl)methyl)pyrimidin-2-yl-amino)ethyl)-5,5-dimethylimidazolidine-2,4-dione Prepared in an analogous manner to Example 300. MS (M+H)+ 519/521.

Example 304

1-(5-(2-Chloro-5-fluoropyrimidin-4-yl)thiazol-2-yl)-1-(4-fluorophenyl)-ethanol

Prepared in an analogous manner to Example 299. MS (M+H)+ 354.

Example 305

1-(2-(5-Fluoro-4-(2-(1-(4-fluorophenyl)-1-hydroxyethyl)thiazol-5-yl)-pyrimidin-2-ylaminoethyl)-5,5-dimethylimidazolidine-2,4-dione Prepared in an analogous manner to Example 300. MS (M+H)+ 489.

Example 306

N-(4-Fluorophenyl)thiazol-2-amine 1-(4-fluorophenyl)thiourea (2.00 g, 11.7 mmol) and 2-chloroacetaldehyde (3.72 mL, 58.6 mmol) in anhydrous ethanol (5 mL) were added to a microwave vial. The reaction mixture was heated to 80° C. in a microwave reactor for 20 min. On cooling, ethyl acetate (2 mL) was added to the crude product reaction mixture and pure product crystallized out. This filtered off, washed with hexane and air-dried to afford the title compound as a crystalline brown solid, 1.568 g. MS (M+H)+ 195.

Example 307

3-((4-Fluorophenyl)(thiazol-2-yl)amino)propan-1-ol

A mixture of N-(4-fluorophenyl)thiazol-2-amine (6.00 g, 30.0 mmol), 3-chloropropanol (3.87 mL, 46.4 mmol), tetra-n-butylammonium hydrogensulfate (1.05 g, 3.09 mmol) in toluene (100 mL) and NaOH (40% w/v in water)(20 mL) was refluxed for 3 h. On cooling, the reaction mixture was diluted with EtOAc (100 mL), washed with water (4×100 mL), brine (100 mL), dried over anhydrous sodium sulphate, filtered and concentrated in vacuo. The crude product was purified by flash chromatography with 50-80% EtOAc in hexane to afford the title compound as a brown oil, 3.287 g. MS (M+H)+ 253.

Example 308

3-((5-(2-Chloro-5-fluoropyrimidin-4-yl)thiazol-2-yl (4-fluorophenyl)-amino)propan-1-ol 3-((5-(2-Chloro-5-fluoropyrimidin-4-yl)thiazol-2-yl(4-fluorophenyl)amino)propan-1-ol was prepared with 2 equivalents of tert-butyl lithium in a manner analogous to Example 299. MS (M+H)+ 383.

Example 309

1-(2-(5-Fluorophenyl)(3-hydroxypropyl)amino)thiazol-5-yl)pyrimidin-2-ylamino)ethyl)-5,5-dimethylimidazolidine-2,4-dione Prepared in an analogous manner to Example 300. MS (M+H)+ 518.

Example 310

1-(2-(5-Fluoro-4-(2-((4-fluorophenyl)(3-(piperazin-1-yl)propyl)amino)thiazol-5-yl)pyrimidin-2-ylamino)ethyl)-5,5-dimethylimidazolidine-2,4-dione 1-(2-(5-fluorophenyl)(3-hydroxypropyl)amino)thiazol-5-yl)pyrimidin-2-ylamino)ethyl)-5,5-dimethylimidazolidine-2,4-dione (325 mg, 0.628 mmol) in NMP (5 mL) at 0° C. was treated with methanesulfonyl chloride (280 mg, 0.386 mmol) and stirred for 3 h. piperazine (166.2 mg, 1.93 mmol) and NaI (20 mg) were added and the reaction was stirred at rt overnight. The crude reaction mixture was diluted with EtOAc (30 mL), washed with water (3×40 mL), dried over anhydrous sodium sulfate, concentrated in vacuo and purified by flash chromatography with 0-80% methanol in dichloromethane to afford the title compound as an amorphous light brown solid, 3.3 mg. MS (M+H)+ 586.

Example 311

1-(2-(5-Fluoro-4-(2-((4-fluorophenyl)(3-morpholinopropyl)amino)-thiazol-5-yl)pyrimidin-2-ylamino) ethyl)-5,5-dimethylimidazolidine-2,4-dione Prepared in an analogous manner to Example 310. MS (M+H)+ 587.

Example 312

1-(2-(4-(2-(Allyl(4-fluorophenyl)amino)thiazol-5-yl)-5-fluoropyrimidin-2-ylamino)ethyl)-5,5-dimethylimidazolidine-2,4-dione Isolated as a by-product of Example 311. MS (M+H)+ 500.

Example 313

5,5-dimethyl-1-(2-((4-(3-phenyl-2-thienyl)-2-pyrimidinyl)amino)ethyl)-2,4-imidazolidinedione

(i) 1-(3-Phenylthiophen-2-yl)ethanone and 1-(4-phenylthiophen-2-yl)ethanone A solution of 3-phenylthiophene (3.10 g, 19.3 mmol) and acetyl chloride (1.38 mL, 23.2 mmol) in dichloromethane (50 mL) was cooled to 0° C. Aluminium (III) chloride (2.58 g, 19.3 mmol) was added in several portions to control an otherwise vigorous exotherm. After addition was complete, the bath was removed and the reaction allowed to stir at ambient temperature for 2 h. The reaction mixture was then diluted with saturated aqueous $NaHCO_3$ and the layers were separated. The organic phase was washed with another portion of $NaHCO_3$ solution and brine. The resulting dichloromethane solution was concentrated in vacuo and the residue was purified by flash chromatography eluting with a gradient of 1-5% EtOAc/hexanes to afford 1.62 g (41% yield) of 1-(3-phenylthiophen-2-yl)ethanone and 1.13 g (29% yield) of 1-(4-phenylthiophen-2-yl)ethanone which were both spectroscpopically identical to literature compounds (See reference: Acta Chemica Scandinavica (1947-1973) 1970, 24, pp. 99-104.)

(ii) 3-(Dimethylamino)-1-(3-phenylthiophen-2-yl) prop-2-en-1-one 1-(3-Phenylthiophen-2-yl)ethanone was dissolved in dimethylformamide dimethyl acetal (6.0 mL) and heated to 100° C. for 40 h. The temperature was reduced to 90° C. and heating continued for an additional 60 h after which the mixture was concentrated in vacuo to provide the crude vinylogous amide in quantitative yield. MS $(M+H)^+$ 258.

(iii) 5,5-Dimethyl-1-(2-((4-(3-phenyl-2-thienyl)-2-pyrimidinyl)amino)ethyl)-2,4-imidazolidinedione A flask charged with 3-(dimethylamino)-1-(3-phenylthiophen-2-yl)prop-2-en-1-one (52 mg, 0.20 mmol), 1-(2-(5,5-dimethyl-2,4-dioxoimidazolidin-1-yl)ethyl)guanidine hydrochloride (100 mg, 0.40 mmol) and sodium hydroxide (40 mg, 1.0 mmol) and IPA (3.0 mL) was heated to reflux under nitrogen. After 18 h, the reaction mixture was allowed to cool and then diluted with dichloromethane and water. The organic layer was separated and washed with one portion of water and two portions of brine. The organics were then concentrated and the residue purified by preparative TLC eluted with 3% MeOH/dichloromethane to afford the product (27 mg, 0.066 mmol, 33% yield). MS $(M+H)^+$ 408.

Example 314

5,5-Dimethyl-1-(2-((4-(4-phenyl-2-thienyl)-2-pyrimidinyl)amino)ethyl)-2,4-imidazolidinedione Prepared from 1-(4-phenylthiophen-2-yl)ethanone, the other regioisomeric product isolated in Example 313 step (i), in a fashion analogous to Example 313. MS $(M+H)^+$ 408.

Example 315

1-(2-(4-(5-(4-Fluorophenylsulfonyl)-3-phenylthiophen-2-yl)pyrimidin-2-ylamino)ethyl)-5,5-dimethylimidazolidine-2,4-dione

(i) 2-(1,1-Dimethoxyethyl)-3-phenylthiophene 1-(4-Phenylthiophen-2-yl)ethanone (1.33 g, 6.57 mmol) was dissolved in MeOH and treated with trimethylorthoformate (1.44 mL, 13.2 mmol) and p-toluenesulfonic acid monohydrate (0.050 g). The resulting solution was stirred at ambient temperature for 16 h at which time the solution was partitioned between $Et_2O$ and saturated aqueous $NaHCO_3$ solution. The organic phase was separated and washed with two portions of water and three portions of brine, then dried over $Na_2SO_4$ and concentrated in vacuo. The resulting white semi-solid was used without further purification. MS $(M+H)^+$ 249.

(ii) 1-(5-(4-Fluorophenylthio)-3-phenylthiophen-2-yl)ethanone

Under an inert atmosphere in a round-bottomed flask equipped with a septum and a magnetic stir bar, 2-(1,1-dimethoxyethyl)-3-phenylthiophene (1.60 g, 6.44 mmol) was dissolved in THF (30 mL) and the solution was cooled to −78° C. before dropwise addition of 2.5 M n-BuLi (3.1 mL, 7.7 mmol). The reaction mixture was maintained at −78° C. for 1 h and then neat 1,2-bis(4-fluorophenyl)disulfane (1.5 mL, 7.7 mmol) was added in portions via syringe [reagent prepared by stirring an ethanolic solution of 4-fluorobenzenethiol and excess potassium carbonate in an open flask for 24 h followed by concentration in vacuo and drying over $MgSO_4$]. After 20 min the reaction mixture was allowed to warm to ambient temperature and treated with saturated aqueous $NaHCO_3$ and $Et_2O$. The organic layer was separated and washed with saturated aqueous $NaHCO_3$, $H_2O$, and brine. The organic solvents were removed in vacuo and then the residue dissolved in $CHCl_3$ (30 mL). The solution was treated with 5% TFA/$H_2O$ (10 mL) and stirred vigorously for 1 h. The reaction mixture was partitioned between $CH_2Cl_2$ and $H_2O$, then the organic layer was separated and washed with saturated aqueous $NaHCO_3$, $H_2O$, and brine. The solution was dried over $Na_2SO_4$ and concentrated to afford 1-(5-(4-fluorophenylthio)-3-phenylthiophen-2-yl)ethanone (2.02 g, 95% yield) as a yellow oil. MS $(M+H)^+$ 329.

(iii) 1-(2-(4-(5-(4-Fluorophenylthio)-3-phenylthiophen-2-yl)pyrimidin-2-ylamino)-ethyl)-5,5-dimethylimidazolidine-2,4-dione Prepared from 1-(5-(4-fluorophenylthio)-3-phenylthiophen-2-yl)ethanone in a fashion analogous to Example 313. MS $(M+H)^+$ 534.

(iv) 1-(2-(4-(5-(4-Fluorophenylsulfonyl)-3-phenylthiophen-2-yl)pyrimidin-2-ylamino)-ethyl)-5,5-dimethylimidazolidine-2,4-dione 1-(2-(4-(5-(4-Fluorophenylthio)-3-phenylthiophen-2-yl) pyrimidin-2-ylamino)ethyl)-5,5-dimethylimidazolidine-2,4-dione (0.100 g, 0.188 mmol) was dissolved in acetone (3.0 mL) and treated with a solution of Oxone™ (0.346 g, 0.563 mmol) in $H_2O$ (1.5 mL). The reaction mixture was allowed to stir at ambient temperature overnight and then diluted with 10 mL $H_2O$. The suspension was filtered and the precipitate washed with additional portions of H₂O. The solid was air-dried and then purified by flash chromatography, eluted with 1-10% MeOH/dichloromethane to afford the product as a bright yellow solid. MS (M+H)⁺ 566.

Example 316

1-(2-(4-(3-Iodothiophen-2-yl)pyrimidin-2-ylamino) ethyl)-5,5-dimethyl-imidazolidine-2,4-dione Prepared from 3-iodothiophene in a fashion analogous to Example 313. MS (M+H)⁺ 458.

Example 317

1-(2-(4-(3-bromophen-2-yl)pyrimidin-2-ylamino) ethyl)-5,5-dimethyl-imidazolidine-2,4-dione Prepared from 3-bromothiophene in a fashion analogous to Example 313. MS (M+H)⁺ 410/412.

Example 318

1-(2-(4-(3-(4-methoxyphenyl)thiophen-2-yl)pyrimidin-2-ylamino)ethyl)-5,5-dimethylimidazolidine-2,4-dione (i) 1-(3-(4-methoxyphenyl)thiophen-2-yl)ethanone A flask was charged with 1-(3-bromothiophen-2-yl)ethanone (1.00 g, 4.88 mmol), 4-methoxyphenylboronic acid (0.740 g, 4.88 mmol), tetrakis(triphenylphosphine)palladium (0) (0.17 g, 0.15 mmol), dimethoxyethane (50 mL), and 2 N aqueous Na₂CO₃ (7.3 mL) and then warmed to 80° C. for 7 h. At that time the reaction mixture was poured into H₂O and extracted with EtOAc. The organic phase was separated and washed with brine, dried over Na₂SO₄ and concentrated in vacuo. The resulting residue was purified via flash chromatography, eluting with 5-15% EtOAc/hexanes to afford the product (0.50 g, 2.2 mmol). MS (M+H)⁺ 233.

(ii) 1-(2-(4-(3-(4-Methoxyphenyl)thiophen-2-yl) pyrimidin-2-ylamino)ethyl)-5,5-dimethylimidazolidine-2,4-dione 1-(3-(4-Methoxyphenyl)thiophen-2-yl)ethanone was converted to 1-(2-(4-(3-(4-methoxyphenyl)thiophen-2-yl)pyrimidin-2-ylamino)ethyl)-5,5-dimethylimidazolidine-2,4-dione using procedures analogous to those in Example 313. MS (M+H)⁺ 438.

Example 319

5,5-Dimethyl-1-(2-(4-(3-methylthiophen-2-yl)pyrimidin-2-ylamino)-ethyl)imidazolidine-2,4-dione 1-(3-Methylthiophen-2-yl)ethanone was converted to 5,5-dimethyl-1-(2-(4-(3-methylthiophen-2-yl)pyrimidin-2-ylamino)ethyl)imidazolidine-2,4-dione using procedures analogous to those in Example 313. MS (M+H)⁺ 346.

Example 320

1-(2-(4-(3,4-Dibromothiophen-2-yl)pyrimidin-2-ylamino)ethyl)-5,5-dimethylimidazolidine-2,4-dione 3,4-Dibromothiophene was converted to 1-(2-(4-(3,4-Dibromothiophen-2-yl)pyrimidin-2-ylamino)ethyl)-5,5-dimethylimidazolidine-2,4-dione using procedures analogous to those in Example 313. MS (M+H)⁺ 488.

Example 321

1-(2-(4-(4-Bromo-3-phenylthiophen-2-yl)pyrimidin-2-ylamino)ethyl)-5,5-dimethylimidazolidine-2,4-dione 1-(3,4-Dibromothiophen-2-yl)ethanone was converted to 1-(4-bromo-3-phenylthiophen-2-yl)ethanone using the procedure described in Example 318, Step 1. This compound was further elaborated into 1-(2-(4-(4-bromo-3-phenylthiophen-2-yl)pyrimidin-2-ylamino)-ethyl)-5,5-dimethylimidazolidine-2,4-dione using procedures analogous to those in Example 313. MS (M+H)⁺ 486/488.

Example 322

1-(2-(4-(3-(3-Hydroxyphenyl)thiophen-2-yl)pyrimidin-2-ylamino)ethyl)-5,5-dimethylimidazolidine-2,4-dione A sealed reaction vessel charged with 1-(2-(4-(3-Bromophen-2-yl)pyrimidin-2-ylamino)-ethyl)-5,5-dimethylimidazolidine-2,4-dione (50 mg, 0.12 mmol), 3-hydroxyphenylboronic acid (34 mg, 0.24 mmol), tetrakis (triphenylphosphine)palladium(0) (5.0 mg, 0.0060 mmol), dimethoxyethane/EtOH/H2O (7:2:3, 1.25 mL), and 2 N aqueous Na₂CO₃ (0.18 mL) was heated to 155° C. for 20 min in a Personal Chemistry microwave reactor. Upon completion, the reaction mixture was poured into H₂O and extracted with EtOAc. The organic phase was separated and washed with brine, dried over Na₂SO₄ and concentrated in vacuo. The resulting residue was purified by preparative thin-layer chromatography, eluting with 5% MeOH/dichloromethane to afford the product as a white solid. MS (M+H)⁺ 424.

Example 323

2-(2-((2-(5,5-Dimethyl-2,4-dioxo-1-imidazolidinyl) ethyl)amino)-4-pyrimidinyl)-3-thiophenecarbonitrile A round-bottomed flask equipped with a nitrogen inlet and a reflux condenser was charged with 1-(2-(4-(3-bromothiophen-2-yl)pyrimidin-2-ylamino)ethyl)-5,5-dimethylimidazol-idine-2,4-dione (50 mg, 0.12 mmol), copper (I) cyanide (33 mg, 0.36 mmol), and dry DMF (2 mL). The reaction mixture was heated to reflux (bath temperature 160° C.). After 4 h, the reaction vessel was removed from the oil bath and allowed to cool to approximately 70° C. and poured into a stirring suspension of iron (III) chloride (0.28 g, 1.70 mmol) in 1.7 N aqueous HCl (5.0 mL). The combined mixture was maintained at 60-70° C. for 30 min at which time the mixture was allowed to cool to ambient temperature and extracted with three 15 mL portions of dichloromethane. The combined extracts were washed with two 40 mL portions of 6 N aqueous HCl, saturated aqueous NaHCO₃, and H₂O, then dried over Na₂SO₄ and concentrated. Chromatographic purification by preparative TLC, eluting with 8% MeOH/dichloromethane, and subsequent crystallization from EtOAc afforded the product as a white solid. MS (M+H)⁺ 357.

Example 324

5,5-Dimethyl-1-(2-((4-(3-(trifluoromethyl)-2-thienyl)-2-pyrimidinyl)amino)ethyl)-2,4-imidazolidinedione A sealed tube charged with 1-(2-(4-(3-iodothiophen-2-yl)pyrimidin-2-ylamino)ethyl)-5,5-dimethylimidazolidine-2,4-dione (0.300 g, 0.656 mmol), copper (I) iodide (0.275 g, 1.44 mmol), spray-dried potassium fluoride (0.075 g, 1.3 mmol), triethyl(trifluoromethyl)silane (0.25 mL, 1.3 mmol), DMF (1.0 mL), and NMP (1.0 mL) was heated to 80° C. and allowed to stir for 72 h. At that time, the mixture was diluted with 20 mL dichloromethane and filtered. The pale green filtrate was then purified through Celite and the plug was washed with 10% MeOH/dichloromethane and $H_2O$. The organic solvents were removed from the biphasic mixture in vacuo and the aqueous residue was then partitioned between dichloromethane and $H_2O$. The organic phase was separated, concentrated and the residue purified by flash chromatography, eluting with 1-6% MeOH/dichloromethane to afford the product as a white solid. MS $(M+H)^+$ 400.

Example 325

5-(2-((2-(5,5-Dimethyl-2,4-dioxo-1-imidazolidinyl)ethyl)amino)-4-pyrimidinyl)-4-phenyl-3-thiophenecarbonitrile 1-(2-(4-(4-Bromo-3-phenylthiophen-2-yl)pyrimidin-2-ylamino)ethyl)-5,5-dimethylimid-azolidine-2,4-dione prepared in Example 321 was converted to 5-(2-((2-(5,5-dimethyl-2,4-dioxo-1-imidazolidinyl)ethyl)amino)-4-pyrimidinyl)-4-phenyl-3-thiophenecarbonitrile by the same method used in Example 323. MS $(M+H)^+$ 433.

Example 326

5-(2-((2-(5,5-Dimethyl-2,4-dioxo-1-imidazolidinyl)ethyl)amino)-4-pyrimidinyl)-4-(4-fluorophenyl)-2-((4-fluorophenyl)sulfanyl)-3-thiophenecarbonitrile (i) Bis(4-fluorophenyl)carbonotrithioate 4-Fluorobenzenethiol (5.00 mL, 46.7 mmol) was added to a stirred suspension of thiocarbonyldiimidazole (4.16 g, 23.5 mmol) in THF (30 mL). The mixture was heated to reflux for 2 h, then cooled to room temperature and partitioned between EtOAc and $H_2O$. The organic layer was washed with $H_2O$ and brine and dried over $Na_2SO_4$. The organic solvents were removed in vacuo to afford an orange oil which crystallized on standing. MS $(M+H)^+$ 298.

(ii) 4-Fluorophenyl 2-cyano-3-(4-fluorophenyl)-3-oxopropanedithioate

Trithiocarbonate (0.644 g, 2.15 mmol) from step (i) was added to a stirred suspension of sodium hydride (0.165 g, 0.412 mmol) in benzene (2.0 mL). Then, 3-(4-fluorophenyl)-3-oxopropanenitrile (0.320 g, 1.96 mmol) was added as a solution in benzene (2.0 mL). The reaction mixture was stirred for 5 min then DMF (2.0 mL) was added slowly. After addition was complete the reaction mixture was heated to reflux for 30 min and then allowed to cool to ambient temperature before being partitioned between $H_2O$ and $Et_2O$. The aqueous layer was separated and washed with two additional portions of $Et_2O$, then acidified with aqueous 2 N HCl. The acidic aqueous layer was then extracted with two portions of EtOAc, which were combined, washed with brine, dried over $Na_2SO_4$, and concentrated. The residue was purified by flash chromatography, eluting with a gradient of 25-100% EtOAc/hexanes to afford the product as a yellow solid (0.20 g, 0.60 mmol, 31% yield). MS $(M-H)^-$ 332.

(iii) 5-Acetyl-4-(4-fluorophenyl)-2-(4-fluorophenylthio)thiophene-3-carbonitrile Chloroacetone (0.100 mL, 1.26 mmol) was added dropwise to a stirred suspension of potassium carbonate (0.210 g, 1.52 mmol) and 4-fluorophenyl 2-cyano-3-(4-fluorophenyl)-3-oxopropanedithioate (0.20 g, 0.60 mmol) from step (ii) in DMF (2.5 mL). The reaction temperature was raised to 50° C. for 50 min. The reaction mixture was then diluted with $Et_2O$ and $H_2O$. The organic layer was separated and washed with $H_2O$ and brine, dried over $Na_2SO_4$, and concentrated. The residue was purified by flash chromatography, eluting with a gradient of 0.75-15% EtOAc/hexanes to afford the product as a yellow oil (102 mg, 0.27 mmol, 46% yield). MS (M–H)- 370.

(iv) 5-(2-((2-(5,5-Dimethyl-2,4-dioxo-1-imidazolidinyl)ethyl)amino)-4-pyrimidinyl)-4-(4-fluorophenyl)-2-((4-fluorophenyl)sulfanyl)-3-thiophenecarbonitrile 5-Acetyl-4-(4-fluorophenyl)-2-(4-fluorophenylthio)thiophene-3-carbonitrile from step (iii) was converted to the final product using procedures analogous to those in Example 313. MS $(M+H)^+$ 577.

Example 327

1-(2-(5-Bromo-4-(5-chloro-4-((dimethylamino)methyl)thiophen-2-yl)pyrimidin-2-ylamino)ethyl)-5,5-dimethylimidazolidine-2,4-dione (i) (2-Chlorothiophen-3-yl)methanol 2-Chlorothiophene-3-carboxylic acid (0.835 g) obtained from 3-bromo-2-chlorothiophene by an established literature procedure (*Journal of Heterocyclic Chemistry* 1976, 13, p. 1099) was dissolved in THF (5.00 mL). The stirred solution was cooled to 0° C. and treated with a slow addition of borane in THF (1.0 M, 6.68 mL, 6.68 mmol). The reaction was allowed to warm to ambient temperature overnight. After a total of 16 h, the reaction mixture was treated with MeOH (10 mL) and allowed to stir for an additional hour. The solvents were removed in vacuo and the residue concentrated twice more from methanolic solution. Purification by flash chromatography, eluting with a gradient of 10-50% EtOAc/hexanes, afforded the product as a colorless oil (0.698 g, 4.72 mmol, 92% yield). MS $(M-OH)^+$ 131.

(ii) (2-Chlorothiophen-3-yl)-N,N-dimethylmethanamine (2-Chlorothiophen-3-yl)methanol (0.698 g, 4.72 mmol) from step (i) was dissolved in THF (5.0 mL) and treated successively with p-toluenesulfonyl chloride (0.989 g, 5.19 mmol), and triethylamine (0.79 mL, 5.66 mmol). The reaction was allowed to stir for 18 h at ambient temperature at which time dimethylamine (2 M in THF, 4.72 mL, 9.44 mL) was added to the reaction mixture. The increasingly cloudy suspension was stirred for 2 h before being partitioned between $Et_2O$ and saturated aqueous $NaHCO_3$. The organic layer was washed with H$_2$O and brine, then dried over Na$_2$SO$_4$ and concentrated in vacuo. The residue was purified by flash chromatography to afford the pure amine as a colorless oil (0.512 g, 2.91 mmol, 62% yield). MS (M+H)$^+$ 176.

(iii) 1-(2-(5-Bromo-4-(5-chloro-4-((dimethylamino) methyl)thiophen-2-yl)pyrimidin-2-ylamino)ethyl)-5, 5-dimethylimidazolidine-2,4-dione (2-Chlorothiophen-3-yl)-N,N-dimethylmethanamine from step (ii) was converted to the final product using procedures analogous to those in Example 24. MS (M+H)$^+$ 501/503.

Example 328

1-(2-((5-Bromo-4-(5-bromo-4-(2-(dimethylamino) ethyl)-2-thienyl)-2-pyrimidinyl)amino)ethyl)-5,5-dimethyl-2,4-imidazolidinedione (i) 2-(2-Bromothiophen-3-yl)acetonitrile Perchloric acid (0.025 mL, 0.28 mmol) was added to a rapidly stirring suspension of N-bromosuccinimide (5.06 g, 28.4 mmol) and 2-(thiophen-3-yl)acetonitrile (3.50 g, 28.4 mmol) in carbon tetrachloride (15 mL). After 4 h at room temperature, the reaction mixture was treated with solid NaHCO$_3$ (100 mg, 1.2 mmol), then filtered and concentrated. The residue was purified by chromatography, eluting with a gradient of 2-15% EtOAc/hexanes to afford pure 2-(2-bromothiophen-3-yl)acetonitrile as a pale green oil (2.44 g, 12.1 mmol, 43% yield). MS (M+H)$^+$ 202/204.

(ii) 2-(2-Bromothiophen-3-yl)ethanamine 2-(2-Bromothiophen-3-yl)acetonitrile (1.44 g, 7.13 mmol) was added slowly to a stirred solution of borane in THF (1.0 M, 15.7 mL, 15.7 mmol). The mixture was then heated to reflux for 14 h. The reaction mixture was allowed to cool to ambient temperature before residual borane was destroyed by careful dropwise addition of MeOH (10 mL). After the quench was complete, HCl gas was bubbled through the solution for 20 min and then the solvent was removed in vacuo. The residue was dissolved again in MeOH (20 mL) and concentrated twice more. The resulting white solid was dissolved in a biphasic mixture of dichloromethane and 1 N aqueous NaOH. The organic layer was separated, washed with brine, dried and concentrated to a colorless oil (1.34 g, 6.50 mmol, 92% yield). MS (M+H)$^+$ 206/208.

(iii) 2-(2-Bromothiophen-3-yl)-N,N-dimethylethanamine

Primary amine (1.34 g, 6.50 mmol) from step (ii) was dissolved in THF (14 mL) and treated with formaldehyde (37% aqueous, 1.46 mL, 19.5 mmol). Sodium triacetoxyborohydride (4.13 g, 19.5 mmol) was added to the stirred solution in portions so as to minimize effervescence and exotherm. 5 min after addition of the hydride was complete, the reaction was diluted with saturated aqueous NaHCO$_3$. The phases were separated and the aqueous layer was extracted with three portions of Et$_2$O. The combined organic layers were washed with brine, dried over Na$_2$SO$_4$, and concentrated. The residue was dissolved in MeOH (4 mL) and the solution was applied to pre-packed SCX ion exchange resin cartridges (4×5 g) which had been previously conditioned with MeOH followed by water. The resin was washed with water (10 mL) followed by MeOH (20 mL), and the product was then eluted with 2 M NH$_3$ in MeOH (20 mL). The combined fractions of pure product were concentrated in vacuo to afford the product as a colorless oil. (1.12 g, 4.78 mmol, 74% yield). MS (M+H)$^+$ 234/236.

(iv) 1-(2-((5-Bromo-4-(5-bromo-4-(2-(dimethylamino)ethyl)-2-thienyl)-2-pyrimidinyl)amino) ethyl)-5,5-dimethyl-2,4-imidazolidinedione 2-(2-Bromothiophen-3-yl)-N,N-dimethylethanamine from step (iii) was converted to the final product using procedures analogous to those in Example 24. MS (M+H)$^+$ 559/561/563.

Example 329

1-(2-((5-Bromo-4-(5-chloro-4-(2-(dimethylamino) ethyl)-2-thienyl)-2-pyrimidinyl)amino)ethyl)-5,5-dimethyl-2,4-imidazolidinedione (i) 2-(2-Chlorothiophen-3-yl)acetonitrile Perchloric acid (0.070 mL, 0.81 mmol) was added to a rapidly stirring suspension of N-chlorosuccinimide (10.8 g, 81.2 mmol) and 2-(thiophen-3-yl)acetonitrile (10.0 g, 81.2 mmol) in carbon tetrachloride (40 mL). After 3 h at room temperature, the reaction mixture was treated with solid NaHCO$_3$ (300 mg, 3.6 mmol), then filtered and concentrated. The residue was purified by chromatography, eluting with a gradient of 5-15% EtOAc/hexanes to afford pure 2-(2-chlorothiophen-3-yl)acetonitrile as a pale yellow oil (4.23 g, 26.8 mmol, 33% yield). MS (M+H)$^+$ 158/160.

(ii) 1-(2-((5-Bromo-4-(5-chloro-4-(2-(dimethylamino)ethyl)-2-thienyl)-2-pyrimidinyl)amino) ethyl)-5,5-dimethyl-2,4-imidazolidinedione 2-(2-Chlorothiophen-3-yl)-N,N-dimethylethanamine from step (i) was converted to the final product using procedures analogous to those in Example 328. MS (M+H)$^+$ 515/517.

Example 330

1-(2-(5-Bromo-4-(3-iodothiophen-2-yl)pyrimidin-2-ylamino)ethyl)-5,5-dimethylimidazolidine-2,4-dione 3-Iodothiophene was converted to the final product using procedures analogous to those in Example 24. MS (M+H)$^+$ 536/538.

Example 331

1-(2-(5-Bromo-4-(4-iodothiophen-2-yl)pyrimidin-2-ylamino)ethyl)-5,5-dimethylimidazolidine-2,4-dione Prepared as a mixture with 1-(2-(5-bromo-4-(3-iodothiophen-2-yl)pyrimidin-2-ylamino)ethyl)-5,5-dimethylimidazolidine-2,4-dione in Example 329 and separated by HPLC. MS (M+H)$^+$ 536/538.

Example 332

1-(2-(4-(3-Bromo-5-chlorothiophen-2-yl)pyrimidin-2-ylamino)ethyl)-5,5-dimethylimidazolidine-2,4-dione (i) 2,3-Dibromo-5-chlorothiophene A solution of 2,3-dibromothiophene (7.23 g, 29.9 mmol) in carbon tetrachloride (15.0 mL) was treated with N-chlorosuccinimide (4.79 g, 35.9 mmol) and 70% perchloric acid (0.26 mL, 3.0 mmol). The reaction mixture was stirred at ambient temperature for 96 h, then treated with solid NaHCO$_3$ (1.0 g, 12 mmol) and filtered. The filter cake was washed with dichloromethane and the combined organic fractions were concentrated in vacuo. The residue was loaded onto a silica plug (100 g SiO$_2$, 8 cm diameter) and eluted with hexanes. The product was isolated as a 7.7:1 mixture with the starting material. $^1$H NMR: δ (CDCl$_3$, 400 MHz) 6.77 (1H, s).

(ii) 1-(2-(4-(3-Bromo-5-chlorothiophen-2-yl)pyrimidin-2-ylamino)ethyl)-5,5-dimethylimidazolidine-2,4-dione 2,3-Dibromo-5-chlorothiophene from step (i) was converted to the final product using procedures analogous to those in Example 24. MS (M+H)$^+$ 444/446.

Example 333

1-(2-(4-(5-(4-Fluorobenzyl)-4-(2-(pyrrolidin-1-yl)ethyl)thiophen-2-yl)-5-bromopyrimidin-2-ylamino)ethyl)-5,5-dimethylimidazolidine-2,4-dione (i) 1-(2-(thiophen-3-yl)ethyl)pyrrolidine A stirred solution of 1-(2-(thiophen-3-yl)ethyl)pyrrolidine (8.74 mL, 78.0 mmol) and p-toluenesulfonyl chloride (14.9 g, 78.0 mmol) in dichloromethane (100 mL) was cooled to 0° C. and treated with triethylamine (13.1 mL, 94.0 mmol). After 15 min the reaction mixture was allowed to warm to ambient temp and stirred for an additional 5 h before addition of pyrrolidine (14.3 mL, 172 mmol) in one portion. The resulting suspension was then stirred for another 16 h and then partitioned between H$_2$O and dichloromethane. The aqueous phase was acidified to pH 1 using concentrated aqueous HCl. The organic phase was further extracted with three portions of 1 N aqueous HCl. The combined aqueous layers were then treated with 10 N aqueous NaOH in order to raise the pH of the solution above 12. The basic aqueous solution was then extracted with three portions of dichloromethane, dried over MgSO$_4$, and concentrated in vacuo. The residue was purified by flash chromatography, eluting with 1-5% (0.5 M ammonia in MeOH)/dichloromethane to afford the product as a colorless oil (7.1 g, 39 mmol, 50% yield). MS (M+H)$^+$ 182.

(ii) (4-Fluorophenyl)(3-(2-(pyrrolidin-1-yl)ethyl)thiophen-2-yl)methanol

A solution of 1-(2-(thiophen-3-yl)ethyl)pyrrolidine (1.0 g, 5.5 mmol) in THF (11.0 mL) was cooled to −78° C. in a dry-ice acetone bath before dropwise addition of n-butyllithium solution (2.5 M in hexanes, 2.4 mL, 6.0 mmol). The reaction mixture was stirred at −78° C. for 1 h and then neat p-fluorobenzaldehyde (0.65 mL, 6.1 mmol) was added dropwise via syringe. The mixture was allowed to warm to room temperature over 16 h and subsequently diluted with saturated aqueous NaHCO$_3$ and EtOAc. The organic layer was separated, washed with brine, and dried over Na$_2$SO$_4$. The residue remaining after solvent removal in vacuo was purified by flash chromatography to afford the desired alkylation product as a white solid (353 mg, 1.16 mmol, 21% yield). MS (M+H)$^+$ 306.

(iii) 1-(2-(2-(4-Fluorobenzyl)thiophen-3-yl)ethyl)pyrrolidine (4-Fluorophenyl)(3-(2-(pyrrolidin-1-yl)ethyl)thiophen-2-yl)methanol from step (ii) was reduced with trimethylsilyliodide in accordance with published procedure (See reference: *Tetrahedron* 1995, 51 (41), 11043-11062.) A dry three-necked flask equipped with an addition funnel and a nitrogen inlet was charged with sodium iodide (0.87 g, 5.8 mmol) and acetonitrile (5.0 mL). Then, chlorotrimethylsilane (0.73 mL, 5.8 mmol) was added via syringe and the reaction mixture was allowed to stir at ambient temperature for about 15 min. At that time, the bright yellow mixture was cooled to 0° C. and a solution of (4-fluorophenyl)(3-(2-(pyrrolidin-1-yl)ethyl)thiophen-2-yl)methanol (353 mg, 1.16 mmol) in acetonitrile (5 mL) was added dropwise over the course of an hour. The reaction mixture was allowed to warm to room temperature over 16 h and then cooled back down below 5° C. before work-up. A solution of NaOH (5 N, 1.5 mL, 7.5 mmol) was added and the reaction mixture cooled to rt before it was diluted with EtOAc and stirred for an additional 10 min. The layers were separated and the aqueous layer extracted with another portion of EtOAc. The combined organic layers were washed with a solution of saturated aqueous Na$_2$S$_2$O$_3$.5H$_2$O, water, and brine, dried over MgSO$_4$, and concentrated. The resulting residue was purified by flash chromatography, eluting with 1-10% (0.5 M ammonia in MeOH)/dichloromethane to afford the product as a pale yellow oil (160 mg, 0.56 mmol, 48% yield). MS (M+H)$^+$ 290.

(iv) 1-(2-(4-(5-(4-Fluorobenzyl)-4-(2-(pyrrolidin-1-yl)ethyl)thiophen-2-yl)-5-bromopyrimidin-2-ylamino)ethyl)-5,5-dimethylimidazolidine-2,4-dione 1-(2-(2-(4-Fluorobenzyl)thiophen-3-yl)ethyl)pyrrolidine from step (iii) was converted to the final product using procedures analogous to those in Example 24. MS (M+H)$^+$ 615/617.

Example 334

1-(2-(5-Bromo-4-(5-chloro-4-(2-(pyrrolidin-1-yl)ethyl)thiophen-2-yl)pyrimidin-2-ylamino)ethyl)-5,5-dimethylimidazolidine-2,4-dione (i) 1-(2-(2-Chlorothiophen-3-yl)ethyl)pyrrolidine A solution of 2-(2-chlorothiophen-3-yl)ethanamine hydrochloride (3.00 g, 15.1 mmol, prepared as described in Example 329) in acetonitrile (30 mL) was treated with anhydrous potassium carbonate (7.50 g, 54.3 mmol), sodium iodide (5.45 g, 36.4) and 1,4-dibromo-butane (2.2 mL, 18 mmol). The resulting suspension was heated to reflux for 18 h, then cooled, filtered and concentrated to a dark brown oil. Purification by flash chromatography eluting with 1-5% (0.5 M ammonia in MeOH)/dichloromethane afforded the product as a colorless oil (0.45 g, 2.09 mmol, 14% yield). MS (M+H)$^+$ 216.

(ii) 1-(2-(5-Bromo-4-(5-chloro-4-(2-(pyrrolidin-1-yl)ethyl)thiophen-2-yl)pyrimidin-2-ylamino)ethyl)-5,5-dimethylimidazolidine-2,4-dione 1-(2-(2-Chlorothiophen-3-yl)ethyl)pyrrolidine from step (i) was converted to the final product using procedures analogous to those in Example 24. MS (M+H)$^+$ 541/543.

Example 335

1-(2-(4-(5-(4-Fluorobenzyl)thiazol-2-yl)-5-bromopyrimidin-2-ylamino)ethyl)-5,5-dimethylimidazolidine-2,4-dione (i) (4-Fluorophenyl)(thiazol-5-yl)methanol A solution of 2-(trimethylsilyl)thiazole (6.12 g, 38.9 mmol) in THF (80 mL) was cooled to −78° C. and treated with a dropwise addition of "BuLi (2.5 M in hexanes, 15.6 mL, 39.0 mmol). The reaction mixture was stirred at −78° C. for 1 h before 4-fluorobenzaldehyde (4.59 mL, 42.8 mmol) was added dropwise. The stirred suspension was allowed to warm gradually to room temperature over 16 h, then treated with 100 mL of saturated aqueous ammonium chloride and 100 mL of EtOAc. The organic layer was washed with water and brine, dried over $Na_2SO_4$, and concentrated. The residue was purified by flash chromatography, eluting with a gradient of 10-50% EtOAc/hexanes to afford the product as a white solid (4.09 g, 19.5 mmol, 50% yield). MS (M+H)$^+$ 210.

(ii) 5-(4-Fluorobenzyl)thiazole (4-Fluorophenyl)(thiazol-5-yl)methanol from step (i) was reduced with trimethylsilyliodide using a slight modification of published procedure (See reference: *Tetrahedron* 1995, 51 (41), 11043-11062.) A dry three-necked flask equipped with an addition funnel and a nitrogen inlet was charged with sodium iodide (6.78 g, 47.8 mmol) and acetonitrile (10 mL). Then, chlorotrimethylsilane (6.0 mL, 48 mmol) was added via syringe and the reaction mixture was allowed to stir at ambient temperature for about 15 min. At that time, the bright yellow mixture was cooled to 0° C. and a solution of (4-fluorophenyl)(thiazol-5-yl)methanol (2.00 g, 9.56 mmol) in acetonitrile (40 mL) and dichloromethane (50 mL) was added dropwise over the course of an hour. The reaction mixture was allowed to warm to room temperature over 16 h and then heated to 40° C. for 72 h. Then the solution was cooled back down to 5° C. for work-up. A solution of NaOH (5 N, 10 mL, 50 mmol) was added and the reaction mixture cooled to rt before it was diluted with EtOAc and stirred for an additional 10 min. The layers were separated and the aqueous layer extracted with another portion of EtOAc. The combined organic layers were washed with a solution of saturated aqueous $Na_2S_2O_3.5H_2O$, water, and brine, dried over $MgSO_4$, and concentrated. The resulting residue was purified by flash chromatography, eluting with 10-30% EtOAc/hexanes to afford the product (1.26 g, 6.50 mmol, 68% yield). MS (M+H)$^+$ 194.

(iii) 1-(2-(4-(5-(4-Fluorobenzyl)thiazol-2-yl)-5-bromopyrimidin-2-ylamino)ethyl)-5,5-dimethylimidazolidine-2,4-dione 5-(4-Fluorobenzyl)thiazole from step (ii) was converted to the final product using procedures analogous to those in Example 24. MS (M+H)$^+$ 519/521.

Example 336

1-(2-(5-Bromo-4-(5-((4-fluorophenyl)(hydroxy)methyl)thiazol-2-yl)pyrimidin-2-ylamino)ethyl)-5,5-dimethylimidazolidine-2,4-dione (4-Fluorophenyl)(thiazol-5-yl)methanol was converted to the final product using procedures analogous to those in Example 24. MS (M+H)$^+$ 535/537.

Example 337

1-(2-(4-(5-(4-Fluorobenzyl)thiazol-2-yl)-5-fluoropyrimidin-2-ylamino)ethyl)-5,5-dimethylimidazolidine-2,4-dione 5-(4-Fluorobenzyl)thiazole was condensed with 2-chloro-5-fluoropyrimidine and subsequently aminated with 1-(2-aminoethyl)-5,5-dimethylimidazolidine-2,4-dione using procedures analogous to those in Example 24. MS (M+H)$^+$ 459.

Example 338

1-(2-(5-Chloro-4-(5-(phenylamino)-1,3,4-thiadiazol-2-yl)pyrimidin-2-ylamino)ethyl)-5,5-dimethylimidazolidine-2,4-dione (i) 5-chloro-2-(methylthio)pyrimidine-4-carbohydrazide 5-Chloro-2-(methylthio)pyrimidine-4-carboxylic acid (4.0 g, 19.6 mmol) and 1,1-carbonyl diimidazole (6.35 g, 39.2 mmol) were dissolved in 80 mL THF and stirred at room temperature. After 3 h, the solution was cooled with an ice bath and hydrazine hydrate (1.90 mL, 39.2 mmol) was added in one quick portion. The solution was allowed to stir for 5 h, gradually warming to room temperature. The reaction mixture was diluted with excess $H_2O$ and extracted with EtOAc several times. These organics were combined and washed with 2 N HCl. The combined aqueous layers were then basified carefully with 5 N NaOH, and extracted once again with EtOAc. This second set of organic layers were combined, dried over magnesium sulfate and concentrated under vacuum to give 2.46 g (58% yield) of product as a white solid. MS (M+H)$^+$ 219.

(ii) 1-(5-Chloro-2-(methylthio)pyrimidine-6-carbonyl)-4-(4-fluorophenyl)thiosemicarbazide 5-Chloro-2-(methylthio)pyrimidine-4-carbohydrazide (8.28 g, 38.0 mmol) and 4-fluoro-phenyl isothiocyanate (5.811 g, 38.0) were added to a 1 liter flask. A minimal amount of EtOH was added, just to ensure proper mixing. This suspension was stirred at room temperature overnight. The EtOH was removed under vacuum to give 13.5 g (95% yield) of product as a light yellow solid. MS (M+H)$^+$ 372.

(iii) 5-(5-Chloro-2-(methylthio)pyrimidin-4-yl)-N-(4-fluorophenyl)-1,3,4-thiadiazol-2-amine 1-(5-Chloro-2-(methylthio)pyrimidine-6-carbonyl)-4-(4-fluorophenyl)thiosemicarbazide (1.08 g, 2.9 mmol) was diluted in 60 mL sulfuric acid. This solution was stirred at room temperature for 5 min before cooling in an ice bath. The reaction mixture was carefully diluted with excess $H_2O$ forming the product as a bright orange ppt. The product was collected by filtration and dried in a vacuum oven overnight to give 0.721 g (71% yield) of product as a bright orange solid. MS (M+H)$^+$ 354.

(iv) 1-(2-(5-Chloro-4-(5-(phenylamino)-1,3,4-thiadiazol-2-yl)pyrimidin-2-ylamino)ethyl)-5,5-dimethylimidazolidine-2,4-dione 5-(5-Chloro-2-(methylthio)pyrimidin-4-yl)-N-(4-fluorophenyl)-1,3,4-thiadiazol-2-amine (0.637 g, 1.7 mmol) was dissolved in 300 mL acetone. Oxone (6.3 g, 10.3 mmol) was dissolved in 300 mL H$_2$O and added in one portion to the acetone solution and allowed to stir overnight at room temperature. The acetone was removed under vacuum, the resulting precipitate was obtained by filtration. LC/MS analysis indicates a mixture of both sulfoxide and sulfone. This solid mixture was dried briefly in a vacuum oven. This material was charged to a microwave reaction vessel along with 1-(2-aminoethyl)-5,5-dimethyl-imidazolidine-2,4-dione (0.588 g, 3.4 mmol), diisopropyl ethylamine (0.60 mL, 3.4 mmol) and 15 mL IPA. This reaction was heated under microwave conditions to 170° C. for 1200 s. Upon cooling 0.545 g (67% yield) of product was obtained by filtration. MS (M+H)$^+$ 477.

Examples 339-341 were prepared in an analogous manner to Example 338.

Example 339

1-(2-(5-Chloro-4-(5-(phenylamino)-1,3,4-thiadiazol-2-yl)pyrimidin-2-ylamino)ethyl)-5,5-dimethylimidazolidine-2,4-dione

MS (M+H)$^+$ 459.

Example 340

1-(2-(5-Chloro-4-(5-(4-methoxyphenylamino)-1,3,4-thiadiazol-2-yl)pyrimidin-2-ylamino)ethyl)-5,5-dimethylimidazolidine-2,4-dione

MS (M+H)$^+$ 489.

Example 341

1-(2-(5-Chloro-4-(5-(cyclohexylamino)-1,3,4-thiadiazol-2-yl)pyrimidin-2-ylamino)ethyl)-5,5-dimethylimidazolidine-2,4-dione

MS (M+H)$^+$ 465.

Example 342

1-(2-(4-(5-Benzyl-1,3,4-thiadiazol-2-yl)-5-chloropyrimidin-2-ylamino)ethyl)-5,5-dimethylimidazolidine-2,4-dione (i) 5-Chloro-2-(methylthio)pyrimidine-4-carbohydrazide 5-Chloro-2-(methylthio)pyrimidine-4-carboxylic acid (4.0 g, 19.6 mmol) and 1,1-carbonyl diimidazole (6.35 g, 39.2 mmol) were dissolved in 80 mL THF and stirred at room temperature. After 3 h, the solution was cooled in an ice bath and hydrazine hydrate (1.90 mL, 39.2 mmol) was added in one quick portion. The solution was allowed to stir for 5 h, gradually warming to room temperature. The reaction mixture was diluted with excess H$_2$O and extracted with EtOAc several times. These organics were combined and washed with 2 N HCl. The combined aqueous layers were then basified carefully with 5 N NaOH, and extracted once again with EtOAc. This second set of organic layers was combined, dried over magnesium sulfate and concentrated under vacuum to give 2.46 g (58% yield) of product as a white solid. MS (M+H)$^+$ 219.

(ii) 5-Chloro-2-(methylthio)-N'-(2-phenylacetyl)pyrimidine-4-carbohydrazide

5-Chloro-2-(methylthio)pyrimidine-4-carbohydrazide (1.0 g, 4.6 mmol) and 2-phenylacetyl chloride (0.61 mL, 4.6 mmol) were dissolved in 20 mL pyridine. The solution was stirred at 60° C. for 3 h. Upon cooling to room temperature, the reaction mixture was diluted with excess H$_2$O. The aqueous layer was extracted with EtOAc 3 times. The combined organic layers were washed with 2 N HCl and H$_2$O, dried over magnesium sulfate and concentrated under vacuum. Flash chromatography was required to obtain 0.442 g (26% yield) of product as a white solid. MS (M+H)$^+$ 337.

(iii) 4-(5-Benzyl-1,3,4-thiadiazol-2-yl)-5-chloro-2-(methylthio)pyrimidine

Lawesson's Reagent (0.487 g (1.2 mmol) and 5-chloro-2-(methylthio)-N'-(2-phenyl-acetyl)pyrimidine-4-carbohydrazide (0.442 g, 1.2 mmol) were dissolved in 8 mL pyridine. This solution was heated to 100° C. for 30 h, giving ~50% conversion. Upon cooling, the reaction mixture was diluted with excess H$_2$O. The aqueous layer was extracted with EtOAc. The combined organic layers were dried with magnesium sulfate and concentrated under vacuum. Flash chromatography was used to obtain 0.190 g (47% yield) product as a brown solid. MS (M+H)$^+$ 335.

(iv) 1-(2-(4-(5-Benzyl-1,3,4-thiadiazol-2-yl)-5-chloropyrimidin-2-ylamino)ethyl)-5,5-dimethylimidazolidine-2,4-dione 4-(5-Benzyl-1,3,4-thiadiazol-2-yl)-5-chloro-2-(methylthio)pyrimidine (0.190 g, 0.57 mmols) was dissolved in 75 mL acetone. Oxone (1.05 g, 1.7 mmol) was dissolved in 75 mL H$_2$O and added to the acetone solution. This mixture was allowed to stir for 5 h. The acetone was removed under vacuum, the resulting precipitate was obtained by filtration. LC/MS analysis indicates a mixture of both sulfoxide and sulfone. This solid mixture was dried briefly in a vacuum oven. This material was charged to a microwave reaction vessel along with 1-(2-aminoethyl)-5,5-dimethyl-imidazolidine-2,4-dione (0.194 g, 1.1 mmol) and diisopropyl ethylamine (0.20 mL, 1.1 mmol) and 15 mL IPA. This reaction was heated under microwave conditions to 170° C. for 1200 s. Upon cooling 0.236 g (90% yield) of product was obtained by filtration. MS (M+H)$^+$ 458.

Example 343

1-(2-(5-Methyl-4-(thiophen-2-yl)pyrimidin-2-ylamino)ethyl)imidazolidin-2-one (i) 3-(Dimethylamino)-2-methyl-1-(thiophen-2-yl)prop-2-en-1-one 1-(Thiophen-2-yl)propan-1-one (0.15 g, 1.069 mmol) was treated with tert-butoxybis-(dimethylamino)methane (0.5 mL) and the mixture stirred at 55° C. overnight. The volatiles

(ii) 5-Methyl-2-(methylthio)-4-(thiophen-2-yl)pyrimidine 3-(Dimethylamino)-2-methyl-1-(thiophen-2-yl)prop-2-en-1-one (0.2 g, 1.02 mmol) was dissolved in isopropyl alcohol (2 mL) at room temperature. Thiourea (0.077 g, 1.02 mmol) followed by potassium tert-butoxide (1.102 mL of a 1.0 M solution in 2-methyl-2-propanol) was added to the mixture, which was then heated to reflux overnight. The reaction was cooled down to rt and iodomethane (0.126 mL, 2.04 mmol) was added to the reaction, which was stirred for an additional 6 h. The volatiles were removed in vacuo and the residue was dissolved in ethyl acetate, washed with saturated aqueous sodium bicarbonate, water and brine. The organic layer was then dried with sodium sulfate, concentrated in vacuo and purified by flash chromatography using a gradient of 5 to 30% ethyl acetate in hexanes. The pure fractions yielded a tan solid (0.15 g). MS (M+H)$^+$ 223.

(iii) 5-Methyl-2-(methylsulfonyl)-4-(thiophen-2-yl)pyrimidine

5-Methyl-2-(methylthio)-4-(thiophen-2-yl)pyrimidine (0.15 g, 0.67 mmol) was dissolved in acetone (10 mL) and then water (10 mL) was added. Oxone (1.2 g, 2.02 mmol) was added in small portions to the reaction mixture, which was allowed to stir overnight at ambient temperature. The white precipitate that formed during the course of the reaction was collected by suction filtration and washed several times with water and then dried in a vacuum oven at 60° C. Yield=0.12 g. MS (M+H)$^+$ 255.

(iv) 1-(2-(5-Methyl-4-(thiophen-2-yl)pyrimidin-2-ylamino)ethyl)imidazolidin-2-one 5-Methyl-2-(methylsulfonyl)-4-(thiophen-2-yl)pyrimidine (0.1 g, 0.39 mmol) and 1-(2-aminoethyl)imidazolidin-2-one (0.06 g, 047 mmol) were added to a microwave tube along with toluene (1 mL). The tube was capped and heated to 200° C. for 10 min in a Personal Chemistry microwave. The mixture was diluted with dichloromethane and purified by flash chromatography using a gradient of 2 to 10% methanol in dichloromethane to obtain an off-white solid. Yield=0.03 g. MS (M+H)$^+$ 304.

Example 344

1-(2-(4-(5-Bromothiophen-2-yl)-5-methylpyrimidin-2-ylamino)ethyl)imidazolidin-2-one

(i) 1-(5-Bromothiophen-2-yl)-3-(dimethylamino)-2-methylprop-2-en-1-one prepared in an analogous manner to Example 343. MS (M+H)$^+$ 274/276.

(ii) 1-(5-Bromothiophen-2-yl)-3-(dimethylamino)-2-methylprop-2-en-1-one

2-Bromo-1-(5-bromothiophen-2-yl)ethanone (5.4 g, 24.6 mmol) was treated with tert-butoxybis(dimethylamino)methane (10 mL) and the mixture stirred at 55° C. overnight. The volatiles were removed in vacuo. The resulting residue was dissolved in dichloromethane and washed successively with a saturated solution of sodium bicarbonate, water and saturated solution of sodium chloride. The organic layer was then dried with sodium sulfate and concentrated in vacuo. The residue was placed under high vacuum to afford a thick brown oil which was used without further purification. Yield=6.39 g. MS (M+H)$^+$ 275/277.

(iii) 4-(5-Bromothiophen-2-yl)-5-methyl-2-(methylthio)pyrimidine 1-(5-Bromothiophen-2-yl)-3-(dimethylamino)-2-methylprop-2-en-1-one (6.39 g, 23 mmol) was dissolved in isopropyl alcohol (30 mL) at room temperature. Thiourea (1.748 g, 23 mmol) followed by potassium tert-butoxide (23 mL of a 1.0 M solution in tetrahydrofuran) was added to the mixture, which was then heated to reflux overnight. The reaction was cooled to rt and iodomethane (2.86 mL, 46 mmol) was added to the reaction in one portion. The mixture was subsequently stirred for an additional 6 h. The volatiles were removed in vacuo and the residue was dissolved in ethyl acetate, washed with saturated aqueous sodium bicarbonate, water and brine. The organic layer was then dried with sodium sulfate, reduced in vacuo and purified by column chromatography on silica gel using a gradient of 10 to 40% of ethyl acetate in hexanes to yield a yellow solid (5 g). MS (M+H)$^+$ 302.

(iv) 4-(5-Bromothiophen-2-yl)-5-methyl-2-(methylsulfonyl)pyrimidine 4-(5-Bromothiophen-2-yl)-5-methyl-2-(methylthio)pyrimidine (2.5 g, 3.3 mmol) dissolved in acetone (50 mL) was treated, via slow addition, with a solution of oxone (15.3 g, 24 mmol) in water (50 mL). The reaction was allowed to stir overnight at ambient temperature. The white precipitate that formed during the course of the reaction was collected by filtration and washed several times with water and then dried in a vacuum oven at 60° C. Yield=2.3 g. MS (M+H)$^+$ 334.

(v) 1-(2-(4-(5-Bromothiophen-2-yl)-5-methylpyrimidin-2-ylamino)ethyl)imidazolidin-2-one 4-(5-Bromothiophen-2-yl)-5-methyl-2-(methylsulfonyl)pyrimidine (2 g, 6 mmol) in toluene (10 mL) was treated with 1-(2-aminoethyl)imidazolidin-2-one (1.489 g, 10.2 mmol) and the reaction stirred at 120° C. overnight. The volatiles were removed in vacuo and the residue purified by flash chromatography using a gradient of 2 to 10% methanol in dichloromethane to obtain a light yellow solid (1.8 g). MS (M+H)$^+$ 383.

Example 345

1-(2-(5-Methyl-4-(5-(thiophen-2-yl)thiophen-2-yl)pyrimidin-2-ylamino)ethyl)imidazolidin-2-one 1-(2-(4-(5-Bromothiophen-2-yl)-5-methylpyrimidin-2-ylamino)ethyl)imidazolidin-2-one (0.1 g, 0.26 mmol), thiophen-2-ylboronic acid (0.066 g, 0.52 mmol), and sodium carbonate (0.26 mL of 2 M solution, 0.52 mmol) were added to a microwave tube containing dimethyl ether (2 mL). The tube was flushed with nitrogen and tetrakis(triphenylphosphine)palladium (0.06 g, 0.054 mmol) was added. The tube was capped and heated to 145° C. for 20 min in a Personal Chemistry microwave. The reaction was diluted with a mixture of 2:1 dichloromethane and methanol (9 mL), filtered through a pad of celite, washed with saturated aqueous sodium bicarbonate, water and brine. The organic layer was dried with sodium sulfate, concentrated in vacuo and purified by flash chromatography on silica gel using a gradient 2 to 10% of methanol in dichloromethane to afford a yellow solid. Yield=0.036 g. MS (M+H)$^+$ 386.

Example 346

1-(2-(5-Methyl-4-(5-phenylthiophen-2-yl)pyrimidin-2-ylamino)ethyl)imidazolidin-2-one Synthesized in an analogous manner to Example 345. MS (M+H)$^+$ 380.

Example 347

1-(2-(4-(5-(4-Fluorophenyl)thiophen-2-yl)-5-methylpyrimidin-2-ylamino)ethyl)imidazolidin-2-one Synthesized in an analogous manner to Example 345. MS (M+H)$^+$ 398.

Example 348

1-(2-(4-(5-(4-Methoxyphenyl)thiophen-2-yl)-5-methylpyrimidin-2-ylamino)ethyl)imidazolidin-2-one Synthesized in an analogous manner to Example 345. MS (M+H)$^+$ 410.

Example 349

1-(2-(5-Methyl-4-(5-(pyridin-3-yl)thiophen-2-yl)pyrimidin-2-ylamino)ethyl)imidazolidin-2-one Synthesized in an analogous manner to Example 345. MS (M+H)$^+$ 381.

Example 350

1-(2-(4-(5-(2-Fluorophenyl)thiophen-2-yl)-5-methylpyrimidin-2-ylamino)ethyl)imidazolidin-2-one Synthesized in an analogous manner to Example 345. MS (M+H)$^+$ 398.

Example 351

1-(2-(4-(5-(4-(Dimethylamino)phenyl)thiophen-2-yl)-5-methylpyrimidin-2-ylamino)ethyl)imidazolidin-2-one Synthesized in an analogous manner to Example 345. MS (M+H)$^+$ 423.

Example 352

1-(2-(5-Methyl-4-(5-(pyridin-4-yl)thiophen-2-yl)pyrimidin-2-ylamino)ethyl)imidazolidin-2-one Synthesized in an analogous manner to Example 345. MS (M+H)$^+$ 381.

Example 353

1-(2-(4-(5-(Furan-2-yl)thiophen-2-yl)-5-methylpyrimidin-2-ylamino)ethyl)imidazolidin-2-one Synthesized in an analogous manner to Example 345. MS (M+H)$^+$ 370.

Example 354

2-(2-(2-Oxoimidazolidin-1-yl)ethylamino)-4-(thiophen-2-yl)pyrimidine-5-carbonitrile (i) 3-(Dimethylamino)-2-(thiophene-2-carbonyl)acrylonitrile Prepared in an analogous manner to Example 343. MS (M+H)$^+$ 207.

(ii) 2-(Methylthio)-4-(thiophen-2-yl)pyrimidine-5-carbonitrile

Prepared in an analogous manner to Example 343. MS (M+H)$^+$ 234.

(iii) 2-(Methylsulfonyl)-4-(thiophen-2-yl)pyrimidine-5-carbonitrile

Synthesized in an analogous manner to Example 343. MS (M+H)$^+$ 266.

(iv) 2-(2-(2-Oxoimidazolidin-1-yl)ethylamino)-4-(thiophen-2-yl)pyrimidine-5-carbonitrile Prepared in an analogous manner to Example 343. MS (M+H)$^+$ 315.

Example 355

2-(2-(2-Oxoimidazolidin-1-yl)ethylamino)-4-(5-(thiophen-2-yl)thiophen-2-yl)pyrimidine-5-carbonitrile (i) 2-Bromo-1-(5-bromothiophen-2-yl)ethanone 1-(5-Bromothiophen-2-yl)ethanone (1 g, 4.87 mmol) was dissolved in glacial acetic acid (5 mL) and treated with bromine (0.25 mL) in acetic acid (2 mL) added dropwise. The reaction was stirred at ambient temperature overnight. The volatiles were removed in vacuo while care was taken so as to keep the bath temperature under 40° C. The residue was dissolved in dichloromethane, washed with saturated aqueous sodium bicarbonate, water and brine. The organic layer was then dried with sodium sulfate, concentrated and purified by flash chromatography using a gradient of 10 to 30% of ethyl acetate in hexanes to yield a off-white solid (0.85 g).

(ii) 3-(5-Bromothiophen-2-yl)-3-oxopropanenitrile

2-Bromo-1-(5-bromothiophen-2-yl)ethanone (5 g, 17.6 mmol) dissolved in ethanol (100 mL) was treated with an aqueous solution (10 mL) of potassium cyanide (6.19 g, 96.8 mmol) and stirred at ambient temperature overnight. The volatiles were removed in vacuo and crushed iced added to the residue which was acidified to pH 4 with acetic acid. The yellow precipitate that formed was collected by suction filtration and purified by flash chromatography on silica gel using a gradient of 10-30% of ethyl acetate in hexanes to yield a light gray solid (3 g).

(iii) 2-(2-Bromothiophene-5-carbonyl)-3-(dimethylamino)acrylonitrile 3-(5-Bromothiophen-2-yl)-3-oxopropanenitrile (4 g, 17 mmol) was treated with dimethyl formamide dimethylacetal and the mixture heated to 100° C. After 1 h, the mixture was allowed to cool down to room temperature. The yellow solid that precipitated was collected by suction filtration and washed well with diethyl ether. Yield=4.6 g. MS (M+H)$^+$ 284.

(iv) 4-(5-Bromothiophen-2-yl)-2-(2-(2-oxoimidazolidin-1-yl)ethylamino)pyrimidine-5-carbonitrile 2-(2-Bromothiophene-5-carbonyl)-3-(dimethylamino) acrylonitrile (3 g, 10 mmol) in N-methylpyrrolidone (15 mL) was treated with 1-(2-(2-oxoimidazolidin-1-yl)ethyl)guanidine hydrochloride (1 M solution in N-methylpyrrolidone, 15 mL, 15 mmol) and cesium carbonate (3.4 g, 10 mmol). The mixture was heated at 100° C. overnight. The reaction was then allowed to cool to room temperature and poured onto crushed ice. The resulting solid that formed was suspended in hot methanol to give a yellow solid (2.3 g). The filtrate was concentrated and purified by flash chromatography using a gradient of 3 to 10% methanol in dichloromethane to obtain an additional 0.9 g of the desired product. Total yield=3.2 g. MS (M+H)$^+$ 394.

(v) 2-(2-(2-oxoimidazolidin-1-yl)ethylamino)-4-(5-(thiophen-2-yl)thiophen-2-yl)pyrimidine-5-carbonitrile 4-(5-Bromothiophen-2-yl)-2-(2-(2-oxoimidazolidin-1-yl) ethylamino)pyrimidine-5-carbonitrile (0.08 g, 0.2 mmol), thiophen-2-ylboronic acid (0.052 g, 04 mmol), sodium carbonate (1.5 mL of 2 M solution, 1 mmol) were added to a microwave tube containing ethanol (1.5 mL). The tube was flushed with nitrogen and tetrakis(triphenylphosphine)palladium (0.06 g, 0.054 mmol) was added. The tube was capped and heated to 130° C. for 30 min in a Personal Chemistry microwave. The reaction was diluted with dichloromethane and washed with saturated aqueous sodium bicarbonate, water and brine. The organic layer was then dried with sodium sulfate, reduced in vacuo and purified by flash chromatography on silica gel using a gradient of 0 to 10% methanol in dichloromethane to afford a yellow solid which recrystallized from ethyl acetate. Yield=0.066 g. MS (M+H)$^+$ 397.

Example 356

1-(2-(5-Phenyl-4-(thiophen-2-yl)pyrimidin-2-ylamino)ethyl)imidazolidin-2-one

(i) 2-Phenyl-1-(thiophen-2-yl)ethanone

1-Bromobenzene (2 g, 12 mmol) in toluene (30 mL) was treated 1-(thiophen-2-yl)ethanone (1.8 g, 14.4 mmol), potassium bis(trimethylsilyl)amide (28.8 mL of 0.5 M solution in toluene, 14.4 mmol), 2,2'-bis(diphenyl)phosphino-1,1'-binaphthyl (racemic BINAP, 1.86 g, 3 mmol). The reaction was heated to 90° C. in an oil bath under a nitrogen atmosphere. After 4 h, the reaction was allowed to cool to room temperature and diluted with ethyl acetate (30 mL). The organic layer was washed with saturated aqueous sodium bicarbonate, water and brine. The organic layer was then dried with sodium sulfate, concentrated and purified by flash chromatography using a gradient of 10 to 40% ethyl acetate in hexanes to yield a yellow oil (1 g). MS (M+H)$^+$ 203.

(ii) 3-(Dimethylamino)-2-phenyl-1-(thiophen-2-yl) prop-2-en-1-one

2-Phenyl-1-(thiophen-2-yl)ethanone (1 g, 4.94 mmol) was treated with dimethylformamide dimethylacetal (5 mL) and heated to 100° C. while stirring. After 4 h, the reaction was allowed to cool down to room temperature. The solid that precipitated out of the reaction mixture was collected by filtration and washed with a 1:1 mixture of diethyl ether and hexanes to afford a yellow crystalline solid (1 g). MS (M+H)$^+$ 258.

(iii) 1-(2-(5-Phenyl-4-(thiophen-2-yl)pyrimidin-2-ylamino)ethyl)imidazolidin-2-one 3-(Dimethylamino)-2-phenyl-1-(thiophen-2-yl)prop-2-en-1-one (1 g, 3.88 mmol) in N-methylpyrrolidone (10 mL) was treated with 1-(2-(2-oxoimidazolidin-1-yl)ethyl)guanidine hydrochloride (1 M solution in N-methylpyrrolidone 5.82 mL, 5.82 mmol) and cesium carbonate (1.26 g, 3.88 mmol). The mixture was heated at 100° C. overnight. The reaction was then allowed to cool to room temperature and poured into cold water. The aqueous layer was extracted three times with dichloromethane. All the organic layers were combined and washed with saturated aqueous sodium bicarbonate, water and brine. The organic layer was then dried with sodium sulfate, reduced in vacuo and purified by flash chromatography using a gradient of 0 to 10% methanol in dichloromethane to obtain a yellow solid. Yield=1.2 g. MS (M+H)$^+$ 366.

Example 357

2-(2-(2-Oxoimidazolidin-1-yl)ethylamino)-4-(5-(piperidin-1-ylsulfonyl)thiophen-2-yl)pyrimidine-5-carbonitrile

(i) 1-(Thiophen-2-ylsulfonyl)piperidine

Thiophene-2-sulfonyl chloride (10 g, 54 mmol) was dissolved in dichloromethane (15 mL) and added dropwise to a round-bottom flask containing a solution of piperidine (10.6 mL, 108 mmol) and diisopropylethylamine (18.8 mL, 108 mmol) in dichloromethane at 0° C. The reaction was stirred at 0° C. for 15 min and then allowed to warm up to room temperature. After 2 h, the reaction was washed successively with a saturated solution of sodium bicarbonate, water, 1 N HCl and a saturated solution of sodium chloride. The organic layer was dried with sodium sulfate, concentrated and placed on a vacuum line to give an off-white solid (11.98 g). MS (M+H)$^+$ 232.

(ii) 1-(5-(Piperidin-1-ylsulfonyl)thiophen-2-yl)ethanone 1-(Thiophen-2-ylsulfonyl)piperidine (5 g, 21.6 mmol) was taken up in anhydrous tetrahydrofuran (90 mL) and the solution, which was kept under a nitrogen atmosphere, was cooled down to −78° C. n-Butyllithium (2.5 M in hexanes, 12.96 mL, 32.4 mmol) was added to the reaction dropwise with a syringe. The reaction was stirred at −78° C. for 10 min and allowed to warm up to −30° C. and stirred for 30 min. The reaction was cooled back down to −78° C. and N,N-dimethylacetamide (4.01 mL, 43.2 mmol) diluted with anhydrous tetrahydrofuran (10 mL) was added slowly to the reaction. The reaction was stirred for 15 min and then allowed to warm up to room temperature over 1 h. The mixture was quenched with acetic acid (10 mL) and diluted with ethyl acetate and a saturated solution of sodium bicarbonate. The layers were separated and the organic layer washed with water and brine. The organic layer was then dried with sodium sulfate, concentrated and purified by flash chromatography using a gradient of 10 to 40% ethyl acetate in hexanes to afford an off-white solid (1.8 g).

(iii) 2-(2-(2-Oxoimidazolidin-1-yl)ethylamino)-4-(5-(piperidin-1-ylsulfonyl)thiophen-2-yl)pyrimidine-5-carbonitrile Prepared in an analogous manner to Example 355. MS (M+H)⁺ 462.

Example 358

1-(2-(5-(Thiazol-2-yl)-4-(thiophen-2-yl)pyrimidin-2-ylamino)ethyl)imidazolidin-2-one (i) 2-(Methylthio)-4-(thiophen-2-yl)pyrimidine-5-carbothioamide 2-(Methylthio)-4-(thiophen-2-yl)pyrimidine-5-carbonitrile (1 g, 4.28 mmol) was dissolved in anhydrous tetrahydrofuran (20 mL) and treated with triethyamine (1.8 mL, 12 mmol). The reaction was cooled down to 0° C. and hydrogen sulfide was bubbled into the reaction for 15 min. The reaction was vented into a bleach bath. The cooling bath was removed and the reaction was stirred overnight. Nitrogen was bubbled into the reaction for 15 min and the volatiles were removed in vacuo. The residue was purified by flash chromatography using a gradient of 20 to 70% ethyl acetate in hexanes to afford a tan solid (0.342 g). MS (M+H)⁺ 268.

(ii) 2-(Methylthio)-5-(thiazol-2-yl)-4-(thiophen-2-yl)pyrimidine 2-(Methylthio)-4-(thiophen-2-yl)pyrimidine-5-carbothioamide (0.3 g, 1.12 mmol) suspended in ethanol (2 mL) was treated with bromoacetaldehyde dimethylacetal (0.158 mL, 1.34 mmol). The reaction was stirred at reflux overnight. No product formation was observed by thin layer chromatography in 20% ethyl acetate/hexanes. Another equivalent of bromoacetaldehyde dimethylacetal was added to the reaction in addition to a few drops of concentrated hydrochloric acid and the reaction kept at reflux for another 3 h. The reaction was cooled down to room temperature and the volatiles removed in vacuo. A solution of saturated sodium bicarbonate was added to the residue, which was extracted with dichloromethane. The organic layer was dried with sodium sulfate and purified by flash chromatography using a gradient of 20 to 60% of ethyl acetate in hexanes. The product was obtained as a brown solid (0.18 g). MS (M+H)⁺ 292.

(iii) 1-(2-(5-(Thiazol-2-yl)-4-(thiophen-2-yl)pyrimidin-2-ylamino)ethyl)imidazolidin-2-one Prepared in an analogous manner to Example 354. MS (M+H)⁺ 373.

Example 359

1-(2-(5-Bromo-4-(thiophen-2-yl)pyrimidin-2-ylamino)ethyl)imidazolidin-2-one (i) 5-Bromo-2-chloro-4-(thiophen-2-yl)pyrimidine Thienyl lithium (1.0 M in THF, 26 mL, 26 mmol) was diluted with anhydrous THF (65 mL) and the mixture cooled down to −78° C. under a nitrogen atmosphere. 5-Bromo-2-chloropyrimidine, dissolved in 10 mL of tetrahydrofuran, was added to the reaction mixture dropwise. The reaction was allowed to stir for 1 h and then warmed to −20° C. Acetic acid (1.5 mL) and methanol (1.2 mL) were successively added to the reaction mixture. The reaction was stirred for 15 min and a solution of 2,3-dichloro-5,6-dicyano-1,4-benzoquinone (5.9 g, 20 mmol) in 10 mL of THF was added. The reaction was stirred for an additional 15 min and then the cooling bath was removed. The mixture was stirred for 1 h and then cooled to 0° C. with an ice bath. 5 N sodium hydroxide (5.2 mL) was added to the reaction mixture and stirred for 5 min. The reaction was then diluted with ethyl acetate (50 mL) and water (50 mL). The organic layer was washed with saturated aqueous sodium bicarbonate, water and brine. The organic layer was then dried with sodium sulfate, concentrated and purified by flash chromatography on silica gel using 5% ethyl acetate in hexanes as an eluent to obtain a yellow solid. Yield=3.6 g. MS (M+H)⁺ 275/277.

(ii) 1-(2-(5-Bromo-4-(thiophen-2-yl)pyrimidin-2-ylamino)ethyl)imidazolidin-2-one 5-Bromo-2-chloro-4-(thiophen-2-yl)pyrimidine (2.0 g, 7.25 mmol) dissolved in N-methyl pyrrolidone (25 mL) was treated with potassium carbonate (2 g, 14.5 mmol) and 1-(2-aminoethyl)imidazolidin-2-one (1.125 g, 8.71 mmol). The reaction was heated to 110° C. overnight. The reaction was poured into ice water and extracted with dichloromethane. The organic layer was washed with saturated aqueous sodium bicarbonate, water and brine and then dried with sodium sulfate. Purification was achieved by flash chromatography using a gradient of 0 to 10% methanol in dichloromethane to obtain a yellow solid. Yield=2 g. MS (M+H)⁺ 368/370.

Example 360

1-(2-(5-(4-Chlorophenyl)-4-(thiophen-2-yl)pyrimidin-2-ylamino)ethyl)imidazolidin-2-one 1-(2-(5-Bromo-4-(thiophen-2-yl)pyrimidin-2-ylamino)ethyl)imidazolidin-2-one (0.1 g, 0.27 mmol), 4-chlorophenylboronic acid (0.085 g, 0.54 mmol), sodium carbonate (0.27 mL of 2.0 M solution, 0.52 mmol) were added to a flask containing dioxane (1 mL). The flask was flushed with nitrogen and tetrakis(triphenylphosphine)palladium (0.062 g, 0.054 mmol) was added. The reaction was heated to 80° C. overnight. The reaction was cooled down to ambient temperature and diluted with ethyl acetate and water. The organic layer was filtered through a pad of celite and washed with saturated aqueous sodium bicarbonate, water and brine. The organic layer was then dried with sodium sulfate, concentrated and purified by column chromatography using a gradient 2 to 10% of methanol in dichloromethane to afford an off-white solid. Yield=0.04 g. MS (M+H)+ 400.

Examples 361-413 were prepared in an analogous manner as Example 360.

Example 361

1-(2-(5-(Pyridin-4-yl)-4-(thiophen-2-yl)pyrimidin-2-ylamino)ethyl)imidazolidin-2-one

MS (M+H)+ 367.

Example 362

4-(2-(2-(2-Oxoimidazolidin-1-yl)ethylamino)-4-(thiophen-2-yl)pyrimidin-5-yl)benzonitrile

MS (M+H)+ 391.

Example 363

1-(2-(5-(3-Chlorophenyl)-4-(thiophen-2-yl)pyrimidin-2-ylamino)ethyl)imidazolidin-2-one

MS (M+H)+ 400.

Example 364

1-(2-(5-(2-Chlorophenyl)-4-(thiophen-2-yl)pyrimidin-2-ylamino)ethyl)imidazolidin-2-one

MS (M+H)+ 400.

Example 365

1-(2-(5-(Pyridin-3-yl)-4-(thiophen-2-yl)pyrimidin-2-ylamino)ethyl)imidazolidin-2-one

MS (M+H)+ 367.

Example 366

1-(2-(5-(4-Fluorophenyl)-4-(thiophen-2-yl)pyrimidin-2-ylamino)ethyl)imidazolidin-2-one

MS (M+H)+ 384.

Example 367

N-(4-(2-(2-(2-Oxoimidazolidin-1-yl)ethylamino)-4-(thiophen-2-yl)pyrimidin-5-yl)phenyl)acetamide

MS (M+H)+ 423.

Example 368

1-(2-(5-(3,4-Dimethoxyphenyl)-4-(thiophen-2-yl)pyrimidin-2-ylamino)ethyl)imidazolidin-2-one

MS (M+H)+ 426.

Example 369

1-(2-(5-(1H-Indol-5-yl)-4-(thiophen-2-yl)pyrimidin-2-ylamino)ethyl)imidazolidin-2-one

MS (M+H)+ 405.

Example 370

1-(2-(5-(3-Nitrophenyl)-4-(thiophen-2-yl)pyrimidin-2-ylamino)ethyl)imidazolidin-2-one

MS (M+H)+ 411.

Example 371

1-(2-(5-(4-Phenoxyphenyl)-4-(thiophen-2-yl)pyrimidin-2-ylamino)ethyl)imidazolidin-2-one

MS (M+H)+ 458.

Example 372

1-(2-(5-(4-Acetylphenyl)-4-(thiophen-2-yl)pyrimidin-2-ylamino)ethyl)imidazolidin-2-one

MS (M+H)+ 408.

Example 373

1-(2-(4-(Thiophen-2-yl)-5-(3-(trifluoromethyl)phenyl)pyrimidin-2-ylamino)ethyl)imidazolidin-2-one

MS (M+H)+ 434.

Example 374

1-(2-(5-(Benzo[d][1,3]dioxol-5-yl)-4-(thiophen-2-yl)pyrimidin-2-ylamino)ethyl)imidazolidin-2-one

MS (M+H)+ 410.

Example 375

1-(2-(5-(Naphthalen-2-yl)-4-(thiophen-2-yl)pyrimidin-2-ylamino)ethyl)imidazolidin-2-one

MS (M+H)+ 416.

Example 376

1-(2-(4-(Thiophen-2-yl)-5-(4-(trifluoromethyl)phenyl)pyrimidin-2-ylamino)ethyl)imidazolidin-2-one

MS (M+H)+ 434.

Example 377

1-(2-(5-(4-Methoxyphenyl)-4-(thiophen-2-yl)pyrimidin-2-ylamino)ethyl)imidazolidin-2-one

MS (M+H)$^+$ 396.

Example 378

1-(2-(5-(3-Fluoro-4-methylphenyl)-4-(thiophen-2-yl)pyrimidin-2-ylamino)ethyl)imidazolidin-2-one

MS (M+H)$^+$ 398.

Example 379

1-(2-(5-(6-Methoxypyridin-3-yl)-4-(thiophen-2-yl)pyrimidin-2-ylamino)ethyl)imidazolidin-2-one

MS (M+H)$^+$ 397.

Example 380

1-(2-(5-(3,5-Difluorophenyl)-4-(thiophen-2-yl)pyrimidin-2-ylamino)ethyl)imidazolidin-2-one

MS (M+H)$^+$ 402.

Example 381

1-(2-(5-(Pyrimidin-5-yl)-4-(thiophen-2-yl)pyrimidin-2-ylamino)ethyl)imidazolidin-2-one

MS (M+H)$^+$ 368.

Example 382

1-(2-(5-(3-Fluoro-4-methylphenyl)-4-(thiophen-2-yl)pyrimidin-2-ylamino)ethyl)imidazolidin-2-one

MS (M+H)$^+$ 398.

Example 383

1-(2-(5-(4-tert-Butylphenyl)-4-(thiophen-2-yl)pyrimidin-2-ylamino)ethyl)imidazolidin-2-one

MS (M+H)$^+$ 422.

Example 384

4-(2-(2-(2-Oxoimidazolidin-1-yl)ethylamino)-4-(thiophen-2-yl)pyrimidin-5-yl)benzonitrile

MS (M+H)$^+$ 391.

Example 385

1-(2-(5-(4-Hydroxyphenyl)-4-(thiophen-2-yl)pyrimidin-2-ylamino)ethyl)imidazolidin-2-one

MS (M+H)$^+$ 382.

Example 386

1-(2-(5-(Naphthalen-1-yl)-4-(thiophen-2-yl)pyrimidin-2-ylamino)ethyl)imidazolidin-2-one

MS (M+H)$^+$ 416.

Example 387

1-(2-(5-(2-Fluorophenyl)-4-(thiophen-2-yl)pyrimidin-2-ylamino)ethyl)imidazolidin-2-one

MS (M+H)$^+$ 384.

Example 388

1-(2-(5-(3-Biphenyl)-4-(thiophen-2-yl)pyrimidin-2-ylamino)ethyl)imidazolidin-2-one

MS (M+H)$^+$ 442.

Example 389

1-(2-(4-(Thiophen-2-yl)-5-m-tolylpyrimidin-2-ylamino)ethyl)imidazolidin-2-one

MS (M+H)$^+$ 380.

Example 390

N-(3-(2-(2-(2-Oxoimidazolidin-1-yl)ethylamino)-4-(thiophen-2-yl)pyrimidin-5-yl)phenyl)methanesulfonamide

MS (M+H)$^+$ 459.

Example 391

1-(2-(5-(3-(Piperidin-1-yl)phenyl)-4-(thiophen-2-yl)pyrimidin-2-ylamino)ethyl)imidazolidin-2-one

MS (M+H)$^+$ 449.

Example 392

1-(2-(5-(3-(3,5-Dimethylisoxazol-4-yl)phenyl)-4-(thiophen-2-yl)pyrimidin-2-ylamino)ethyl)imidazolidin-2-one

MS (M+H)$^+$ 385.

Example 393

1-(2-(5-Phenyl-4-(5-(piperidin-1-ylsulfonyl)thiophen-2-yl)pyrimidin-2-ylamino)ethyl)imidazolidin-2-one

MS (M+H)$^+$ 513.

Example 394

1-(2-(5-(3-(Piperidin-1-yl)phenyl)-4-(5-(piperidin-1-ylsulfonyl)thiophen-2-yl)pyrimidin-2-ylamino)ethyl)imidazolidin-2-one

MS (M+H)$^+$ 596.

Example 395

1-(2-(4-(5-(3,4-Dihydroquinolin-1(2H)-ylsulfonyl)thiophen-2-yl)-5-phenylpyrimidin-2-ylamino)ethyl)imidazolidin-2-one

MS (M+H)$^+$ 561.

Example 396

1-(2-(5-(1H-Indol-5-yl)-4-(5-(piperidin-1-ylsulfonyl)thiophen-2-yl)pyrimidin-2-ylamino)ethyl)imidazolidin-2-one

MS (M+H)$^+$ 552.

Example 397

1-(2-(4-(5-(Piperidin-1-ylsulfonyl)thiophen-2-yl)-5-(quinolin-8-yl)pyrimidin-2-ylamino)ethyl)imidazolidin-2-one

MS (M+H)$^+$ 564.

Example 398

1-(2-(4-(5-(Piperidin-1-ylsulfonyl)thiophen-2-yl)-5-(pyridin-4-yl)pyrimidin-2-ylamino)ethyl)imidazolidin-2-one

MS (M+H)$^+$ 514.

Example 399

1-(2-(5-(3-Hydroxyphenyl)-4-(5-(piperidin-1-ylsulfonyl)thiophen-2-yl)pyrimidin-2-ylamino)ethyl)imidazolidin-2-one

MS (M+H)$^+$ 529.

Example 400

1-(2-(5-(3-(Hydroxymethyl)phenyl)-4-(5-(piperidin-1-ylsulfonyl)thiophen-2-yl)pyrimidin-2-ylamino)ethyl)imidazolidin-2-one

MS (M+H)$^+$ 543.

Example 401

N-(3-(2-(2-(2-Oxoimidazolidin-1-yl)ethylamino)-4-(5-(piperidin-1-ylsulfonyl)thiophen-2-yl)pyrimidin-5-yl)phenyl)acetamide

MS (M+H)$^+$ 570.

Example 402

1-(2-(5-(3-(Dimethylamino)phenyl)-4-(5-(piperidin-1-ylsulfonyl)thiophen-2-yl)pyrimidin-2-ylamino)ethyl)imidazolidin-2-one

MS (M+H)$^+$ 556.

Example 403

3-(2-(2-(2-Oxoimidazolidin-1-yl)ethylamino)-4-(5-(piperidin-1-ylsulfonyl)thiophen-2-yl)pyrimidin-5-yl)benzoic acid

MS (M+H)$^+$ 557.

Example 404

1-(2-(5-(1H-Indol-5-yl)-4-(5-(phenylsulfonyl)thiophen-2-yl)pyrimidin-2-ylamino)ethyl)imidazolidin-2-one

MS (M+H)$^+$ 545.

Example 405

1-(2-(5-(3-Hydroxyphenyl)-4-(5-(phenylsulfonyl)thiophen-2-yl)pyrimidin-2-ylamino)ethyl)imidazolidin-2-one

MS (M+H)$^+$ 522.

Example 406

1-(2-(5-(3-Methoxyphenyl)-4-(5-(phenylsulfonyl)thiophen-2-yl)pyrimidin-2-ylamino)ethyl)-5,5-dimethylimidazolidine-2,4-dione

MS (M+H)$^+$ 578.

Example 407

1-(2-(5-(3-Hydroxyphenyl)-4-(5-(phenylsulfonyl)thiophen-2-yl)pyrimidin-2-ylamino)ethyl)-5,5-dimethylimidazolidine-2,4-dione

MS (M+H)$^+$ 564.

Example 408

1-(2-(4-(5-(4-Fluorophenylsulfonyl)thiophen-2-yl)-5-(3-hydroxyphenyl)pyrimidin-2-ylamino)ethyl)-5,5-dimethylimidazolidine-2,4-dione

MS (M+H)$^+$ 582.

Example 409

3-(2-(2-(5,5-Dimethyl-2,4-dioxoimidazolidin-1-yl)ethylamino)-4-(5-(4-fluorophenylsulfonyl)thiophen-2-yl)pyrimidin-5-yl)benzonitrile

MS (M+H)$^+$ 591.

Example 410

1-(2-(4-(5-(3-Fluorophenylsulfonyl)thiophen-2-yl)-5-(3-hydroxyphenyl)pyrimidin-2-ylamino)ethyl)-5,5-dimethylimidazolidine-2,4-dione

MS (M+H)$^+$ 582.

Example 411

1-(2-(4-(5-(4-Chlorophenylsulfonyl)thiophen-2-yl)-5-(3-hydroxyphenyl)pyrimidin-2-ylamino)ethyl)-5,5-dimethylimidazolidine-2,4-dione

MS (M+H)$^+$ 598.

Example 412

3-(4-(Benzo[b]thiophen-2-yl)-2-(2-(5,5-dimethyl-2,4-dioxoimidazolidin-1-yl)ethylamino)pyrimidin-5-yl)benzonitrile

MS (M+H)$^+$ 483.

Example 413

1-(2-(5-(3-Methoxyphenyl)-4-(5-(piperidin-1-ylsulfonyl)thiophen-2-yl)pyrimidin-2-ylamino)ethyl)imidazolidin-2-one

MS (M+H)$^+$ 543.

Example 414

1-(2-(5-Bromo-4-(5-chlorothiophen-2-yl)pyrimidin-2-ylamino)ethyl)imidazolidin-2-one 5-Bromo-2-chloro-4-(5-chlorothiophen-2-yl)pyrimidine A solution of 2-chlorothiophene (0.467 mL, 5 mmol) in anhydrous tetrahydrofuran (5 mL) with treated with a solution of lithium diisopropylamide (2 M in THF, 2.75 mL, 5.5 mmol) at –40° C. under a nitrogen atmosphere. After 15 min, the reaction was allowed to warm up to –10° C. and held at that temperature for 20 min. The reaction was then cooled back down to –40° C. and 5-bromo-2-chloropyrimidine (1.06 g, 5.5 mmol), dissolved in anhydrous THF (10 mL) was added to the reaction slowly. After 2 h, a mixture of 1:1 methanol/acetic acid (2 mL) was added to the reaction. After 15 min, a solution of 2,3-dichloro-5,6-dicyano-1,4-benzoquinone (1.36 g, 6 mmol) in 10 mL of THF was added. The reaction was stirred for an additional 15 min and then the cooling bath was removed. The mixture was stirred for 1 h and then cooled to 0° C. with an ice bath. 5 N sodium hydroxide (5 mL) was added to the reaction mixture which was stirred for an additional 5 min. The reaction was then diluted with ethyl acetate (20 mL) and water (20 mL). The organic layer was washed with saturated aqueous sodium bicarbonate, water and brine. The organic layer was dried with sodium sulfate, concentrated and purified by flash chromatography using a gradient of 5 to 20% ethyl acetate in hexanes to obtain a yellow solid. Yield=0.6 g. MS (M+H)$^+$ 311/313.

1-(2-(5-Bromo-4-(5-chlorothiophen-2-yl)pyrimidin-2-ylamino)ethyl)imidazolidin-2-one 5-Bromo-2-chloro-4-(5-chlorothiophen-2-yl)pyrimidine (0.4 g, 1.3 mmol), N-methyl pyrrolidone (3 mL), potassium carbonate (0.358 g, 2.6 mmol) and 1-(2-aminoethyl)-imidazolidin-2-one (0.2 g, 1.54 mmol) were all placed in a microwave tube. The reaction was heated to 150° C. for 20 min in a Personal Chemistry microwave. A saturated solution of sodium bicarbonate was added to the reaction mixture, which was extracted three times with dichloromethane. The organic layer was dried with sodium sulfate and purified by flash chromatography on silica gel using gradient of 0 to 10% methanol in dichloromethane to obtain a white solid. Yield=0.41 g. MS (M+H)$^+$ 402/404.

Example 415

1-(2-(5-Phenyl-4-(5-phenylthiophen-2-yl)pyrimidin-2-ylamino)ethyl)imidazolidin-2-one Prepared in an analogous manner to Example 345. MS (M+H)$^+$ 442.

Example 416

1-(2-(4-(5-(Thiophen-2-yl)thiophen-2-yl)pyrimidin-2-ylamino)ethyl)pyrrolidin-2-one (i) 2-(2-Oxopyrrolidin-1-yl)acetonitrile Dimethylformamide (4.65 mL, 60 mmol) was taken up in acetonitrile (100 mL) and the solution cooled to 0° C. with an ice bath. Oxalyl chloride (4.8 mL, 55 mmol), diluted with acetonitrile (20 mL) was added to the reaction dropwise. The mixture was stirred for 30 min, then 2-(2-oxopyrrolidin-1-yl)acetamide (7.11 g, 50 mmol) in 30 mL of acetonitrile was added slowly to the reaction. The mixture was allowed to stir for 30 min and pyridine (6.1 mL, 100 mmol) was added to the reaction in one portion. The reaction was stirred for an additional 30 min and the volatiles were removed in vacuo. Water was added to the residue which was extracted with ethyl acetate. The aqueous layer was acidified to pH 2 with 1 N HCl and further extracted with ethyl acetate. All the organic layers were combined, washed with brine, dried with sodium sulfate, concentrated and placed on a high vacuum line to afford a clear oil. Yield=4.4 g 1-(2-Aminoethyl)pyrrolidin-2-one hydrochloride 2-(2-Oxopyrrolidin-1-yl)acetonitrile (0.25 g, 2.01 mmol) was dissolved in methanol (5 mL) and concentrated hydrochloric acid (1 mL) in a Parr shaker vessel. Under a flow of nitrogen, a catalytic amount platinum oxide (25 mg) was added to the reaction mixture. The reaction was placed on a Parr Shaker apparatus, degassed under vacuum and flushed with nitrogen. Then, the reaction was hydrogenated at 50 psi overnight. The reaction was passed through a plug of celite and concentrated to give a white solid. Yield=0.259 g MS (M+H)$^+$ 129.

(iii) 1-(2-(4-(5-(Thiophen-2-yl)thiophen-2-yl)pyrimidin-2-ylamino)ethyl)pyrrolidin-2-one Prepared in an analogous manner to Example 414. MS (M+H)$^+$ 371.

Example 417

1-(2-(5-Bromo-4-(5-chlorothiophen-2-yl)pyrimidin-2-ylamino)ethyl)-5,5-dimethylimidazolidin-2-one Prepared in analogous manner to Example 359. MS (M+H)+ 431/433.

Example 418

1-(2-(5-Bromo-4-(5-chlorothiophen-2-yl)pyrimidin-2-ylamino)ethyl)-5,5-dimethylimidazolidine-2,4-dione Prepared in an analogous manner to Example 359. MS (M+H)+ 444/446.

Example 419

1-(2-(4-(5-(Thiophen-2-yl)thiophen-2-yl)-5-(trifluoromethyl)pyrimidin-2-ylamino)ethyl)imidazolidin-2-one

(i) 2-Chloro-4-(5-(thiophen-2-yl)thiophen-2-yl)-5-(trifluoromethyl)pyrimidine Prepared in an analogous manner to Example 360. MS (M+H)+ 346.

(ii) 1-(2-(4-(5-(Thiophen-2-yl)thiophen-2-yl)-5-(trifluoromethyl)pyrimidin-2-ylamino)ethyl)imidazolidin-2-one Prepared in analogous manner to Example 359. MS (M+H)+ 440.

Example 420

1-(2-(5-Bromo-4-(thieno[2,3-c]pyridin-2-yl)pyrimidin-2-ylamino)ethyl)-5,5-dimethylimidazolidine-2,4-dione

(i) 2,2-Dimethoxy-N-(thiophen-2-ylmethyl)ethanamine

Thiophene-2-carboxaldehyde (22.4 g, 200 mmol) was dissolved in anhydrous ethanol (200 mL) and treated with 2,2-dimethoxyethanamine (26.6 g, 200 mmol) and para-toluenesulfonic acid hydrate (0.1 g, catalytic) and the mixture heated to reflux for 4 h. The reaction was allowed to cool down to room temperature and sodium borohydride (7.6 g, 200 mmol) was added in small portions to the reaction. Following complete addition, the reaction was stirred at room temperature for 15 min, then at reflux for 2 h. The reaction was allowed to cool down to room temperature and all the volatiles removed in vacuo. The residue was dissolved in ethyl acetate and was washed with saturated aqueous sodium bicarbonate, water and brine. The organic layer was then dried with sodium sulfate, passed through a pad of silica gel, concentrated and placed on a vacuum line to afford an off-white solid. Yield=40.1 g. MS (M+H)+ 202.

(ii) N-(2,2-Dimethoxyethyl)-4-methyl-N-(thiophen-2-ylmethyl)benzenesulfonamide 2,2-Dimethoxy-N-(thiophen-2-ylmethyl)ethanamine (5 g, 24 mmol) was dissolved in anhydrous dichloromethane and pyridine (5.82 mL, 72 mmol) was added to the reaction. The mixture was cooled down to 0° C. and was treated with para-toluenesulfonyl chloride (5.6 g, 29 mmol) added portionwise. The reaction was allowed to stir at 0° C. for 4 h and was then washed 3 times with 1 N HCl, water and a saturated solution of sodium bicarbonate. The organic layer was dried with sodium sulfate. Purification by flash chromatography using a gradient of 5-30% ethyl acetate in hexanes yielded a white crystalline solid (7.4 g) MS (M+H)+ 356.

(iii) Thieno[2,3-c]pyridine

N-(2,2-Dimethoxyethyl)-4-methyl-N-(thiophen-2-ylmethyl)benzenesulfonamide (7 g, 19 mmol) was dissolved in dioxane (10 mL) and treated with concentrated HCl (10 mL). The mixture for heated to reflux for 12 h. The mixture was allowed to cool down to room temperature, diluted with water (20 mL) and brought to pH 7 with 2 N sodium hydroxide. The mixture was then extracted with ethyl acetate. The organic layer was washed with saturated aqueous sodium bicarbonate, water and brine. The organic layer was dried with sodium sulfate, concentrated and purified by flash chromatography using a gradient of 10 to 60% ethyl acetate in hexanes to obtain a tan solid. Yield=1 g. MS (M+H)+ 136.

(iv) 2-(5-Bromo-2-chloropyrimidin-4-yl)thieno[2,3-c]pyridine

Diisopropylamine (1.02 mL, 7.27 mmol) was added to a flask containing anhydrous THF (10 mL) and the mixture, while kept under an atmosphere of nitrogen, was cooled to −78° C. n-BuLi (2.5 M in hexanes, 2.9 mL, 7.27 mmol) was added dropwise to the mixture, which was stirred for 30 min. Thieno[2,3-c]pyridine (0.82 g, 6.06 mmol) dissolved in anhydrous THF (10 mL) was added to the reaction mixture dropwise. The reaction was stirred at −78° C. for 10 min and then at −40° C. for 20 min. 5-Bromo-2-chloropyrimidine, dissolved in anhydrous THF (5 mL) was added to the reaction slowly. The mixture was allowed to stir at −40° C. for 2 h and then was quenched with a 1:1 mixture of acetic acid/methanol (5 mL). The mixture was stirred for 15 min and a solution of 2,3-dichloro-5,6-dicyano-1,4-benzoquinone (1.72 g, 6.66 mmol) in 10 mL of THF was added. The reaction was stirred for an additional 15 min and then the cooling bath was removed. The mixture was stirred for 1 h and then cooled to 0° C. with an ice bath. 5 N sodium hydroxide (50 mL) was added to the reaction mixture, which was stirred for an additional 5 min. The reaction was then diluted with ethyl acetate (30 mL) and water (30 mL). The organic layer was washed with saturated aqueous sodium bicarbonate, water and brine. The organic layer was then dried with sodium sulfate, concentrated and purified by column chromatography using a gradient of 5 to 40% ethyl acetate in hexanes to obtain a light brown solid. Yield=0.5 g. MS (M+H)+ 326/328.

(v) 1-(2-(5-Bromo-4-(thieno[2,3-c]pyridin-2-yl)pyrimidin-2-ylamino)ethyl)-5,5-dimethylimidazolidine-2,4-dione 2-(5-Bromo-2-chloropyrimidin-4-yl)thieno[2,3-c]pyridine (0.38 g, 1.16 mmol), 1-(2-aminoethyl)-5,5-dimethylimidazolidine-2,4-dione (0.393 g, 2.3 mmol), diisopropylethylamine (0.4 mL, 2.3 mmol) and isopropyl alcohol (2 mL) were all placed in a microwave tube and heated to 170° C. for 20 min. The volatiles were removed in vacuo and the residue dissolved in 9:1 mixture of dichloromethane, preadsorbed onto silica gel and purified by flash chromatography using a gradient of 0 to 10% methanol in dichloromethane to obtain a yellow solid. Yield=0.4 g. MS (M+H)+ 461/463.

Example 421

1-(2-(5-Bromo-4-(thieno[3,2-c]pyridin-2-yl)pyrimidin-2-ylamino)ethyl)-5,5-dimethylimidazolidine-2,4-dione (i)
2,2-Dimethoxy-N-(thiophen-3-ylmethyl)ethanamine Prepared in an analogous manner to Example 420. MS (M+H)+ 202.

(ii) N-(2,2-Dimethoxyethyl)-4-methyl-N-(thiophen-3-ylmethyl)benzenesulfonamide

Prepared in an analogous manner to Example 420. MS (M+H) 356.

(iii) Thieno[3,2-c]pyridine

Prepared in an analogous manner to Example 420. MS (M+H) 136.

(iv) 2-(5-Bromo-2-chloropyrimidin-4-yl)thieno[3,2-c]pyridine

Prepared in an analogous manner to Example 420. MS (M+H)+ 326/328.

(v) 1-(2-(5-Bromo-4-(thieno[3,2-c]pyridin-2-yl)pyrimidin-2-ylamino)ethyl)-5,5-dimethylimidazolidine-2,4-dione Prepared in an analogous manner to Example 420. MS (M+H)+ 461/463.

Example 422

1-(2-(5-(3-Hydroxyphenyl)-4-(thieno[3,2-c]pyridin-2-yl)pyrimidin-2-ylamino)ethyl)-5,5-dimethylimidazolidine-2,4-dione (i) 1-(2-(5-(3-Hydroxyphenyl)-4-(thieno[3,2-c]pyridin-2-yl)pyrimidin-2-ylamino)ethyl)-5,5-dimethylimidazolidine-2,4-dione Prepared in an analogous manner to Example 360. MS (M+H)+ 475.

(ii) 5,5-Dimethyl-1-(2-(4-(thieno[3,2-c]pyridin-2-yl) pyrimidin-2-ylamino)ethyl)imidazolidine-2,4-dione Isolated as a side product. MS (M+H)+ 383.

Example 423

1-(2-(4-(Benzo[b]thiophen-2-yl)-5-bromopyrimidin-2-yloxy)ethyl)imidazolidin-2-one 1-(2-Hydroxyethyl)imidazolidin-2-one (0.6 g, 4.6 mmol) was taken up in anhydrous THF (5 mL) and added dropwise to a reaction flask containing a suspension of sodium hydride (0.147 g (60% in oil), 3.68 mmol) in anhydrous THF (10 mL) at 0° C. The ice bath was removed and the reaction allowed to warm up to room temperature over a 2 h period. 4-(benzo[b] thiophen-2-yl)-5-bromo-2-chloropyrimidine (0.3 g, 9.2 mmol), dissolved in THF was added dropwise. The reaction was stirred overnight. The reaction was then diluted with ethyl acetate and saturated sodium bicarbonate. The organic layer was then washed with water and brine. The organic portion was dried with sodium sulfate and then purified by flash chromatography on silica gel using a gradient of 0 to 10% methanol in dichloromethane to give a white solid. Yield=0.085 g. MS (M+H)+ 420.

Example 424

1-(2-(4-(Benzo[b]thiophen-2-yl)-5-(trifluoromethyl) pyrimidin-2-yloxy)ethyl)-5,5-dimethylimidazolidine-2,4-dione (i) 2-(Methylthio)-5-(trifluoromethyl)pyrimidine Prepared in an analogous manner to a literature procedure: Tetrahedron Letters 37 (11) 1996 pp 1827-1832. MS (M+H)+ 195.

(ii) 4-(Benzo[b]thiophen-2-yl)-2-(methylthio)-5-(trifluoromethyl)pyrimidine

Prepared in an analogous manner to Example 420. n-BuLi was used rather than lithium diisopropylamide. MS (M+H)+ 327.

(iii) 4-(Benzo[b]thiophen-2-yl)-5-(trifluoromethyl) pyrimidin-2-ol 4-(Benzo[b]thiophen-2-yl)-2-(methylthio)-5-(trifluoromethyl)pyrimidine (0.45 g, 1.3 mmol) suspended in dioxane (3 mL) was treated with 5 N sodium hydroxide (3 mL) and the reaction heated to 75° C. After stirring overnight, there was still some starting material present in the reaction mixture by LC-MS. An additional 3 mL of 5 N sodium hydroxide was added to the reaction mixture and the temperature was increased to 90° C. After 6 h, the reaction was cooled to room temperature and acidified to pH 4 with 1 N hydrochloric acid. The precipitate that formed was collected by suction filtration, washed well with water and dried in a vacuum oven to give a white solid. Yield=0.31 g. MS (M+H)+ 297.

(iv) 4-(Benzo[b]thiophen-2-yl)-2-chloro-5-(trifluoromethyl)pyrimidine 4-(Benzo[b]thiophen-2-yl)-5-(trifluoromethyl)pyrimidin-2-ol (0.28 g, 0.94 mmol) was treated with phosphorous oxychloride (6 mL) and the mixture was heated to 100° C. overnight. The volatiles were removed in vacuo and residual phosphorous oxychloride was azeotroped with toluene. The resulting residue was dissolved in chloroform, washed successively with cold water, saturated aqueous solution of sodium bicarbonate, water again and brine. The organic solution was dried with sodium sulfate and passed through a plug of silica gel. The filtrate was concentrated to yield a yellow solid (0.2 g). MS (M+H)+ 315.

(v) 1-(2-(4-(Benzo[b]thiophen-2-yl)-5-(trifluoromethyl)pyrimidin-2-yloxy)ethyl)-5,5-dimethylimidazolidine-2,4-dione 4-(Benzo[b]thiophen-2-yl)-2-chloro-5-(trifluoromethyl) pyrimidine (0.1 g, 0.31 mmol), 1-(2-aminoethyl)-5,5-dimethylimidazolidine-2,4-dione (0.106 g, 0.62 mmol) and toluene (3 mL) were all placed in a microwave tube and heated in a Personal Chemistry microwave at 170° C. for 20 min. The volatiles were removed in vacuo and purification was achieved by flash chromatography using a gradient of 2 to 10% methanol in dichlorormethane. The product was obtained as a white solid (0.065 g). MS (M+H)$^+$ 452.

Example 425

1-(2-(4-(Benzo[b]thiophen-2-yl)-5-(trifluoromethyl) pyrimidin-2-yloxy)ethyl)imidazolidin-2-one Prepared in an analogous manner to Example 424. MS (M+H)$^+$ 408.

Example 426

1-(2-(5-Bromo-4-(6-methoxybenzo[b]thiophen-2-yl) pyrimidin-2-ylamino)ethyl)-5,5-dimethylimidazolidine-2,4-dione (i) N,N-Diethyl-4-methoxybenzamide 4-Methoxybenzoic acid (6 g, 39 mmol) was treated with diethylamine (4.45 mL, 43 mmol), TBTU (15 g, 46.8 mmol), disopropylethylamine (10.2 mL, 58.5 mmol) in DMF (40 mL). The mixture was stirred at ambient temperature overnight. The reaction was poured into ice water and the resulting mixture extracted several times with ethyl acetate. The organic layer was washed with a solution of saturated sodium bicarbonate, water and then brine. The organic layer was then dried with sodium sulfate, concentrated and purified by flash chromatography using a gradient of 30 to 70% ethyl acetate in hexanes to obtain a brown oil. Yield=7.8 g. MS (M+H)$^+$ 208.

(ii) N,N-Diethyl-4-methoxy-2-(methylthio)benzamide

Sec-BuLi (1.4 M in cyclohexane, 11.34 mL, 15 mmol) was carefully added to a mixture of N,N,N',N'-tetramethylethane-1,2-diamine (2.2 mL, 15 mmol) in anhydrous THF at −78° C. N,N-Diethyl-4-methoxybenzamide (3 g, 14.4 mmol) dissolved in 5 mL of anhydrous THF was added dropwise to the reaction mixture which was allowed to stir for 1 h. Dimethyl sulfide (2.5 mL, 28.8 mmol) was then added to the reaction. After stirring for 15 min, the cooling bath was removed and the mixture was stirred overnight. The reaction was diluted with ethyl acetate and washed with a solution of saturated sodium bicarbonate, water and then brine. The organic layer was then dried with sodium sulfate, concentrated and purified by flash chromatography using a gradient of 20 to 80% ethyl acetate in hexanes to obtain the product as a light yellow oil. Yield=2.51 g. MS (M+H)$^+$ 254.

(iii) 6-Methoxybenzo[b]thiophen-3(2H)-one n-BuLi (1.6 M in hexanes, 13 mL, 20.8 mmol) was added slowly to a solution of diisopropylamine (2.91 mL, 20.8 mmol) in THF at −78° C. The mixture was stirred under nitrogen for 30 min and N,N-diethyl-4-methoxy-2-(methylthio)benzamide (2.4 g, 9.47 mmol), dissolved in 10 mL of anhydrous THF was added to the reaction dropwise. Stirring was continued at −78° C. for 1 h and the cooling bath was removed. After 12 h, the reaction was cooled back down to −78° C. and a 1:1 mixture of methanol and acetic acid (10 mL) was added to the mixture. The reaction was stirred for 15 min and the cooling bath was removed and allowed to warm up to room temperature. The reaction was diluted with ethyl acetate and the organic layer was washed with saturated aqueous sodium bicarbonate, water and brine. The organic layer was then dried with sodium sulfate, concentrated and purified by flash chromatography using a gradient of 15 to 40% ethyl acetate in hexanes to obtain an off white solid. Yield=1.4 g. MS (M−H)-179.

(iv) 6-Methoxybenzo[b]thiophene

6-Methoxybenzo[b]thiophen-3(2H)-one (1.4 g, 7.76 mmol) was dissolved in a mixture of methanol (18 mL) and 2.5 M sodium hydroxide (3 mL). The mixture was treated with sodium borohydride (0.589 g, 15 mmol) in 10 mL of methanol and 3 mL of 2.5 M sodium hydroxide. The reflux was heated to reflux for 1 h and then at 60° C. overnight. The reaction was cooled down to room temperature and the methanol removed in vacuo. The remaining aqueous layer was acidified to pH 4 with 1 N hydrochloric acid. The aqueous layer was extracted with ethyl acetate and washed with 1 N HCl. The organic layer was further washed with water, saturated sodium bicarbonate, water and brine. The organic layer was dried with sodium sulfate, concentrated and purified by flash chromatography using a gradient of 20 to 50% ethyl acetate in hexanes to afford a clear oil (0.843 g).

(v) 5-Bromo-2-chloro-4-(6-methoxybenzo[b] thiophen-2-yl)pyrimidine

Prepared in an analogous manner to Example 424. MS (M+H)$^+$ 356/358.

(vi) 1-(2-(5-Bromo-4-(6-methoxybenzo[b]thiophen-2-yl)pyrimidin-2-ylamino)ethyl)-5,5-dimethylimidazolidine-2,4-dione Prepared in an analogous manner to Example 424. MS (M+H)$^+$ 490.

Example 427

1-(2-(4-(5-Aminobenzo[b]thiophen-2-yl)-5-(trifluoromethyl)pyrimidin-2-ylamino)ethyl)-5,5-dimethylimidazolidine-2,4-dione (i) 2-(Methylthio)-4-(5-nitrobenzo[b]thiophen-2-yl)-5-(trifluoromethyl)pyrimidine Prepared in an analogous manner to Example 420. MS (M+H)$^+$ 372.

(ii) 2-(Methylsulfonyl)-4-(5-nitrobenzo[b]thiophen-2-yl)-5-(trifluoromethyl)pyrimidine Prepared in an analogous manner to Example 343. MS (M+H)$^+$ 404.

(iii) 5,5-Dimethyl-1-(2-(4-(5-nitrobenzo[b]thiophen-2-yl)-5-(trifluoromethyl)pyrimidin-2-ylamino)ethyl) imidazolidine-2,4-dione Prepared in an analogous manner to Example 424. MS (M+H)$^+$ 495.

(iv) 1-(2-(4-(5-Aminobenzo[b]thiophen-2-yl)-5-(trifluoromethyl)pyrimidin-2-ylamino)ethyl)-5,5-dimethylimidazolidine-2,4-dione 5,5-Dimethyl-1-(2-(4-(5-nitrobenzo[b]thiophen-2-yl)-5-(trifluoromethyl)pyrimidin-2-ylamino)ethyl)imidazolidine-2,4-dione (0.25 g, 0.5 mmol) was suspended in ethanol (7 mL) and treated with indium (0.406 g, 3.5 mmol) and 3 mL of a saturated aqueous solution of ammonium chloride. The mixture was stirred at reflux under nitrogen. After 3 h, the mixture was allowed to cool down to room temperature, passed through a pad of celite, and the volatiles removed in vacuo. The resulting solid was suspended in hot methanol, filtered off and dried on a vacuum line to afford a rust colored solid. Yield=0.18 g. MS (M+H)$^+$ 465.

Example 428

1-(2-(4-(5-(4-Fluorophenylsulfonyl)thiophen-2-yl)-5-(trifluoromethyl)pyrimidin-2-ylamino)ethyl)-5,5-dimethylimidazolidine-2,4-dione (i) 4-(5-(4-Fluorophenylsulfonyl)thiophen-2-yl)-2-(methylthio)-5-(trifluoromethyl)pyrimidine Prepared in an analogous manner to Example 424. MS (M+H)$^+$ 434.

(ii) 4-(5-(4-Fluorophenylsulfonyl)thiophen-2-yl)-2-(methylsulfonyl)-5-(trifluoromethyl)pyrimidine Prepared in an analogous manner to Example 343. MS (M+H)$^+$ 466.

(iii) 1-(2-(4-(5-(4-Fluorophenylsulfonyl)thiophen-2-yl)-5-(trifluoromethyl)pyrimidin-2-ylamino)ethyl)-5,5-dimethylimidazolidine-2,4-dione Prepared in an analogous manner to Example 424. MS (M+H)$^+$ 558.

Example 429

1-(2-(4-(6-Methoxybenzo[b]thiophen-2-yl)-5-(trifluoromethyl)pyrimidin-2-ylamino)ethyl)-5,5-dimethylimidazolidine-2,4-dione (i) 4-(6-Methoxybenzo[b]thiophen-2-yl)-2-(methylthio)-5-(trifluoromethyl)pyrimidine Prepared in a manner analogous to Example 424. MS (M+H)$^+$ 357.

(ii) 4-(6-Methoxybenzo[b]thiophen-2-yl)-2-(methylsulfonyl)-5-(trifluoromethyl)pyrimidine Prepared in a analogous manner to Example 343. MS (M+H)$^+$ 389.

(iii) 1-(2-(4-(6-Methoxybenzo[b]thiophen-2-yl)-5-(trifluoromethyl)pyrimidin-2-ylamino)ethyl)-5,5-dimethylimidazolidine-2,4-dione Prepared in an analogous manner to Example 424. MS (M+H)$^+$ 480.

Example 430

1-(2-(4-(Benzo[b]thiophen-2-yl)-5-bromopyrimidin-2-ylamino)ethyl)-tetrahydropyrimidin-2(1H)-one and 1-(3-(4-(benzo[b]thiophen-2-yl)-5-bromopyrimidin-2-ylamino)propyl)imidazolidin-2-one (i) 3-(2-Aminoethyl)-tetrahydropyrimidin-2(1H)-one and 1-(3-aminopropyl)imidazolidin-2-one N1-(2-aminoethyl)propane-1,3-diamine (5 g, 42.1 mmol) was treated with urea (2.5 g, 42.1 mmol) and the mixture heated to 130° C. for 1 h. The temperature was further increased to 160° C. and stirred for 2 h. Unreacted N1-(2-aminoethyl)propane-1,3-diamine was distilled off from the reaction mixture which was used without further purification. Yield=5.9 g. MS (M+H)$^+$ 144.

(ii) 1-(2-(4-(Benzo[b]thiophen-2-yl)-5-bromopyrimidin-2-ylamino)ethyl)-tetrahydropyrimidin-2(1H)-one and 1-(3-(4-(benzo[b]thiophen-2-yl)-5-bromopyrimidin-2-ylamino)propyl)imidazolidin-2-one Prepared in an analogous manner to Example 424. The two products obtained were separated by column chromatography. Both product have the same MS (M+H)$^+$ 432/434.

Example 431

1-(2-(5-Bromo-4-(5-methoxybenzo[b]thiophen-2-yl)pyrimidin-2-ylamino)ethyl)-5,5-dimethylimidazolidine-2,4-dione (i) 5-Bromo-2-chloro-4-(5-methoxybenzo[b]thiophen-2-yl)pyrimidine Prepared in an analogous manner to Example 424. MS (M+H)$^+$ 355/357.

(ii) 1-(2-(5-Bromo-4-(5-methoxybenzo[b]thiophen-2-yl)pyrimidin-2-ylamino)ethyl)-5,5-dimethylimidazolidine-2,4-dione Prepared in an analogous manner to Example 424. MS (M+H)$^+$ 490/492.

Example 432

1-(2-(5-(3-Aminophenyl)-4-(5-methoxybenzo[b]thiophen-2-yl)pyrimidin-2-ylamino)ethyl)-5,5-dimethylimidazolidine-2,4-dione Prepared in an analogous manner to Example 345. MS (M+H)$^+$ 503.

Example 433

1-(2-(5-(3-Hydroxyphenyl)-4-(5-methoxybenzo[b]thiophen-2-yl)pyrimidin-2-ylamino)ethyl)-5,5-dimethylimidazolidine-2,4-dione Prepared in an analogous manner to Example 345. MS (M+H)$^+$ 504.

Example 434

1-(2-(4-(5-Methoxybenzo[b]thiophen-2-yl)-5-(trifluoromethyl)pyrimidin-2-ylamino)ethyl)-5,5-dimethylimidazolidine-2,4-dione (i) 4-(5-Methoxybenzo[b]thiophen-2-yl)-2-(methylthio)-5-(trifluoromethyl)pyrimidine Prepared in a manner analogous to Example 424. MS (M+H)$^+$ 357.

(ii) 4-(5-Methoxybenzo[b]thiophen-2-yl)-2-(methylsulfonyl)-5-(trifluoromethyl)pyrimidine Prepared in a analogous manner to Example 343. MS (M+H)$^+$ 389.

(iii) 1-(2-(4-(5-Methoxybenzo[b]thiophen-2-yl)-5-(trifluoromethyl)pyrimidin-2-ylamino)ethyl)-5,5-dimethylimidazolidine-2,4-dione Prepared in an analogous manner to Example 424. MS (M+H)$^+$ 480.

Example 435

2-(2-(5,5-Dimethyl-2,4-dioxoimidazolidin-1-yl)ethylamino)-4-(5-iodothiophen-2-yl)pyrimidine-5-carbonitrile (i) 2-Bromo-1-(5-iodothiophen-2-yl)ethanone Prepared in an analogous manner to Example 355.

(ii) 3-(5-Iodothiophen-2-yl)-3-oxopropanenitrile

Prepared in an analogous manner to Example 355.

(iii) 3-(Dimethylamino)-2-(2-iodothiophene-5-carbonyl)acrylonitrile

Prepared in an analogous manner to Example 355. MS (M+H)$^+$ 332.

(iv) 2-(2-(5,5-Dimethyl-2,4-dioxoimidazolidin-1-yl)ethylamino)-4-(5-iodothiophen-2-yl)pyrimidine-5-carbonitrile Prepared in an analogous manner to Example 355. MS (M+H)$^+$ 483.

Example 436

1-(2-(5-Bromo-4-(5-(2-morpholinoethoxy)benzo[b]thiophen-2-yl)pyrimidin-2-ylamino)ethyl)-5,5-dimethylimidazolidine-2,4-dione (i) 5-(2-Chloroethoxy)benzo[b]thiophene Benzo[b]thiophen-5-ol (0.5 g, 3.3 mmol, prepared in an analogous manner to a literature preparation: Synthetic Communications 21(7), 959-964, 1991) was dissolved in anhydrous acetonitrile (10 mL) was treated with chloroethyltosylate (0.94 g, 3.99 mmol) and cesium carbonate (2.15 g, 6.6 mmol). The mixture was stirred at reflux under nitrogen. After 2 h, the reaction was allowed to cool down to room temperature. The volatiles were removed in vacuo and the residue dissolved in ethyl acetate. The organic solution was washed with a saturated aqueous solution of sodium bicarbonate, water and brine. The ethyl acetate layer was then dried with sodium sulfate and purified by flash chromatography using a gradient of 5 to 25% of ethyl acetate in hexanes to obtain a white solid. Yield=0.676 g.

(ii) 4-(2-(Benzo[b]thiophen-5-yloxy)ethyl)morpholine 5-(2-Chloroethoxy)benzo[b]thiophene (0.25 g, 1.17 mmol) was dissolved in DMF (3 mL) and treated with morpholine (0.205 mL, 2.35 mmol) and sodium iodide (0.035 g, 0.235 mmol). The mixture was heated to 70° C. and stirred overnight. The reaction was cooled down to room temperature and poured into a saturated aqueous solution of sodium bicarbonate (20 mL), which was extracted several times with ethyl acetate. All the organic extracts were combined and washed with a saturated aqueous solution of sodium bicarbonate, water and brine. The ethyl acetate layer was then dried with sodium sulfate and purified by flash chromatography using a gradient of 0 to 8% methanol in dichloromethane to obtain a clear oil. Yield=0.237 g. MS (M+H)$^+$ 264.

(iii) 5-Bromo-2-chloro-4-(5-(2-morpholinoethoxy)benzo[b]thiophen-2-yl)pyrimidine Prepared in an analogous manner to Example 424. MS (M+H)$^+$ 455.

(iv) 1-(2-(5-Bromo-4-(5-(2-morpholinoethoxy)benzo[b]thiophen-2-yl)pyrimidin-2-ylamino)ethyl)-5,5-dimethylimidazolidine-2,4-dione Prepared in analogous manner to Example 359. MS (M+H)$^+$ 539.

Example 437

1-(2-(5-Bromo-4-(5-(2-chloroethoxy)benzo[b]thiophen-2-yl)pyrimidin-2-ylamino)ethyl)-5,5-dimethylimidazolidine-2,4-dione (i) 5-Bromo-2-chloro-4-(5-(2-chloroethoxy)benzo[b]thiophen-2-yl)pyrimidine Prepared in an analogous manner to Example 424. MS (M+H)$^+$ 405/407.

(ii) 1-(2-(5-Bromo-4-(5-(2-chloroethoxy)benzo[b]thiophen-2-yl)pyrimidin-2-ylamino)ethyl)-5,5-dimethylimidazolidine-2,4-dione Prepared in an analogous manner to Example 359. MS (M+H)$^+$ 538/540.

Example 438

1-(2-(5-Bromo-4-(5-(2-(4-methylpiperazin-1-yl)ethoxy)benzo[b]thiophen-2-yl)pyrimidin-2-ylamino)ethyl)-5,5-dimethylimidazolidine-2,4-dione 1-(2-{5-Bromo-4-[5-(2-chloroethoxy)benzo[b]thiophen-2-yl]pyrimidin-2-ylamino}ethyl)-5,5-dimethylimidazolidine-2,4-dione (0.15 g, 0.27 mmol) was dissolved in DMF (2 mL) and treated with N-methylpiperazine (0.061 mL, 0.55 mmol) and catalytic amount of sodium iodide (0.025 g). The mixture was heated to 70° C. and stirred overnight. The reaction was cooled down to room temperature and poured into a saturated aqueous solution of sodium bicarbonate (15 mL). The resulting precipitate was collected by filtration, dissolved in DMF (2 mL) and purified by preparative HPLC. The clean fractions were treated with 2 M ammonia in methanol and the organic volatiles removed to give a suspension of a white solid in the aqueous layer, which was collected by filtration, washed well with water and dried overnight in a vacuum oven at 60° C. Yield=0.062 g. MS (M+H)$^+$ 603/605.

Examples 439-449 were prepared in a manner analogous to Example 438. Purification was achieved either by reverse phase HPLC as in Example 438 or by preparative thin layer chromatography.

Example 439

1-(2-(4-(5-(2-(1H-Imidazol-1-yl)ethoxy)benzo[b]thiophen-2-yl)-5-bromopyrimidin-2-ylamino)ethyl)-5,5-dimethylimidazolidine-2,4-dione

MS (M+H)$^+$ 570/572.

Example 440

1-(2-(5-Bromo-4-(5-(2-(dimethylamino)ethoxy)benzo[b]thiophen-2-yl)pyrimidin-2-ylamino)ethyl)-5,5-dimethylimidazolidine-2,4-dione

MS (M+H)$^+$ 547/549.

Example 441

1-(2-(4-(5-(2-(Azetidin-1-yl)ethoxy)benzo[b]thiophen-2-yl)-5-bromopyrimidin-2-ylamino)ethyl)-5,5-dimethylimidazolidine-2,4-dione

MS (M+H)$^+$ 559/561.

Example 442

1-(2-(5-Bromo-4-(5-(2-(2-methylpyrrolidin-1-yl)ethoxy)benzo[b]thiophen-2-yl)pyrimidin-2-ylamino)ethyl)-5,5-dimethylimidazolidine-2,4-dione

MS (M+H)$^+$ 587/589.

Example 443 tert-Butyl 4-(2-(2-(5-bromo-2-(2-(5,5-dimethyl-2,4-dioxoimidazolidin-1-yl)ethylamino)pyrimidin-4-yl)benzo[b]thiophen-5-yloxy)ethyl)piperazine-1-carboxylate

MS (M+H)$^+$ 689/691.

Example 444

1-(2-(5-Bromo-4-(5-(2-(diethylamino)ethoxy)benzo[b]thiophen-2-yl)pyrimidin-2-ylamino)ethyl)-5,5-dimethylimidazolidine-2,4-dione

MS (M+H)$^+$ 575/577.

Example 445

1-(2-(5-Bromo-4-(5-(2-(piperidin-1-yl)ethoxy)benzo[b]thiophen-2-yl)pyrimidin-2-ylamino)ethyl)-5,5-dimethylimidazolidine-2,4-dione

MS (M+H)$^+$ 587/589.

Example 446

1-(2-(5-Bromo-4-(5-(2-(3-hydroxypyrrolidin-1-yl)ethoxy)benzo[b]thiophen-2-yl)pyrimidin-2-ylamino)ethyl)-5,5-dimethylimidazolidine-2,4-dione

MS (M+H)$^+$ 589/591.

Example 447

1-(2-(5-Bromo-4-(5-(2-(isopropyl(methyl)amino)ethoxy)benzo[b]thiophen-2-yl)pyrimidin-2-ylamino)ethyl)-5,5-dimethylimidazolidine-2,4-dione

MS (M+H)$^+$ 577/577.

Example 448

1-(2-(5-Bromo-4-(5-(2-(pyrrolidin-1-yl)ethoxy)benzo[b]thiophen-2-yl)pyrimidin-2-ylamino)ethyl)-5,5-dimethylimidazolidine-2,4-dione

MS (M+H)$^+$ 573/575.

Example 449

1-(2-(5-Bromo-4-(5-(2-(isopropylamino)ethoxy)benzo[b]thiophen-2-yl)pyrimidin-2-ylamino)ethyl)-5,5-dimethylimidazolidine-2,4-dione

MS (M+H)$^+$ 561/563.

Example 450

1-(2-(5-Bromo-4-(5-(2-(piperazin-1-yl)ethoxy)benzo[b]thiophen-2-yl)pyrimidin-2-ylamino)ethyl)-5,5-dimethylimidazolidine-2,4-dione tert-butyl 4-(2-(2-(5-bromo-2-(2-(5,5-dimethyl-2,4-dioxoimidazolidin-1-yl)ethylamino)-pyrimidin-4-yl)benzo[b]thiophen-5-yloxy)ethyl)piperazine-1-carboxylate (0.23 g, 3.3 mmol) dissolved in dichloromethane (3 mL) was treated with trifluoroacetic acid (3 mL) and the mixture stirred at room temperature overnight. The volatiles were removed in vacuo and the residue dissolved in dichloromethane. The organic solution was washed with water, saturated sodium bicarbonate and brine. The solution was dried with sodium sulfate and purified by column chromatography using a gradient of 8% to 20% methanol in dichloromethane to give an off-white solid (0.143 g). MS (M+H)$^+$ 588/590.

Example 451

1-(2-(4-(5-(2-(Dimethylamino)ethoxy)benzo[b]thiophen-2-yl)-5-(3-hydroxyphenyl)pyrimidin-2-ylamino)ethyl)-5,5-dimethylimidazolidine-2,4-dione Prepared in an analogous manner to Example 345. MS (M+H)$^+$ 561.

Example 452

N-(3-(2-(2-(5,5-Dimethyl-2,4-dioxoimidazolidin-1-yl)ethylamino)-4-(5-(2-(dimethylamino)ethoxy)benzo[b]thiophen-2-yl)pyrimidin-5-yl)phenyl)acetamide Prepared in an analogous manner to Example 345. MS (M+H)+ 602.

Example 453

1-(2-(5-Bromo-4-(5-((S)-pyrrolidin-2-ylmethoxy)benzo[b]thiophen-2-yl)pyrimidin-2-ylamino)ethyl)-5,5-dimethylimidazolidine-2,4-dione (S)-tert-Butyl 2-((benzo[b]thiophen-5-yloxy)methyl)pyrrolidine-1-carboxylate Polystyrene supported triphenylphosphine (2.9 mmol/g, 1.70 g, 4.95 mmol) was treated with diisopropylazodicarboxylate (0.779 mL, 3.96 mmol) at 0° C. in anhydrous dichloromethane. A mixture of (S)-tert-butyl 2-(hydroxymethyl)pyrrolidine-1-carboxylate (0.5 g, 3.3 mmol), benzo[b]thiophen-5-ol (0.5 g, 3.3 mmol) and triethylamine (0.689 mL, 4.95 mmol) in dichloromethane (5 mL) was then added to the reaction. The mixture was then allowed to warm up to room temperature and stirred overnight. The reaction was then filtered off and the filtrate purified by column chromatography on silica gel using a gradient of 15 to 50% ethyl acetate in hexanes to obtain a clear oil that solidied into an off-white solid on standing. Yield=0.48 g. MS (M+H)+ 334.

(ii) (2S)-tert-Butyl 2-((2-(5-bromo-2-chloropyrimidin-4-yl)benzo[b]thiophen-5-yloxy)methyl)pyrrolidine-1-carboxylate Prepared in an analogous manner to Example 424. MS (M+H)+ 524/526.

(2S)-tert-Butyl 2-((2-(5-bromo-2-(2-(5,5-dimethyl-2,4-dioxoimidazolidin-1-yl)ethylamino)pyrimidin-4-yl)benzo[b]thiophen-5-yloxy)methyl)pyrrolidine-1-carboxylate Prepared in an analogous manner to Example 359. MS (M+H)+ 659/651.

1-(2-(5-Bromo-4-(5-((S)-pyrrolidin-2-ylmethoxy)benzo[b]thiophen-2-yl)pyrimidin-2-ylamino)ethyl)-5,5-dimethylimidazolidine-2,4-dione Prepared in an analogous manner to Example 450. MS (M+H)+ 559/561.

Example 454

5,5-Dimethyl-1-(2-(4-(5-(2-(pyrrolidin-1-yl)ethoxy)benzo[b]thiophen-2-yl)-5-(trifluoromethyl)pyrimidin-2-ylamino)ethyl)imidazolidine-2,4-dione (i) 4-(5-(2-Chloroethoxy)benzo[b]thiophen-2-yl)-2-(methylthio)-5-(trifluoromethyl)pyrimidine Prepared in an analogous manner to Example 424. MS (M+H)+ 405.

(ii) 4-(5-(2-Chloroethoxy)benzo[b]thiophen-2-yl)-2-(methylsulfonyl)-5-(trifluoromethyl)pyrimidine Prepared in an analogous manner as Example 343. MS (M+H)+ 437.

(iii) 1-(2-(4-(5-(2-Chloroethoxy)benzo[b]thiophen-2-yl)-5-(trifluoromethyl)pyrimidin-2-ylamino)ethyl)-5,5-dimethylimidazolidine-2,4-dione Prepared in an analogous manner as Example 358. MS (M+H)+ 528.

(iv) 5,5-Dimethyl-1-(2-(4-(5-(2-(pyrrolidin-1-yl)ethoxy)benzo[b]thiophen-2-yl)-5-(trifluoromethyl)pyrimidin-2-ylamino)ethyl)imidazolidine-2,4-dione Prepared in an analogous manner as Example 438. MS (M+H)+ 563.

Example 455

1-(2-(4-(5-(2-(Isopropylamino)ethoxy)benzo[b]thiophen-2-yl)-5-(trifluoromethyl)pyrimidin-2-ylamino)ethyl)-5,5-dimethylimidazolidine-2,4-dione Prepared in an analogous manner to Example 438. MS (M+H)+ 551.

Example 456

1-(2-(5-Bromo-4-(5-isopropyl-4,5,6,7-tetrahydrothieno[3,2-c]pyridin-2-yl)pyrimidin-2-ylamino)ethyl)-5,5-dimethylimidazolidine-2,4-dione (i) 4,5,6,7-Tetrahydrothieno[3,2-c]pyridine Formaldehyde (37% in H₂O, 3.82 g, 47 mmol) was added dropwise to a flask equipped with a magnetic stirring bar containing neat 2-(thiophen-2-yl)ethanamine (5 g, 39.3 mmol). The mixture was heated to 90° C. for 2 h and then allowed to cool down to room temperature. The reaction was then diluted with water and ethyl acetate. The organic layer was collected and dried with sodium sulfate, reduced in vacuo to give a thick oil. The thick oil was dissolved in anhydrous DMF (25 mL) and added dropwise to a DMF solution saturated with HCl gas (HCl gas was bubbled in DMF for 15 min at 10° C.). The reaction was stirred for 1 h and then poured unto crushed ice and rendered basic (pH 10) with 5 N NaOH. The mixture was extracted three times with dichloromethane. All the organic layers were combined, washed with a saturated aqueous solution of sodium bicarbonate, water and brine. The organic layer was then dried with sodium sulfate, reduced in vacuo and placed on a vacuum line to give a thick oil. Yield 5.47 g. MS (M+H)+ 140.

(ii) tert-Butyl 6,7-dihydrothieno[3,2-c]pyridine-5(4H)-carboxylate 4,5,6,7-Tetrahydrothieno[3,2-c]pyridine (5.47 g, 39.2 mmol) was dissolved in DMF (20 mL) and treated di-tert-butyl dicarbonate (12.86 g, 58.9 mmol), 4-dimethylaminopyridine (100 mg) and triethylamine (11 mL, 78.4 mmol). The mixture was stirred at room temperature overnight. The reaction was then poured into crushed ice and diluted with an aqueous saturated solution of sodium bicarbonate. The mixture was extracted 3 times with dichloromethane, washed with water and dried with sodium sulfate. Purification was achieved by flash chromatography using a gradient of 15 to 40% of ethyl acetate in hexanes to give a waxy white solid (7.5 g). MS (M+H)$^+$ 240.

(iii) tert-Butyl 2-(5-bromo-2-chloropyrimidin-4-yl)-6,7-dihydrothieno[3,2-c]pyridine-5(4H)-carboxylate Prepared in manner analogous to Example 424. MS (M+H)$^+$ 429/431.

(iv) tert-Butyl 2-(5-bromo-2-(2-(5,5-dimethyl-2,4-dioxoimidazolidin-1-yl)ethylamino)pyrimidin-4-yl)-6,7-dihydrothieno[3,2-c]pyridine-5(4H)-carboxylate Prepared in an analogous manner to Example 358. MS (M+H)$^+$ 565/567.

(v) 1-(2-(5-Bromo-4-(4,5,6,7-tetrahydrothieno[3,2-c]pyridin-2-yl)pyrimidin-2-ylamino)ethyl)-5,5-dimethylimidazolidine-2,4-dione Prepared in an analogous manner to Example 450. MS (M+H)$^+$ 465/467.

(vi) 1-(2-(5-Bromo-4-(5-isopropyl-4,5,6,7-tetrahydrothieno[3,2-c]pyridin-2-yl)pyrimidin-2-ylamino)ethyl)-5,5-dimethylimidazolidine-2,4-dione 1-(2-(5-Bromo-4-(4,5,6,7-tetrahydrothieno[3,2-c]pyridin-2-yl)pyrimidin-2-ylamino)ethyl)-5,5-dimethylimidazolidine-2,4-dione (0.15 g, 032 mmol) was treated with acetone (1 mL), sodium triacetoxyborohydride (0.136 g, 0.64 mmol) in dicholoethane (5 mL). The reaction was stirred at room temperature overnight. The mixture was diluted with dichloromethane and water. The layers were separated and the organic layer was washed with a saturated aqueous solution of sodium bicarbonate, water and brine. The mixture was dried with sodium sulfate and purified by preparative HPLC. Yield=0.05 g.
MS (M+H)$^+$ 507/509.

Example 457

1-(2-(5-Chloro-4-(2-(methyl(phenyl)amino)thiazol-5-yl)pyrimidin-2-ylamino)ethyl)-5,5-dimethylimidazolidine-2,4-dione (i) 5-(5-Chloro-2-(methylthio)pyrimidin-4-yl)-N-methyl-N-phenylthiazol-2-amine Prepared in an analogous manner to Example 424. MS (M+H)$^+$ 349.

(ii) 5-(5-Chloro-2-(methylsulfonyl)pyrimidin-4-yl)-N-methyl-N-phenylthiazol-2-amine Prepared in analogous manner to Example 343. MS (M+H)$^+$ 380.

(iii) 1-(2-(5-Chloro-4-(2-(methyl(phenyl)amino)thiazol-5-yl)pyrimidin-2-ylamino)ethyl)-5,5-dimethylimidazolidine-2,4-dione Prepared in an analogous manner to Example 358. MS (M+H)$^+$ 472.

Example 458

1-(2-(5-Fluoro-4-(5-(2-(isopropylamino)ethoxy)benzo[b]thiophen-2-yl)pyrimidin-2-ylamino)ethyl)-5,5-dimethylimidazolidine-2,4-dione (i) 2-Chloro-4-(5-(2-chloroethoxy)benzo[b]thiophen-2-yl)-5-fluoropyrimidine Prepared in an analogous manner to Example 424. MS (M+H)$^+$ 342.

(ii) 1-(2-(4-(5-(2-Chloroethoxy)benzo[b]thiophen-2-yl)-5-fluoropyrimidin-2-ylamino)ethyl)-5,5-dimethylimidazolidine-2,4-dione Prepared in an analogous manner to Example 424. MS (M+H)$^+$ 478.

(iii) 1-(2-(5-Fluoro-4-(5-(2-(isopropylamino)ethoxy)benzo[b]thiophen-2-yl)pyrimidin-2-ylamino)ethyl)-5,5-dimethylimidazolidine-2,4-dione Prepared in analogous manner to Example 450. MS (M+H)$^+$ 501.

Example 459

1-(2-(5-Bromo-4-(5-isopropyl-7-phenyl-4,5,6,7-tetrahydrothieno[3,2-c]pyridin-2-yl)pyrimidin-2-ylamino)ethyl)-5,5-dimethylimidazolidine-2,4-dione (i) 1-Phenyl-2-(thiophen-3-ylmethylamino)ethanol
Prepared in an analogous manner to Example 420.
MS (M+H)$^+$ 234.

(ii) 7-Phenyl-4,5,6,7-tetrahydrothieno[3,2-c]pyridine

1-Phenyl-2-(thiophen-3-ylmethylamino)ethanol (4.5 g, 19.2 mmol) was added to a flask containing polyphosphoric acid (20 g) and the mixture was heated to 80° C. After 1 h, the reaction was cooled down to room temperature and treated with crushed ice. The mixture was then rendered basic using ammonium hydroxide. The aqueous mixture was extracted twice with dichloromethane. The organic layers were combined and washed with water and brine. The organic portion was dried with sodium sulfate, reduced in vacuo and placed on a vacuum line to give an oil. Yield=3.5 g. MS (M+H)$^+$ 216.

(iii) 1-Phenyl-2-(thiophen-3-ylmethylamino)ethanol

Prepared in an analogous manner to Example 456. MS (M+H)$^+$ 316.

(iv) tert-Butyl 2-(5-bromo-2-chloropyrimidin-4-yl)-7-phenyl-6,7-dihydrothieno[3,2-c]pyridine-5(4H)-carboxylate Prepared in analogous manner to Example 424. MS (M+H)$^+$ 507.

(v) tert-Butyl 2-(5-bromo-2-(2-(5,5-dimethyl-2,4-dioxoimidazolidin-1-yl)ethylamino)pyrimidin-4-yl)-7-phenyl-6,7-dihydrothieno[3,2-c]pyridine-5(4H)-carboxylate Prepared in an analogous manner to Example 358. MS (M+H)+ 642.

(vi) 1-(2-(5-Bromo-4-(7-phenyl-4,5,6,7-tetrahydrothieno[3,2-c]pyridin-2-yl)pyrimidin-2-ylamino)ethyl)-5,5-dimethylimidazolidine-2,4-dione Prepared in an analogous manner to Example 450. MS (M+H)+ 542.

(vii) 1-(2-(5-Bromo-4-(5-isopropyl-7-phenyl-4,5,6,7-tetrahydrothieno[3,2-c]pyridin-2-yl)pyrimidin-2-ylamino)ethyl)-5,5-dimethylimidazolidine-2,4-dione Prepared in analogous manner to Example 456. MS (M+H)+ 584.

Example 460

1-(2-(5-Chloro-4-(7-phenyl-4,5,6,7-tetrahydrothieno[3,2-c]pyridin-2-yl)pyrimidin-2-ylamino)ethyl)-5,5-dimethylimidazolidine-2,4-dione (i) tert-Butyl 2-(5-chloro-2-(methylthio)pyrimidin-4-yl)-7-phenyl-6,7-dihydrothieno[3,2-c]pyridine-5(4H)-carboxylate Prepared in an analogous manner to Example 424. MS (M+H)+ 474.

(ii) tert-Butyl 2-(5-chloro-2-(methylsulfonyl)pyrimidin-4-yl)-7-phenyl-6,7-dihydrothieno[3,2-c]pyridine-5(4H)-carboxylate Prepared in analogous manner to Example 343. MS (M+H)+ 506.

(iii) tert-Butyl 2-(5-chloro-2-(2-(5,5-dimethyl-2,4-dioxoimidazolidin-1-yl)ethylamino)pyrimidin-4-yl)-7-phenyl-6,7-dihydrothieno[3,2-c]pyridine-5(4H)-carboxylate Prepared in an analogous manner as Example 358. MS (M+H)+ 597.

(iv) 1-(2-(5-Chloro-4-(7-phenyl-4,5,6,7-tetrahydrothieno[3,2-c]pyridin-2-yl)pyrimidin-2-ylamino)ethyl)-5,5-dimethylimidazolidine-2,4-dione Prepared in an analogous manner to Example 450. MS (M+H)+ 497.

Example 461

1-(2-(5-Bromo-4-(7-chlorobenzo[b]thiophen-2-yl)pyrimidin-2-ylamino)ethyl)-5,5-dimethylimidazolidine-2,4-dione (i) Methyl 7-chlorobenzo[b]thiophene-2-carboxylate 3-Chloro-2-fluorobenzaldehyde (1 g, 6.3 mmol) was dissolved in DMSO (10 mL) and treated with methylthioglycolate, followed by diethylamine (0.58 mL, 6.3 mmol). The reaction was heated to 70° C. and stirred overnight. The reaction was allowed to cool down to room temperature and diluted with water (25 mL). The solid that precipitated out of solution was collected by filtration and washed well with water. The solid was then purified by flash chromatography using a gradient of 2 to 20% ethyl acetate in hexanes to afford a white solid (0.8 g).

(ii) 7-Chlorobenzo[b]thiophene-2-carboxylic acid

Methyl 7-chlorobenzo[b]thiophene-2-carboxylate (3 g, 13 mmol) was dissolved is ethanol (15 mL) and treated 5 N sodium hydroxide (5 mL). The reaction was heated at reflux overnight. The volatiles were removed in vacuo and the aqueous residue was acidified to pH 2 using 5 N HCl. The resulting white solid was filtered off, washed well with water and dried in a vacuum oven at 60° C. Yield=2.6 g. MS (M−H)-210.

(iii) 7-Chlorobenzo[b]thiophene

7-Chlorobenzo[b]thiophene-2-carboxylic acid (2.5 g, 11.8 mmol) was suspended in quinoline (20 mL) and treated with copper (0.779 g, 13 mmol). The mixture was heated to 190° C. After 1.5 h, the mixture was allowed to cool down to room temperature and diluted with 200 mL of 2 N HCl. The mixture was extracted three times with ethyl acetate. All the organic layers were combined and washed with 1 N HCl, water and brine, then dried with sodium sulfate. Purification was achieved by flash chromatography using 10 to 20% ethyl acetate in hexanes. Yield=1.8 g.

(iv) 5-Bromo-2-chloro-4-(7-chlorobenzo[b]thiophen-2-yl)pyrimidine

Prepared in an analogous manner to Example 424. MS (M+H)+ 358/360.

(v) 1-(2-(5-Bromo-4-(7-chlorobenzo[b]thiophen-2-yl)pyrimidin-2-ylamino)ethyl)-5,5-dimethylimidazolidine-2,4-dione Prepared in analogous manner to Example 358. MS (M+H)+ 494/496.

Example 462

1-(2-(5-(3-Hydroxyphenyl)-4-(5-(piperidin-1-ylmethyl)thiophen-2-yl)pyrimidin-2-ylamino)ethyl)imidazolidin-2-one (i) 1-(Thiophen-2-ylmethyl)piperidine 2-Thiophenecarboxaldehyde (1 g, 8.9 mmol) was dissolved in dichloroethane and treated with piperidine and sodium triacetoxyborohydride. The reaction was stirred at room temperature overnight. The reaction was diluted with dichloromethane and aqueous saturated sodium bicarbonate. The organic layer was separated out, washed with water and brine and dried with sodium sulfate. The volatile were removed in vacuo and the residue was purified by column chromatography on silica gel using a gradient of 2 to 8% of methanol in dichloromethane to obtain a brown oil. Yield=1.5 g. MS (M+H)+ 182.

(ii) 5-Bromo-2-chloro-4-(5-(piperidin-1-ylmethyl) thiophen-2-yl)pyrimidine

Prepared in an analogous manner to Example 424. MS (M+H)+ 371/373.

(iii) 1-(2-(5-Bromo-4-(5-(piperidin-1-ylmethyl) thiophen-2-yl)pyrimidin-2-ylamino)ethyl)imidazolidin-2-one 5-Bromo-2-chloro-4-(5-(piperidin-1-ylmethyl)thiophen-2-yl)pyrimidine (0.3 g, 0.8 mmol), 1-(2-aminoethyl)imidazolidin-2-one (0.123 g, 0.96 mmol) and isopropyl alcohol were all placed in a microwave tube. The tube was capped and heated to 170° C. in a Personal Chemistry microwave for 10 min. The reaction then diluted with dichloromethane washed with water, saturated sodium bicarbonate, water and brine. The organic layer was dried with sodium sulfate and purified by flash chromatography using a gradient of 2 to 12% methanol in dichloromethane to give a light yellow solid (0.23 g). MS (M+H)+ 465/476.

(iv) 1-(2-(5-(3-Hydroxyphenyl)-4-(5-(piperidin-1-ylmethyl)thiophen-2-yl)pyrimidin-2-ylamino)ethyl) imidazolidin-2-one Prepared in an analogous manner to Example 345. MS (M+S)+ 479.

Example 463

1-(2-(5-Bromo-4-(5-(piperidin-1-ylmethyl)thiophen-2-yl)pyrimidin-2-ylamino)ethyl)-5,5-dimethylimidazolidine-2,4-dione Prepared in an analogous manner to Example 462. MS (M+H)+ 507/509.

Example 464

1-(2-(5-Bromo-4-(2-(piperidin-1-ylmethyl)thiazol-5-yl)pyrimidin-2-ylamino)ethyl)-5,5-dimethylimidazolidine-2,4-dione (i) 1-(Thiazol-2-ylmethyl)piperidine Prepared in an analogous manner to Example 462. MS (M+H)+ 183.

(ii) 5-Bromo-2-chloro-4-(2-(piperidin-1-ylmethyl) thiazol-5-yl)pyrimidine

Prepared in an analogous manner to Example 424. MS (M+H)+ 372/374.

(iii) 1-(2-(5-Bromo-4-(2-(piperidin-1-ylmethyl)thiazol-5-yl)pyrimidin-2-ylamino)ethyl)-5,5-dimethylimidazolidine-2,4-dione Prepared in a manner analogous to Example 462. MS (M+H) 508/510.

Example 465

1-(2-(5-Bromo-4-(7-phenyl-4,5-dihydrothieno[2,3-c] pyridin-2-yl)pyrimidin-2-ylamino)ethyl)-5,5-dimethylimidazolidine-2,4-dione (i) 2-(Thiophen-3-yl)ethanamine hydrochloride Borane.THF (1 M in THF, 242 mL, 242 mmol) was added to a 1 L 3-neck flask equipped with a temperature probe, a reflux condenser, a magnetic stir and an addition funnel. 2-(thiophen-3-yl)acetonitrile (15 g, 121 mmol), dissolved in 200 mL of THF was added dropwise to the reaction mixture. After the addition was complete, the reaction was heated to reflux for 6 h and then at room temperature overnight. The volatiles were removed in vacuo and methanol (150 mL) was carefully added to the mixture. HCl gas was bubbled into the methanolic solution for 15 min. The volatiles were removed in vacuo to obtain a white solid. Yield=17.4 g. MS (M+H)+ 164.

(ii) N-(2-(Thiophen-3-yl)ethyl)benzamide 2-(Thiophen-3-yl)ethanamine hydrochloride (3 g, 18 mmol) was taken in THF (40 mL) and treated with triethylamine (9.92 mL, 71.2 mmol). The reaction was cooled down to 0° C. and benzoyl chloride (2.55 mL, 21.9 mmol), diluted with THF was added dropwise to the reaction. The reaction was stirred for 3 h and the volatiles removed in vacuo. The residue was dissolved in ethyl acetate and washed with an aqueous saturated solution of sodium bicarbonate, water and brine. The organic solution was dried with sodium sulfate and purified by flash chromatography using a gradient of 25 to 70% ethyl acetate in hexanes to afford an off-white solid (4 g). MS (M+H)+ 232.

(iii) 7-Phenyl-4,5-dihydrothieno[2,3-c]pyridine

N-(2-(Thiophen-3-yl)ethyl)benzamide (1.5 g, 6.48 mmol) suspended in xylenes (20 mL) was treated with phosphorous oxychloride (3.62 mL, 38 mmol) and phosphorous pentoxide (5.39 g, 19 mmol). The mixture was heated to reflux for 3 h and the volatiles were removed in vacuo. The residue was diluted with cold water and ethyl acetate. 5 N sodium hydroxide was added and the mixture and the layers were separated. The aqueous layer was extracted twice more with ethyl acetate. All the organic layers were combined and washed with aqueous solution of sodium bicarbonate, water, then brine. The organic layer was dried with sodium sulfate and purified by flash chromatography using a gradient of 20 to 60% of ethyl acetate in hexanes to afford a light yellow clear oil (1.28 g). MS (M+H)+ 214.

(iv) 2-(5-Bromo-2-chloropyrimidin-4-yl)-7-phenyl-4,5-dihydrothieno[2,3-c]pyridine Prepared in analogous manner to Example 424. MS (M+H)+ 403/405.

(v) 1-(2-(5-Bromo-4-(7-phenyl-4,5-dihydrothieno[2,3-c]pyridin-2-yl)pyrimidin-2-yl-amino)ethyl)-5,5-dimethylimidazolidine-2,4-dione Prepared in an analogous manner to Example 462. MS (M+H)+ 539/541.

5.1 Human Polo-Like Kinase 1 (Plk1) Inhibitor Primary Dose-Response Assay

Inhibitor compounds were dissolved in 100% DMSO and serially diluted 3 fold in a polypropylene 96-well microtiter plate (drug plate). Rows 6 and 12 (HI controls and LO controls respectively) were reserved as controls and contained only DMSO. Two microliters of inhibitor compounds from the drug plate were transferred to another polypropylene 96-well microtiter plate (assay plate) containing 33 μL of kinase reaction buffer (KRB; 50 mM Tris/HCl pH 7.5, 5 mM $MgCl_2$, 1 mM EGTA, 0.2 mg/mL BSA, 10 mM α-glycerophosphate, 5 mM DTT). Immediately 10 μL of 5× substrate buffer (KRB with 50 μM ATP, 2.5 μM GSTcJun-avitag) and 5 μL 10× enzyme (100 nM truncated recombinant PLK1-344 protein) was added. Row 6 (HI control) contained enzyme, substrate and kinase reaction buffer while row 12 (LO control) contained enzyme, kinase reaction buffer without substrate.

After a 60 min incubation at room temperature with shaking, the reaction was terminated by transfer of a 5 μL aliquot of the kinase reaction into a black polypropylene 96-well microtiter plate (detection plate) containing 45 μL of Kinase Detection Buffer (KDB) (100 mM Hepes pH 7.5, 100 mM NaCl, 0.1% BSA, 0.05% Tween 20) supplemented with 20 nM Streptavidin Allophycocyanin (SA-APC) and 250 pM europium labeled anti-MPM2 antibody. After 60 min at room temperature, the wells were excited with coherent 320 nm light, and the ratio of delayed (50 ms post excitation) emissions at 620 nm (native europium fluorescence) and 665 nm (europium fluorescence transferred to allophycocyanin—an index of substrate phosphorylation) determined.

The proportion of substrate phosphorylated in the kinase reaction in the presence of compound compared with that phosphorylated in the presence of DMSO vehicle alone (HI control) was calculated using the formula: % control (POC)=(cpd−average LO)/(average HI−averageLO)*100. Data (consisting of POC and inhibitor concentration in μM) was fitted to a 4-parameter equation (y=A+((B−A)/(1+ ((x/C)^D))), where A is the minimum y (POC) value, B is the maximum y (POC), C is the x (cpd concentration) at the point of inflection and D is the slope factor) using a Levenburg-Marquardt non-linear regression algorithm. The inhibition constant (Ki) of the inhibitor was estimated from the $IC_{50}$ (cpd concentration at the point of inflection; C) using the Cheng-Prussof equation: $Ki=IC_{50}/(1+S/Km)$, where S is the ATP substrate concentration, and Km is the Michaelis constant for ATP as determined experimentally.

The compounds of Examples 1-465 exhibited plk1 kinase activity with $IC_{50}$ values less than 1 μM.

The foregoing has demonstrated the pertinent and important features of the present invention. Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

All references cited herein are incorporated herein by reference in their entirety and for all purposes to the same extent as if each individual publication or patent or patent application was specifically and individually indicated to be incorporated by reference in its entirety for all purposes.

What is claimed is:
1. A compound of Formula I

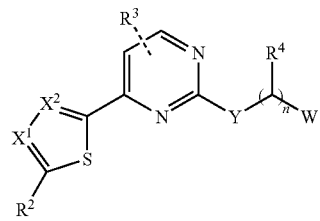

wherein:
$X^1$ is N;
$X^2$ is CH or N;
Y is O, S, $CH(R^7)$,
W is selected from CN,

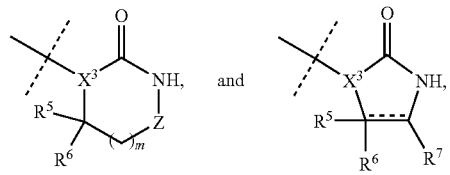

wherein m is 0 or 1, $X^3$ is CH or N, and Z is $CH_2$ or C(O);

$R^2$ is selected from the group consisting of H, halo, CN, $C_1$-$C_6$ alkyl which may be interrupted by one or more hetero atoms, —$(CR^8R^9)_t$(aryl), —$(CR^8R^9)_t$(heteroaryl), —$(CR^8R^9)_t$(cycloalkyl), —$(CR^8R^9)_t$(heterocyclyl), —$(CR^8R^9)_tN(R^{10})(R^{11})$, —$(CR^8R^9)_tSO_2(R^{10})$, —$(CR^8R^9)_tSO_2(N)(R^{10})(R^{11})$, —$(CR^8R^9)_tSO_2$(cycloalkyl), —$(CR^8R^9)_tSO(R^{10})$, and —$(CR^8R^9)_tS(R^{10})$;

$R^3$ is H, OH, halo, $NO_2$, $NH_2$, CN, $C_1$-$C_6$ alkyl, $C_1$-$C_6$ alkoxy, $C_1$-$C_6$ alkylamino, $C_2$-$C_6$ alkenyl, $C_2$-$C_6$ alkynyl, or an aryl or heteroaryl;

$R^4$, $R^7$, $R^8$, and $R^9$ are independently selected from —H and $C_1$-$C_6$ alkyl;

$R^5$ and $R^6$ are independently selected from —H, $C_1$-$C_6$ alkyl, alkenyl, aryl, heteroaryl, cycloalkyl, and heterocyclyl, or $R^5$ and $R^6$ together with the atom to which they are linked join to form a 3 to 6-membered carbocyclic ring or heterocyclic ring containing a NH, O or S heteroatom;

$R^{10}$ and $R^{11}$ are independently selected from $C_1$-$C_6$ alkyl, aryl, heteroaryl, cycloalkyl, and heterocyclyl;

wherein n is an integer from 1 to 6, and each t is an integer from 0 to 2;

wherein the above alkyl, alkenyl, aryl, heteroaryl, cycloalkyl, heterocyclyl, heterocyclic, and carbocyclic moieties are optionally substituted by 1-3 substituents selected from alkanoyl, alkylamine, amino, aryl, heteroaryl, cycloalkyl, heterocyclyl, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms, carboxyl, cyano, halo, hydroxy, nitro, —N=N—$NH_2$, —$C(O)_2$—($C_1$-$C_6$ alkyl), —$C(O)_2$(aryl), —$C(O)_2$-(heteroaryl), —$C(O)_2$-(cycloalkyl), —$C(O)_2$-(heterocyclyl), —O—($C_1$-$C_6$ haloalkyl), —O—($C_1$-$C_6$ alkyl)aryl, —O—($C_1$-$C_6$ alkyl)heteroaryl, —O—($C_1$-$C_6$ alkyl)cycloalkyl, —O—($C_1$-$C_6$ alkyl)heterocyclyl, —O—($C_1$-$C_6$ alkyl)amino, —O—($C_1$-$C_6$ alkyl)alkylamino, —O—($C_1$-$C_6$ alkyl)dialkylamino, —O-aryl, —O-heteroaryl, —NHC(O)—($C_1$-$C_6$ alkyl), —NHC(O)—($C_1$-$C_6$ alkylene), —NHC(O)-(aryl), —NHC(O)-(heteroaryl), —NHC(O)-(cycloalkyl), —NHC(O)-(heterocyclyl), —NHC(O)—($C_1$-$C_6$ alkyl)aryl, —NHC(O)—($C_1$-$C_6$ alkyl) heteroaryl, —NHC(O)—($C_1$-$C_6$ alkyl)cycloalkyl, —NHC(O)—($C_1$-$C_6$ alky)heterocyclyl, —NHC(O)—($C_1$-$C_6$ alkyl)amino,—NHC(O)—($C_1$-$C_6$ alkyl)alkylamine, —NHC(O)—($C_1$-$C_6$ alkyl)dialkylamine, —NHC(O)—($C_1$-$C_6$ alkyl)C(O)amino, —NHC(O)—($C_1$-$C_6$ akyl)C(O)alkylamine, —NHC(O)—($C_1$-$C_6$ alkyl)C(O)dialkamine, —NHC(O)—($C_1$-$C_6$ alkyl)N(H)—($C_1$-$C_6$ alkyl)C(O)$_2$—($C_1$-$C_6$ alkyl), —NHC(O)—($C_1$-$C_6$ alkyl)S(O)$_2$($C_1$-$C_6$ alkyl), —NHC(O)—($C_1$-$C_6$ alkyl)-S-(heterocyclyl), —NHS(O)$_2$—($C_1$-$C_6$ alkyl), —NHS(O)$_2$-(aryl), —NHS(O)$_2$-(heteroaryl), —NHS(O)$_2$-(cycloalkyl), —NHS(O)$_2$(heterocyclyl), —NHS(O)($C_1$-$C_6$ alkyl), —NHS(O)(aryl), —NHS(O)(heteroaryl), —NHS(O)(cycloalkyl), —NHS(O)(heterocyclyl), —NHS($C_1$-$C_6$ alkyl), —NHS(aryl), —NHS(heteroaryl), —NHS(cycloalkyl), and —NH—S-(heterocyclyl), wherein each of the above aryl, heteroaryl, cycloalkyl, or heterocyclyl moieties can be further optionally substituted by 1-5 substituents selected from amino, $C_1$-$C_6$ alkylamine, $C_1$-$C_6$ dialkylamine, $C_1$-$C_6$ alkyl, $C_1$-$C_6$ alkoxy, $C_2$-$C_6$ alkenyl, $C_1$-$C_6$ hydroxyl, and $C_1$-$C_6$ hydroxyalkyl, or a pharmaceutically acceptable salt thereof.

2. The compound of claim 1 or pharmaceutically acceptable salt thereof, wherein n is 2 and $R^4$ is H.

3. The compound of claim 1 or pharmaceutically acceptable salt thereof, wherein $R^3$ is halo, haloalkyl, aryl, or CN.

4. The compound of claim 1 or pharmaceutically acceptable salt thereof, wherein W is

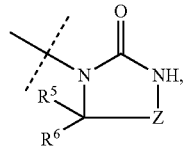

Z is $CH_2$, or C(O); and $R^5$ and $R^6$ are independently selected from —H and $C_1$-$C_6$ alkyl.

5. The compound of claim 1 or pharmaceutically acceptable salt thereof, wherein $R^5$ and $R^6$ are each —$CH_3$.

6. The compound of claim 1 or pharmaceutically acceptable salt-thereof, wherein $X^2$ is N.

7. The compound of claim 1 or pharmaceutically acceptable salt thereof, wherein $X^2$ is CH.

8. The compound of claim 1 or pharmaceutically acceptable salt thereof, wherein $R^1$ and $R^2$ are each independently selected from the group consisting of $C_1$-$C_6$ alkyl, —$(CR^8R^9)_t$(aryl), —$(CR^8R^9)_t$(heterocyclyl), —$(CR^8R^9)_t$N($R^{10}$)($R^{11}$), $(CR^8R^9)_tSO_2(R^{10})$, —$(CR^8R^9)_tS(R^{10})$; wherein t is an integer from 0 to 2; and wherein $R^{10}$ and $R^{11}$ are independently selected from $C_1$-$C_6$ alkyl, aryl, and heterocyclyl.

9. A pharmaceutical composition comprising a pharmaceutically-acceptable carrier and a compound of claim 1.

10. The composition of claim 9, further comprising at least one additional therapeutic agent.

11. A method for treating a kinase-mediated disorder selected from rheumatoid arthritis and breast cancer, in a mammal in need thereof comprising administering to the mammal a therapeutically effective amount of a compound of claim 1.

12. The method of claim 11 wherein the disorder is breast cancer.

\* \* \* \* \*